(12) United States Patent
Braig et al.

(10) Patent No.: US 7,972,296 B2
(45) Date of Patent: Jul. 5, 2011

(54) FLUID COMPONENT ANALYSIS SYSTEM AND METHOD FOR GLUCOSE MONITORING AND CONTROL

(75) Inventors: James R. Braig, Piedmont, CA (US); Richard Keenan, Livermore, CA (US); Peter Rule, Los Altos Hills, CA (US); Gil Rivas, Danville, CA (US); Mahesh Seetharaman, Danville, CA (US)

(73) Assignee: OptiScan Biomedical Corporation, Hayward, CA (US)

( * ) Notice: Subject to any disclaimer, the term of this patent is extended or adjusted under 35 U.S.C. 154(b) by 0 days.

(21) Appl. No.: 12/249,831

(22) Filed: Oct. 10, 2008

(65) Prior Publication Data

US 2009/0131861 A1 May 21, 2009

Related U.S. Application Data

(60) Provisional application No. 60/979,044, filed on Oct. 10, 2007, provisional application No. 60/979,380, filed on Oct. 11, 2007, provisional application No. 61/025,260, filed on Jan. 31, 2008, provisional application No. 60/979,348, filed on Oct. 11, 2007, provisional application No. 61/096,461, filed on Sep. 12, 2008, provisional application No. 61/099,491, filed on Sep. 23, 2008.

(51) Int. Cl.
*A61M 31/00* (2006.01)
(52) U.S. Cl. ............................................. 604/66; 604/65
(58) Field of Classification Search ............... 417/477.2; 600/431–435; 604/65–67, 118–121, 131–147, 604/151–155, 890.1–892.1
See application file for complete search history.

(56) References Cited

U.S. PATENT DOCUMENTS

| 2,797,149 A | 6/1957 | Skeggs |
| 3,634,039 A | 1/1972 | Broady |
| 4,055,175 A | 10/1977 | Clemens et al. |
| 4,151,845 A | 5/1979 | Clemens |
| 4,245,634 A * | 1/1981 | Albisser et al. ............ 604/66 |
| 4,403,984 A | 9/1983 | Ash et al. |
| 4,464,170 A | 8/1984 | Clemens et al. |
| 4,526,568 A | 7/1985 | Clemens et al. |
| 4,573,968 A | 3/1986 | Parker |

(Continued)

FOREIGN PATENT DOCUMENTS

DE 197 56 872 A1 7/1999

(Continued)

OTHER PUBLICATIONS

International Search Report and Written Opinion in PCT/US2008/079641 dated Feb. 25, 2009.

(Continued)

*Primary Examiner* — Nicholas D Lucchesi
*Assistant Examiner* — Gerald Landry, II
(74) *Attorney, Agent, or Firm* — Knobbe, Martens, Olson & Bear, LLP

(57) ABSTRACT

Disclosed are methods and apparatus for determining analyte concentration in a sample such as bodily fluid. Systems and methods disclosed herein can also include a treatment dosing system to infuse or inject a treatment drug (e.g. insulin or glucose) and provide glycemic control. The dose of the treatment drug may be based on the concentration of the analyte or the average value for the concentration of the analyte and/or the rate of change of the value of the concentration of the analyte.

38 Claims, 48 Drawing Sheets

U.S. PATENT DOCUMENTS

| | | | |
|---|---|---|---|
| 4,633,878 A | 1/1987 | Bombardieri | |
| 4,657,529 A | 4/1987 | Prince et al. | |
| 4,854,170 A | 8/1989 | Brimhall | |
| 4,900,292 A | 2/1990 | Berry et al. | |
| 4,919,596 A | 4/1990 | Slate et al. | |
| 4,925,444 A | 5/1990 | Orkin et al. | |
| 4,940,527 A | 7/1990 | Kazlauskas | |
| 4,976,720 A | 12/1990 | Machold et al. | |
| 4,981,140 A | 1/1991 | Wyatt | |
| 5,097,834 A | 3/1992 | Skrabal et al. | |
| 5,102,406 A | 4/1992 | Arnold | |
| 5,109,850 A | 5/1992 | Blanco et al. | |
| 5,134,079 A | 7/1992 | Cusack et al. | |
| 5,165,406 A | 11/1992 | Wong | |
| 5,207,642 A | 5/1993 | Orkin et al. | |
| 5,237,993 A | 8/1993 | Skrabal | |
| 5,273,517 A | 12/1993 | Barone | |
| 5,299,571 A | 4/1994 | Mastrototaro | |
| 5,380,665 A | 1/1995 | Cusack et al. | |
| 5,385,539 A | 1/1995 | Maynard | |
| 5,505,828 A | 4/1996 | Wong et al. | |
| 5,609,572 A | 3/1997 | Lang | |
| 5,665,065 A | 9/1997 | Colman et al. | |
| 5,697,899 A * | 12/1997 | Hillman et al. | 604/28 |
| 5,758,643 A | 6/1998 | Wong et al. | |
| 5,817,007 A | 10/1998 | Fodgaard et al. | |
| 5,820,622 A | 10/1998 | Gross et al. | |
| 5,902,253 A * | 5/1999 | Pfeiffer et al. | 600/584 |
| 6,017,318 A | 1/2000 | Gauthier | |
| 6,032,059 A | 2/2000 | Henning et al. | |
| 6,040,578 A | 3/2000 | Malin | |
| 6,049,727 A | 4/2000 | Crothall | |
| 6,058,934 A | 5/2000 | Sullivan | |
| 6,077,055 A | 6/2000 | Vilks | |
| 6,101,406 A | 8/2000 | Hacker et al. | |
| 6,124,134 A | 9/2000 | Stark | |
| 6,128,519 A | 10/2000 | Say | |
| 6,142,939 A | 11/2000 | Eppstein et al. | |
| 6,200,287 B1 | 3/2001 | Keller et al. | |
| 6,214,629 B1 | 4/2001 | Freitag et al. | |
| 6,261,065 B1 | 7/2001 | Nayak et al. | |
| 6,262,798 B1 | 7/2001 | Shepherd et al. | |
| 6,270,455 B1 | 8/2001 | Brown et al. | |
| 6,402,689 B1 | 6/2002 | Scarantino et al. | |
| 6,491,656 B1 | 12/2002 | Morris | |
| 6,540,672 B1 | 4/2003 | Simonsen et al. | |
| 6,546,268 B1 | 4/2003 | Ishikawa et al. | |
| 6,558,351 B1 | 5/2003 | Steil et al. | |
| 6,560,471 B1 | 5/2003 | Heller et al. | |
| 6,561,978 B1 | 5/2003 | Conn et al. | |
| 6,718,189 B2 | 4/2004 | Rohrscheib et al. | |
| 6,751,490 B2 | 6/2004 | Esenaliev | |
| 6,780,156 B2 | 8/2004 | Haueter et al. | |
| 6,890,291 B2 | 5/2005 | Robinson et al. | |
| 6,958,809 B2 | 10/2005 | Sterling | |
| 6,989,891 B2 | 1/2006 | Braig | |
| 6,990,366 B2 | 1/2006 | Say et al. | |
| 7,061,593 B2 | 6/2006 | Braig | |
| 7,115,205 B2 | 10/2006 | Robinson et al. | |
| 7,171,252 B1 | 1/2007 | Scarantino et al. | |
| 7,190,988 B2 | 3/2007 | Say et al. | |
| 7,267,665 B2 | 9/2007 | Steil et al. | |
| 7,278,983 B2 * | 10/2007 | Ireland et al. | 604/66 |
| 7,291,107 B2 | 11/2007 | Hellwig | |
| 7,291,497 B2 | 11/2007 | Holmes et al. | |
| 7,303,922 B2 | 12/2007 | Jeng et al. | |
| 7,354,420 B2 | 4/2008 | Steil et al. | |
| 7,388,202 B2 | 6/2008 | Sterling et al. | |
| 7,402,153 B2 | 7/2008 | Steil et al. | |
| 7,404,796 B2 | 7/2008 | Ginsberg | |
| 7,481,787 B2 | 1/2009 | Gable et al. | |
| 7,491,187 B2 | 2/2009 | Van Den Berghe et al. | |
| 7,500,949 B2 | 3/2009 | Gottlieb et al. | |
| 7,547,281 B2 | 6/2009 | Hayes et al. | |
| 7,608,042 B2 | 10/2009 | Goldberger et al. | |
| 7,785,258 B2 | 8/2010 | Braig et al. | |
| 2001/0051377 A1 | 12/2001 | Hammer | |
| 2002/0128543 A1 | 9/2002 | Leonhardt | |
| 2002/0147423 A1 | 10/2002 | Burbank | |
| 2003/0086074 A1 | 5/2003 | Braig et al. | |
| 2003/0086075 A1 | 5/2003 | Braig et al. | |
| 2003/0090649 A1 | 5/2003 | Sterling et al. | |
| 2003/0130616 A1 | 7/2003 | Steil et al. | |
| 2003/0208113 A1 | 11/2003 | Mault et al. | |
| 2003/0208154 A1 | 11/2003 | Close et al. | |
| 2004/0147034 A1 | 7/2004 | Gore et al. | |
| 2004/0220517 A1 | 11/2004 | Starkweather | |
| 2004/0241736 A1 | 12/2004 | Hendee et al. | |
| 2004/0249308 A1 | 12/2004 | Forssell | |
| 2005/0003470 A1 | 1/2005 | Nelson et al. | |
| 2005/0049179 A1 | 3/2005 | Davidson et al. | |
| 2005/0105095 A1 | 5/2005 | Pesach et al. | |
| 2005/0171503 A1 | 8/2005 | Van Den Berghe et al. | |
| 2005/0192557 A1 * | 9/2005 | Brauker et al. | 604/503 |
| 2005/0203360 A1 | 9/2005 | Brauker et al. | |
| 2005/0272640 A1 | 12/2005 | Doyle | |
| 2006/0009727 A1 | 1/2006 | O'Mahony et al. | |
| 2006/0079809 A1 * | 4/2006 | Goldberger et al. | 600/576 |
| 2006/0197015 A1 * | 9/2006 | Sterling et al. | 250/252.1 |
| 2006/0200070 A1 | 9/2006 | Callicoat et al. | |
| 2006/0229531 A1 | 10/2006 | Goldberger et al. | |
| 2007/0060796 A1 | 3/2007 | Kim | |
| 2007/0060872 A1 * | 3/2007 | Hall et al. | 604/66 |
| 2007/0116601 A1 * | 5/2007 | Patton | 422/81 |
| 2007/0142720 A1 | 6/2007 | Ridder et al. | |
| 2007/0173761 A1 | 7/2007 | Kanderian | |
| 2007/0191716 A1 | 8/2007 | Goldberger et al. | |
| 2007/0225675 A1 | 9/2007 | Robinson et al. | |
| 2008/0051764 A1 | 2/2008 | Dent et al. | |
| 2008/0058625 A1 | 3/2008 | McGarraugh et al. | |
| 2008/0071157 A1 | 3/2008 | McGarraugh et al. | |
| 2008/0071158 A1 | 3/2008 | McGarraugh et al. | |
| 2008/0188796 A1 | 8/2008 | Steil et al. | |
| 2008/0200838 A1 | 8/2008 | Goldberger et al. | |
| 2008/0249386 A1 | 10/2008 | Besterman et al. | |
| 2008/0269585 A1 | 10/2008 | Ginsberg | |
| 2009/0006061 A1 | 1/2009 | Thukral et al. | |
| 2009/0069743 A1 | 3/2009 | Krishnamoorthy et al. | |
| 2009/0156922 A1 | 6/2009 | Goldberger et al. | |
| 2009/0228214 A1 | 9/2009 | Say et al. | |
| 2009/0326343 A1 | 12/2009 | Gable et al. | |
| 2010/0121170 A1 | 5/2010 | Rule | |

FOREIGN PATENT DOCUMENTS

| | | |
|---|---|---|
| EP | 0 549 341 A1 | 6/1993 |
| EP | 1 491 144 | 12/2004 |
| WO | WO 00/32258 A | 6/2000 |
| WO | WO 02/43866 | 6/2002 |
| WO | WO 02/082990 A1 | 10/2002 |
| WO | WO 03/016882 | 2/2003 |
| WO | WO 03/039362 | 5/2003 |
| WO | WO 03/045233 A1 | 6/2003 |
| WO | WO 2004/043250 A1 | 5/2004 |
| WO | WO 2004/092715 A1 | 10/2004 |
| WO | WO 2005/051170 | 6/2005 |
| WO | WO 2005/110601 A1 | 11/2005 |
| WO | WO 2009/049252 A1 | 4/2009 |

OTHER PUBLICATIONS

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et. al.,"Clinical Performance of an In line Ex-Vivo Point of Care Monitor: A Multicenter Study," Clinical Chemistry 48:11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

International Searching Authority, Invitation to Pay Additional Fees, International Application No. PCT/US2006/004929, mailed Jul. 27, 2006.

Farkas et al. "Single-Versus Triple-Lumen Central Catheter-Related Sepsis: A Prospective Randomized Study in a Critically III Population" The American Journal of Medicine Sep. 1992 vol. 93 p. 277-282.

Davidson, Paul C., et al., A computer-directed intravenous insulin system shown to be safe, simple, and effective in 120,618 h of operation, *Diabetes Care*, vol. 28, No. 10, Oct. 2005, pp. 2418-2423.

Davidson, Paul C., et al., *Glucommander: A Computer-Directed IV Insulin System Shown to be Safe, Simple, and Effective in 120,618 Hours of Operation*, Atlanta Diabetes Associates presentation.

Groke, A. "Microbial Contamination of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, *The New England Journal of Medicine*, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study".

Wilson, George S., et al., Progress toward the Development of an Implantable Sensor for Glucose, *Clin. Chem.*, vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

"Normoglycaemia in Intensive Care Evaluation and Survival Using Glucose Algorithm Regulation—NICE-SUGAR," downloaded Mar. 23, 2009.

Letters to the Editor regarding "Glucose Control in Critically Ill Patients," N Engl J Med 361:1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

* cited by examiner

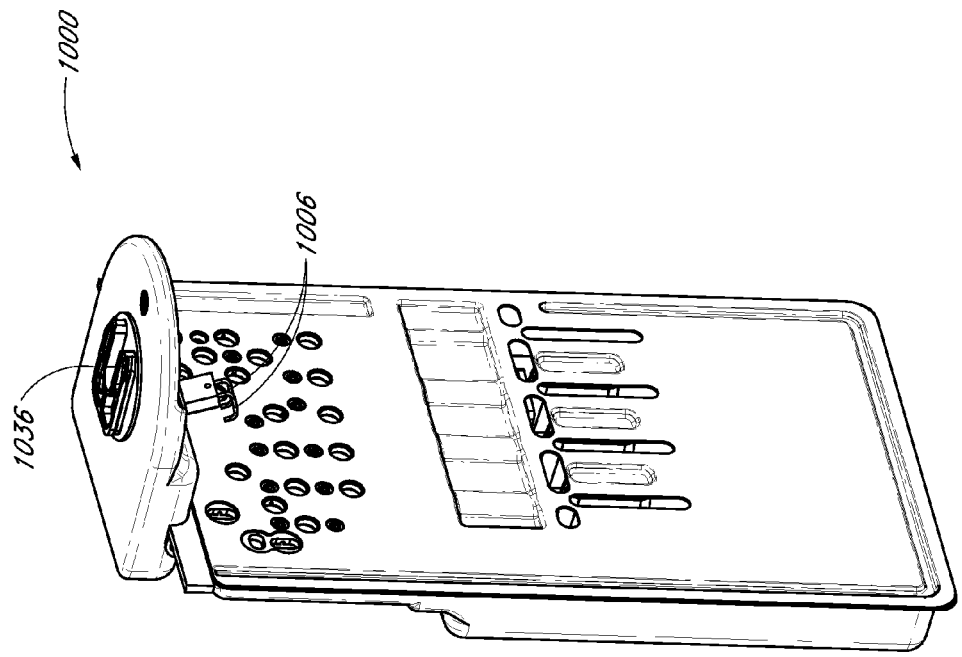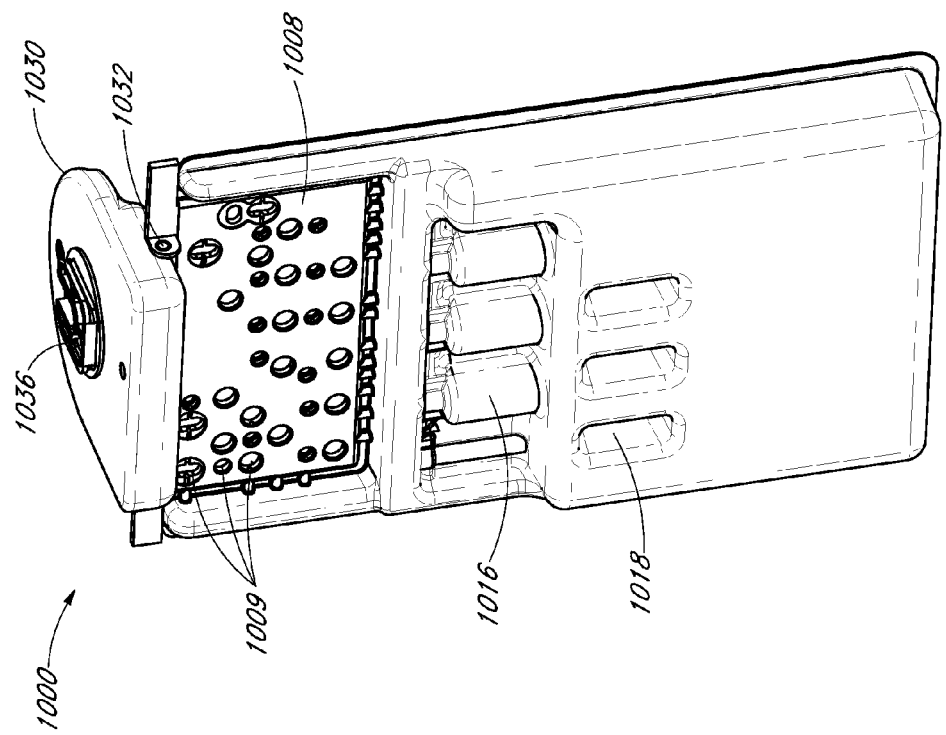
FIG. 10

FLUID COMPONENT ANALYSIS SYSTEM AND METHOD FOR GLUCOSE MONITORING AND CONTROL

CROSS-REFERENCE TO RELATED APPLICATIONS

This application claims the benefit under 35 U.S.C. §119 (e) of U.S. Provisional Patent Application No. 60/979,044, entitled "System and User Interface For Infusion and Analysis," filed Oct. 10, 2007; U.S. Provisional Patent Application No. 60/979,380, entitled "Fluid Component Analysis System and Bolus Injection," filed Oct. 11, 2007; U.S. Provisional Patent Application No. 61/025,260, entitled "Fluid Component Analysis System and Method for Glucose Monitoring and Control," filed Jan. 31, 2008; U.S. Provisional Patent Application No. 60/979,348, entitled "System and Method for Glucose Monitoring and Control," filed Oct. 11, 2007; U.S. Provisional Patent Application No. 61/096,461, entitled "Analyte Monitoring System and Treatment Dosing Protocol," filed Sep. 12, 2008; and U.S. Provisional Patent Application No. 61/099,491, entitled "An Analyte Monitoring System Including a Treatment Dosing Assistant," filed Sep. 23, 2008. Each of the foregoing applications, as well as U.S. Provisional Patent Application No. 60/978,385, entitled "Dilution Calibration for an Analyte Detection System," filed Oct. 8, 2007, is hereby incorporated by reference in its entirety and made part of this specification.

BACKGROUND

1. Field

Some embodiments of the disclosure relate generally to methods and devices for determining a concentration of an analyte in a sample, such as an analyte in a sample of bodily fluid, as well as methods and devices which can be used to support the making of such determinations. This disclosure also relates generally to a user interface for use with such apparatus. Some embodiments of this disclosure also relate generally to bolus injection and basal infusion systems and related apparatus. Some embodiments in this disclosure also relate to an analyte detection system configured to provide glycemic control and/or Tight Glycemic Control (TGC). Some aspects of this disclosure relate to an analyte detection system that is configured to determine a dosing protocol based on one or more measurements of the concentration of an analyte. Some aspects of this disclosure relate to a system and method that provides feedback to a healthcare provider regarding the treatment dose being administered to the patient. Some aspects of this disclosure also relate generally to systems and methods for calibrating analyte concentration when dilution of the sample has occurred.

2. Description of Related Art

It is advantageous to measure the levels of certain analytes, such as glucose, in a bodily fluid, such as blood). This can be done, for example, in a hospital or clinical setting when there is a risk that the levels of certain analytes may move outside a desired range, which in turn can jeopardize the health of a patient. Systems for measuring analyte levels may include a user interface (UI) that permits a user such as, for example, a patient, a health care provider, and so forth, to interact with the system. Currently known systems for analyte monitoring in a hospital or clinical setting may suffer from various drawbacks.

SUMMARY

Example embodiments described herein have several features, no single one of which is indispensible or solely responsible for their desirable attributes. Without limiting the scope of the claims, some of the advantageous features will now be summarized.

Embodiments of an analyte detection and treatment dosing system comprising a fluid transport network configured to provide fluid communication with a body fluid in a patient through a patient end are disclosed. The disclosed embodiments can further comprise at least one pump system coupled to the fluid transport network, the pump system having a sampling mode in which the pump system is operable to withdraw a sample of bodily fluid from the patient end and transport said sample of bodily fluid toward the body fluid analyzer, and an infusion mode in which the pump system is operable to transport an infusion fluid to the patient. The disclosed embodiments can further comprise a body fluid analyzer accessible via the fluid transport network, the body fluid analyzer configured to measure a characteristic of at least one analyte in the body fluid and determine the concentration of the at least one analyte from the measured characteristic; and a treatment dosing system in communication with the body fluid analyzer, said treatment dosing system including a treatment dosing protocol stored in a computer memory and configured to automatically determine a recommended dose of an infusion substance configured to provide glycemic control, wherein the body fluid analyzer determines the recommended dose based at least in part on the measured concentration of the analyte and the stored treatment dosing protocol, wherein the treatment dosing system comprising a treatment pump having a variable pump rate to deliver the recommended dose of the infusion substance to the patient.

Embodiments of an analyte detection and treatment dosing system comprising a fluid transport network configured to provide fluid communication with a body fluid in a patient through a patient end are disclosed. Disclosed embodiments comprise at least one pump system coupled to the fluid transport network, the pump system having a sampling mode in which the pump system is operable to withdraw a sample of bodily fluid from the patient end and transport said sample of bodily fluid towards the body fluid analyzer, and an infusion mode in which the pump system is operable to transport an infusion fluid to the patient. The disclosed embodiments also comprise a body fluid analyzer accessible via the fluid transport network, the body fluid analyzer configured to measure a characteristic of at least one analyte in the body fluid and determine the concentration of the at least one analyte from the measured characteristic; and a treatment dosing system in communication with the body fluid analyzer, said treatment dosing system including a treatment dosing protocol stored in a computer memory and configured to automatically determine a recommended dose of an infusion substance configured to provide glycemic control, wherein the recommended dose is determined based at least in part on one or more determinations by the body fluid analyzer of the concentration of the analyte and the treatment dosing protocol. In some embodiments, the treatment dosing system comprises a basal delivery system and a bolus injection system, both systems configured to deliver infusion substances to the patient through said patient end and through the same intravenous access line.

Embodiments of an analyte detection and control system to determine and regulate the concentration of one or more analytes in a sample of bodily fluid are disclosed. The disclosed embodiments, can comprise a control system, an analyte detector configured to measure a characteristic of at least one analyte in the sample of bodily fluid and determine a concentration of the analyte in the sample based on the measured characteristic, a fluid handling system operatively coupled to the analyte detector, said fluid handling system comprising a fluid passageway in communication with a patient through a patient end, a pump unit configured to engage the fluid handling system and draw a sample of bodily fluid from the patient periodically at draw intervals of less than 1 hour for analysis, a source of infusion fluid configured to adjust glycemic levels in the patient, said infusion fluid source in fluid communication with the fluid handling system and a treatment dosing system in communication with the body fluid analyzer, said treatment dosing system including a treatment dosing protocol and configured to determine a recommended dose for the infusion fluid, wherein the recommended dose is determined based at least in part on one or more determinations by the body fluid analyzer of the concentration of the analyte and the treatment dosing protocol.

An embodiment of a method of analyzing an analyte in the body fluid of a patient is disclosed. The method comprises placing a body fluid analyzer in fluid communication with the body fluid in the patient; transporting a sample of the body fluid toward the body fluid analyzer; with the body fluid analyzer, measuring a characteristic of an analyte in the bodily fluid and determining the concentration of the analyte in the body fluid, while the analyzer is in fluid communication with the body fluid in the patient; and with a treatment dosing system in communication with the body fluid analyzer, determining a recommended dose for an infusion fluid based at least in part on one or more determinations by the body fluid analyzer of the concentration of the analyte and a treatment dosing protocol.

An embodiment of a method of monitoring and regulating the concentration of one or more analytes in a sample of bodily fluid is disclosed. The method comprises providing a fluid connection to a patient; periodically withdrawing a certain volume of bodily fluid from the patient at draw intervals of less than 1 hour; sensing a property of the withdrawn fluid using one or more sensors; dividing the withdrawn volume of fluid into an analysis portion and a return portion; measuring a characteristic of said analysis portion to determine the concentration of an analyte in said analysis portion; determining a recommended dose for an infusion fluid for an infusion fluid based at least in part on one or more determinations by the body fluid analyzer of the concentration of the analyte and a treatment dosing protocol; and providing an instruction to an infusion fluid system to infuse the recommended dose of infusion fluid into the patient at a prescribed infusion fluid delivery rate.

Embodiments of an analyte detection and treatment dosing system are disclosed. Disclosed embodiments comprise a fluid transport network configured to provide fluid communication with a body fluid in a patient; a body fluid analyzer accessible via the fluid transport network, the body fluid analyzer configured to measure a characteristic of at least one analyte in the body fluid and determine the concentration of the at least one analyte from the measured characteristic; a treatment dosing system in communication with the body fluid analyzer, said treatment dosing system including a treatment dosing protocol and configured to determine a recommended dose for an infusion fluid configured to provide glycemic control, wherein the recommended dose is determined based at least in part on one or more determinations by the body fluid analyzer of the concentration of the analyte and the treatment dosing protocol; a treatment pump coupled to the fluid transport network, the treatment pump operable to transport the infusion fluid to the patient through the patient end; and a fluid system controller comprising a graphic user interface, said fluid system controller configured to actuate the treatment pump and control the pump rate of the pump, wherein the fluid system controller and the body fluid analyzer are both included within a single housing, the graphic user interface is located on the same housing, and the graphic user interface is configured to display the determined analyte concentration and the recommended dose. In some embodiments, the graphic user interface includes an input element configured to accept user input, the user interface further configured to adjust the actual dose of the infusion fluid based at least in part on the user input. In some embodiments the graphic user interface is configured to display both the recommended dose and the actual dose, where both the recommended dose and the actual dose are expressed as infusion rates. In some embodiments, the graphic user interface includes an input element configured to accept user input, the user interface configured to actuate the pump unit based at least in part on the user input.

Embodiments of an analyte monitoring system comprising a fluidic system in fluid communication with a source of bodily fluid, said fluidic system being configured to obtain a sample of bodily fluid from the source; an analyte detection system configured to analyze the sample of bodily fluid or a component of the sample of bodily fluid; and a fluid infusion system are disclosed. In some disclosed embodiments, the analyte detection system is configured to determine the concentration of an analyte in said sample of the bodily fluid or a component of the sample of the bodily fluid. In some embodiments, the analyte detection system is configured to access a measurement database and calculate an average concentration of the analyte based on the determined concentration and one or more previous values for the concentration of the analyte stored in the measurement database.

Embodiments of an analyte monitoring system comprising a fluidic system in fluid communication with a source of bodily fluid, said fluidic system being configured to obtain a first sample of bodily fluid from the source at a first time; an analyte detection system configured to analyze the first sample of bodily fluid or a component of the first sample of bodily fluid; and a fluid infusion system are disclosed. In some embodiments, the analyte detection system is configured to determine the concentration of an analyte in said first sample of the bodily fluid or a component of the first sample of the bodily fluid and store the value of the determined concentration in a measurement database. In some disclosed embodiments, the fluidic system further obtains a second sample of the bodily fluid at a second time and presents said second sample to the analyte detection system for analysis. In the disclosed embodiments, the analyte detection system analyzes the second sample or a component of the second sample and determines the concentration of the analyte in the second sample or the component of the second sample, calculates a rate of change of the concentration of the analyte and determines a treatment dose based on the rate of change of the concentration of the analyte if the concentration of the analyte in the second sample is not within a prescribed range. In some embodiments, the analyte detection system communicates with the fluid infusion system to deliver the determined treatment dose.

Embodiments of an analyte monitoring system comprising a fluidic system in fluid communication with a source of bodily fluid, said fluidic system being configured to obtain a sample of bodily fluid from the source several times in a give time interval are disclosed. Some disclosed embodiments can comprise an analyte detection system configured to analyze the sample of bodily fluid or a component of the sample of bodily fluid and determine the concentration of an analyte in said sample of the bodily fluid or a component of the sample of the bodily fluid, wherein the analyte detection system is further configured to access a measurement history and store the estimated concentration of the analyte in the measurement history. Some disclosed embodiments comprise a feedback system; and a user interface configured to accept an input from a user; wherein the feedback system calculates a predicted value for the concentration of the analyte at a future time based on the input from the user and one or more previous values for the concentration of the analyte stored in the measurement history, and wherein the feedback system alerts the user through the user interface if the predicted value for the concentration is not within an acceptable range.

Embodiments of an analyte monitoring system comprising a fluidic system in fluid communication with a source of bodily fluid, said fluidic system being configured to obtain a sample of bodily fluid from the source several times in a give time interval are disclosed. The disclosed embodiments further comprise an analyte detection system configured to analyze the sample of bodily fluid or a component of the sample of bodily fluid and determine the concentration of an analyte in said sample of the bodily fluid or a component of the sample of the bodily fluid, wherein the analyte detection system is further configured to access a measurement history and store the estimated concentration of the analyte in the measurement history. The disclosed embodiments can also comprise a fluid infusion system comprising a plurality of infusion fluid sources, each infusion fluid source configured to provide one or more drugs or chemicals; a user feedback system; a watch list comprising a catalog of spectra related to various known substances that may present medical hazards, alone or in combination, the watch list being electronically accessible to the user feedback system; and a user interface configured to provide information to a user and accept input from the user. In some embodiments, the feedback system is configured to obtain one or more spectroscopic measurements of the contents of the plurality of infusion fluid sources, compare the spectroscopic measurements with the watch list, and alert the user through the user interface if any substance in the watch list is detected in the plurality of infusion fluid sources.

Embodiments of a combined glucose monitoring and adjustment system comprising a fluid control device with pumps, valves, and fluid passageways configured to draw fluid from a fluid source and deliver a portion of that fluid to an analyte monitoring system are disclosed. The disclosed embodiments can further comprise an optical glucose meter configured to irradiate the fluid or a portion thereof and detect secondary radiation, either transmitted or reflected, and determine, based on that secondary radiation, a concentration of an analyte in the fluid. The disclosed embodiments can further comprise a glucose adjustment system. In some embodiments, the glucose adjustment system can comprise a repository of a treatment substance selected from the group consisting of insulin and a sugar; a pump configured to adjust the level of glucose in the fluid source by infusing insulin and/or sugar; and a controller configured to control the pump. In some embodiments, the body fluid analyzer is configured for calibration no more than twice per day. In some embodiments, the body fluid analyzer is configured for calibration no more than once per day. In some embodiments, the body fluid analyzer is configured for calibration no more than once every 36 hours. In some embodiments, the body fluid analyzer is configured for calibration no more than once every two days. In some embodiments, the body fluid analyzer is configured for calibration no more than once every three days.

BRIEF DESCRIPTION OF THE DRAWINGS

The following drawings and the associated descriptions are provided to illustrate embodiments of the present disclosure and do not limit the scope of the claims.

FIG. 10 illustrates an embodiment of a removable cartridge that can interface with a monitoring device.

Figure 1:
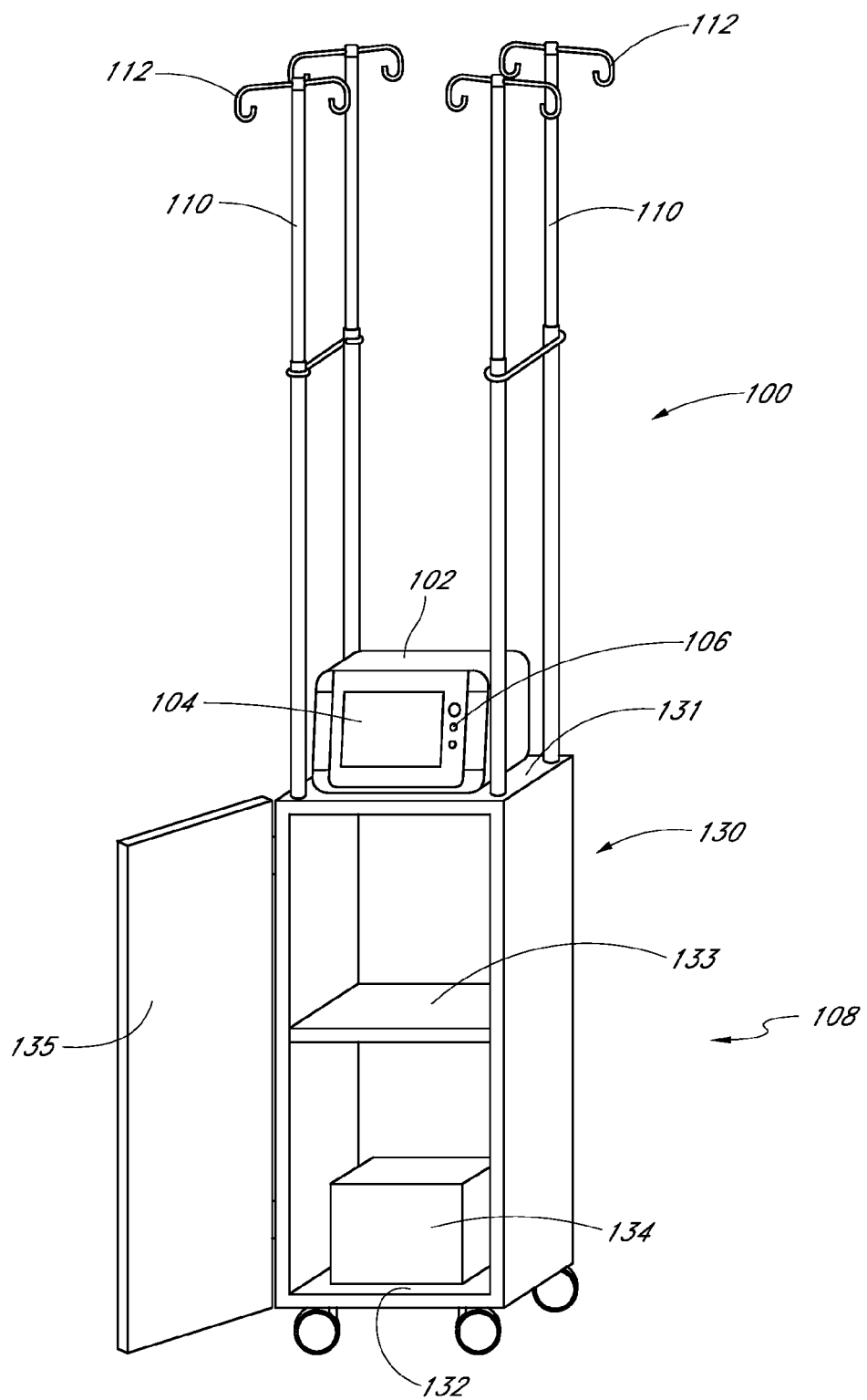
FIG. 1 shows an embodiment of an apparatus for withdrawing and analyzing fluid samples.

These and other features will now be described with reference to the drawings summarized above. The drawings and the associated descriptions are provided to illustrate embodiments and not to limit the scope of any claim. Throughout the drawings, reference numbers may be reused to indicate correspondence between referenced elements. In addition, where applicable, the first one or two digits of a reference numeral for an element can frequently indicate the figure number in which the element first appears.

DETAILED DESCRIPTION OF PREFERRED EMBODIMENTS

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The systems and methods discussed herein can be used anywhere, including, for example, in laboratories, hospitals, healthcare facilities, intensive care units (ICUs), or residences. Moreover, the systems and methods discussed herein can be used for invasive techniques, as well as non-invasive techniques or techniques that do not involve a body or a patient such as, for example, in vitro techniques.

Analyte Monitoring Apparatus

FIG. 1 shows an embodiment of an apparatus 100 for withdrawing and analyzing fluid samples. The apparatus 100 includes a monitoring device 102. In some embodiments, the monitoring device 102 can be an "OptiScanner®" monitor available from OptiScan Biomedical Corporation of Hayward, Calif. In some embodiments, the device 102 can measure one or more physiological parameters, such as the concentration of one or more substance(s) in a sample fluid. The sample fluid can be, for example, whole blood from a patient 302 (see, e.g., FIG. 3) and/or a component of whole blood such as, e.g., blood plasma. In some embodiments, the device 100 can also deliver an infusion fluid to a patient.

In the illustrated embodiment, the monitoring device 102 includes a display 104 such as, for example, a touch-sensitive liquid crystal display. The display 104 can provide an interface that includes alerts, indicators, charts, and/or soft buttons. The device 102 also can include one or more inputs and/or outputs 106 that provide connectivity and/or permit user interactivity.

In the embodiment shown in FIG. 1, the device 102 is mounted on a stand 108. The stand 108 may comprise a cart such as, for example, a wheeled cart 130 as shown in FIG. 1. In some embodiments, the stand 108 is configured to roll on a wheeled pedestal 240 (shown in FIG. 2). The stand 108 advantageously can be easily moved and includes one or more poles 110 and/or hooks 112. The poles 110 and hooks 112 can be configured to accommodate other medical devices and/or implements, including, for example, infusion pumps, saline bags, arterial pressure sensors, other monitors and medical devices, and so forth. Some stands or carts may become unstable if intravenous (IV) bags, IV pumps, and other medical devices are hung too high on the stand or cart. In some embodiments, the apparatus 100 can be configured to have a low center of gravity, which may overcome possible instability. For example, the stand 108 can be weighted at the bottom to at least partially offset the weight of IV bags, IV pumps and medical devices that may be attached to the hooks 112 that are placed above the monitoring device 102. Adding weight toward the bottom (e.g., near the wheels) may help prevent the apparatus 100 from tipping over.

In some embodiments, the apparatus 100 includes the cart 130, which has an upper shelf 131 on which the monitoring device 102 may be placed (or attached) and a bottom shelf 132 on which a battery 134 may be placed (or attached). The battery 134 may be used as a main or backup power supply for the monitoring device 102 (which may additionally or alternatively accept electrical power from a wall socket). Two or more batteries are used in certain embodiments. The apparatus 100 may be configured so that the upper and lower shelves 131, 132 are close to ground level, and the battery provides counterweight. Other types of counterweights may be used. For example, in some embodiments, portions of the cart 130 near the floor (e.g., a lower shelf) are weighted, formed from a substantial quantity of material (e.g., thick sheets of metal), and/or formed from a relatively high-density metal (e.g., lead). In some embodiments the bottom shelf 132 is approximately 6 inches to 1 foot above ground level, and the upper shelf 131 is approximately 2 feet to 4 feet above ground level. In some embodiments the upper shelf 131 may be configured to support approximately 40 pounds (lbs), and the bottom shelf 132 may be configured to support approximately 20 lbs. One possible advantage of embodiments having such a configuration is that IV pumps, bags containing saline, blood and/or drugs, and other medical equipment weighing approximately 60 lbs, collectively, can be hung on the hooks 112 above the shelves without making the apparatus 100 unstable. The apparatus 100 may be moved by applying a horizontal force on the apparatus 100, for example, by pushing and/or pulling the poles 110. In many cases, a user may exert force on an upper portion of the apparatus 100, for example, close to shoulder-height. By counterbalancing the weight as described above, the apparatus 100 may be moved in a reasonably stable manner.

In the illustrated embodiment, the cart 130 includes the bottom shelf 132 and an intermediate shelf 133, which are enclosed on three sides by walls and on a fourth side by a door 135. The door 135 can be opened (as shown in FIG. 1) to provide access to the shelves 132, 133. In other embodiments, the fourth side is not enclosed (e.g., the door 135 is not used). Many cart variations are possible. In some embodiments the battery 134 can be placed on the bottom shelf 134 or the intermediate shelf 133.

Figure 2:
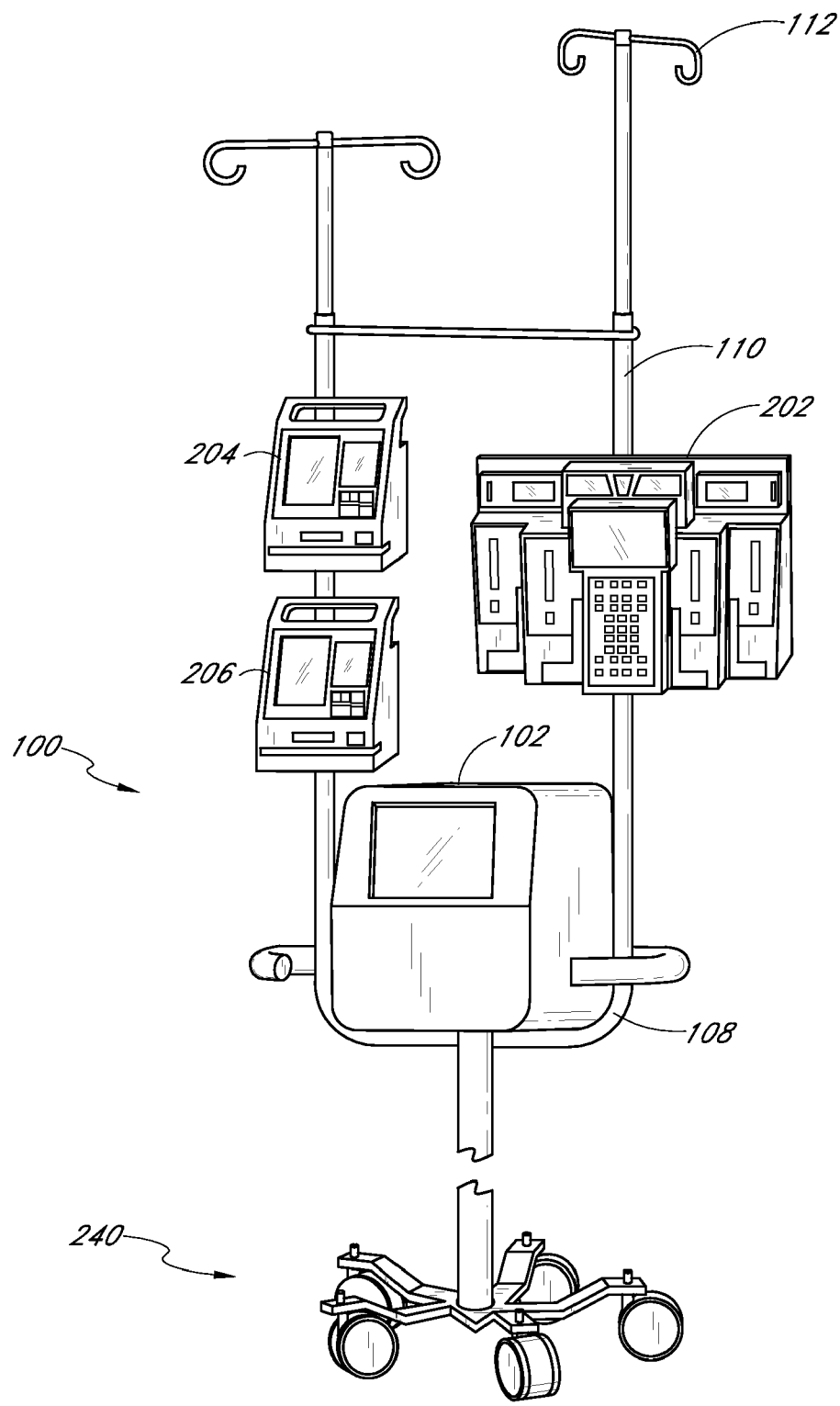
FIG. 2 illustrates how various other devices can be supported on or near an embodiment of apparatus illustrated in FIG. 1.

FIG. 2 illustrates how various other devices can be supported on or near the apparatus 100 illustrated in FIG. 1. For example, the poles 110 of the stand 108 can be configured (e.g., of sufficient size and strength) to accommodate multiple devices 202, 204, 206. In some embodiments, one or more COLLEAGUE® volumetric infusion pumps available from Baxter International Inc. of Deerfield, Ill. can be accommodated. In some embodiments, one or more Alaris® PC units available from Cardinal Health, Inc. of Dublin, Ohio can be accommodated. Furthermore, various other medical devices (including the two examples mentioned here), can be integrated with the disclosed monitoring device 102 such that multiple devices function in concert for the benefit of one or multiple patients without the devices interfering with each other.

Figure 3:
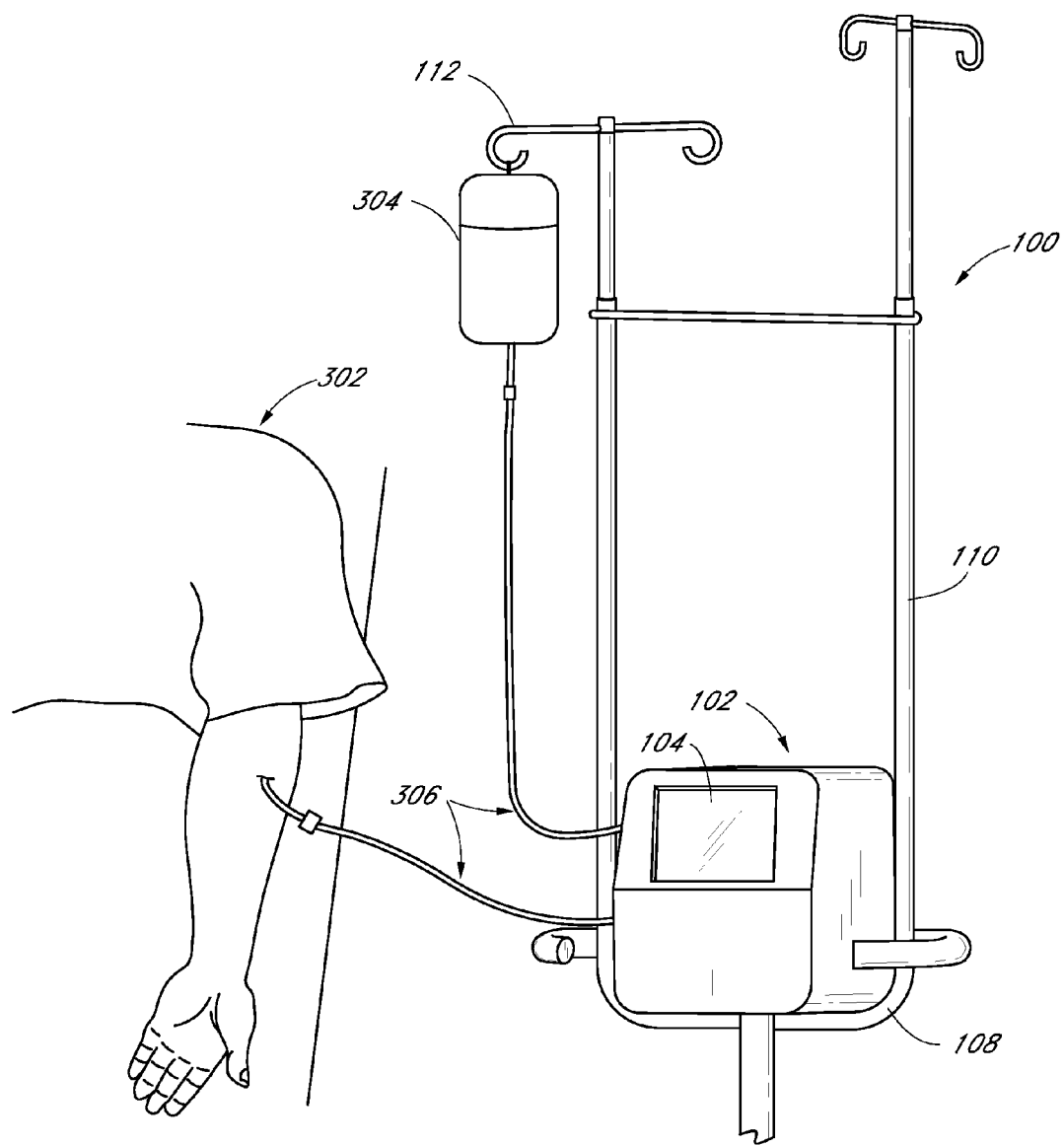
FIG. 3 illustrates an embodiment of the apparatus in FIG. 1 configured to be connected to a patient.
Figure 3A:
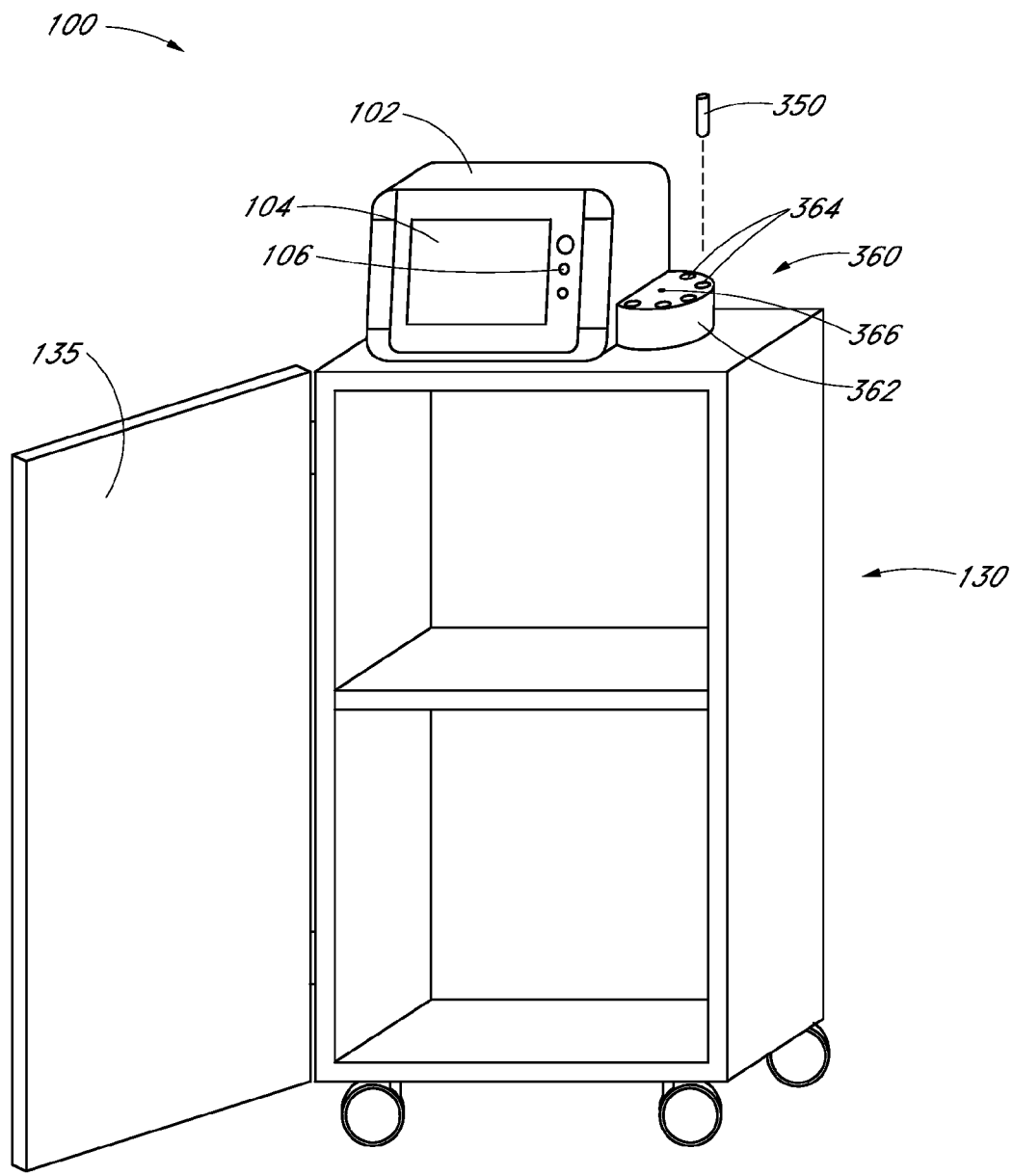
FIG. 3A illustrates an embodiment of the apparatus in FIG. 1 that is not configured to be connected to a patient but which receives a fluid sample from an extracorporeal fluid container such as, for example, a test tube. This embodiment of the apparatus can advantageously provide in vitro analysis of a fluid sample.

FIG. 3 illustrates the apparatus 100 of FIG. 1 as it can be connected to a patient 302. The monitoring device 102 can be used to determine the concentration of one or more substances in a sample fluid. The sample fluid can come can come from the patient 302, as illustrated in FIG. 3, or the sample fluid can come from a fluid container, as illustrated in FIG. 3A. In some preferred embodiments, the sample fluid is whole blood.

In some embodiments (see, e.g., FIG. 3), the monitoring device 102 can also deliver an infusion fluid to the patient 302. An infusion fluid container 304 (e.g., a saline bag), which can contain infusion fluid (e.g., saline and/or medication), can be supported by the hook 112. The monitoring device 102 can be in fluid communication with both the container 304 and the sample fluid source (e.g., the patient 302), through tubes 306. The infusion fluid can comprise any combination of fluids and/or chemicals. Some advantageous examples include (but are not limited to): water, saline, dextrose, lactated Ringer's solution, drugs, and insulin.

The example monitoring device 102 schematically illustrated in FIG. 3 allows the infusion fluid to pass to the patient 302 and/or uses the infusion fluid itself (e.g., as a flushing fluid or a standard with known optical properties, as discussed further below). In some embodiments, the monitoring device 102 may not employ infusion fluid. The monitoring device 102 may thus draw samples without delivering any additional fluid to the patient 302. The monitoring device 102 can include, but is not limited to, fluid handling and analysis apparatuses, connectors, passageways, catheters, tubing, fluid control elements, valves, pumps, fluid sensors, pressure sensors, temperature sensors, hematocrit sensors, hemoglobin sensors, calorimetric sensors, gas (e.g., "bubble") sensors, fluid conditioning elements, gas injectors, gas filters, blood plasma separators, and/or communication devices (e.g., wireless devices) to permit the transfer of information within the monitoring device 102 or between the monitoring device 102 and a network.

In some embodiments, the apparatus 100 is not connected to a patient and may receive fluid samples from a container such as a decanter, flask, beaker, tube, cartridge, test strip, etc., or any other extracorporeal fluid source. The container may include a biological fluid sample such as, e.g., a body fluid sample. For example, FIG. 3A schematically illustrates an embodiment of the monitoring device 102 that is configured to receive a fluid sample from one or more test tubes 350. This embodiment of the monitoring device 102 is configured to perform in vitro analysis of a fluid (or a fluid component) in the test tube 350. The test tube 350 may comprise a tube, vial, bottle, or other suitable container or vessel. The test tube 350 may include an opening disposed at one end of the tube through which the fluid sample may be added prior to delivery of the test tube to the monitoring device 102. In some embodiments, the test tubes 350 may also include a cover adapted to seal the opening of the tube. The cover may include an aperture configured to permit a tube, nozzle, needle, pipette, or syringe to dispense the fluid sample into the test tube 350. The test tubes 350 may comprise a material such as, for example, glass, polyethylene, or polymeric compounds. In various embodiments, the test tubes 350 may be re-usable units or may be disposable, single-use units. In certain embodiments, the test tubes 350 may comprise commercially available low pressure/vacuum sample bottles, test bottles, or test tubes.

In the embodiment shown in FIG. 3A, the monitoring device 102 comprises a fluid delivery system 360 configured to receive a container (e.g., the test tube 350) containing a fluid sample and deliver the fluid sample to a fluid handling system (such as, e.g., fluid handling system 404 described below). In some embodiments, the fluid handling system delivers a portion of the fluid sample to an analyte detection system for in vitro measurement of one or more physiological parameters (e.g., an analyte concentration). Prior to measurement, the fluid handling system may, in some embodiments, separate the fluid sample into components, and a measurement may be performed on one or more of the components. For example, the fluid sample in the test tube 350 may comprise whole blood, and the fluid handling system may separate blood plasma from the sample (e.g., by filtering and/or centrifuging).

In the embodiment illustrated in FIG. 3A, the fluid delivery system 360 comprises a carousel 362 having one or more openings 364 adapted to receive the test tube 350. The carousel 362 may comprise one, two, four, six, twelve, or more openings 364. In the illustrated embodiment, the carousel 362 is configured to rotate around a central axis or spindle 366 so that a test tube 350 inserted into one of the openings 364 is delivered to the monitoring device 102. In certain embodiments, the fluid handling system of the monitoring device 102 comprises a sampling probe that is configured to collect a portion of the fluid sample from the test tube 350 (e.g., by suction or aspiration). The collected portion may then be transported in the device 102 as further described below (see, e.g., FIGS. 4-7). For example, in one embodiment suitable for use with whole blood, the collected portion of the whole blood sample is transported to a centrifuge for separation into blood plasma, a portion of the blood plasma is transported to an infrared spectroscope for measurement of one or more analytes (e.g., glucose), and the measured blood plasma is then transported to a waste container for disposal.

In other embodiments of the apparatus 100 shown in FIG. 3A, the fluid delivery system 360 may comprise a turntable, rack, or caddy adapted to receive the test tube 350. In yet other embodiments, the monitoring device 102 may comprise an inlet port adapted to receive the test tube 350. Additionally, in other embodiments, the fluid sample may be delivered to the apparatus 100 using a test cartridge, a test strip, or other suitable container. Many variations are possible.

In some embodiments, one or more components of the apparatus 100 can be located at another facility, room, or other suitable remote location. One or more components of the monitoring device 102 can communicate with one or more other components of the monitoring device 102 (or with other devices) by communication interface(s) such as, but not limited to, optical interfaces, electrical interfaces, and/or wireless interfaces. These interfaces can be part of a local network, internet, wireless network, or other suitable networks.

System Overview

Figure 4:
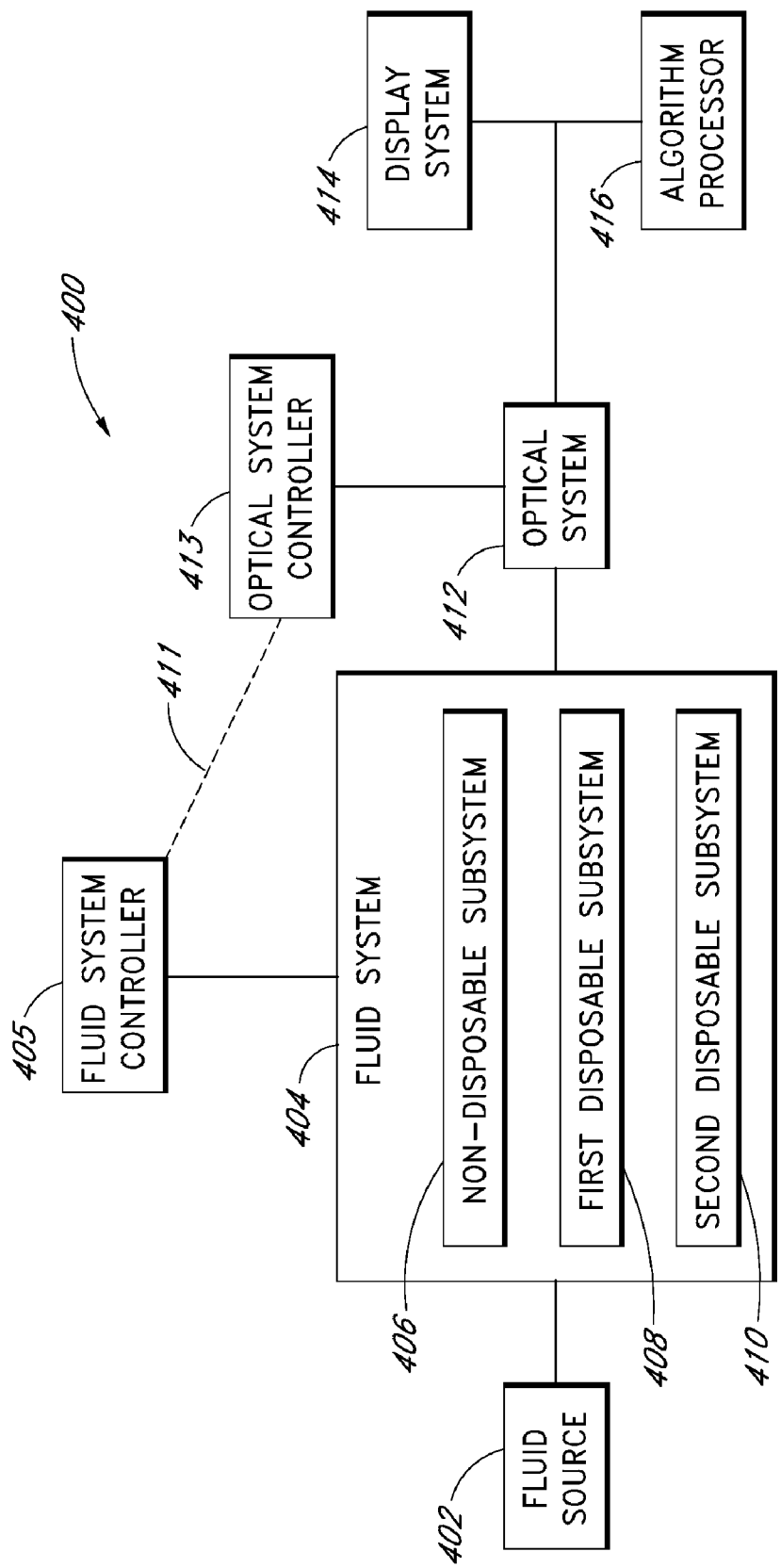
FIG. 4 is a block diagram of an embodiment of a system for withdrawing and analyzing fluid samples.

FIG. 4 is a block diagram of a system 400 for sampling and analyzing fluid samples. The monitoring device 102 can comprise such a system. The system 400 can include a fluid source 402 connected to a fluid-handling system 404. The fluid-handling system 404 includes fluid passageways and other components that direct fluid samples. Samples can be withdrawn from the fluid source 402 and analyzed by an optical system 412. The fluid-handling system 404 can be controlled by a fluid system controller 405, and the optical system 412 can be controlled by an optical system controller 413. The sampling and analysis system 400 can also include a display system 414 and an algorithm processor 416 that assist in fluid sample analysis and presentation of data.

In some embodiments, the sampling and analysis system 400 is a mobile point-of-care apparatus that monitors physiological parameters such as, for example, blood glucose concentration. Components within the system 400 that may contact fluid and/or a patient, such as tubes and connectors, can be coated with an antibacterial coating to reduce the risk of infection. Connectors between at least some components of the system 400 can include a self-sealing valve, such as a spring valve, in order to reduce the risk of contact between port openings and fluids, and to guard against fluid escaping from the system. Other components can also be included in a system for sampling and analyzing fluid in accordance with the described embodiments.

The sampling and analysis system 400 can include a fluid source 402 (or more than one fluid source) that contain(s) fluid to be sampled. The fluid-handling system 404 of the sampling and analysis system 400 is connected to, and can draw fluid from, the fluid source 402. The fluid source 402 can be, for example, a blood vessel such as a vein or an artery, a container such as a decanter, flask, beaker, tube, cartridge, test strip, etc., or any other corporeal or extracorporeal fluid source. For example, in some embodiments, the fluid source 402 may be a vein or artery in the patient 302 (see, e.g., FIG. 3). In other embodiments, the fluid source 402 may comprise an extracorporeal container 350 of fluid delivered to the system 400 for analysis (see, e.g., FIG. 3B). The fluid to be sampled can be, for example, blood, plasma, interstitial fluid, lymphatic fluid, or another fluid. In some embodiments, more than one fluid source can be present, and more than one fluid and/or type of fluid can be provided.

In some embodiments, the fluid-handling system 404 withdraws a sample of fluid from the fluid source 402 for analysis, centrifuges at least a portion of the sample, and prepares at least a portion of the sample for analysis by an optical sensor such as a spectrophotometer (which can be part of an optical system 412, for example). These functions can be controlled by a fluid system controller 405, which can also be integrated into the fluid-handling system 404. The fluid system controller 405 can also control the additional functions described below.

In some embodiments, at least a portion of the sample is returned to the fluid source 402. At least some of the sample, such as portions of the sample that are mixed with other materials or portions that are otherwise altered during the sampling and analysis process, or portions that, for any reason, are not to be returned to the fluid source 402, can also be placed in a waste bladder (not shown in FIG. 4). The waste bladder can be integrated into the fluid-handling system 404 or supplied by a user of the system 400. The fluid-handling system 404 can also be connected to a saline source, a detergent source, and/or an anticoagulant source, each of which can be supplied by a user, attached to the fluid-handling system 404 as additional fluid sources, and/or integrated into the fluid-handling system 404.

Components of the fluid-handling system 404 can be modularized into one or more non-disposable, disposable, and/or replaceable subsystems. In the embodiment shown in FIG. 4, components of the fluid-handling system 404 are separated into a non-disposable subsystem 406, a first disposable subsystem 408, and a second disposable subsystem 410.

The non-disposable subsystem 406 can include components that, while they may be replaceable or adjustable, do not generally require regular replacement during the useful lifetime of the system 400. In some embodiments, the non-disposable subsystem 406 of the fluid-handling system 404 includes one or more reusable valves and sensors. For example, the non-disposable subsystem 406 can include one or more valves (or non-disposable portions thereof), (e.g., pinch-valves, rotary valves, etc.), sensors (e.g., ultrasonic bubble sensors, non-contact pressure sensors, optical blood dilution sensors, etc). The non-disposable subsystem 406 can also include one or more pumps (or non-disposable portions thereof). For example, some embodiments can include pumps available from Hospira. In some embodiments, the components of the non-disposable subsystem 406 are not directly exposed to fluids and/or are not readily susceptible to contamination.

The first and second disposable subsystems 408, 410 can include components that are regularly replaced under certain circumstances in order to facilitate the operation of the system 400. For example, the first disposable subsystem 408 can be replaced after a certain period of use, such as a few days, has elapsed. Replacement may be necessary, for example, when a bladder within the first disposable subsystem 408 is filled to capacity. Such replacement may mitigate fluid system performance degradation associated with and/or contamination wear on system components.

In some embodiments, the first disposable subsystem 408 includes components that may contact fluids such as patient blood, saline, flushing solutions, anticoagulants, and/or detergent solutions. For example, the first disposable subsystem 408 can include one or more tubes, fittings, cleaner pouches and/or waste bladders. The components of the first disposable subsystem 408 can be sterilized in order to decrease the risk of infection and can be configured to be easily replaceable.

In some embodiments, the second disposable subsystem 410 can be designed to be replaced under certain circumstances. For example, the second disposable subsystem 410 can be replaced when the patient being monitored by the system 400 is changed. The components of the second disposable subsystem 410 may not need replacement at the same intervals as the components of the first disposable subsystem 408. For example, the second disposable subsystem 410 can include a sample holder and/or at least some components of a centrifuge, components that may not become filled or quickly worn during operation of the system 400. Replacement of the second disposable subsystem 410 can decrease or eliminate the risk of transferring fluids from one patient to another during operation of the system 400, enhance the measurement performance of system 400, and/or reduce the risk of contamination or infection.

In some embodiments, the sample holder of the second disposable subsystem 410 receives the sample obtained from the fluid source 402 via fluid passageways of the first disposable subsystem 408. The sample holder is a container that can hold fluid for the centrifuge and can include a window to the sample for analysis by a spectrometer. In some embodiments, the sample holder includes windows that are made of a material that is substantially transparent to electromagnetic radiation in the mid-infrared range of the spectrum. For example, the sample holder windows can be made of calcium fluoride.

An injector can provide a fluid connection between the first disposable subsystem 408 and the sample holder of the second disposable subsystem 410. In some embodiments, the injector can be removed from the sample holder to allow for free spinning of the sample holder during centrifugation.

In some embodiments, the components of the sample are separated by centrifuging for a period of time before measurements are performed by the optical system 412. For example, a fluid sample (e.g., a blood sample) can be centrifuged at a relatively high speed. The sample can be spun at a certain number of revolutions per minute (RPM) for a given length of time to separate blood plasma for spectral analysis. In some embodiments, the fluid sample is spun at about 7200 RPM. In some embodiments, the sample is spun at about 5000 RPM. In some embodiments, the fluid sample is spun at about 4500 RPM. In some embodiments, the fluid sample is spun at more than one rate for successive time periods. The length of time can be approximately 5 minutes. In some embodiments, the length of time is approximately 2 minutes. Separation of a sample into the components can permit measurement of solute (e.g., glucose) concentration in plasma, for example, without interference from other blood components. This kind of post-separation measurement, (sometimes referred to as a "direct measurement") has advantages over a solute measurement taken from whole blood because the proportions of plasma to other components need not be known or estimated in order to infer plasma glucose concentration. In some embodiments, the separated plasma can be analyzed electrically using one or more electrodes instead of, or in addition to, being analyzed optically. This analysis may occur within the same device, or within a different device. For example, in certain embodiments, an optical analysis device can separate blood into components, analyze the components, and then allow the components to be transported to another analysis device that can further analyze the components (e.g., using electrical and/or electrochemical measurements).

An anticoagulant, such as, for example, heparin can be added to the sample before centrifugation to prevent clotting. The fluid-handling system 404 can be used with a variety of anticoagulants, including anticoagulants supplied by a hospital or other user of the monitoring system 400. A detergent solution formed by mixing detergent powder from a pouch connected to the fluid-handling system 404 with saline can be used to periodically clean residual protein and other sample remnants from one or more components of the fluid-handling system 404, such as the sample holder. Sample fluid to which anticoagulant has been added and used detergent solution can be transferred into the waste bladder.

The system 400 shown in FIG. 4 includes an optical system 412 that can measure optical properties (e.g., transmission) of a fluid sample (or a portion thereof). In some embodiments, the optical system 412 measures transmission in the mid-infrared range of the spectrum. In some embodiments, the optical system 412 includes a spectrometer that measures the transmission of broadband infrared light through a portion of a sample holder filled with fluid. The spectrometer need not come into direct contact with the sample. As used herein, the term "sample holder" is a broad term that carries its ordinary meaning as an object that can provide a place for fluid. The fluid can enter the sample holder by flowing.

In some embodiments, the optical system 412 includes a filter wheel that contains one or more filters. In some embodiments, more than ten filters can be included, for example twelve or fifteen filters. In some embodiments, more than 20 filters (e.g., twenty-five filters) are mounted on the filter wheel. The optical system 412 includes a light source that passes light through a filter and the sample holder to a detector. In some embodiments, a stepper motor moves the filter wheel in order to position a selected filter in the path of the light. An optical encoder can also be used to finely position one or more filters. In some embodiments, one or more tunable filters may be used to filter light into multiple wavelengths. The one or more tunable filters may provide the multiple wavelengths of light at the same time or at different times (e.g., sequentially). The light source included in the optical system 412 may emit radiation in the ultraviolet, visible, near-infrared, mid-infrared, and/or far-infrared regions of the electromagnetic spectrum. In some embodiments, the light source can be a broadband source that emits radiation in a broad spectral region (e.g., from about 1500 nm to about 6000 nm). In other embodiments, the light source may emit radiation at certain specific wavelengths. The light source may comprise one or more light emitting diodes (LEDs) emitting radiation at one or more wavelengths in the radiation regions described herein. In other embodiments, the light source may comprise one or more laser modules emitting radiation at one or more wavelengths. The laser modules may comprise a solid state laser (e.g., a Nd:YAG laser), a semiconductor based laser (e.g., a GaAs and/or InGaAsP laser), and/or a gas laser (e.g., an Ar-ion laser). In some embodiments, the laser modules may comprise a fiber laser. The laser modules may emit radiation at certain fixed wavelengths. In some embodiments, the emission wavelength of the laser module(s) may be tunable over a wide spectral range (e.g., about 30 nm to about 100 nm). In some embodiments, the light source included in the optical system 412 may be a thermal infrared emitter. The light source can comprise a resistive heating element, which, in some embodiments, may be integrated on a thin dielectric membrane on a micromachined silicon structure. In one embodiment the light source is generally similar to the electrical modulated thermal infrared radiation source, IRSource™, available from the Axetris Microsystems division of Leister Technologies, LLC (Itasca, Ill.).

The optical system 412 can be controlled by an optical system controller 413. The optical system controller can, in some embodiments, be integrated into the optical system 412. In some embodiments, the fluid system controller 405 and the optical system controller 413 can communicate with each other as indicated by the line 411. In some embodiments, the function of these two controllers can be integrated and a single controller can control both the fluid-handling system 404 and the optical system 412. Such an integrated control can be advantageous because the two systems are preferably integrated, and the optical system 412 is preferably configured to analyze the very same fluid handled by the fluid-handling system 404. Indeed, portions of the fluid-handling system 404 (e.g., the sample holder described above with respect to the second disposable subsystem 410 and/or at least some components of a centrifuge) can also be components of the optical system 412. Accordingly, the fluid-handling system 404 can be controlled to obtain a fluid sample for analysis by optical system 412, when the fluid sample arrives, the optical system 412 can be controlled to analyze the sample, and when the analysis is complete (or before), the fluid-handling system 404 can be controlled to return some of the sample to the fluid source 402 and/or discard some of the sample, as appropriate.

Figure 24:
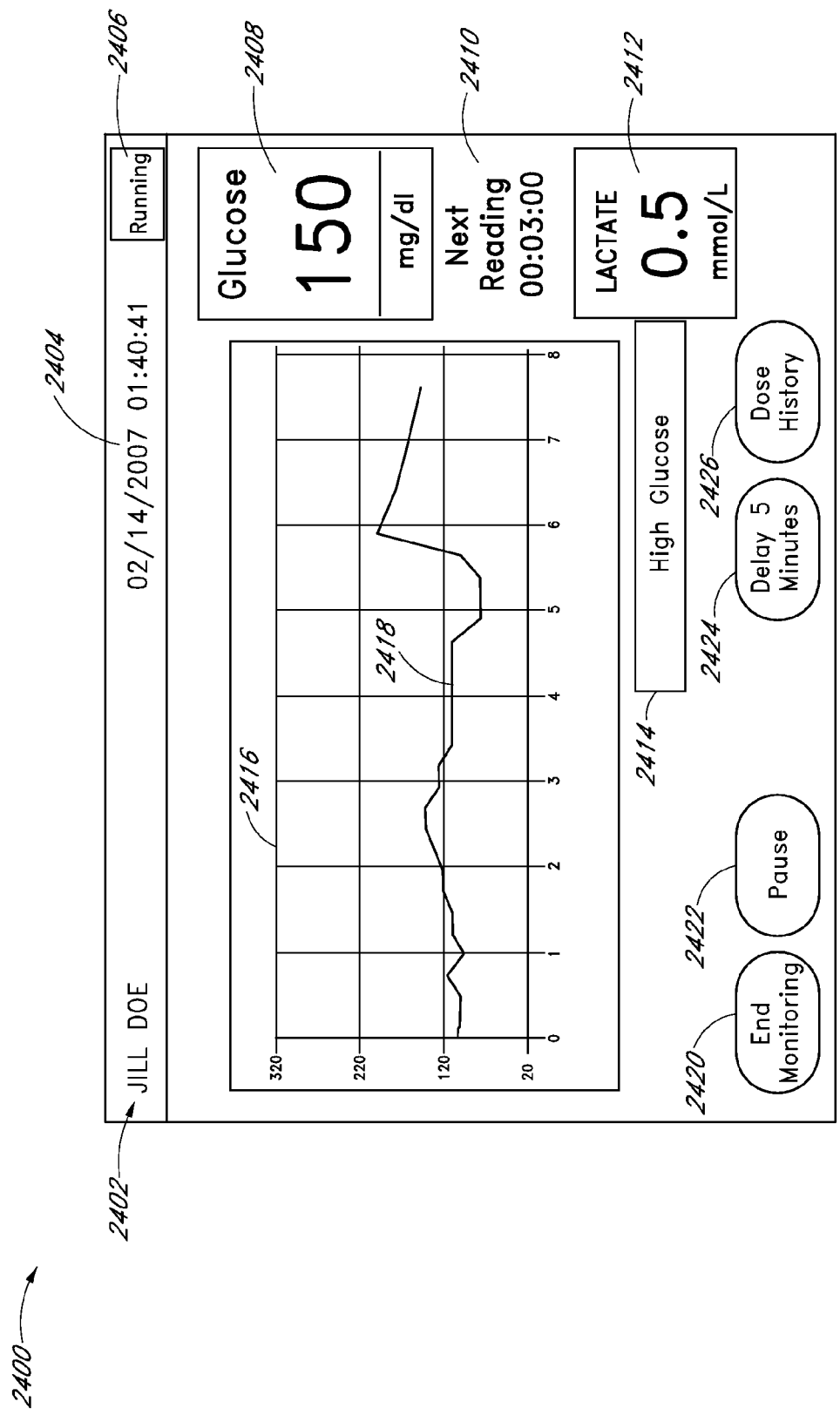
FIGS. 24 and 25 schematically illustrate the visual appearance of embodiments of a user interface for a system for withdrawing and analyzing fluid samples.
Figure 25:
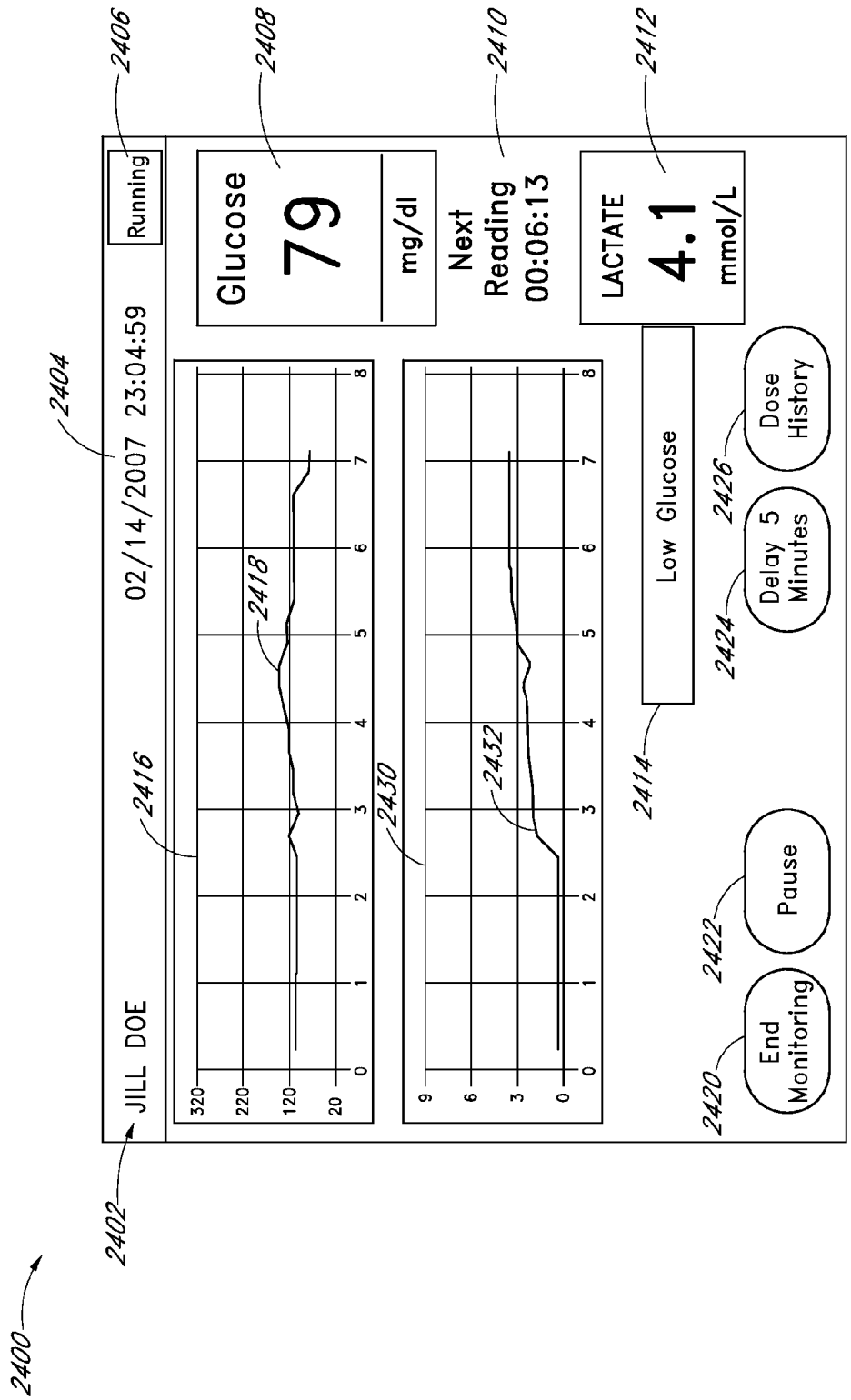

The system 400 shown in FIG. 4 includes a display system 414 that provides for communication of information to a user of the system 400. In some embodiments, the display 414 can be replaced by or supplemented with other communication devices that communicate in non-visual ways. The display system 414 can include a display processor that controls or produces an interface to communicate information to the user. The display system 414 can include a display screen. One or more parameters such as, for example, blood glucose concentration, system 400 operating parameters, and/or other operating parameters can be displayed on a monitor (not shown) associated with the system 400. An example of one way such information can be displayed is shown in FIGS. 24 and 25. In some embodiments, the display system 414 can communicate measured physiological parameters and/or operating parameters to a computer system over a communications connection.

The system 400 shown in FIG. 4 includes an algorithm processor 416 that can receive spectral information, such as optical density (OD) values (or other analog or digital optical data) from the optical system 412 and or the optical system controller 413. In some embodiments, the algorithm processor 416 calculates one or more physiological parameters and can analyze the spectral information. Thus, for example and without limitation, a model can be used that determines, based on the spectral information, physiological parameters of fluid from the fluid source 402. The algorithm processor 416, a controller that may be part of the display system 414, and any embedded controllers within the system 400 can be connected to one another with a communications bus.

Some embodiments of the systems described herein (e.g., the system 400), as well as some embodiments of each method described herein, can include a computer program accessible to and/or executable by a processing system, e.g., a one or more processors and memories that are part of an embedded system. Indeed, the controllers may comprise one or more computers and/or may use software. Thus, as will be appreciated by those skilled in the art, various embodiments may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various embodiments may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Fluid Handling System

Figure 5:
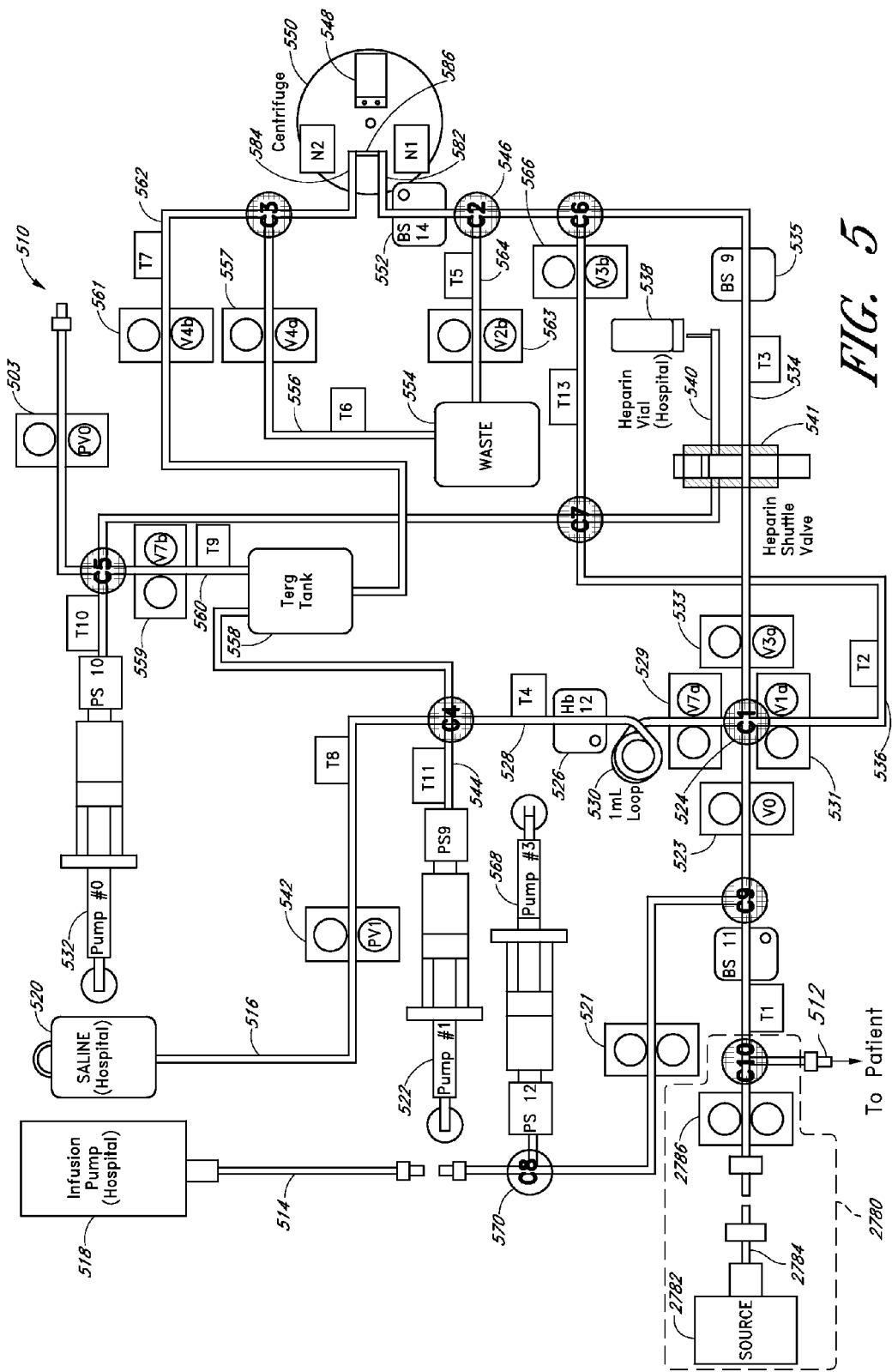
FIG. 5 schematically illustrates an embodiment of a fluid system that can be part of a system for withdrawing and analyzing fluid samples.

The generalized fluid-handling system 404 can have various configurations. In this context, FIG. 5 schematically illustrates the layout of an example embodiment of a fluid system 510. In this schematic representation, various components are depicted that may be part of a non-disposable subsystem 406, a first disposable subsystem 408, a second disposable subsystem 410, and/or an optical system 412. The fluid system 510 is described practically to show an example cycle as fluid is drawn and analyzed.

In addition to the reference numerals used below, the various portions of the illustrated fluid system 510 are labeled for convenience with letters to suggest their roles as follows: T# indicates a section of tubing. C# indicates a connector that joins multiple tubing sections. V# indicates a valve. BS# indicates a bubble sensor or ultrasonic air detector. N# indicates a needle (e.g., a needle that injects sample into a sample holder). PS# indicates a pressure sensor (e.g., a reusable pressure sensor). Pump# indicates a fluid pump (e.g., a syringe pump with a disposable body and reusable drive). "Hb 12" indicates a sensor for hemoglobin (e.g., a dilution sensor that can detect hemoglobin optically).

The term "valve" as used herein is a broad term and is used, in accordance with its ordinary meaning, to refer to any flow regulating device. For example, the term "valve" can include, without limitation, any device or system that can controllably allow, prevent, or inhibit the flow of fluid through a fluid passageway. The term "valve" can include some or all of the following, alone or in combination: pinch valves, rotary valves, stop cocks, pressure valves, shuttle valves, mechanical valves, electrical valves, electromechanical flow regulators, etc. In some embodiments, a valve can regulate flow using gravitational methods or by applying electrical voltages or by both.

The term "pump" as used herein is a broad term and is used, in accordance with its ordinary meaning, to refer to any device that can urge fluid flow. For example, the term "pump" can include any combination of the following: syringe pumps, peristaltic pumps, vacuum pumps, electrical pumps, mechanical pumps, hydraulic pumps, etc. Pumps and/or pump components that are suitable for use with some embodiments can be obtained, for example, from or through Hospira.

The function of the valves, pumps, actuators, drivers, motors (e.g., the centrifuge motor), etc. described below is controlled by one or more controllers (e.g., the fluid system controller 405, the optical system controller 413, etc.) The controllers can include software, computer memory, electrical and mechanical connections to the controlled components, etc.

At the start of a measurement cycle, most lines, including a patient tube 512 (T1), an Arrival sensor tube 528 (T4), an anticoagulant valve tube 534 (T3), and a sample cell 548 can be filled with saline that can be introduced into the system through the infusion tube 514 and the saline tube 516, and which can come from an infusion pump 518 and/or a saline bag 520. The infusion pump 518 and the saline bag 520 can be provided separately from the system 510. For example, a hospital can use existing saline bags and infusion pumps to interface with the described system. The infusion valve 521 can be open to allow saline to flow into the tube 512 (T1).

Before drawing a sample, the saline in part of the system 510 can be replaced with air. Thus, for example, the following valves can be closed: air valve 503 (PV0), the detergent tank valve 559 (V7b), 566 (V3b), 523 (V0), 529 (V7a), and 563 (V2b). At the same time, the following valves can be open: valves 531 (V1a), 533 (V3a) and 577 (V4a). Simultaneously, a second pump 532 (pump #0) pumps air through the system 510 (including tube 534 (T3), sample cell 548, and tube 556 (T6)), pushing saline through tube 534 (T3) and sample cell 548 into a waste bladder 554.

Next, a sample can be drawn. With the valves 542 (PV1), 559 (V7b), and 561 (V4b) closed, a first pump 522 (pump #1) is actuated to draw sample fluid to be analyzed (e.g. blood) from a fluid source (e.g., a laboratory sample container, a living patient, etc.) up into the patient tube 512 (T1), through the tube past the two flanking portions of the open pinch-valve 523 (V0), through the first connector 524 (C1), into the looped tube 530, past the arrival sensor 526 (Hb12), and into the arrival sensor tube 528 (T4). The arrival sensor 526 may be used to detect the presence of blood in the tube 528 (T4). For example in some embodiments, the arrival sensor 526 may comprise a hemoglobin sensor. In some other embodiments, the arrival sensor 526 may comprise a color sensor that detects the color of fluid flowing through the tube 528 (T4). During this process, the valve 529 (V7a) and 523 (V0) are open to fluid flow, and the valves 531 (V1a), 533 (V3a), 542 (PV1), 559 (V7b), and 561 (V4b) can be closed and therefore block (or substantially block) fluid flow by pinching the tube.

Before drawing the sample, the tubes 512 (T1) and 528 (T4) are filled with saline and the hemoglobin (Hb) level is zero. The tubes that are filled with saline are in fluid communication with the sample source (e.g., the fluid source 402). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually nondiluted sample fluid. In the example illustrated here, the sample fluid is blood.

The arrival sensor 526 (Hb12) can detect and/or verify the presence of blood in the tubes. For example, in some embodiments, the arrival sensor 526 can determine the color of the fluid in the tubes. In some embodiments, the arrival sensor 526 (Hb12) can detect the level of Hemoglobin in the sample fluid. As blood starts to arrive at the arrival sensor 526 (Hb12), the sensed hemoglobin level rises. A hemoglobin level can be selected, and the system can be pre-set to determine when that level is reached. A controller such as the fluid system controller 405 of FIG. 4 can be used to set and react to the pre-set value, for example. In some embodiments, when the sensed hemoglobin level reaches the pre-set value, substantially undiluted sample is present at the first connector 524 (C1). The preset value can depend, in part, on the length and diameter of any tubes and/or passages traversed by the sample. In some embodiments, the pre-set value can be reached after approximately 2 mL of fluid (e.g., blood) has been drawn from a fluid source. A nondiluted sample can be, for example, a blood sample that is not diluted with saline solution, but instead has the characteristics of the rest of the blood flowing through a patient's body. A loop of tubing 530 (e.g., a 1-mL loop) can be advantageously positioned as illustrated to help insure that undiluted fluid (e.g., undiluted blood) is present at the first connector 524 (C1) when the arrival sensor 526 registers that the preset Hb threshold is crossed. The loop of tubing 530 provides additional length to the Arrival sensor tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1).

In some embodiments, when nondiluted blood is present at the first connector 524 (C1), a sample is mixed with an anticoagulant and is directed toward the sample cell 548. An amount of anticoagulant (e.g., heparin) can be introduced into the tube 534 (T3), and then the undiluted blood is mixed with the anticoagulant. A heparin vial 538 (e.g., an insertable vial provided independently by the user of the system 510) can be connected to a tube 540. An anticoagulant valve 541 (which can be a shuttle valve, for example) can be configured to connect to both the tube 540 and the anticoagulant valve tube 534 (T3). The valve can open the tube 540 to a suction force (e.g., created by the pump 532), allowing heparin to be drawn from the vial 538 into the valve 541. Then, the anticoagulant valve 541 can slide the heparin over into fluid communication with the anticoagulant valve tube 534 (T3). The anticoagulant valve 541 can then return to its previous position. Thus, heparin can be shuttled from the tube 540 into the anticoagulant valve tube 534 (T3) to provide a controlled amount of heparin into the tube 534 (T3).

With the valves 542 (PV1), 559 (V7b), 561 (V4b), 523 (V0), 531 (V1a), 566 (V3b), and 563 (V2b) closed, and the valves 529 (V7a) and 553 (V3a) open, first pump 522 (pump #1) pushes the sample from tube 528 (T4) into tube 534 (T3), where the sample mixes with the heparin injected by the anticoagulant valve 541 as it flows through the system 510. As the sample proceeds through the tube 534 (T3), the air that was previously introduced into the tube 534 (T3) is displaced. The sample continues to flow until a bubble sensor 535 (BS9) indicates a change from air to a liquid, and thus the arrival of a sample at the bubble sensor. In some embodiments, the volume of tube 534 (T3) from connector 524 (C1) to bubble sensor 535 (BS9) is a known and/or engineered amount, and may be approximately 500 μL, 200 μL or 100 μL, for example.

When bubble sensor 535 (BS9) indicates the presence of a sample, the remainder of the sampled blood can be returned to its source (e.g., the patient veins or arteries). The first pump 522 (pump #1) pushes the blood out of the Arrival sensor tube 528 (T4) and back to the patient by opening the valve 523 (V0), closing the valves 531 (V1a) and 533 (V3a), and keeping the valve 529 (V7a) open. The Arrival sensor tube 528 (T4) is preferably flushed with approximately 2 mL of saline. This can be accomplished by closing the valve 529 (V7a), opening the valve 542 (PV1), drawing saline from the saline source 520 into the tube 544, closing the valve 542 (PV1), opening the valve 529 (V7a), and forcing the saline down the Arrival sensor tube 528 (T4) with the pump 522. In some embodiments, less than two minutes elapse between the time that blood is drawn from the patient and the time that the blood is returned to the patient.

Following return of the unused patient blood sample, the sample is pushed up the anticoagulant valve tube 534 (T3), through the second connector 546 (C2), and into the sample cell 548, which can be located on the centrifuge rotor 550. This fluid movement is facilitated by the coordinated action (either pushing or drawing fluid) of the pump 522 (pump #1), the pump 532 (pump #0), and the various illustrated valves. In particular, valve 531 (V1a) can be opened, and valves 503 (PV0) and 559 (V7b) can be closed. Pump movement and valve position corresponding to each stage of fluid movement can be coordinated by one ore multiple controllers, such as the fluid system controller 405 of FIG. 4.

After the unused sample is returned to the patient, the sample can be divided into separate slugs before being delivered into the sample cell 548. Thus, for example, valve 553 (V3a) is opened, valves 566 (V3b), 523 (V0) and 529 (V7a) are closed, and the pump 532 (pump #0) uses air to push the sample toward sample cell 548. In some embodiments, the sample (for example, 200 μL or 100 μL) is divided into multiple (e.g., more than two, five, or four) "slugs" of sample, each separated by a small amount of air. As used herein, the term "slug" refers to a continuous column of fluid that can be relatively short. Slugs can be separated from one another by small amounts of air (or bubbles) that can be present at intervals in the tube. In some embodiments, the slugs are formed by injecting or drawing air into fluid in the first connector 546 (C2).

In some embodiments, when the leading edge of the sample reaches blood sensor 553 (BS14), a small amount of air (the first "bubble") is injected at a connector C6. This bubble helps define the first "slug" of liquid, which extends from the bubble sensor to the first bubble. In some embodiments, the valves 533 (V3a) and 556 (V3b) are alternately opened and closed to form a bubble at connector C6, and the sample is pushed toward the sample cell 548. Thus, for example, with pump 532 actuated, valve 566 V(3b) is briefly opened and valve 533 (V3a) is briefly closed to inject a first air bubble into the sample.

In some embodiments, the volume of the tube 534 (T3) from the connector 546 (C2) to the bubble sensor 552 (BS14) is less than the volume of tube 534 (T3) from the connector 524 (C1) to the bubble sensor 535 (BS9). Thus, for example and without limitation, the volume of the tube 534 (T3) from the connector 524 (C1) to the bubble sensor 535 (BS9) can be in the range of approximately 80 μL to approximately 120 μL, (e.g., 100 μL,) and the volume of the tube 534 (T3) from the connector 546 (C2) to the bubble sensor 552 (BS14) can be in the range of approximately 5 μL to approximately 25 μL (e.g., 15 μL). In some embodiments, multiple blood slugs are created. For example, more than two blood slugs can be created, each having a different volume. In some embodiments, five blood slugs are created, each having approximately the same volume of approximately 20 μL each. In some embodiments, three blood slugs are created, the first two having a volume of 10 μL and the last having a volume of 20 μL. In some embodiments, four blood slugs are created; the first three blood slugs can have a volume of approximately 15 μL and the fourth can have a volume of approximately 35 μL.

A second slug can be prepared by opening the valve 553 (V3a), closing the valve 566 (V3b), with pump 532 (pump #0) operating to push the first slug through a first sample cell holder interface tube 582 (N1), through the sample cell 548, through a second sample cell holder interface tube 584 (N2), and toward the waste bladder 554. When the first bubble reaches the bubble sensor 552 (BS 14), the open/closed configurations of valves 553 (V3a) and 566 (V3b) are reversed, and a second bubble is injected into the sample, as before. A third slug can be prepared in the same manner as the second (pushing the second bubble to bubble sensor 552 (BS 14) and injecting a third bubble). After the injection of the third air bubble, the sample can be pushed through system 510 until the end of the sample is detected by bubble sensor 552 (BS 14). The system can be designed such that when the end of the sample reaches this point, the last portion of the sample (a fourth slug) is within the sample cell 548, and the pump 532 can stop forcing the fluid column through the anticoagulant valve tube 534 (T3) so that the fourth slug remains within the sample cell 548. Thus, the first three blood slugs can serve to flush any residual saline out the sample cell 548. The three leading slugs can be deposited in the waste bladder 554 by passing through the tube 556 (T6) and past the tube-flanking portions of the open pinch valve 557 (V4a).

In some embodiments, the fourth blood slug is centrifuged for a given length of time (e.g., more than 1 minute, five minutes, or 2 minutes, to take three advantageous examples) at a relatively fast speed (e.g., 7200 RPM, 5000 RPM, or 4500 RPM, to take three examples). Thus, for example, the sample cell holder interface tubes 582 (N1) and 584 (N2) disconnect the sample cell 548 from the tubes 534 (T3) and 562 (T7), permitting the centrifuge rotor 550 and the sample cell 548 to spin together. Spinning separates a sample (e.g., blood) into its components, isolates the plasma, and positions the plasma in the sample cell 548 for measurement. The centrifuge 550 can be stopped with the sample cell 548 in a beam of radiation (not shown) for analysis. The radiation, a detector, and logic can be used to analyze a portion of the sample (e.g., the plasma) spectroscopically (e.g., for glucose, lactate, or other analyte concentration). In some embodiments, some or all of the separated components (e.g., the isolated plasma) may be transported to a different analysis chamber. For example, another analysis chamber can have one or more electrodes in electrical communication with the chamber's contents, and the separated components may be analyzed electrically. At any suitable point, one or more of the separated components can be transported to the waste bladder 554 when no longer needed. In some chemical analysis systems and apparatus, the separated components are analyzed electrically. Analysis devices may be connected serially, for example, so that the analyzed substance from an optical analysis system (e.g., an "OptiScanner®" fluid analyzer) can be transferred to an independent analysis device (e.g., a chemical analysis device) for subsequent analysis. In certain embodiments, the analysis devices are integrated into a single system. Many variations are possible.

In some embodiments, portions of the system 510 that contain blood after the sample cell 548 has been provided with a sample are cleaned to prevent blood from clotting. Accordingly, the centrifuge rotor 550 can include two passageways for fluid that may be connected to the sample cell holder interface tubes 582 (N1) and 584 (N2). One passageway is sample cell 548, and a second passageway is a shunt

586. An embodiment of the shunt 586 is illustrated in more detail in FIG. 16 (see reference numeral 1586).

The shunt 586 can allow cleaner (e.g., a detergent such as tergazyme A) to flow through and clean the sample cell holder interface tubes without flowing through the sample cell 548. After the sample cell 548 is provided with a sample, the interface tubes 582 (N1) and 584 (N2) are disconnected from the sample cell 548, the centrifuge rotor 550 is rotated to align the shunt 586 with the interface tubes 582 (N1) and 584 (N2), and the interface tubes are connected with the shunt. With the shunt in place, the detergent tank 559 is pressurized by the second pump 532 (pump #0) with valves 561 (V4*b*) and 563 (V2*b*) open and valves 557 (V4*a*) and 533 (V3*a*) closed to flush the cleaning solution back through the interface tubes 582 (N1) and 584 (N2) and into the waste bladder 554. Subsequently, saline can be drawn from the saline bag 520 for a saline flush. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7*a*), 533 (V3*a*), 557 (V4*a*), and the following valves are closed: 542 (PV1), 523 (V0), 531 (V1*a*), 566 (V3*b*), 563 (V2*b*), and 561 (V4*b*).

Following analysis, the second pump 532 (pump #0) flushes the sample cell 548 and sends the flushed contents to the waste bladder 554. This flush can be done with a cleaning solution from the detergent tank 558. In some embodiments, the detergent tank valve 559 (V7*b*) is open, providing fluid communication between the second pump 532 and the detergent tank 558. The second pump 532 forces cleaning solution from the detergent tank 558 between the tube-flanking portions of the open pinch valve 561 and through the tube 562 (T7). The cleaning flush can pass through the sample cell 548, through the second connector 546, through the tube 564 (T5) and the open valve 563 (V2*b*), and into the waste bladder 554.

Subsequently, the first pump 522 (pump #1) can flush the cleaning solution out of the sample cell 548 using saline in drawn from the saline bag 520. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7*a*), 533 (V3*a*), 557 (V4*a*), and the following valves are closed: 542 (PV1), 523 (V0), 531 (V1*a*), 566 (V3*b*), 563 (V2*b*), and 561 (V4*b*).

When the fluid source is a living entity such as a patient, a low flow of saline (e.g., 1-5 mL/hr) is preferably moved through the patient tube 512 (T1) and into the patient to keep the patient's vessel open (e.g., to establish a keep vessel open, or "KVO" flow). This KVO flow can be temporarily interrupted when fluid is drawn into the fluid system 510. The source of this KVO flow can be the infusion pump 518, the third pump 568 (pump #3), or the first pump 522 (pump #1). In some embodiments, the infusion pump 518 can run continuously throughout the measurement cycle described above. This continuous flow can advantageously avoid any alarms that may be triggered if the infusion pump 518 senses that the flow has stopped or changed in some other way. In some embodiments, when the infusion valve 521 closes to allow pump 522 (pump #1) to withdraw fluid from a fluid source (e.g., a patient), the third pump 568 (pump #3) can withdraw fluid through the connector 570, thus allowing the infusion pump 518 to continue pumping normally as if the fluid path was not blocked by the infusion valve 521. If the measurement cycle is about two minutes long, this withdrawal by the third pump 568 can continue for approximately two minutes. Once the infusion valve 521 is open again, the third pump 568 (pump #3) can reverse and insert the saline back into the system at a low flow rate. Preferably, the time between measurement cycles is longer than the measurement cycle itself (for example, the time interval can be longer than ten minutes, shorter than ten minutes, shorter than five minutes, longer than two minutes, longer than one minute, etc.). Accordingly, the third pump 568 can insert fluid back into the system at a lower rate than it withdrew that fluid. This can help prevent an alarm by the infusion pump.

Figure 6:
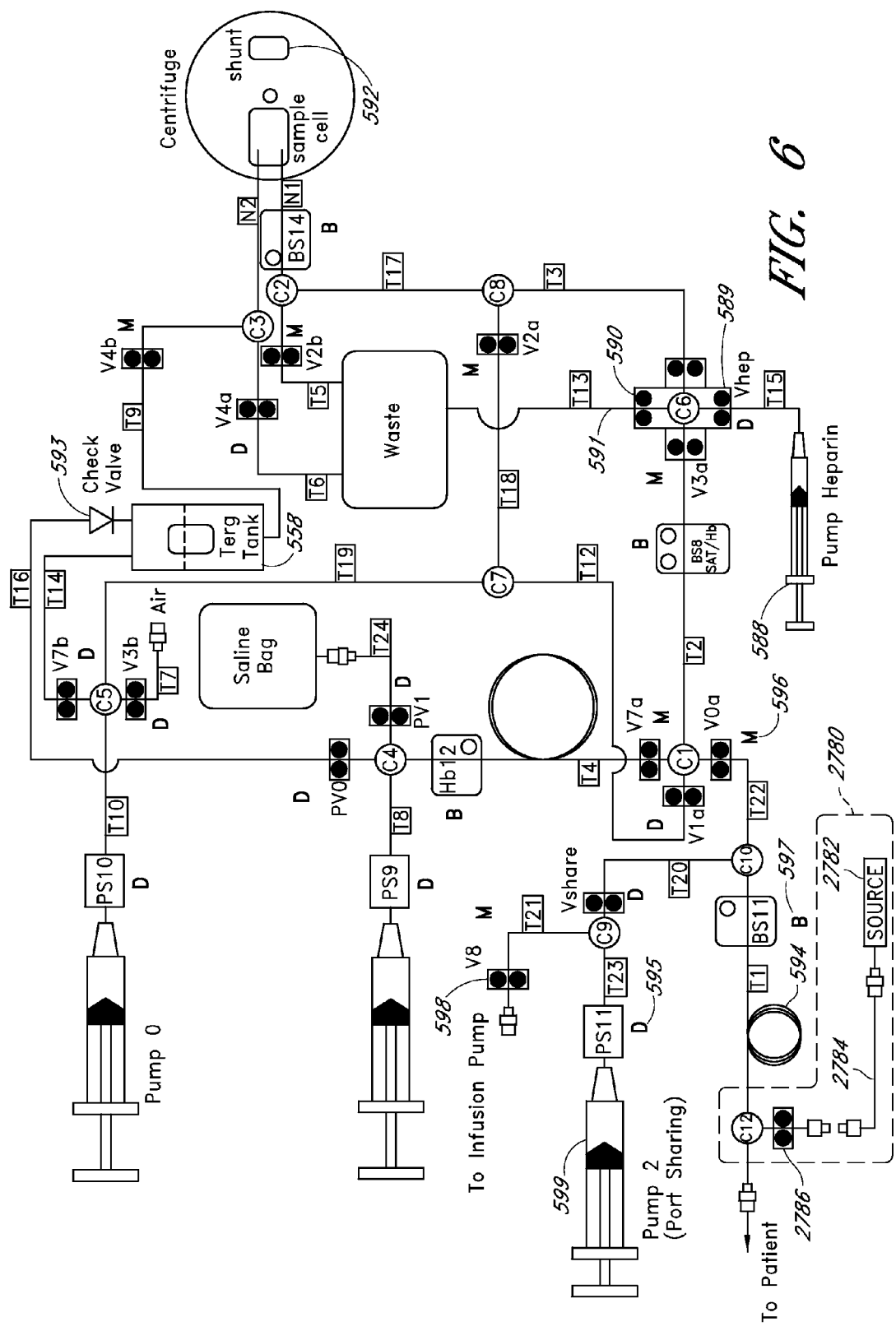
FIG. 6 schematically illustrates another embodiment of a fluid system that can be part of a system for withdrawing and analyzing fluid samples.

FIG. 6 schematically illustrates another embodiment of a fluid system that can be part of a system for withdrawing and analyzing fluid samples. In this embodiment, the anticoagulant valve 541 has been replaced with a syringe-style pump 588 (Pump Heparin) and a series of pinch valves around a junction between tubes. For example, a heparin pinch valve 589 (Vhep) can be closed to prevent flow from or to the pump 588, and a heparin waste pinch valve 590 can be closed to prevent flow from or to the waste container from this junction through the heparin waste tube 591. This embodiment also illustrates the shunt 592 schematically. Other differences from FIG. 5 include the check valve 593 located near the detergent tank 558 and the patient loop 594. The reference letters D, for example, the one indicated at 595, refer to components that are advantageously located on the door. The reference letters M, for example, the one indicated at 596, refer to components that are advantageously located on the monitor. The reference letters B, for example, the one indicated at 597, refer to components that can be advantageously located on both the door and the monitor.

In some embodiments, the system 400 (see FIG. 4), the apparatus 100 (see FIG. 1), or even the monitoring device 102 (see FIG. 1) itself can also actively function not only to monitor analyte levels (e.g., glucose), but also to change and/or control analyte levels. Thus, the monitoring device 102 can be both a monitoring and an infusing device. In some embodiments, the fluid handling system 510 can include an optional analyte control subsystem 2780 that will be further described below (see discussion of analyte control).

In certain embodiments, analyte levels in a patient can be adjusted directly (e.g., by infusing or extracting glucose) or indirectly (e.g., by infusing or extracting insulin). FIG. 6 illustrates one way of providing this function. The infusion pinch valve 598 (V8) can allow the port sharing pump 599 (compare to the third pump 568 (pump #3) in FIG. 5) to serve two roles. In the first role, it can serve as a "port sharing" pump. The port sharing function is described with respect to the third pump 568 (pump #3) of FIG. 5, where the third pump 568 (pump #3) can withdraw fluid through the connector 570, thus allowing the infusion pump 518 to continue pumping normally as if the fluid path was not blocked by the infusion valve 521. In the second role, the port sharing pump 599 can serve as an infusion pump. The infusion pump role allows the port sharing pump 599 to draw a substance (e.g., glucose, saline, etc.) from another source when the infusion pinch valve 598 is open, and then to infuse that substance into the system or the patient when the infusion pinch valve 598 is closed. This can occur, for example, in order to change the level of a substance in a patient in response to a reading by the monitor that the substance is too low. In some embodiments, one or more of the pumps may comprise a reversible infusion pump configured to interrupt the flow of the infusion fluid and draw a sample of blood for analysis.

Mechanical/Fluid System Interface

Figure 7:
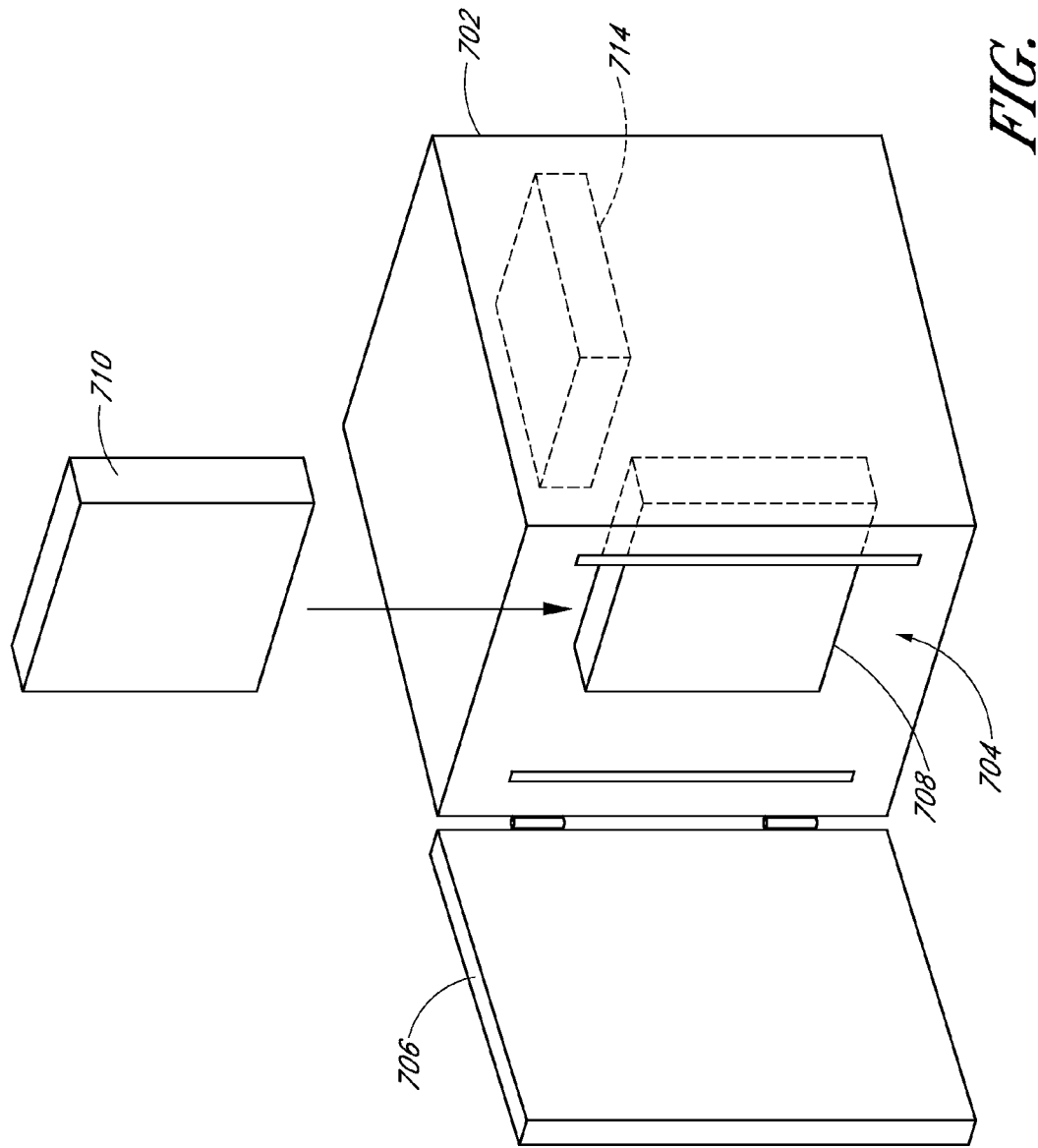
FIG. 7 is an oblique schematic depiction of an embodiment of a monitoring device.

FIG. 7 is an oblique schematic depiction of a modular monitoring device 700, which can correspond to the monitoring device 102. The modular monitoring device 700 includes a body portion 702 having a receptacle 704, which can be accessed by moving a movable portion 706. The receptacle 704 can include connectors (e.g., rails, slots, protrusions, resting surfaces, etc.) with which a removable portion 710 can interface. In some embodiments, portions of a fluidic system that directly contact fluid are incorporated into one or more removable portions (e.g., one or more disposable cassettes, sample holders, tubing cards, etc.). For example, a removable portion 710 can house at least a portion of the fluid system 510 described previously, including portions that contact sample fluids, saline, detergent solution, and/or anticoagulant.

In some embodiments, a non-disposable fluid-handling subsystem 708 is disposed within the body portion 702 of the monitoring device 700. The first removable portion 710 can include one or more openings that allow portions of the non-disposable fluid-handling subsystem 708 to interface with the removable portion 710. For example, the non-disposable fluid-handling subsystem 708 can include one or more pinch valves that are designed to extend through such openings to engage one or more sections of tubing. When the first removable portion 710 is present in a corresponding first receptacle 704, actuation of the pinch valves can selectively close sections of tubing within the removable portion. The non-disposable fluid-handling subsystem 708 can also include one or more sensors that interface with connectors, tubing sections, or pumps located within the first removable portion 710. The non-disposable fluid-handling subsystem 708 can also include one or more actuators (e.g., motors) that can actuate moveable portions (e.g., the plunger of a syringe) that may be located in the removable portion F10. A portion of the non-disposable fluid-handling subsystem 708 can be located on or in the moveable portion F06 (which can be a door having a slide or a hinge, a detachable face portion, etc.).

In the embodiment shown in FIG. 7, the monitoring device 700 includes an optical system 714 disposed within the body portion 702. The optical system 714 can include a light source and a detector that are adapted to perform measurements on fluids within a sample holder (not shown). The light source may comprise a fixed wavelength light source and/or a tunable light source. The light source may comprise one or more sources including, for example, broadband sources, LEDs, and lasers. In some embodiments, the sample holder comprises a removable portion, which can be associated with or disassociated from the removable portion F10. The sample holder can include an optical window through which the optical system 714 can emit radiation for measuring properties of a fluid in the sample holder. The optical system 714 can include other components such as, for example, a power supply, a centrifuge motor, a filter wheel, and/or a beam splitter.

In some embodiments, the removable portion 710 and the sample holder are adapted to be in fluid communication with each other. For example, the removable portion 710 can include a retractable injector that injects fluids into a sample holder. In some embodiments, the sample holder can comprise or be disposed in a second removable portion (not shown). In some embodiments, the injector can be retracted to allow the centrifuge to rotate the sample holder freely.

The body portion 702 of the monitoring device 700 can also include one or more connectors for an external battery (not shown). The external battery can serve as a backup emergency power source in the event that a primary emergency power source such as, for example, an internal battery (not shown) is exhausted.

FIG. 7 shows an embodiment of a system having subcomponents illustrated schematically. By way of a more detailed (but nevertheless non-limiting) example, FIG. 8 and FIG. 9 show more details of the shape and physical configuration of a sample embodiment.

Figure 8:
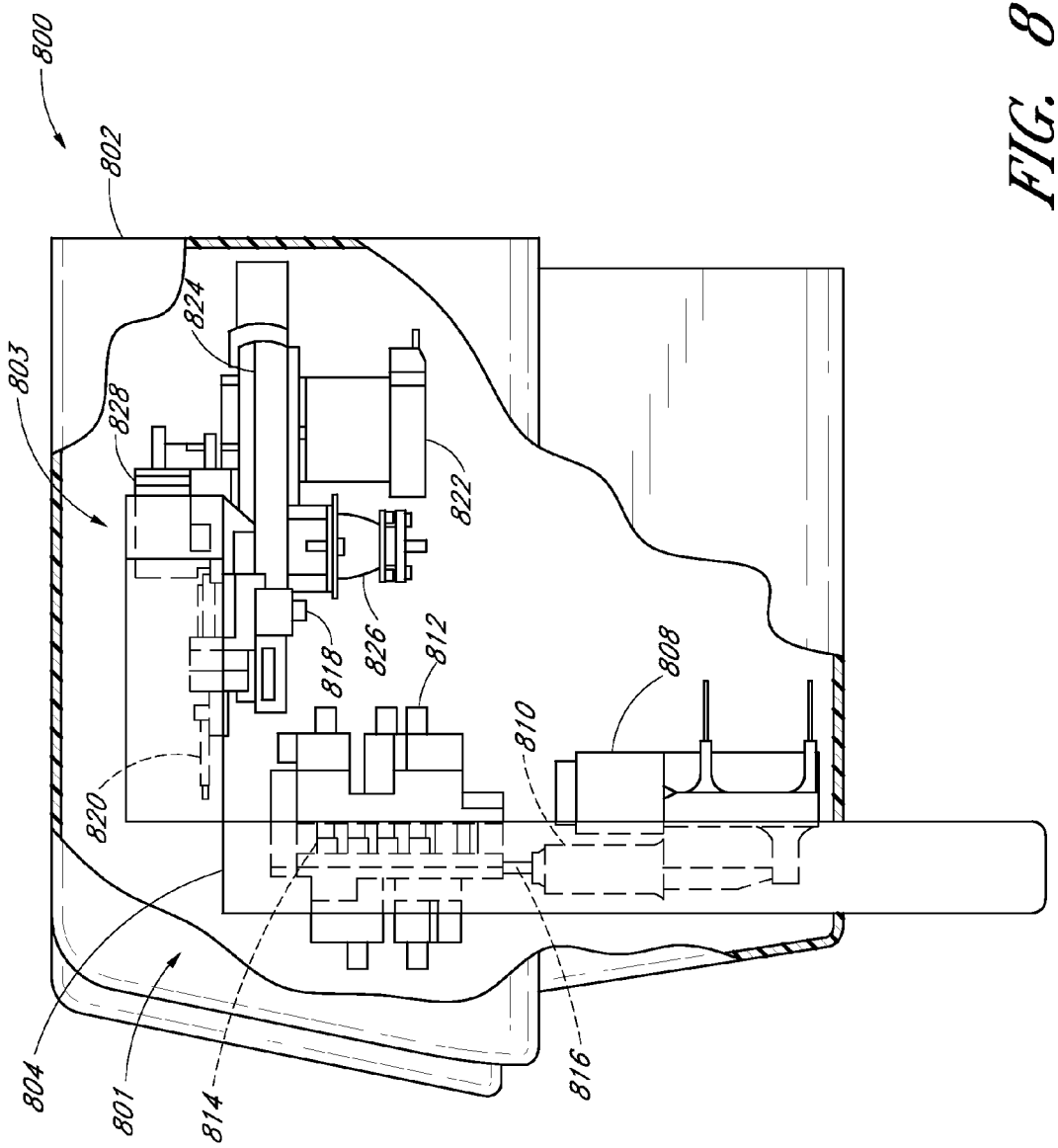
FIG. 8 shows a cut-away side view of an embodiment of a monitoring device.
Figure 9:
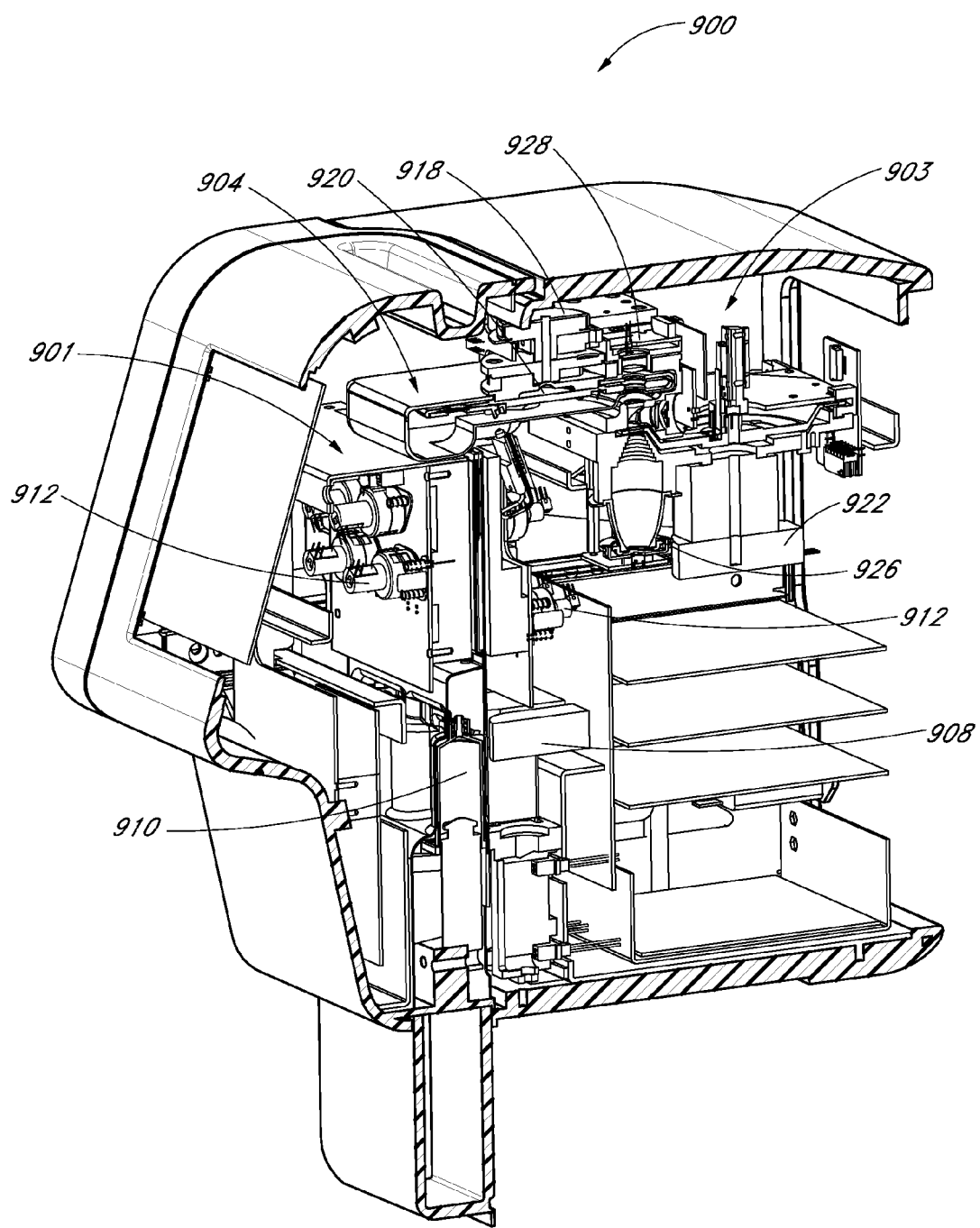
FIG. 9 shows a cut-away perspective view of an embodiment of a monitoring device.

FIG. 8 shows a cut-away side view of a monitoring device 800 (which can correspond, for example, to the device 102 shown in FIG. 1). The device 800 includes a casing 802. The monitoring device 800 can have a fluid system. For example, the fluid system can have subsystems, and a portion or portions thereof can be disposable, as schematically depicted in FIG. 4. As depicted in FIG. 8, the fluid system is generally located at the left-hand portion of the casing 802, as indicated by the reference 801. The monitoring device 800 can also have an optical system. In the illustrated embodiment, the optical system is generally located in the upper portion of the casing 802, as indicated by the reference 803. Advantageously, however, the fluid system 801 and the optical system 803 can both be integrated together such that fluid flows generally through a portion of the optical system 803, and such that radiation flows generally through a portion of the fluid system 801.

Depicted in FIG. 8 are examples of ways in which components of the device 800 mounted within the casing 802 can interface with components of the device 800 that comprise disposable portions. Not all components of the device 800 are shown in FIG. 8. A disposable portion 804 having a variety of components is shown in the casing 802. In some embodiments, one or more actuators 808 housed within the casing 802, operate syringe bodies 810 located within a disposable portion 804. The syringe bodies 810 are connected to sections of tubing 816 that move fluid among various components of the system. The movement of fluid is at least partially controlled by the action of one or more pinch valves 812 positioned within the casing 802. The pinch valves 812 have arms 814 that extend within the disposable portion 804. Movement of the arms 814 can constrict a section of tubing 816.

In some embodiments, a sample cell holder 820 can engage a centrifuge motor 818 mounted within the casing 802 of the device 800. A filter wheel motor 822 disposed within the housing 802 rotates a filter wheel 824, and in some embodiments, aligns one or more filters with an optical path. An optical path can originate at a source 826 within the housing 802 that can be configured to emit a beam of radiation (e.g., infrared radiation, visible radiation, ultraviolet radiation, etc.) through the filter and the sample cell holder 820 and to a detector 828. A detector 828 can measure the optical density of the light when it reaches the detector.

FIG. 9 shows a cut-away perspective view of an alternative embodiment of a monitoring device 900. Many features similar to those illustrated in FIG. 8 are depicted in this illustration of an alternative embodiment. A fluid system 901 can be partially seen. The disposable portion 904 is shown in an operative position within the device. One of the actuators 808 can be seen next to a syringe body 910 that is located within the disposable portion 904. Some pinch valves 912 are shown next to a fluid-handling portion of the disposable portion 904. In this figure, an optical system 903 can also be partially seen. The sample holder 920 is located underneath the centrifuge motor 918. The filter wheel motor 922 is positioned near the radiation source 926, and the detector 928 is also illustrated.

FIG. 10 illustrates two views of a cartridge 1000 that can interface with a fluid system such as the fluid system 510 of FIG. 5. The cartridge 1000 can be configured for insertion into a receptacle of the device 800 of FIG. 8 and/or the device 900 shown in FIG. 9. In some embodiments, the cartridge 1000 can comprise a portion that is disposable and a portion that is reusable. In some embodiments, the cartridge 1000 can be disposable. The cartridge 1000 can fill the role of the removable portion 710 of FIG. 7, for example. In some embodiments, the cartridge 1000 can be used for a system having only one disposable subsystem, making it a simple matter for a health care provider to replace and/or track usage time of the disposable portion. In some embodiments, the cartridge 1000 includes one or more features that facilitate insertion of the cartridge 1000 into a corresponding receptacle. For example, the cartridge 1000 can be shaped so as to promote insertion of the cartridge 1000 in the correct orientation. The cartridge 1000 can also include labeling or coloring affixed to or integrated with the cartridge's exterior casing that help a handler insert the cartridge 1000 into a receptacle properly.

The cartridge 1000 can include one or more ports for connecting to material sources or receptacles. Such ports can be provided to connect to, for example, a saline source, an infusion pump, a sample source, and/or a source of gas (e.g., air, nitrogen, etc.). The ports can be connected to sections of tubing within the cartridge 1000. In some embodiments, the sections of tubing are opaque or covered so that fluids within the tubing cannot be seen, and in some embodiments, sections of tubing are transparent to allow interior contents (e.g., fluid) to be seen from outside.

Figure 15:
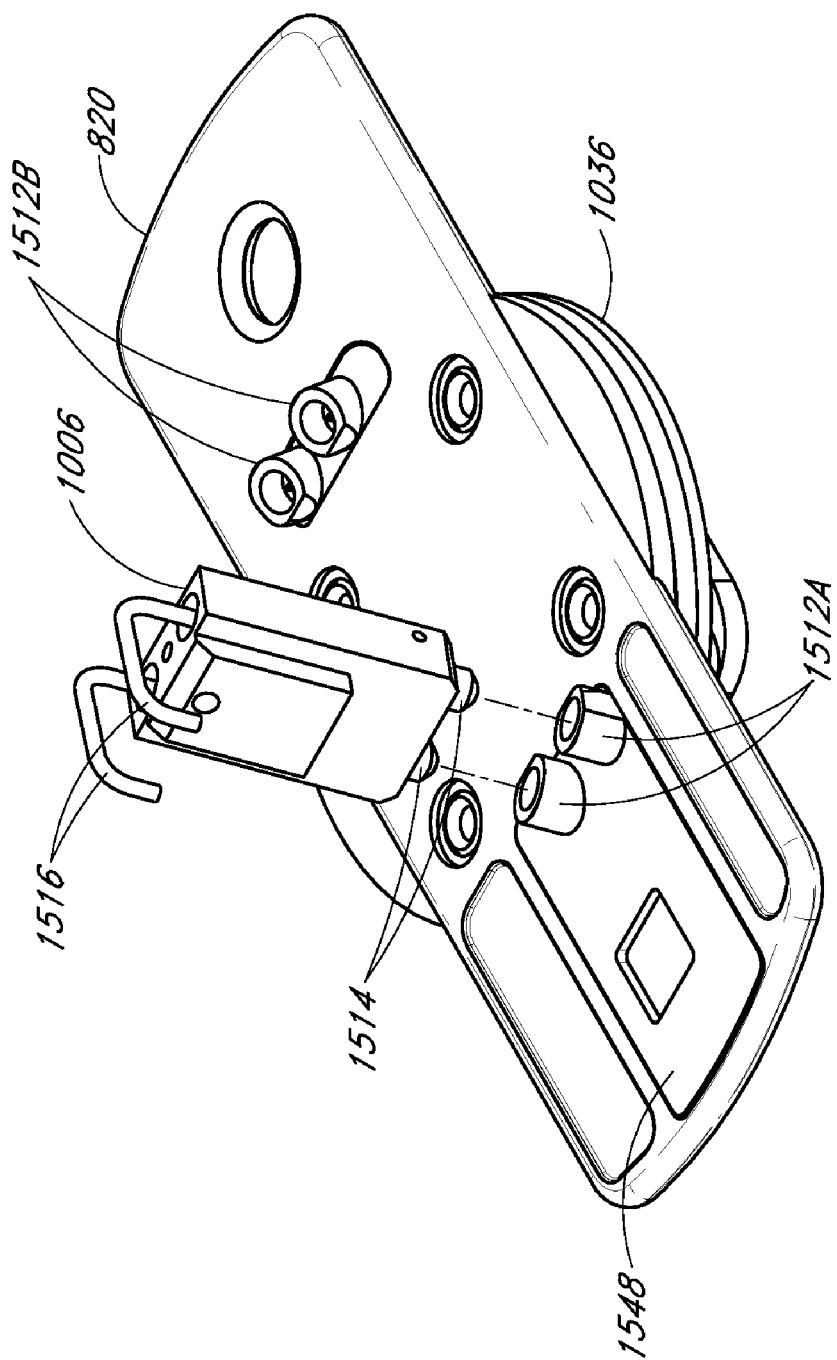
FIG. 15 shows an underneath perspective view of a sample cell holder attached to a centrifuge interface, with a view of an interface with a sample injector.

The cartridge 1000 shown in FIG. 10 can include a sample injector 1006. The sample injector 1006 can be configured to inject at least a portion of a sample into a sample holder (see, e.g., the sample cell 548), which can also be incorporated into the cartridge 1000. The sample injector 1006 can include, for example, the sample cell holder interface tubes 582 (N1) and 584 (N2) of FIG. 5, embodiments of which are also illustrated in FIG. 15.

The housing of the cartridge 1000 can include a tubing portion 1008 containing within it a card having one or more sections of tubing. In some embodiments, the body of the cartridge 1000 includes one or more apertures 1009 through which various components, such as, for example, pinch valves and sensors, can interface with the fluid-handling portion contained in the cartridge 1000. The sections of tubing found in the tubing portion 1008 can be aligned with the apertures 1009 in order to implement at least some of the functionality shown in the fluid system 510 of FIG. 5.

The cartridge 1000 can include a pouch space (not shown) that can comprise one or more components of the fluid system 510. For example, one or more pouches and/or bladders can be disposed in the pouch space (not shown). In some embodiments, a cleaner pouch and/or a waste bladder can be housed in a pouch space. The waste bladder can be placed under the cleaner pouch such that, as detergent is removed from the cleaner pouch, the waste bladder has more room to fill. The components placed in the pouch space (not shown) can also be placed side-by-side or in any other suitable configuration.

The cartridge 1000 can include one or more pumps 1016 that facilitate movement of fluid within the fluid system 510. Each of the pump housings 1016 can contain, for example, a syringe pump having a plunger. The plunger can be configured to interface with an actuator outside the cartridge 1000. For example, a portion of the pump that interfaces with an actuator can be exposed to the exterior of the cartridge 1000 housing by one or more apertures 1018 in the housing.

The cartridge 1000 can have an optical interface portion 1030 that is configured to interface with (or comprise a portion of) an optical system. In the illustrated embodiment, the optical interface portion 1030 can pivot around a pivot structure 1032. The optical interface portion 1030 can house a sample holder (not shown) in a chamber that can allow the sample holder to rotate. The sample holder can be held by a centrifuge interface 1036 that can be configured to engage a centrifuge motor (not shown). When the cartridge 1000 is being inserted into a system, the orientation of the optical interface portion 1030 can be different than when it is functioning within the system.

In some embodiments, the cartridge 1000 is designed for single patient use. The cartridge 1000 may also be disposable and/or designed for replacement after a period of operation. For example, in some embodiments, if the cartridge 1000 is installed in a continuously operating monitoring device that performs four measurements per hour, the waste bladder may become filled or the detergent in the cleaner pouch depleted after about three days. The cartridge 1000 can be replaced before the detergent and waste bladder are exhausted. In some embodiments, a portion of the cartridge 1000 can be disposable while another portion of the cartridge 1000 is disposable, but lasts longer before being discarded. In some embodiments, a portion of the cartridge 1000 may not be disposable at all. For example, a portion thereof may be configured to be cleaned thoroughly and reused for different patients. Various combinations of disposable and less- or non-disposable portions are possible.

The cartridge 1000 can be configured for easy replacement. For example, in some embodiments, the cartridge 1000 is designed to have an installation time of only minutes. For example, the cartridge can be designed to be installed in less than about five minutes, or less than two minutes. During installation, various fluid lines contained in the cartridge 1000 can be primed by automatically filling the fluid lines with saline. The saline can be mixed with detergent powder from the cleaner pouch in order to create a cleaning solution.

The cartridge 1000 can also be designed to have a relatively brief shut down time. For example, the shut down process can be configured to take less than about fifteen minutes, or less than about ten minutes, or less than about five minutes. The shut down process can include flushing the patient line; sealing off the insulin pump connection, the saline source connection, and the sample source connection; and taking other steps to decrease the risk that fluids within the used cartridge 1000 will leak after disconnection from the monitoring device.

Some embodiments of the cartridge 1000 can comprise a flat package to facilitate packaging, shipping, sterilizing, etc. Advantageously, however, some embodiments can further comprise a hinge or other pivot structure. Thus, as illustrated, an optical interface portion 1030 can be pivoted around a pivot structure 1032 to generally align with the other portions of the cartridge 1000. The cartridge can be provided to a medical provider sealed in a removable wrapper, for example.

In some embodiments, the cartridge 1000 is designed to fit within standard waste containers found in a hospital, such as a standard biohazard container. For example, the cartridge 1000 can be less than one foot long, less than one foot wide, and less than two inches thick. In some embodiments, the cartridge 1000 is designed to withstand a substantial impact, such as that caused by hitting the ground after a four foot drop, without damage to the housing or internal components. In some embodiments, the cartridge 1000 is designed to withstand significant clamping force applied to its casing. For example, the cartridge 1000 can be built to withstand five pounds per square inch of force without damage. In some embodiments, the cartridge 1000 can be designed to be less sturdy and more biodegradable. In some embodiments, the cartridge 1000 can be formed and configured to withstand more or less than five pounds of force per square inch without damage. In some embodiments, the cartridge 1000 is non pyrogenic and/or latex free.

Figure 11:
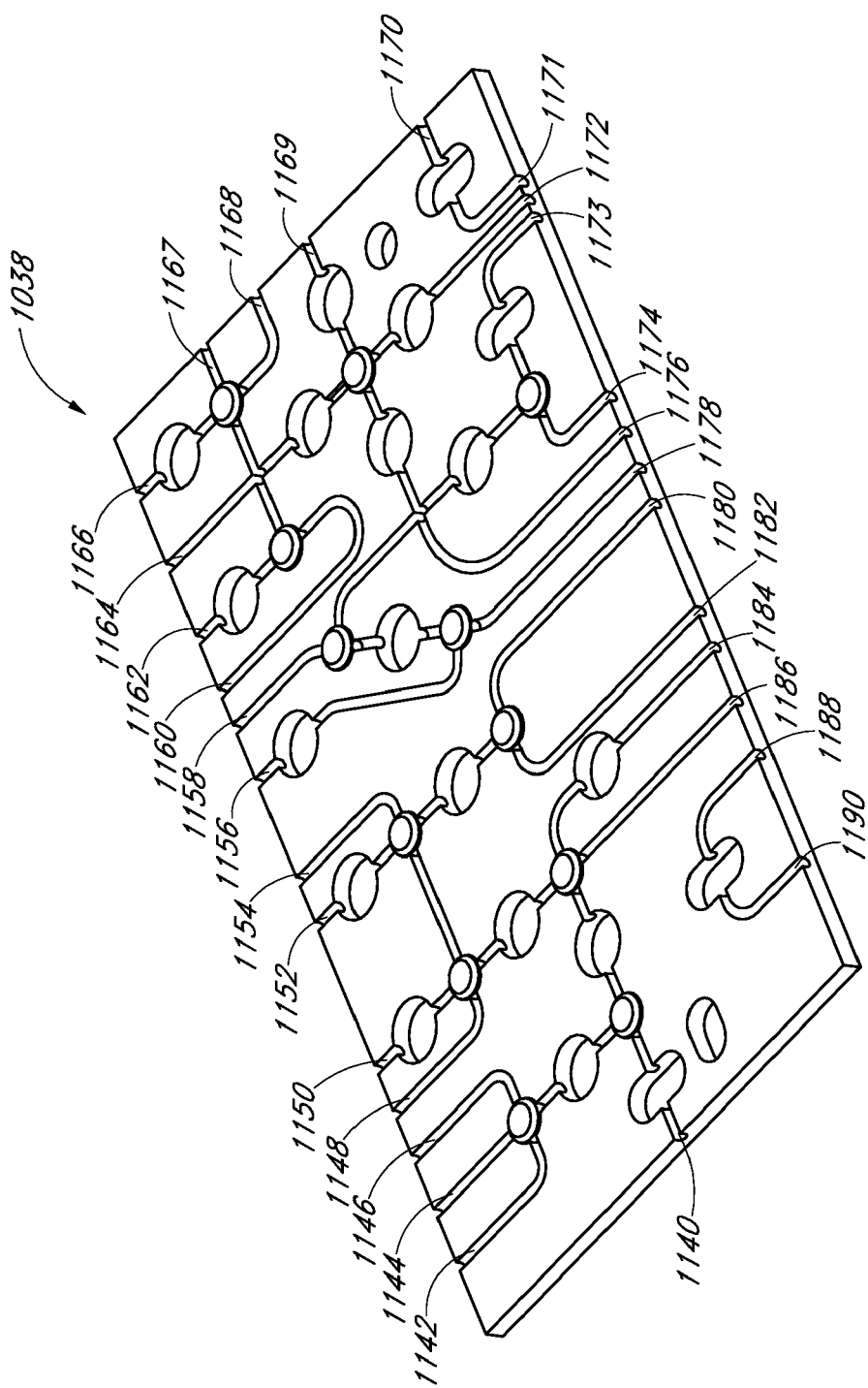
FIG. 11 illustrates an embodiment of a fluid routing card that can be part of the removable cartridge of FIG. 10.

FIG. 11 illustrates an embodiment of a fluid-routing card 1038 that can be part of the removable cartridge of FIG. 10. For example, the fluid-routing card 1038 can be located generally within the tubing portion 1008 of the cartridge 1000. The fluid-routing card 1038 can contain various passages and/or tubes through which fluid can flow as described with respect to FIG. 5 and/or FIG. 6, for example. Thus, the illustrated tube opening openings can be in fluid communication with the following fluidic components, for example:

| Tube Opening Reference Numeral | Can Be In Fluid Communication With |
| --- | --- |
| 1142 | third pump 568 (pump #3) |
| 1144 | infusion pump 518 |
| 1146 | Presx |
| 1148 | air pump |
| 1150 | Vent |
| 1152 | detergent (e.g., tergazyme) source or waste tube |
| 1154 | Presx |
| 1156 | detergent (e.g., tergazyme) source or waste tube |
| 1158 | waste receptacle |
| 1160 | first pump 522 (pump #1) (e.g., a saline pump) |
| 1162 | saline source or waste tube |
| 1164 | anticoagulant (e.g., heparin) pump (see FIG. 6) and/or shuttle valve |
| 1166 | detergent (e.g., tergazyme) source or waste tube |
| 1167 | Presx |
| 1168 | Arrival sensor tube 528 (T4) |
| 1169 | tube 536 (T2) |
| 1170 | Arrival sensor tube 528 (T4) |
| 1171 | Arrival sensor tube 528 (T4) |
| 1172 | anticoagulant (e.g., heparin) pump |
| 1173 | T17 (see FIG. 6) |
| 1174 | Sample cell holder interface tube 582 (N1) |
| 1176 | anticoagulant valve tube 534 (T3) |
| 1178 | Sample cell holder interface tube 584 (N2) |
| 1180 | T17 (see FIG. 6) |
| 1182 | anticoagulant valve tube 534 (T3) |
| 1184 | Arrival sensor tube 528 (T4) |
| 1186 | tube 536 (T2) |
| 1188 | anticoagulant valve tube 534 (T3) |
| 1190 | anticoagulant valve tube 534 (T3) |

The depicted fluid-routing card 1038 can have additional openings that allow operative portions of actuators and/or valves to protrude through the fluid-routing card 1038 and interface with the tubes.

Figure 12:
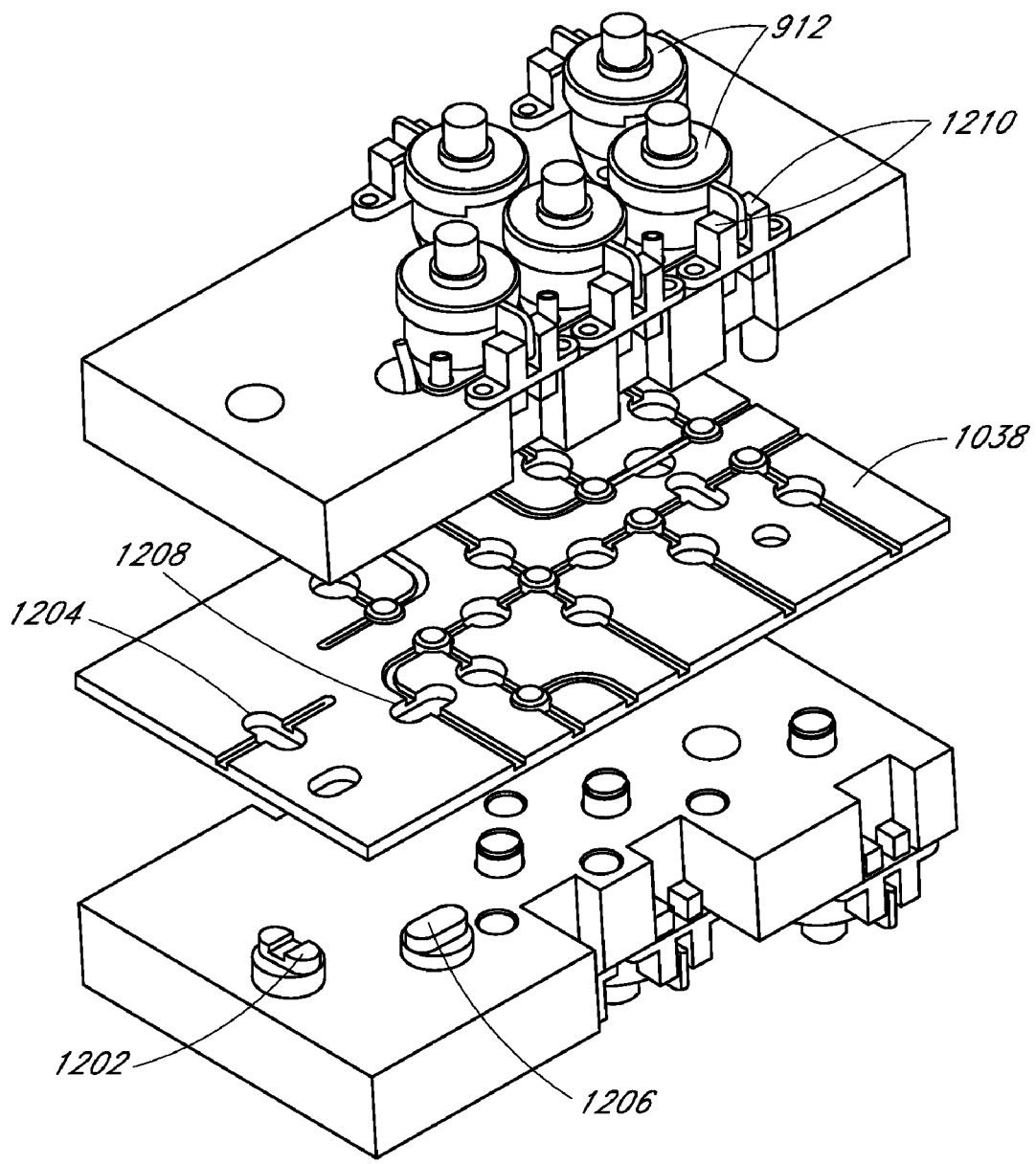
FIG. 12 illustrates how non-disposable actuators can interface with the fluid routing card of FIG. 11.

FIG. 12 illustrates how actuators, which can sandwich the fluid-routing card 1038 between them, can interface with the fluid-routing card 1038 of FIG. 11. Pinch valves 812 can have an actuator portion that protrudes away from the fluid-routing card 1038 containing a motor. Each motor can correspond to a pinch platen 1202, which can be inserted into a pinch platen receiving hole 1204. Similarly, sensors, such as a bubble sensor 1206 can be inserted into receiving holes (e.g., the bubble sensor receiving hole 1208). Movement of the pinch valves 812 can be detected by the position sensors 1210.

Figure 13:
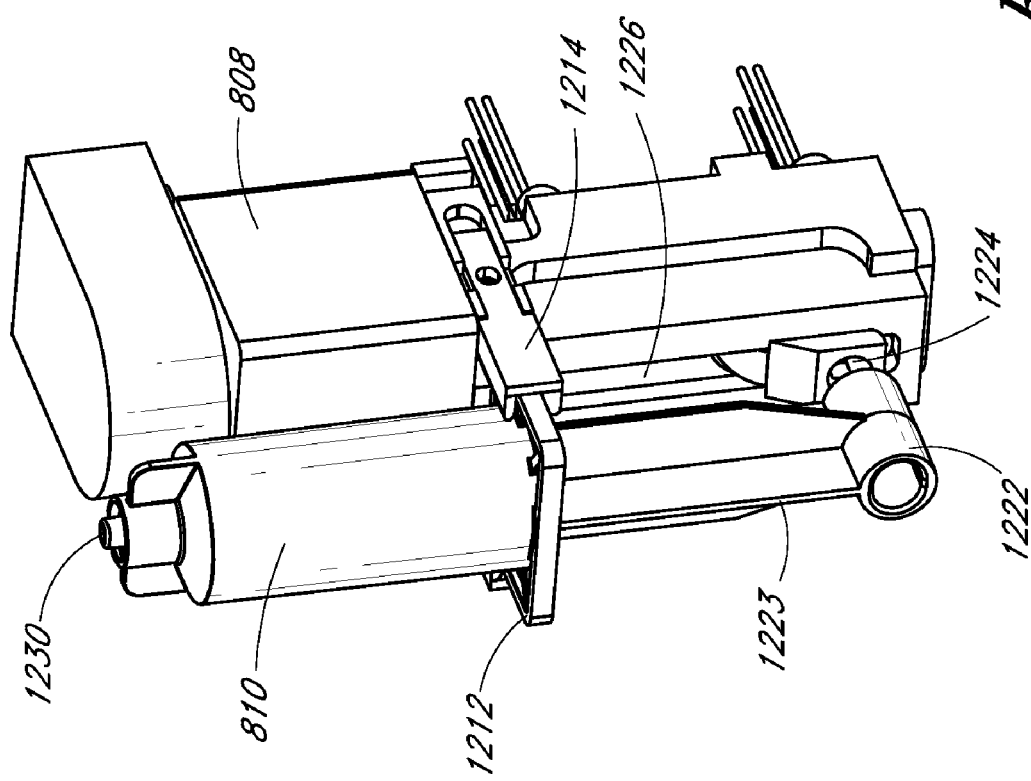
FIG. 13 illustrates a modular pump actuator connected to a syringe housing that can form a portion of a removable cartridge.

FIG. 13 illustrates an actuator 808 that is connected to a corresponding syringe body 810. The actuator 808 is an example of one of the actuators 808 that is illustrated in FIG. 8 and in FIG. 9, and the syringe body 810 is an example of one of the syringe bodies 810 that are visible in FIG. 8 and in FIG. 9. A ledge portion 1212 of the syringe body 810 can be engaged (e.g., slid into) a corresponding receiving portion 1214 in the actuator 808. In some embodiments, the receiving portion 1214 can slide outward to engage the stationary ledge portion 1212 after the disposable cartridge 804 is in place. Similarly, a receiving tube 1222 in the syringe plunger 1223 can be slide onto (or can receive) a protruding portion 1224 of the actuator 808. The protruding portion 1224 can slide along a track 1226 under the influence of a motor inside the actuator 808, thus actuating the syringe plunger 1223 and causing fluid to flow into or out of the syringe tip 1230.

Figure 14:
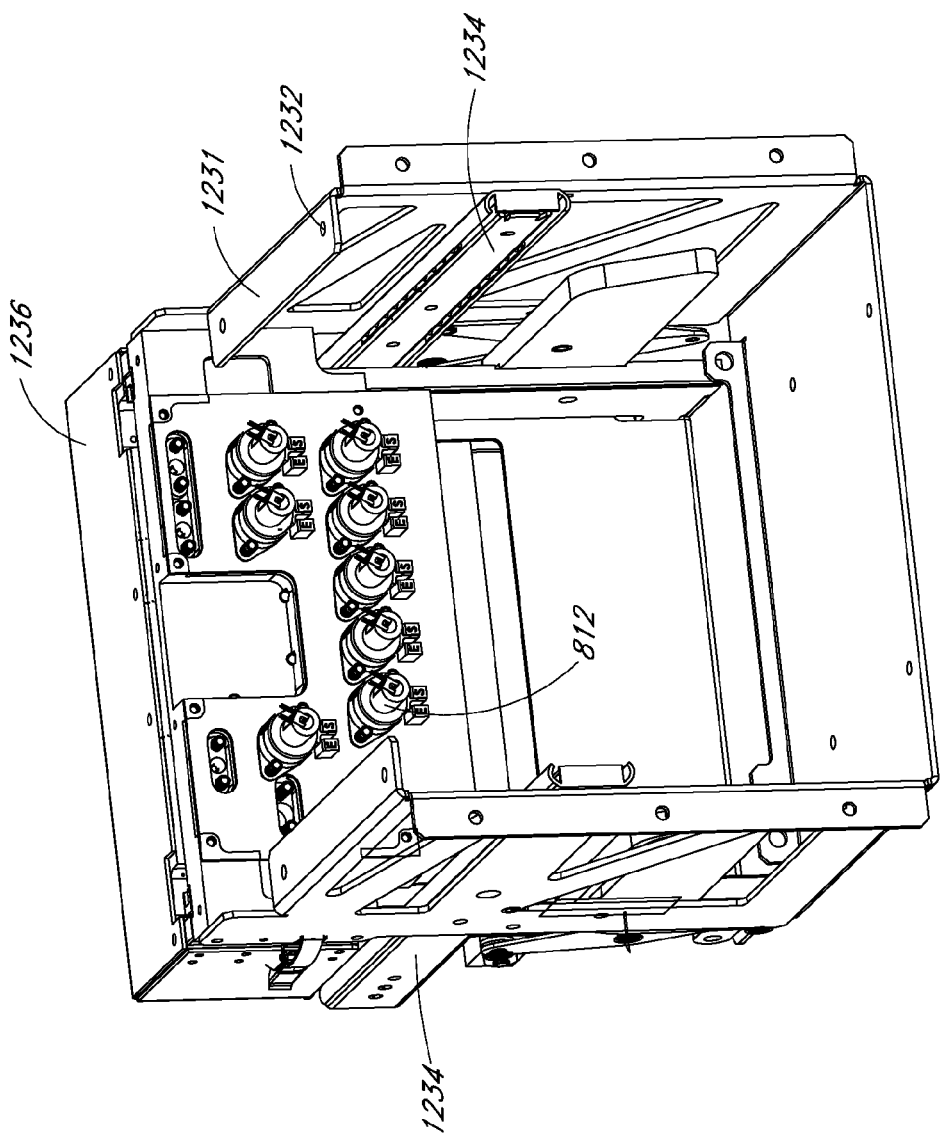
FIG. 14 shows a rear perspective view of internal scaffolding and some pinch valve pump bodies.

FIG. 14 shows a rear perspective view of internal scaffolding 1231 and the protruding bodies of some pinch valves 812. The internal scaffolding 1231 can be formed from metal and can provide structural rigidity and support for other components. The scaffolding 1231 can have holes 1232 into which screws can be screwed or other connectors can be inserted. In some embodiments, a pair of sliding rails 1234 can allow relative movement between portions of an analyzer. For example, a slidable portion 1236 (which can correspond to the movable portion 706, for example) can be temporarily slid away from the scaffolding 1231 of a main unit in order to allow an insertable portion (e.g., the cartridge 804) to be inserted.

FIG. 15 shows an underneath perspective view of the sample cell holder 820, which is attached to the centrifuge interface 1036. The sample cell holder 820 can have an opposite side (see FIG. 17) that allows it to slide into a receiving portion of the centrifuge interface 1036. The sample cell holder 820 can also have receiving nubs 1512A that provide a pathway into a sample cell 1548 held by the sample cell holder 820. Receiving nubs 1512B can provide access to a shunt 1586 (see FIG. 16) inside the sample cell holder 820. The receiving nubs 1512A and 1512B can receive and or dock with fluid nipples 1514. The fluid nipples 1514 can protrude at an angle from the sample injector 1006, which can in turn protrude from the cartridge 1000 (see FIG. 10). The tubes 1516 shown protruding from the other end of the sample injector 1006 can be in fluid communication with the sample cell holder interface tubes 582 (N1) and 584 (N2) (see FIG. 5 and FIG. 6), as well as 1074 and 1078 (see FIG. 11).

Figure 16:
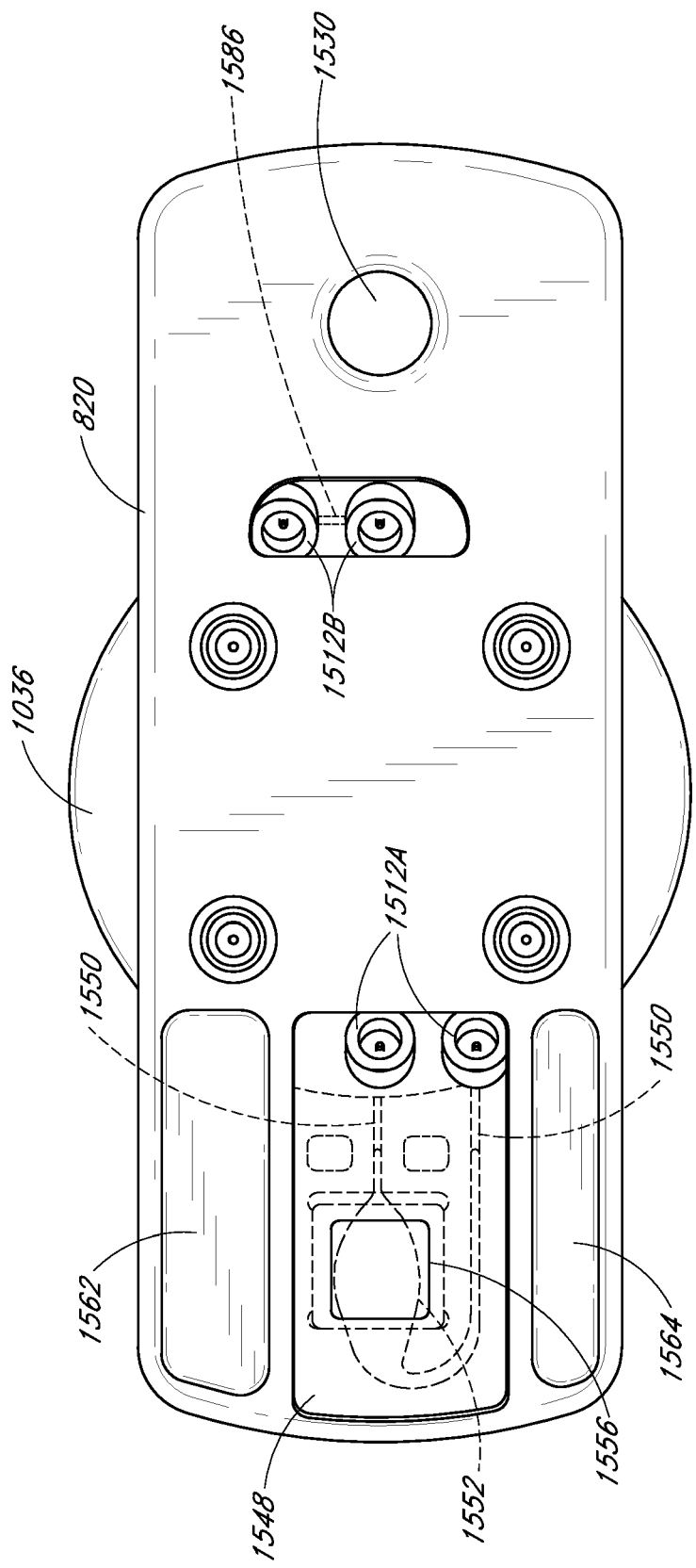
FIG. 16 shows a plan view of a sample cell holder with hidden and/or non-surface portions illustrated using dashed lines.

FIG. 16 shows a plan view of the sample cell holder 820 with hidden and/or non-surface portions illustrated using dashed lines. The receiving nubs 1512A communicate with passages 1550 inside the sample cell 1548 (which can correspond, for example to the sample cell 548 of FIG. 5). The passages widen out into a wider portion 1552 that corresponds to a window 1556. The window 1556 and the wider portion 1552 can be configured to house the sample when radiation is emitted along a pathlength that is generally non-parallel to the sample cell 1548. The window 1556 can allow calibration of the instrument with the sample cell 1548 in place, even before a sample has arrived in the wider portion 1552.

An opposite opening 1530 can provide an alternative optical pathway between a radiation source and a radiation detector (e.g., the radiation source 826 of FIG. 18) and may be used, for example, for obtaining a calibration measurement of the source and detector without an intervening window or sample. Thus, the opposite opening 1530 can be located generally at the same radial distance from the axis of rotation as the window 1556.

The receiving nubs 1512B communicate with a shunt passage 1586 inside the sample cell holder 820 (which can correspond, for example, to the shunt 586 of FIG. 5).

Other features of the sample cell holder 820 can provide balancing properties for even rotation of the sample cell holder 820. For example, the wide trough 1562 and the narrower trough 1564 can be sized or otherwise configured so that the weight and/or mass of the sample cell holder 820 is evenly distributed from left to right in the view of FIG. 16, and/or from top to bottom in this view of FIG. 16.

Figure 17:
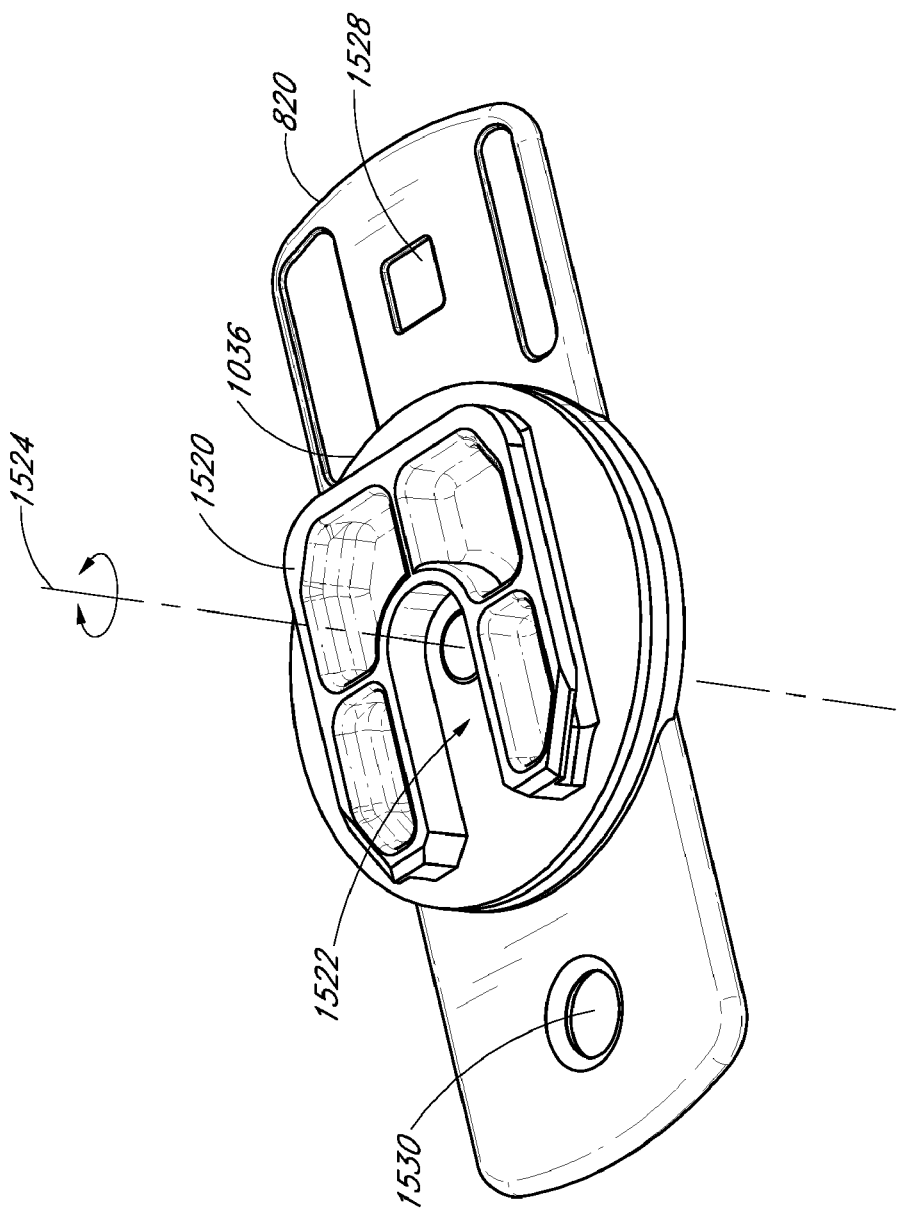
FIG. 17 shows a top perspective view of the centrifuge interface connected to the sample holder.

FIG. 17 shows a top perspective view of the centrifuge interface 1036 connected to the sample cell holder 820. The centrifuge interface 1036 can have a bulkhead 1520 with a rounded slot 1522 into which an actuating portion of a centrifuge can be slid from the side. The centrifuge interface 1036 can thus be spun about an axis 1524, along with the sample cell holder 820, causing fluid (e.g., whole blood) within the sample cell 1548 to separate into concentric strata, according to relative density of the fluid components (e.g., plasma, red blood cells, buffy coat, etc.), within the sample cell 1548. The sample cell holder 820 can be transparent, or it can at least have transparent portions (e.g., the window 1556 and/or the opposite opening 1530) through which radiation can pass, and which can be aligned with an optical pathway between a radiation source and a radiation detector (see, e.g., FIG. 20). In addition, a round opening 1530 through centrifuge rotor 1520 provides an optical pathway between the radiation source and radiation detector and may be used, for example, for obtaining a calibration measurement of the source and detector without an intervening window or sample.

Figure 18:
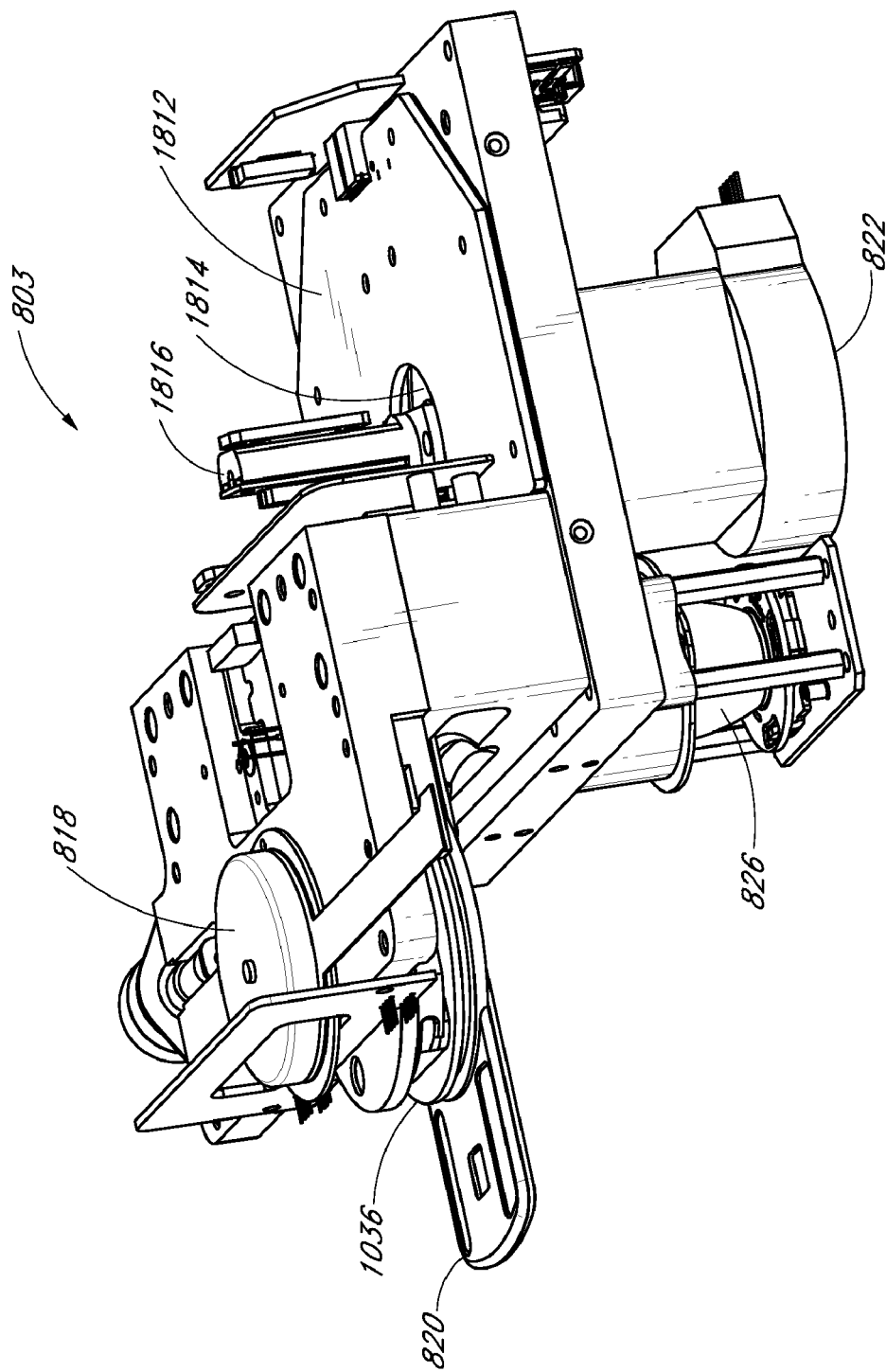
FIG. 18 shows a perspective view of an example optical system.

FIG. 18 shows a perspective view of an example optical system 803. Such a system can be integrated with other systems as shown in FIG. 9, for example. The optical system 803 can fill the role of the optical system 412, and it can be integrated with and/or adjacent to a fluid system (e.g., the fluid-handling system 404 or the fluid system 801). The sample cell holder 820 can be seen attached to the centrifuge interface 1036, which is in turn connected to, and rotatable by the centrifuge motor 818. A filter wheel housing 1812 is attached to the filter wheel motor 822 and encloses a filter wheel 1814. A protruding shaft assembly 1816 can be connected to the filter wheel 1814. The filter wheel 1814 can have multiple filters (see FIG. 19). The radiation source 826 is aligned to transmit radiation through a filter in the filter wheel 1814 and then through a portion of the sample cell holder 820. Transmitted and/or reflected and/or scattered radiation can then be detected by a radiation detector.

Figure 19:
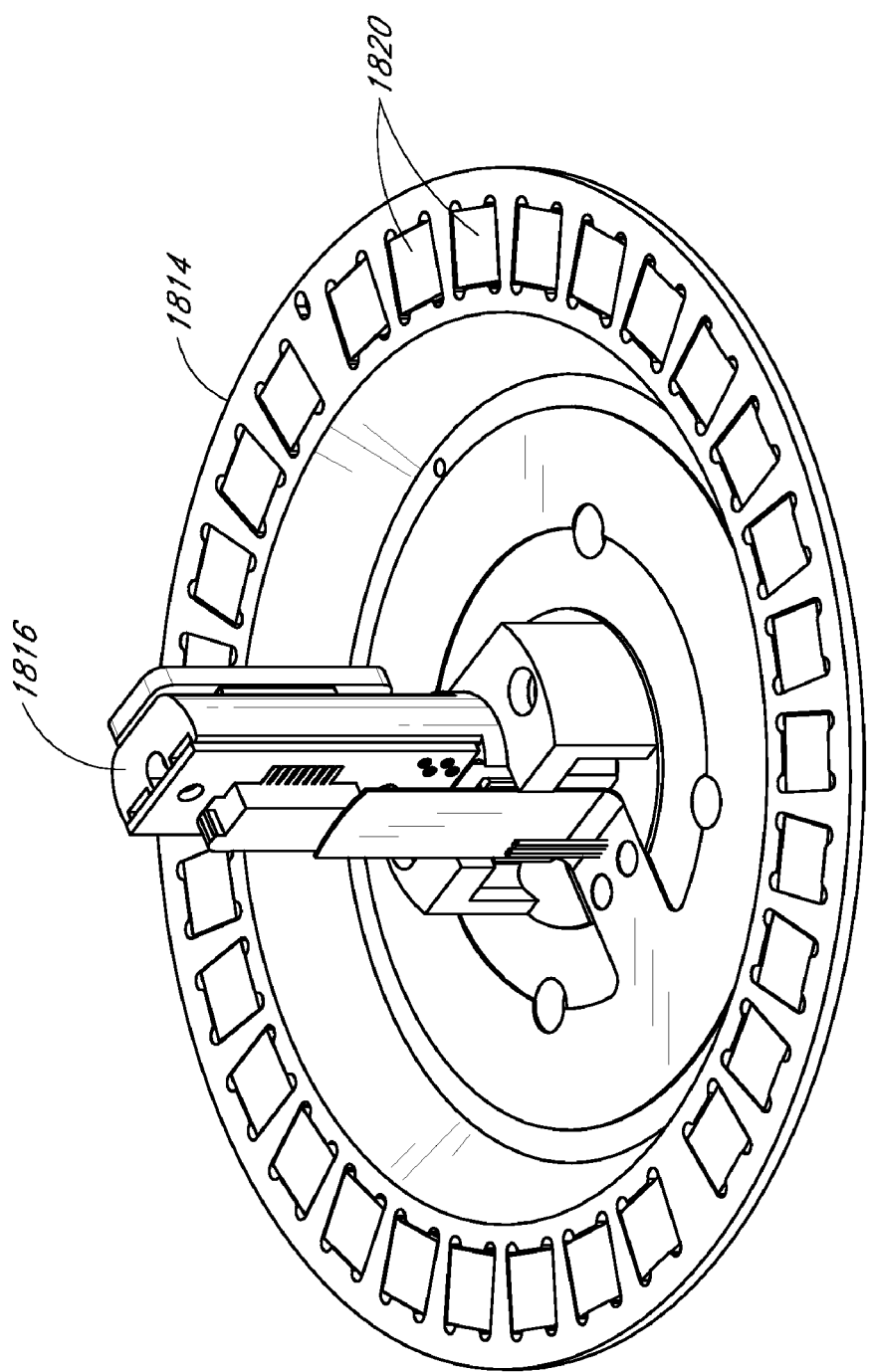
FIG. 19 shows a filter wheel that can be part of the optical system of FIG. 18.

FIG. 19 shows a view of the filter wheel 1814 when it is not located within the filter wheel housing 1812 of the optical system 803. Additional features of the protruding shaft assembly 1816 can be seen, along with multiple filters 1820. In some embodiments, the filters 1820 can be removably and/or replaceably inserted into the filter wheel 1814.

Spectroscopic System

As described above with reference to FIG. 4, the system 400 comprises the optical system 412 for analysis of a fluid sample. In various embodiments, the optical system 412 comprises one or more optical components including, for example, a spectrometer, a photometer, a reflectometer, or any other suitable device for measuring optical properties of the fluid sample. The optical system 412 may perform one or more optical measurements on the fluid sample including, for example, measurements of transmittance, absorbance, reflectance, scattering, and/or polarization. The optical measurements may be performed in one or more wavelength ranges including, for example, infrared (IR) and/or optical wavelengths. As described with reference to FIG. 4 (and further described below), the measurements from the optical system 412 are communicated to the algorithm processor 416 for analysis. For example, in some embodiments the algorithm processor 416 computes concentration of analyte(s) (and/or interferent(s)) of interest in the fluid sample. Analytes of interest can include, for example, glucose and/or lactate in whole blood and/or in blood plasma. In some embodiments the algorithm processor 416 can advantageously calibrate a measured analyte concentration for some or all of the effects of sample dilution. In some embodiments, the algorithm processor 416 may correct a measured analyte concentration for dilution to provide an estimate of analyte concentration that is more representative of the concentration in the patient's body than would otherwise be the case without correcting for dilution.

Figure 20:
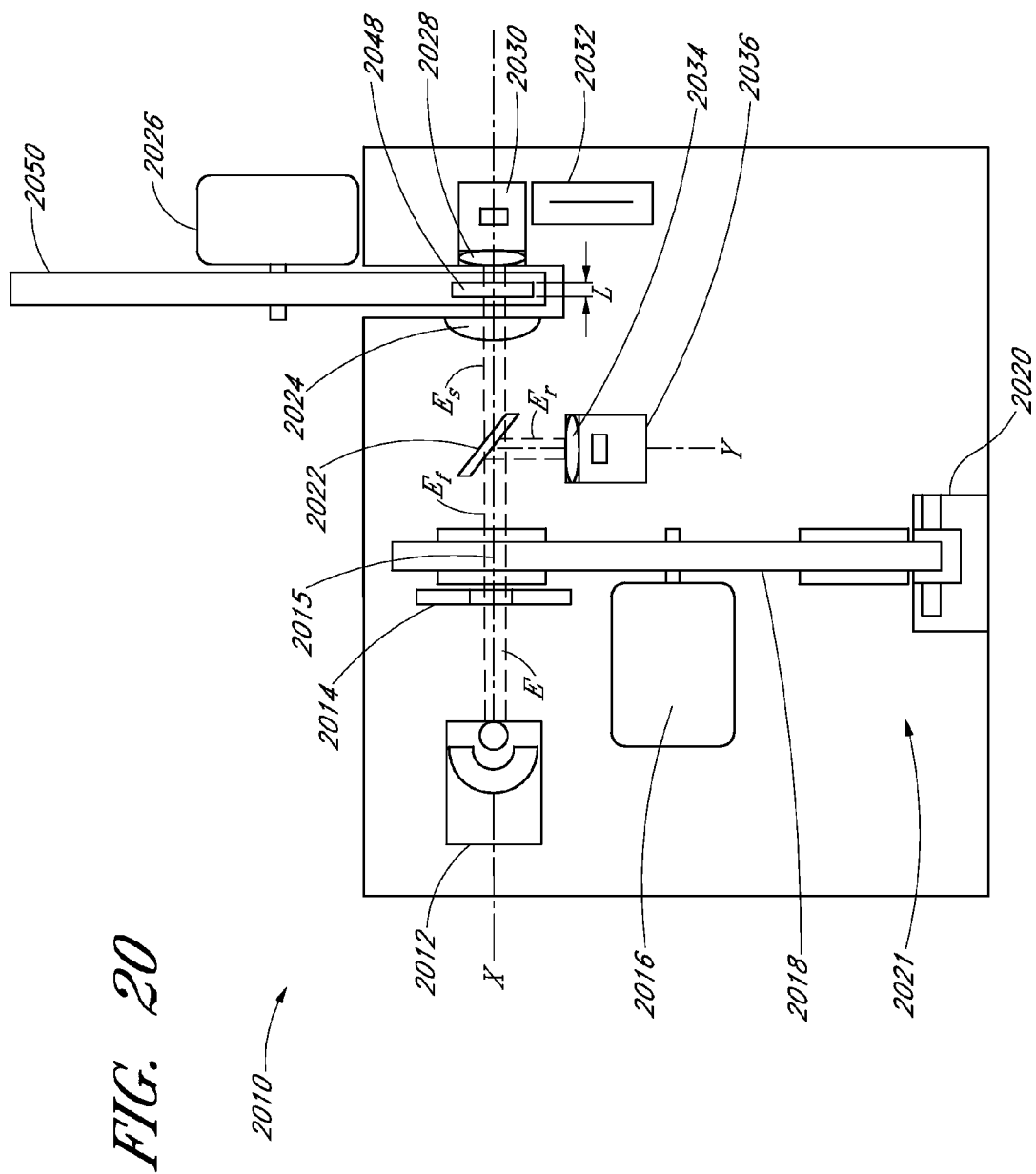
FIG. 20 schematically illustrates an embodiment of an optical system that comprises a spectroscopic analyzer adapted to measure spectra of a fluid sample.

FIG. 20 schematically illustrates an embodiment of the optical system 412 that comprises a spectroscopic analyzer 2010 adapted to measure spectra of a fluid sample such as, for example, blood or blood plasma. The analyzer 2010 comprises an energy source 2012 disposed along an optical axis X of the analyzer 2010. When activated, the energy source 2012 generates an electromagnetic energy beam E, which advances from the energy source 2012 along the optical axis X. In some embodiments, the energy source 2012 comprises an infrared energy source, and the energy beam E comprises an infrared beam. In some embodiments, the infrared energy beam E comprises a mid-infrared energy beam or a near-infrared energy beam. In some embodiments, the energy beam E can include optical and/or radio frequency wavelengths.

The energy source 2012 may comprise a broad-band and/or a narrow-band source of electromagnetic energy. In some embodiments, the energy source 2012 comprises optical elements such as, e.g., filters, collimators, lenses, mirrors, etc., that are adapted to produce a desired energy beam E. For example, in some embodiments, the energy beam E is an infrared beam in a wavelength range between about 2 μm and 20 m. In some embodiments, the energy beam E comprises an infrared beam in a wavelength range between about 4 μm and 10 μm. In the infrared wavelength range, water generally is the main contributor to the total absorption together with features from absorption of other blood components, particularly in the 6 μm-10 μm range. The 4 μm to 10 μm wavelength band has been found to be advantageous for determining glucose concentration, because glucose has a strong absorption peak structure from about 8.5 μm to 10 μm, whereas most other blood components have a relatively low and flat absorption spectrum in the 8.5 μm to 10 μm range. Two exceptions are water and hemoglobin, which are interferents in this range.

The energy beam E may be temporally modulated to provide increased signal-to-noise ratio (S/N) of the measurements provided by the analyzer 2010 as further described below. For example, in some embodiments, the beam E is modulated at a frequency of about 10 Hz or in a range from about 1 Hz to about 30 Hz. A suitable energy source 2012 may be an electrically modulated thin-film thermoresistive element such as the HawkEye IR-50 available from Hawkeye Technologies of Milford, Conn.

As depicted in FIG. 20, the energy beam E propagates along the optical axis X and passes through an aperture 2014 and a filter 2015 thereby providing a filtered energy beam $E_f$. The aperture 2014 helps collimate the energy beam E and can include one or more filters adapted to reduce the filtering burden of the filter 2015. For example, the aperture 2014 may comprise a broadband filter that substantially attenuates beam energy outside a wavelength band between about 4 μm to about 10 μm. The filter 2015 may comprise a narrow-band filter that substantially attenuates beam energy having wavelengths outside of a filter passband (which may be tunable or user-selectable in some embodiments). The filter passband may be specified by a half-power bandwidth ("HPBW"). In some embodiments, the filter 2015 may have an HPBW in a range from about 0.1 μm to about 2 μm, or 0.01 μm to about 1 μm. In some embodiments, the bandwidths are in a range from about 0.2 μm to 0.5 μm, or 0.1 μm to 0.35 μm. Other filter bandwidths may be used. The filter 2015 may comprise a varying-passband filter, an electronically tunable filter, a liquid crystal filter, an interference filter, and/or a gradient filter.

In some embodiments, the filter 2015 comprises one or a combination of a grating, a prism, a monochrometer, a Fabry-Perot etalon, and/or a polarizer. Other optical elements may be utilized as well.

In the embodiment shown in FIG. 20, the analyzer 2010 comprises a filter wheel assembly 2021 configured to dispose one or more filters 2015 along the optical axis X. The filter wheel assembly 2021 comprises a filter wheel 2018, a filter wheel motor 2016, and a position sensor 2020. The filter wheel 2018 may be substantially circular and have one or more filters 2015 or other optical elements (e.g., apertures, gratings, polarizers, mirrors, etc.) disposed around the circumference of the wheel 2018. In some embodiments, the number of filters 2015 in the filter wheel 2016 may be, for example, 1, 2, 5, 10, 15, 20, 25, or more. The motor 2016 is configured to rotate the filter wheel 2018 to dispose a desired filter 2015 (or other optical element) in the energy beam E so as to produce the filtered beam $E_f$. In some embodiments, the motor 2016 comprises a stepper motor. The position sensor 2020 determines the angular position of the filter wheel 2016, and communicates a corresponding filter wheel position signal to the algorithm processor 416, thereby indicating which filter 2015 is in position on the optical axis X. In various embodiments, the position sensor 2020 may be a mechanical, optical, and/or magnetic encoder. An alternative to the filter wheel 2018 is a linear filter translated by a motor. The linear filter can include an array of separate filters or a single filter with properties that change along a linear dimension.

The filter wheel motor 2016 rotates the filter wheel 2018 to position the filters 2015 in the energy beam E to sequentially vary the wavelengths or the wavelength bands used to analyze the fluid sample. In some embodiments, each individual filter 2015 is disposed in the energy beam E for a dwell time during which optical properties in the passband of the filter are measured for the sample. The filter wheel motor 2016 then rotates the filter wheel 2018 to position another filter 2015 in the beam E. In some embodiments, 25 narrow-band filters are used in the filter wheel 2018, and the dwell time is about 2 seconds for each filter 2015. A set of optical measurements for all the filters can be taken in about 2 minutes, including sampling time and filter wheel movement. In some embodiments, the dwell time may be different for different filters 2015, for example, to provide a substantially similar S/N ratio for each filter measurement. Accordingly, the filter wheel assembly 2021 functions as a varying-passband filter that allows optical properties of the sample to be analyzed at a number of wavelengths or wavelength bands in a sequential manner.

In some embodiments of the analyzer 2010, the filter wheel 2018 includes 25 finite-bandwidth infrared filters having a Gaussian transmission profile and full-width half-maximum (FWHM) bandwidth of 28 cm$^{-1}$ corresponding to a bandwidth that varies from 0.14 µm at 7.08 µm to 0.28 µm at 10 µm. The central wavelength of the filters are, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990.

With further reference to FIG. 20, the filtered energy beam $E_f$ propagates to a beamsplitter 2022 disposed along the optical axis X. The beamsplitter 2022 separates the filtered energy beam $E_f$ into a sample beam $E_s$ and a reference beam $E_r$. The reference beam $E_r$ propagates along a minor optical axis Y, which in this embodiment is substantially orthogonal to the optical axis X. The energies in the sample beam $E_s$ and the reference beam $E_r$ may comprise any suitable fraction of the energy in the filtered beam $E_f$. For example, in some embodiments, the sample beam $E_s$ comprises about 80%, and the reference beam $E_r$ comprises about 20%, of the filtered beam energy $E_f$. A reference detector 2036 is positioned along the minor optical axis Y. An optical element 2034, such as a lens, may be used to focus or collimate the reference beam $E_r$ onto the reference detector 2036. The reference detector 2036 provides a reference signal, which can be used to monitor fluctuations in the intensity of the energy beam E emitted by the source 2012. Such fluctuations may be due to drift effects, aging, wear, or other imperfections in the source 2012. The algorithm processor 416 may utilize the reference signal to identify changes in properties of the sample beam $E_s$ that are attributable to changes in the emission from the source 2012 and not to the properties of the fluid sample. By so doing, the analyzer 2010 may advantageously reduce possible sources of error in the calculated properties of the fluid sample (e.g., concentration). In other embodiments of the analyzer 2010, the beamsplitter 2022 is not used, and substantially all of the filtered energy beam $E_f$ propagates to the fluid sample.

As illustrated in FIG. 20, the sample beam $E_s$ propagates along the optical axis X, and a relay lens 2024 transmits the sample beam $E_s$ into a sample cell 2048 so that at least a fraction of the sample beam $E_s$ is transmitted through at least a portion of the fluid sample in the sample cell 2048. A sample detector 2030 is positioned along the optical axis X to measure the sample beam $E_s$ that has passed through the portion of the fluid sample. An optical element 2028, such as a lens, may be used to focus or collimate the sample beam $E_s$ onto the sample detector 2030. The sample detector 2030 provides a sample signal that can be used by the algorithm processor 416 as part of the sample analysis.

In the embodiment of the analyzer 2010 shown in FIG. 20, the sample cell 2048 is located toward the outer circumference of the centrifuge wheel 2050 (which can correspond, for example, to the sample cell holder 820 described herein). The sample cell 2048 preferably comprises windows that are substantially transmissive to energy in the sample beam $E_s$. For example, in implementations using mid-infrared energy, the windows may comprise calcium fluoride. As described herein with reference to FIG. 5, the sample cell 2048 is in fluid communication with an injector system that permits filling the sample cell 2048 with a fluid sample (e.g., whole blood) and flushing the sample cell 2048 (e.g., with saline or a detergent). The injector system may disconnect after filling the sample cell 2048 with the fluid sample to permit free spinning of the centrifuge wheel 2050.

The centrifuge wheel 2050 can be spun by a centrifuge motor 2026. In some embodiments of the analyzer 2010, the fluid sample (e.g., a whole blood sample) is spun at a certain number of revolutions per minute (RPM) for a given length of time to separate blood plasma for spectral analysis. In some embodiments, the fluid sample is spun at about 7200 RPM. In some embodiments, the fluid sample is spun at about 5000 RPM or 4500 RPM. In some embodiments, the fluid sample is spun at more than one rate for successive time periods. The length of time can be approximately 5 minutes. In some embodiments, the length of time is approximately 2 minutes. In some embodiments, an anti-clotting agent such as heparin may be added to the fluid sample before centrifuging to reduce clotting. With reference to FIG. 20, the centrifuge wheel 2050 is rotated to a position where the sample cell 2048 intercepts the sample beam $E_s$, allowing energy to pass through the sample cell 2048 to the sample detector 2030.

The embodiment of the analyzer 2010 illustrated in FIG. 20 advantageously permits direct measurement of the concentration of analytes in the plasma sample rather than by inference of the concentration from measurements of a whole blood sample. An additional advantage is that relatively small volumes of fluid may be spectroscopically analyzed. For example, in some embodiments the fluid sample volume is between about 1 μL and 80 μL and is about 25 μL in some embodiments. In some embodiments, the sample cell 2048 is disposable and is intended for use with a single patient or for a single measurement.

In some embodiments, the reference detector 2036 and the sample detector 2030 comprise broadband pyroelectric detectors. As known in the art, some pyroelectric detectors are sensitive to vibrations. Thus, for example, the output of a pyroelectric infrared detector is the sum of the exposure to infrared radiation and to vibrations of the detector. The sensitivity to vibrations, also known as "microphonics," can introduce a noise component to the measurement of the reference and sample energy beams $E_r$, $E_s$ using some pyroelectric infrared detectors. Because it may be desirable for the analyzer 2010 to provide high signal-to-noise ratio measurements, such as, e.g., S/N in excess of 100 dB, some embodiments of the analyzer 2010 utilize one or more vibrational noise reduction apparatus or methods. For example, the analyzer 2010 may be mechanically isolated so that high S/N spectroscopic measurements can be obtained for vibrations below an acceleration of about 1.5 G.

In some embodiments of the analyzer 2010, vibrational noise can be reduced by using a temporally modulated energy source 2012 combined with an output filter. In some embodiments, the energy source 2012 is modulated at a known source frequency, and measurements made by the detectors 2036 and 2030 are filtered using a narrowband filter centered at the source frequency. For example, in some embodiments, the energy output of the source 2012 is sinusoidally modulated at 10 Hz, and outputs of the detectors 2036 and 2030 are filtered using a narrow bandpass filter of less than about 1 Hz centered at 10 Hz. Accordingly, microphonic signals that are not at 10 Hz are significantly attenuated. In some embodiments, the modulation depth of the energy beam E may be greater than 50% such as, for example, 80%. The duty cycle of the beam may be between about 30% and 70%. The temporal modulation may be sinusoidal or any other waveform. In embodiments utilizing temporally modulated energy sources, detector output may be filtered using a synchronous demodulator and digital filter. The demodulator and filter are software components that may be digitally implemented in a processor such as the algorithm processor 416. Synchronous demodulators, coupled with low pass filters, are often referred to as "lock in amplifiers."

The analyzer 2010 may also include a vibration sensor 2032 (e.g., one or more accelerometers) disposed near one (or both) of the detectors 2036 and 2030. The output of the vibration sensor 2032 is monitored, and suitable actions are taken if the measured vibration exceeds a vibration threshold. For example, in some embodiments, if the vibration sensor 2032 detects above-threshold vibrations, the system discards any ongoing measurement and "holds off" on performing further measurements until the vibrations drop below the threshold. Discarded measurements may be repeated after the vibrations drop below the vibration threshold. In some embodiments, if the duration of the "hold off" is sufficiently long, the fluid in the sample cell 2030 is flushed, and a new fluid sample is delivered to the cell 2030 for measurement. The vibration threshold may be selected so that the error in analyte measurement is at an acceptable level for vibrations below the threshold. In some embodiments, the threshold corresponds to an error in glucose concentration of 5 mg/dL. The vibration threshold may be determined individually for each filter 2015.

Certain embodiments of the analyzer 2010 include a temperature system (not shown in FIG. 20) for monitoring and/or regulating the temperature of system components (such as the detectors 2036, 2030) and/or the fluid sample. Such a temperature system can include temperature sensors, thermoelectrical heat pumps (e.g., a Peltier device), and/or thermistors, as well as a control system for monitoring and/or regulating temperature. In some embodiments, the control system comprises a proportional-plus-integral-plus-derivative (PID) control. For example, in some embodiments, the temperature system is used to regulate the temperature of the detectors 2030, 2036 to a desired operating temperature, such as 35 degrees Celsius.

Optical Measurement

The analyzer 2010 illustrated in FIG. 20 can be used to determine optical properties of a substance in the sample cell 2048. The substance can include whole blood, plasma, saline, water, air or other substances. In some embodiments, the optical properties include measurements of an absorbance, transmittance, and/or optical density in the wavelength passbands of some or all of the filters 2015 disposed in the filter wheel 2018. As described above, a measurement cycle comprises disposing one or more filters 2015 in the energy beam E for a dwell time and measuring a reference signal with the reference detector 2036 and a sample signal with the sample detector 2030. The number of filters 2015 used in the measurement cycle will be denoted by N, and each filter 2015 passes energy in a passband around a center wavelength $\lambda_i$, where i is an index ranging over the number of filters (e.g., from 1 to N). The set of optical measurements from the sample detector 2036 in the passbands of the N filters 2015 provide a wavelength-dependent spectrum of the substance in the sample cell 2048. The spectrum will be denoted by $C_s(\lambda_i)$, where $C_s$ may be a transmittance, absorbance, optical density, or some other measure of an optical property of the substance. In some embodiments, the spectrum is normalized with respect to one or more of the reference signals measured by the reference detector 2030 and/or with respect to spectra of a reference substance (e.g., air or saline). The measured spectra are communicated to the algorithm processor 416 for calculation of the concentration of the analyte(s) of interest in the fluid sample.

In some embodiments, the analyzer 2010 performs spectroscopic measurements on the fluid sample (known as a "wet" reading) and on one or more reference samples. For example, an "air" reading occurs when the sample detector 2036 measures the sample signal without the sample cell 2048 in place along the optical axis X. (This can occur, for example, when the opposite opening 1530 is aligned with the optical axis X). A "water" or "saline" reading occurs when the sample cell 2048 is filled with water or saline, respectively. The algorithm processor 416 may be programmed to calculate analyte concentration using a combination of these spectral measurements. In some embodiments, an advantage of combining the "wet reading" with at least the "water" or "saline" reading is to calibrate a measured analyte concentration for some or all of the effects of dilution.

In some embodiments, a pathlength corrected spectrum is calculated using wet, air, and reference readings. For example, the transmittance at wavelength $\lambda_i$, denoted by $T_i$, may be calculated according to $T_i = (S_i(\text{wet})/R_i(\text{wet}))/(S_i(\text{air})/R_i(\text{air}))$, where $S_i$ denotes the sample signal from the sample detector 2036 and $R_i$ denotes the corresponding reference signal from the reference detector 2030. In some embodiments, the algorithm processor 416 calculates the optical density, $OD_i$, as a logarithm of the transmittance, e.g., according to $OD_i = -\text{Log}(T_i)$. In one implementation, the analyzer 2010 takes a set of wet readings in each of the N filter passbands and then takes a set of air readings in each of the N filter passbands. In other embodiments, the analyzer 2010 may take an air reading before (or after) the corresponding wet reading.

The optical density $OD_i$ is the product of the absorption coefficient at wavelength $\lambda_i$, $\alpha_i$, times the pathlength L over which the sample energy beam $E_s$ interacts with the substance in the sample cell 2048, e.g., $OD_i = \alpha_i L$. The absorption coefficient $\alpha_i$ of a substance may be written as the product of an absorptivity per mole times a molar concentration of the substance. FIG. 20 schematically illustrates the pathlength L of the sample cell 2048. The pathlength L may be determined from spectral measurements made when the sample cell 2048 is filled with a reference substance. For example, because the absorption coefficient for water (or saline) is known, one or more water (or saline) readings can be used to determine the pathlength L from measurements of the transmittance (or optical density) through the cell 2048. In some embodiments, several readings are taken in different wavelength passbands, and a curve-fitting procedure is used to estimate a best-fit pathlength L. The pathlength L may be estimated using other methods including, for example, measuring interference fringes of light passing through an empty sample cell 2048.

The pathlength L may be used to determine the absorption coefficients of the fluid sample at each wavelength. Molar concentration of an analyte of interest can be determined from the absorption coefficient and the known molar absorptivity of the analyte. In some embodiments, a sample measurement cycle comprises a saline reading (at one or more wavelengths), a set of N wet readings (taken, for example, through a sample cell 2048 containing saline solution), followed by a set of N air readings (taken, for example, through the opposite opening 1530). As discussed above, the sample measurement cycle can be performed in a given length of time that may depend, at least in part, on filter dwell times. For example, the measurement cycle may take five minutes when the filter dwell times are about five seconds. In some embodiments, the measurement cycle may take about two minutes when the filter dwell times are about two seconds. After the sample measurement cycle is completed, a detergent cleaner may be flushed through the sample cell 2048 to reduce buildup of organic matter (e.g., proteins) on the windows of the sample cell 2048. The detergent is then flushed to a waste bladder.

In some embodiments, the system stores information related to the spectral measurements so that the information is readily available for recall by a user. The stored information can include wavelength-dependent spectral measurements (including fluid sample, air, and/or saline readings), computed analyte values, system temperatures and electrical properties (e.g., voltages and currents), and any other data related to use of the system (e.g., system alerts, vibration readings, S/N ratios, etc.). The stored information may be retained in the system for a time period such as, for example, 30 days. After this time period, the stored information may be communicated to an archival data storage system and then deleted from the system. In some embodiments, the stored information is communicated to the archival data storage system via wired or wireless methods, e.g., over a hospital information system (HIS).

Analyte Analysis

The algorithm processor 416 (FIG. 4) (or any other suitable processor or processors) may be configured to receive from the analyzer 2010 the wavelength-dependent optical measurements $Cs(\lambda_i)$ of the fluid sample. In some embodiments, the optical measurements comprise spectra such as, for example, optical densities $OD_i$ measured in each of the N filter passbands centered around wavelengths $\lambda_i$. The optical measurements $Cs(\lambda_i)$ are communicated to the processor 416, which analyzes the optical measurements to detect and quantify one or more analytes in the presence of interferents. In some embodiments, one or more poor quality optical measurements $Cs(\lambda_i)$ are rejected (e.g., as having a S/N ratio that is too low), and the analysis performed on the remaining, sufficiently high-quality measurements. In another embodiment, additional optical measurements of the fluid sample are taken by the analyzer 2010 to replace one or more of the poor quality measurements.

Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte, in at least a portion of the wavelength range of the measurements. The presence of such an interferent can introduce errors in the quantification of the analyte. More specifically, the presence of one or more interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As an example of these classes of interferents, consider the analysis of a blood sample (or a blood component sample or a blood plasma sample) for the analyte glucose. Endogenous interferents include those blood components having origins within the body that affect the quantification of glucose, and can include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly, but not necessarily, present in the sample type under analysis. In the example of analyzing samples of blood or blood plasma drawn from patients who are receiving medical treatment, a medicament such as acetaminophen is possibly, but not necessarily, present in this sample type. In contrast, water is necessarily present in such blood or plasma samples.

Certain disclosed analysis methods are particularly effective if each analyte and interferent has a characteristic signature in the measurement (e.g., a characteristic spectroscopic feature), and if the measurement is approximately affine (e.g., includes a linear term and an offset) with respect to the concentration of each analyte and interferent. In such methods, a calibration process is used to determine a set of one or more calibration coefficients and a set of one or more optional offset values that permit the quantitative estimation of an analyte. For example, the calibration coefficients and the offsets may be used to calculate an analyte concentration from spectroscopic measurements of a material sample (e.g., the concentration of glucose in blood plasma). In some of these methods, the concentration of the analyte is estimated by multiplying the calibration coefficient by a measurement value (e.g., an optical density) to estimate the concentration of the analyte. Both the calibration coefficient and measurement can comprise arrays of numbers. For example, in some embodiments, the measurement comprises spectra $C_s(\lambda_i)$ measured at the wavelengths $\lambda_i$, and the calibration coefficient and optional offset comprise an array of values corresponding to each wavelength $\lambda_i$. In some embodiments, as further described below, a hybrid linear analysis (HLA) technique is used to estimate analyte concentration in the presence of a set of interferents, while retaining a high degree of sensitivity to the desired analyte. The data used to accommodate the set of possible interferents can include (a) signatures of each of the members of the family of potential additional substances and (b) a typical quantitative level at which each additional substance, if present, is likely to appear. In some embodiments, the calibration coefficient (and optional offset) are adjusted to minimize or reduce the sensitivity of the calibration to the presence of interferents that are identified as possibly being present in the fluid sample.

In some embodiments, the analyte analysis method uses a set of training spectra each having known analyte concentration and produces a calibration that minimizes the variation in estimated analyte concentration with interferent concentration. The resulting calibration coefficient indicates sensitivity of the measurement to analyte concentration. The training spectra need not include a spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the analyte analysis process. The term "Sample Population" is a broad term and includes, without limitation, a large number of samples having measurements that are used in the computation of calibration values (e.g., calibration coefficients and optional offsets). In some embodiments, the term Sample Population comprises measurements (such as, e.g., spectra) from individuals and may comprise one or more analyte measurements determined from those same individuals. Additional demographic information may be available for the individuals whose sample measurements are included in the Sample Population. For an embodiment involving the spectroscopic determination of glucose concentration, the Sample Population measurements may include a spectrum (measurement) and a glucose concentration (analyte measurement).

Various embodiments of Sample Populations may be used in various embodiments of the systems and methods described herein. Several examples of Sample Populations will now be described. These examples are intended to illustrate certain aspects of possible Sample Population embodiments but are not intended to limit the types of Sample Populations that may be generated. In certain embodiments, a Sample Population may include samples from one or more of the example Sample Populations described below.

In some embodiments of the systems and methods described herein, one or more Sample Populations are included in a "Population Database." The Population Database may be implemented and/or stored on a computer-readable medium. In certain embodiments, the systems and methods may access the Population Database using wired and/or wireless techniques. Certain embodiments may utilize several different Population Databases that are accessible locally and/or remotely. In some embodiments, the Population Database includes one or more of the example Sample Populations described below. In some embodiments, two or more databases can be combined into a single database, and in other embodiments, any one database can be divided into multiple databases.

An example Sample Population may comprise samples from individuals belonging to one or more demographic groups including, for example, ethnicity, nationality, gender, age, etc. Demographic groups may be established for any suitable set of one or more distinctive factors for the group including, for example, medical, cultural, behavioral, biological, geographical, religious, and genealogical traits. For example, in certain embodiments, a Sample Population includes samples from individuals from a specific ethnic group (e.g., Caucasians, Hispanics, Asians, African Americans, etc.). In another embodiment, a Sample Population includes samples from individuals of a specific gender or a specific race. In some embodiments, a Sample Population includes samples from individuals belonging to more than one demographic group (e.g., samples from Caucasian women).

Another example Sample Population can comprise samples from individuals having one or more medical conditions. For example, a Sample Population may include samples from individuals who are healthy and unmedicated (sometimes referred to as a Normal Population). In some embodiments, the Sample Population includes samples from individuals having one or more health conditions (e.g., diabetes). In some embodiments, the Sample Population includes samples from individuals taking one or more medications. In certain embodiments, Sample Population includes samples from individuals diagnosed to have a certain medical condition or from individuals being treated for certain medical conditions or some combination thereof The Sample Population may include samples from individuals such as, for example, ICU patients, maternity patients, and so forth.

An example Sample Population may comprise samples that have the same interferent or the same type of interferents. In some embodiments, a Sample Population can comprise multiple samples, all lacking an interferent or a type of interferent. For example, a Sample Population may comprise samples that have no exogenous interferents, that have one or more exogenous interferents of either known or unknown concentration, and so forth. The number of interferents in a sample depends on the measurement and analyte(s) of interest, and may number, in general, from zero to a very large number (e.g., greater than 300). All of the interferents typically are not expected to be present in a particular material sample, and in many cases, a smaller number of interferents (e.g., 0, 1, 2, 5, 10, 15, 20, or 25) may be used in an analysis. In certain embodiments, the number of interferents used in the analysis is less than or equal to the number of wavelength-dependent measurements N in the spectrum $Cs(\lambda_i)$.

Certain embodiments of the systems and methods described herein are capable of analyzing a material sample using one or more Sample Populations (e.g., accessed from the Population Database). Certain such embodiments may use information regarding some or all of the interferents which may or may not be present in the material sample. In some embodiments, a list of one or more possible interferents, referred to herein as forming a "Library of Interferents," can be compiled. Each interferent in the Library can be referred to as a "Library Interferent." The Library Interferents may include exogenous interferents and endogenous interferents that may be present in a material sample. For example, an interferent may be present due to a medical condition causing abnormally high concentrations of the exogenous and endogenous interferents. In some embodiments, the Library of Interferents may not include one or more interferents that are known to be present in all samples. Thus, for example, water, which is a glucose interferent for many spectroscopic measurements, may not be included in the Library of Interferents. In certain embodiments, the systems and methods use samples in the Sample Population to train calibration methods.

The material sample being measured, for example a fluid sample in the sample cell 2048, may also include one or more Library Interferents which may include, but is not limited to, an exogenous interferent or an endogenous interferent. Examples of exogenous interferent can include medications, and examples of endogenous interferents can include urea in persons suffering from renal failure. In addition to components naturally found in the blood, the ingestion or injection of some medicines or illicit drugs can result in very high and rapidly changing concentrations of exogenous interferents.

In some embodiments, measurements of a material sample (e.g., a bodily fluid sample), samples in a Sample Population, and the Library Interferents comprise spectra (e.g., infrared spectra). The spectra obtained from a sample and/or an interferent may be temperature dependent. In some embodiments, it may be beneficial to calibrate for temperatures of the individual samples in the Sample Population or the interferents in the Library of Interferents. In some embodiments, a temperature calibration procedure is used to generate a temperature calibration factor that substantially accounts for the sample temperature. For example, the sample temperature can be measured, and the temperature calibration factor can be applied to the Sample Population and/or the Library Interferent spectral data. In some embodiments, a water or saline spectrum is subtracted from the sample spectrum to account for temperature effects of water in the sample.

In other embodiments, temperature calibration may not be used. For example, if Library Interferent spectra, Sample Population spectra, and sample spectra are obtained at approximately the same temperature, an error in a predicted analyte concentration may be within an acceptable tolerance. If the temperature at which a material sample spectrum is measured is within, or near, a temperature range (e.g., several degrees Celsius) at which the plurality of Sample Population spectra are obtained, then some analysis methods may be relatively insensitive to temperature variations. Temperature calibration may optionally be used in such analysis methods.

Figure 21:
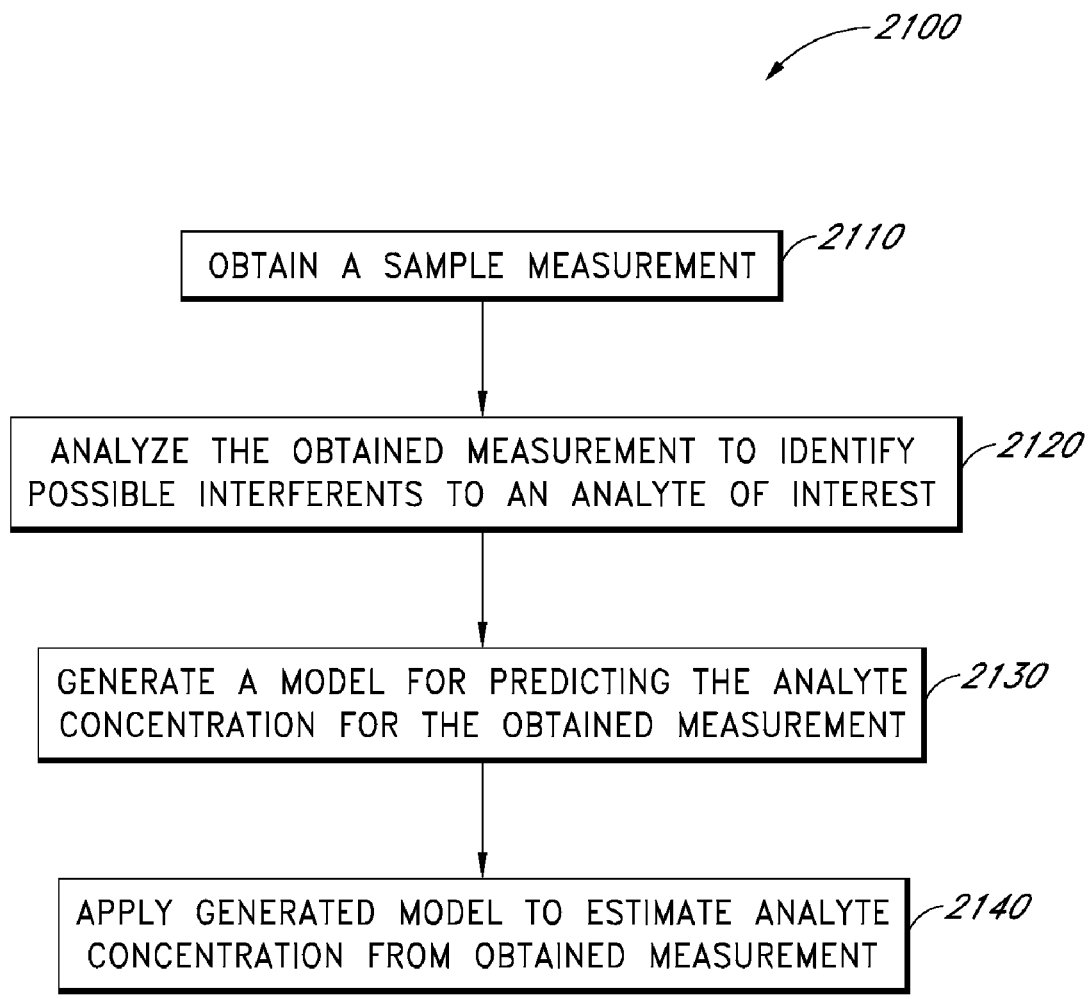
FIG. 21 is a flowchart that schematically illustrates an embodiment of a method for estimating the concentration of an analyte in the presence of interferents.

Systems and Methods for Estimating Analyte Concentration in the Presence of Interferents FIG. 21 is a flowchart that schematically illustrates an embodiment of a method 2100 for estimating the concentration of an analyte in the presence of interferents. In block 2110, a measurement of a sample is obtained, and in block 2120 data relating to the obtained measurement is analyzed to identify possible interferents to the analyte. In block 2130, a model is generated for predicting the analyte concentration in the presence of the identified possible interferents, and in block 2140 the model is used to estimate the analyte concentration in the sample from the measurement. In certain embodiments of the method 2100, the model generated in block 2130 is selected to reduce or minimize the effect of identified interferents that are not present in a general population of which the sample is a member.

An example embodiment of the method 2100 of FIG. 21 for the determination of an analyte (e.g., glucose) in a blood sample will now be described. This example embodiment is intended to illustrate various aspects of the method 2100 but is not intended as a limitation on the scope of the method 2100 or on the range of possible analytes. In this example, the sample measurement in block 2110 is an absorption spectrum, $Cs(\lambda_i)$, of a measurement sample S that has, in general, one analyte of interest, glucose, and one or more interferents.

In block 2120, a statistical comparison of the absorption spectrum of the sample S with a spectrum of the Sample Population and combinations of individual Library Interferent spectra is performed. The statistical comparison provides a list of Library Interferents that are possibly contained in sample S and can include either no Library Interferents or one or more Library Interferents. In this example, in block 2130, one or more sets of spectra are generated from spectra of the Sample Population and their respective known analyte concentrations and known spectra of the Library Interferents identified in block 2120. In block 2130, the generated spectra are used to calculate a model for predicting the analyte concentration from the obtained measurement. In some embodiments, the model comprises one or more calibration coefficients $\kappa(\lambda_i)$ that can be used with the sample measurements $Cs(\lambda_i)$ to provide an estimate of the analyte concentration, $g_{est}$. In block 2140, the estimated analyte concentration is determined form the model generated in block 2130. For example, in some embodiments of HLA, the estimated analyte concentration is calculated according to a linear formula: $g_{est}=\kappa(\lambda_i) \cdot C_s(\lambda_i)$. Because the absorption measurements and calibration coefficients may represent arrays of numbers, the multiplication operation indicated in the preceding formula may comprise a sum of the products of the measurements and coefficients (e.g., an inner product or a matrix product). In some embodiments, the calibration coefficient is determined so as to have reduced or minimal sensitivity to the presence of the identified Library Interferents.

Figure 22:
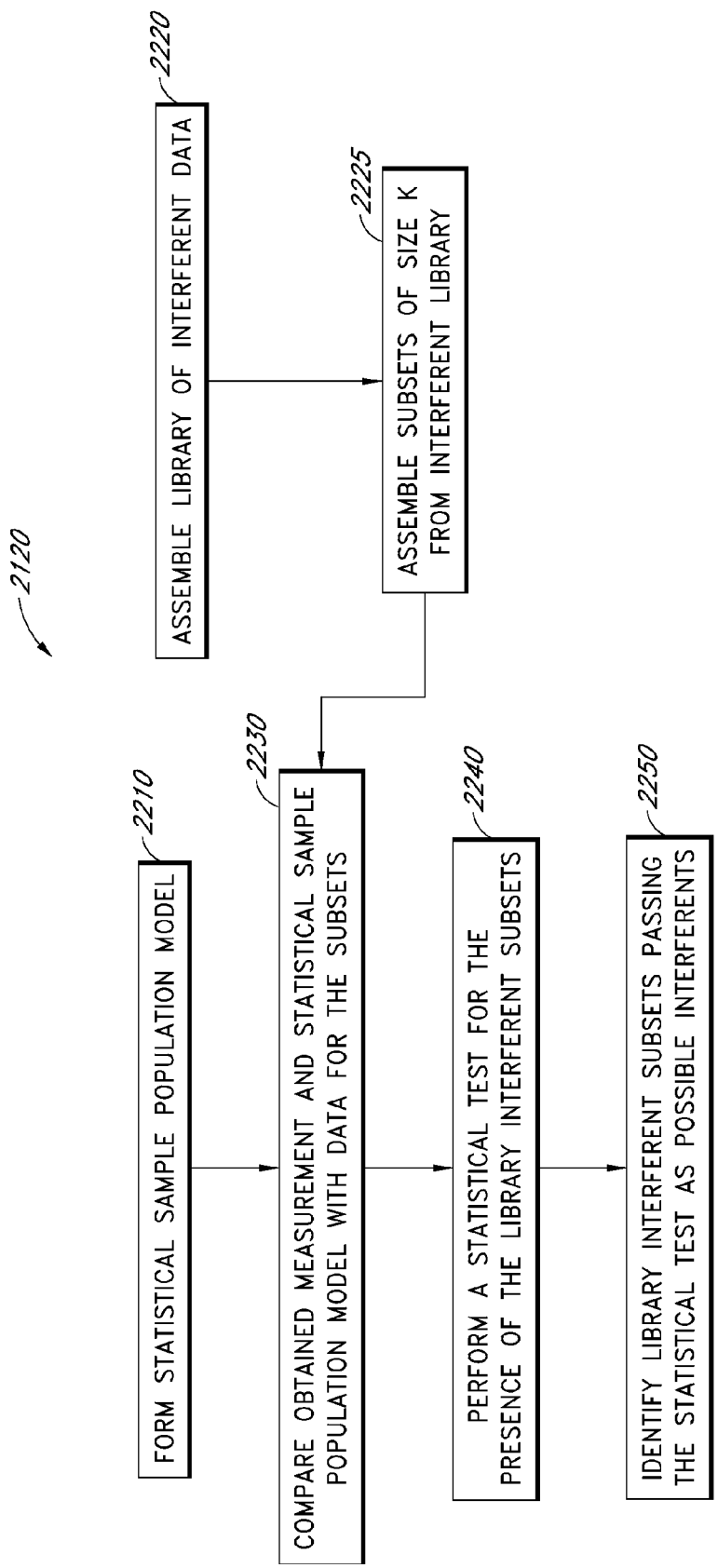
FIG. 22 is a flowchart that schematically illustrates an embodiment of a method for performing a statistical comparison of the absorption spectrum of a sample with the spectrum of a sample population and combinations of individual library interferent spectra.

An example embodiment of block 2120 of the method 2100 will now be described with reference to FIG. 22. In this example, block 2120 includes forming a statistical Sample Population model (block 2210), assembling a library of interferent data (block 2220), assembling all subsets of size K of the library interferents (block 2225), comparing the obtained measurement and statistical Sample Population model with data for each set of interferents from an interferent library (block 2230), performing a statistical test for the presence of each interferent from the interferent library (block 2240), and identifying possible interferents that pass the statistical test (block 2250). The size K of the subsets may be an integer such as, for example, 1, 2, 3, 4, 5, 6, 10, 16, or more. The acts of block 2220 can be performed once or can be updated as necessary. In certain embodiments, the acts of blocks 2230, 2240, and 2250 are performed sequentially for all subsets of Library Interferents that pass the statistical test (block 2240). In this example, in block 2210, a Sample Population Database is formed that includes a statistically large Sample Population of individual spectra taken over the same wavelength range as the sample spectrum, $C_s(\lambda_i)$. The Database also includes an analyte concentration corresponding to each spectrum. For example, if there are P Sample Population spectra, then the spectra in the Database can be represented as $C=\{C_1, C_2, \ldots, C_P\}$, and the analyte concentration corresponding to each spectrum can be represented as $g=\{g_1, g_2, \ldots, g_P\}$. In some embodiments, the Sample Population does not have any of the Library Interferents present, and the material sample has interferents contained in the Sample Population and one or more of the Library Interferents.

In some embodiments of block 2210, the statistical sample model comprises a mean spectrum and a covariance matrix calculated for the Sample Population. For example, if each spectrum measured at N wavelengths $\lambda_i$ is represented by an N×1 array, C, then the mean spectrum, $\mu$, is an N×1 array having values at each wavelength averaged over the range of spectra in the Sample Population. The covariance matrix, V, is calculated as the expected value of the deviation between C and μ and can be written as $V=E((C-\mu)(C-\mu)^T)$ where $E(\cdot)$ represents the expected value and the superscript T denotes transpose. In other embodiments, additional statistical parameters may be included in the statistical model of the Sample Population spectra.

Additionally, a Library of Interferents may be assembled in block 2220. A number of possible interferents can be identified, for example, as a list of possible medications or foods that might be ingested by the population of patients at issue. Spectra of these interferents can be obtained, and a range of expected interferent concentrations in the blood, or other expected sample material, can be estimated. In certain embodiments, the Library of Interferents includes, for each of "M" interferents, the absorption spectrum normalized to unit interferent concentration of each interferent, $IF=\{IF_1, IF_2, \ldots, IF_M\}$, and a range of concentrations for each interferent from $Tmax=\{Tmax_1, Tmax_2, \ldots, Tmax_M\}$ to $Tmin=\{Tmin_1, Tmin_2, \ldots, Tmin_M\}$. Information in the Library may be assembled once and accessed as needed. For example, the Library and the statistical model of the Sample Population may be stored in a storage device associated with the algorithm processor 416 (see, FIG. 4).

Continuing in block 2225, the algorithm processor 416 assembles one or more subsets comprising a number K of spectra taken from the Library of Interferents. The number K may be an integer such as, for example, 1, 2, 3, 4, 5, 6, 10, 16, or more. In some embodiments, the subsets comprise all combinations of the M Library spectra taken K at a time. In these embodiments, the number of subsets having K spectra is $M!/(K!(M-K)!)$, where ! represents the factorial function.

Continuing in block 2230, the obtained measurement data (e.g., the sample spectrum) and the statistical Sample Population model (e.g., the mean spectrum and the covariance matrix) are compared with data for each subset of interferents determined in block 2225 in order to determine the presence of possible interferents in the sample (block 2240). In some embodiments, the statistical test for the presence of an interferent subset in block 2240 comprises determining the concentrations of each subset of interferences that minimize a statistical measure of "distance" between a modified spectrum of the material sample and the statistical model of the Sample Population (e.g., the mean μ and the covariance V). The term "concentration" used in this context refers to a computed value, and, in some embodiments, that computed value may not correspond to an actual concentration. The concentrations may be calculated numerically. In some embodiments, the concentrations are calculated by algebraically solving a set of linear equations. The statistical measure of distance may comprise the well-known Mahalanobis distance (or square of the Mahalanobis distance) and/or some other suitable statistical distance metric (e.g., Hotelling's T-square statistic). In certain implementations, the modified spectrum is given by $C'_s(T)=C_s-IF\cdot T$ where $T=(T_1, T_2, \ldots T_K)^T$ is a K-dimensional column vector of interferent concentrations and $IF=\{IF_1, IF_2, \ldots IF_K\}$ represents the K interferent absorption spectra of the subset. In some embodiments, concentration of the $i^{th}$ interferent is assumed to be in a range from a minimum value, $Tmin_i$, to a maximum value, $Tmax_i$. The value of $Tmin_i$ may be zero, or may be a value between zero and $Tmax_i$, such as a fraction of $Tmax_i$, or may be a negative value. Negative values represent interferent concentrations that are smaller than baseline interferent values in the Sample Population.

In block 2250, a list of a number $N_S$ of possible interferent subsets ξ may be identified as the particular subsets that pass one or more statistical tests (in block 2240) for being present in the material sample. One or more statistical tests may be used, alone or in combination, to identify the possible interferents. For example, if a statistical test indicates that an $i^{th}$ interferent is present in a concentration outside the range $Tmin_i$ to $Tmax_i$, then this result may be used to exclude the $i^{th}$ interferent from the list of possible interferents. In some embodiments, only the single most probable interferent subset is included on the list, for example, the subset having the smallest statistical distance (e.g., Mahalanobis distance). In an embodiment, the list includes the subsets ξ having statistical distances smaller than a threshold value. In certain embodiments, the list includes a number $N_S$ of subsets having the smallest statistical distances, e.g., the list comprises the "best" candidate subsets. The number $N_S$ may be any suitable integer such as 10, 20, 50, 100, 200, or more. An advantage of selecting the "best" $N_S$ subsets is reduced computational burden on the algorithm processor 416. In some embodiments, the list includes all the Library Interferents. In certain such embodiments, the list is selected to comprise combinations of the $N_S$ subsets taken L at a time. For example, in some embodiments, pairs of subsets are taken (e.g., L=2). An advantage of selecting pairs of subsets is that pairing captures the most likely combinations of interferents and the "best" candidates are included multiple times in the list of possible interferents. In embodiments in which combinations of L subsets are selected, the number of combinations of subsets in the list of possible interferent subsets is $N_S!/(L!(N_S-L)!)$.

In other embodiments, the list of possible interferent subsets ξ is determined using a combination of some or all of the above criteria. In another embodiment, the list of possible interferent subsets ξ includes each of the subsets assembled in block 2225. Many selection criteria are possible for the list of possible interferent subsets ξ.

Figure 23:
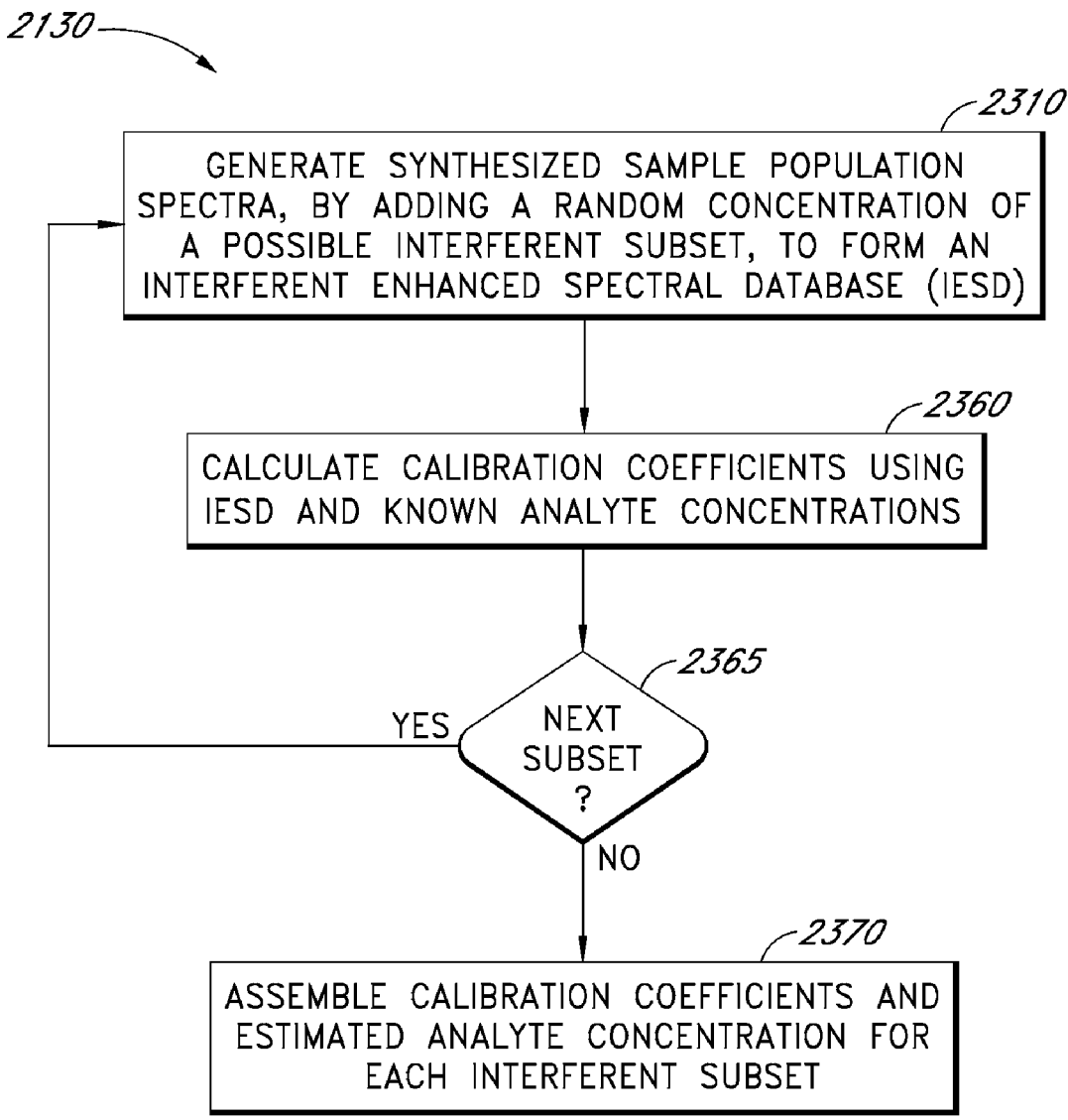
FIG. 23 is a flowchart that schematically illustrates an example embodiment of a method for estimating analyte concentration in the presence of the possible interferents.

Returning to FIG. 21, the method 2100 continues in block 2130 where analyte concentration is estimated in the presence of the possible interferent subsets ξ determined in block 2250. FIG. 23 is a flowchart that schematically illustrates an example embodiment of the acts of block 2130. In block 2310, synthesized Sample Population measurements are generated to form an Interferent Enhanced Spectral Database (IESD). In block 2360, the IESD and known analyte concentrations are used to generate calibration coefficients for the selected interferent subset. As indicated in block 2365, blocks 2310 and 2360 may be repeated for each interferent subset ξ identified in the list of possible interferent subsets (e.g., in block 2250 of FIG. 22). In this example embodiment, when all the interferent subsets ξ have been processed, the method continues in block 2370, wherein an average calibration coefficient is applied to the measured spectra to determine a set of analyte concentrations.

In one example embodiment for block 2310, synthesized Sample Population spectra are generated by adding random concentrations of each interferent in one of the possible interferent subsets ξ. These spectra are referred to herein as an Interferent-Enhanced Spectral Database or IESD. In one example method, the IESD is formed as follows. A plurality of Randomly-Scaled Single Interferent Spectra (RSIS) are formed for each interferent in the interferent subset ξ. Each RSIS is formed by combinations of the interferent having spectrum IF multiplied by the maximum concentration Tmax, which is scaled by a random factor between zero and one. In certain embodiments, the scaling places the maximum concentration at the $95^{th}$ percentile of a log-normal distribution in order to generate a wide range of concentrations. In some embodiments, the log-normal distribution has a standard deviation equal to half of its mean value.

In this example method, individual RSIS are then combined independently and in random combinations to form a large family of Combination Interferent Spectra (CIS), with each spectrum in the CIS comprising a random combination of RSIS, selected from the full set of identified Library Interferents. An advantage of this method of selecting the CIS is that it produces adequate variability with respect to each interferent, independently across separate interferents.

The CIS and replicates of the Sample Population spectra are combined to form the IESD. Since the interferent spectra and the Sample Population spectra may have been obtained from measurements having different optical pathlengths, the CIS may be scaled to the same pathlength as the Sample Population spectra. The Sample Population Database is then replicated R times, where R depends on factors including the size of the Database and the number of interferents. The IESD includes R copies of each of the Sample Population spectra, where one copy is the original Sample Population Data, and the remaining R-1 copies each have one randomly chosen CIS spectra added. Accordingly, each of the IESD spectra has an associated analyte concentration from the Sample Population spectra used to form the particular IESD spectrum. In some embodiments, a 10-fold replication of the Sample Population Database is used for 130 Sample Population spectra obtained from 58 different individuals and 18 Library Interferents. A smaller replication factor may be used if there is greater spectral variety among the Library Interferent spectra, and a larger replication factor may be used if there is a greater number of Library Interferents.

After the IESD is generated in block 2310, in block 2360, the IESD spectra and the known, random concentrations of the subset interferents are used to generate a calibration coefficient for estimating the analyte concentration from a sample measurement. The calibration coefficient is calculated in some embodiments using a hybrid linear analysis (HLA) technique. In certain embodiments, the HLA technique uses a reference analyte spectrum to construct a set of spectra that are free of the desired analyte, projecting the analyte's spectrum orthogonally away from the space spanned by the analyte-free calibration spectra, and normalizing the result to produce a unit response. Further description of embodiments of HLA techniques may be found in, for example, "Measurement of Analytes in Human Serum and Whole Blood Samples by Near-Infrared Raman Spectroscopy," Chapter 4, Andrew J. Berger, Ph. D. thesis, Massachusetts Institute of Technology, 1998, and "An Enhanced Algorithm for Linear Multivariate Calibration," by Andrew J. Berger, et al., Analytical Chemistry, Vol. 70, No. 3, Feb. 1, 1998, pp. 623-627, the entirety of each of which is hereby incorporated by reference herein. In other embodiments, the calibration coefficients may be calculated using other techniques including, for example, regression techniques such as, for example, ordinary least squares (OLS), partial least squares (PLS), and/or principal component analysis.

In block 2365, the processor 416 determines whether additional interferent subsets $\xi$ remain in the list of possible interferent subsets. If another subset is present in the list, the acts in blocks 2310-2360 are repeated for the next subset of interferents using different random concentrations. In some embodiments, blocks 2310-2360 are performed for only the most probable subset on the list.

The calibration coefficient determined in block 2360 corresponds to a single interferent subset $\xi$ from the list of possible interferent subsets and is denoted herein as a single-interferent-subset calibration coefficient $\kappa_{avg}(\xi)$. In this example method, after all subsets $\xi$ have been processed, the method continues in block 2370, in which the single-interferent-subset calibration coefficient is applied to the measured spectra $C_s$ to determine an estimated, single-interferent-subset analyte concentration, $g(\xi)=\kappa_{avg}(\xi) \cdot C_s$, for the interferent subset $\xi$. The set of the estimated, single-interferent-subset analyte concentrations $g(\xi)$ for all subsets in the list may be assembled into an array of single-interferent-subset concentrations. As noted above, in some embodiments the blocks 2310-2370 are performed once for the most probable single-interferent-subset on the list (e.g., the array of single-interferent analyte concentrations has a single member).

Returning to block 2140 of FIG. 21, the array of single-interferent-subset concentrations, $g(\xi)$, is combined to determine an estimated analyte concentration, $g_{est}$, for the material sample. In certain embodiments, a weighting function $p(\xi)$ is determined for each of the interferent subsets $\xi$ on the list of possible interferent subsets. The weighting functions may be normalized such that $\Sigma p(\xi)=1$, where the sum is over all subsets $\xi$ that have been processed from the list of possible interferent subsets. In some embodiments, the weighting functions can be related to the minimum Mahalanobis distance or an optimal concentration. In certain embodiments, the weighting function $p(\xi)$, for each subset $\xi$, is selected to be a constant, e.g., $1/N_S$ where $N_S$ is the number of subsets processed from the list of possible interferent subsets. In other embodiments, other weighting functions $p(\xi)$ can be selected.

In certain embodiments, the estimated analyte concentration, $g_{est}$, is determined (in block 2140) by combining the single-interferent-subset estimates, $g(\xi)$, and the weighting functions, $p(\xi)$, to generate an average analyte concentration. The average concentration may be computed according to $g_{est}=\Sigma g(\xi) p(\xi)$, where the sum is over the interferent subsets processed from the list of possible interferent subsets. In some embodiments, the weighting function $p(\xi)$ is a constant value for each subset (e.g., a standard arithmetic average is used for determining average analyte concentration). By testing the above described example method on simulated data, it has been found that the average analyte concentration advantageously has errors that may be reduced in comparison to other methods (e.g., methods using only a single most probable interferent).

Although the flowchart in FIG. 21 schematically illustrates an embodiment of the method 2100 performed with reference to the blocks 2110-2140 described herein, in other embodiments, the method 2100 can be performed differently. For example, some or all of the blocks 2110-2140 can be combined, performed in a different order than shown, and/or the functions of particular blocks may be reallocated to other blocks and/or to different blocks. Embodiments of the method 2100 may utilize different blocks than are shown in FIG. 21.

For example, in some embodiments of the method 2100, the calibration coefficient is computed without synthesizing spectra and/or partitioning the data into calibration sets and test sets. Such embodiments are referred to herein as "Parameter-Free Interferent Rejection" (PFIR) methods. In one example embodiment using PFIR, for each of the possible interferent subsets $\xi$, the following calculations may be performed to compute an estimate of a calibration coefficient for each subset $\xi$. An average concentration may be estimated according to $g_{est}=\Sigma g(\xi) p(\xi)$, where the sum is over the interferent subsets processed from the list of possible interferent subsets.

An example of an alternative embodiment of block 2130 includes the following steps and calculations.

Step 1: For a subset's $N_{IF}$ interferents, form a scaled interferent spectra matrix. In certain embodiments, the scaled interferent spectra matrix is the product of an interferent spectral matrix, IF, multiplied by an interferent concentration matrix, $T_{max}$, and can be written as: IF $T_{max}$. In certain such embodiments, the interferent concentration matrix $T_{max}$ is a diagonal matrix having entries given by the maximum plasma concentrations for the various interferents.

Step 2: Calculate a covariance for the interferent component. If X denotes the IESD, the covariance of X, cov(X), is defined as the expectation $E((X-mean(X))(X-mean(X))^T)$ and is $$cov(X) \approx XX^T/(N-1) - mean(X)mean(X)^T.$$

As described above, the IESD (e.g., X) is obtained as a combination of Sample Population Spectra, C, with Combination Interferent Spectra (CIS): $X_j = C_j + IF_j \xi_j$, therefore the covariance is:

$$cov(X) \approx CC^T/(N-1) + IF\Xi\Xi^T IF^T/(N-1) - mean(X)mean(X)^T,$$

which can be written as, $$cov(X) \approx cov(C) + IF cov(\Xi) IF^T.$$

If the weights in the weighting matrix $\Xi$ are independent and identically distributed, the covariance of $\Xi$, cov($\Xi$), is a diagonal matrix having along the diagonal the variance, v, of the samples in $\Xi$. The last equation may be written as $$cov(X) \approx V_0 + v\Phi,$$

where $V_0$ is the covariance of the original sample population and $\phi$ is the covariance of the IF spectral set.

Step 3: The group's covariance may be at least partially corrected for the presence of a single replicate of the Sample Population spectra with the IESD as formed from $N_{IF}$ replicates of the Sample Population Spectra with Combined Interferent Spectra. This partial correction may be achieved by multiplying the second term in the covariance formula given above by a correction factor $\rho$:

$$V = V_0 + \rho v\Phi,$$

where $\rho$ is a scalar weighting function that depends on the number of interferents in the group. In some embodiments, the scalar weighting function is $\rho = N_{IF}/(N_{IF}+1)$. In certain embodiments, the variance v of the weights is assumed to be the variance of a log-normal random variable having a 95th percentile at a value of 1.0, and a standard deviation equal to half of the mean value.

Step 4: The eigenvectors and the corresponding eigenvalues of the covariance matrix V are determined using any suitable linear algebraic methods. The number of eigenvectors (and eigenvalues) is equal to the number of wavelengths L in the spectral measurements. The eigenvectors may be sorted based on decreasing order of their corresponding eigenvalues.

Step 5: The matrix of eigenvectors is decomposed so as to provide an orthogonal matrix Q. For example, in some embodiments, a QR-decomposition is performed, thereby yielding the matrix Q having orthonormal columns and rows.

Step 6: The following matrix operations are performed on the orthogonal matrix Q. For n=2 to L-1, the product $P^{\parallel}_n = Q(:,1:n) Q(:,1:n)^T$ is calculated, where Q(:,1:n) denotes the submatrix comprising the first n columns of the full matrix Q. The orthogonal projection, $P^{\perp}_n$, away from the space spanned by Q(:,1:n) is determined by subtracting $P^{\parallel}_n$ from the L×L identity matrix I. The $n^{th}$ calibration vector is then determined from $\kappa_n = P^{\perp}_n \alpha_X / \alpha_X^T P^{\perp}_n \alpha_X$, and the $n^{th}$ error variance $E_n$ is determined as the projection of the full covariance V onto the subspace spanned by $\kappa_n$ as follows: $E_n = \kappa_n^T V \kappa_n$.

The steps 4-6 of this example are an embodiment of the HLA technique.

In some embodiments, the calibration coefficient $\kappa$ is selected as the calibration vector corresponding to the minimum error variance $E_n$. Thus, for example, the average group calibration coefficient $\kappa$ may be found by searching among all the error variances for the error variance $E_n$ that has the minimum value. The calibration coefficient is then selected as the $n^{th}$ calibration vector $\kappa_n$ corresponding to the minimum error variance $E_n$. In other embodiments, the calibration coefficient is determined by averaging some or all of the calibration vectors $\kappa_n$.

Examples of Algorithm Results and Effects of Sample Population

Embodiments of the above-described methods have been used to estimate blood plasma glucose concentrations in humans. Four example experiments will now be described. The population of individuals from whom samples were obtained for analysis (estimation of glucose concentration) will be referred to as the "target population." Infrared spectra obtained from the target population will be referred to as the "target spectra." In the four example experiments, the target population included 41 intensive care unit (ICU) patients. Fifty-five samples were obtained from the target population.

Example Experiment 1

In this example experiment, a partial least squares (PLS) regression method was applied to the infrared target spectra of the target patients' blood plasma to obtain the glucose estimates. In example experiment 1, estimated glucose concentration was not corrected for effects of interferents. The Sample Population used for the analysis included infrared spectra and independently measured glucose concentrations for 92 individuals selected from the general population. This Sample Population will be referred to as a "Normal Population."

Figure 23A:
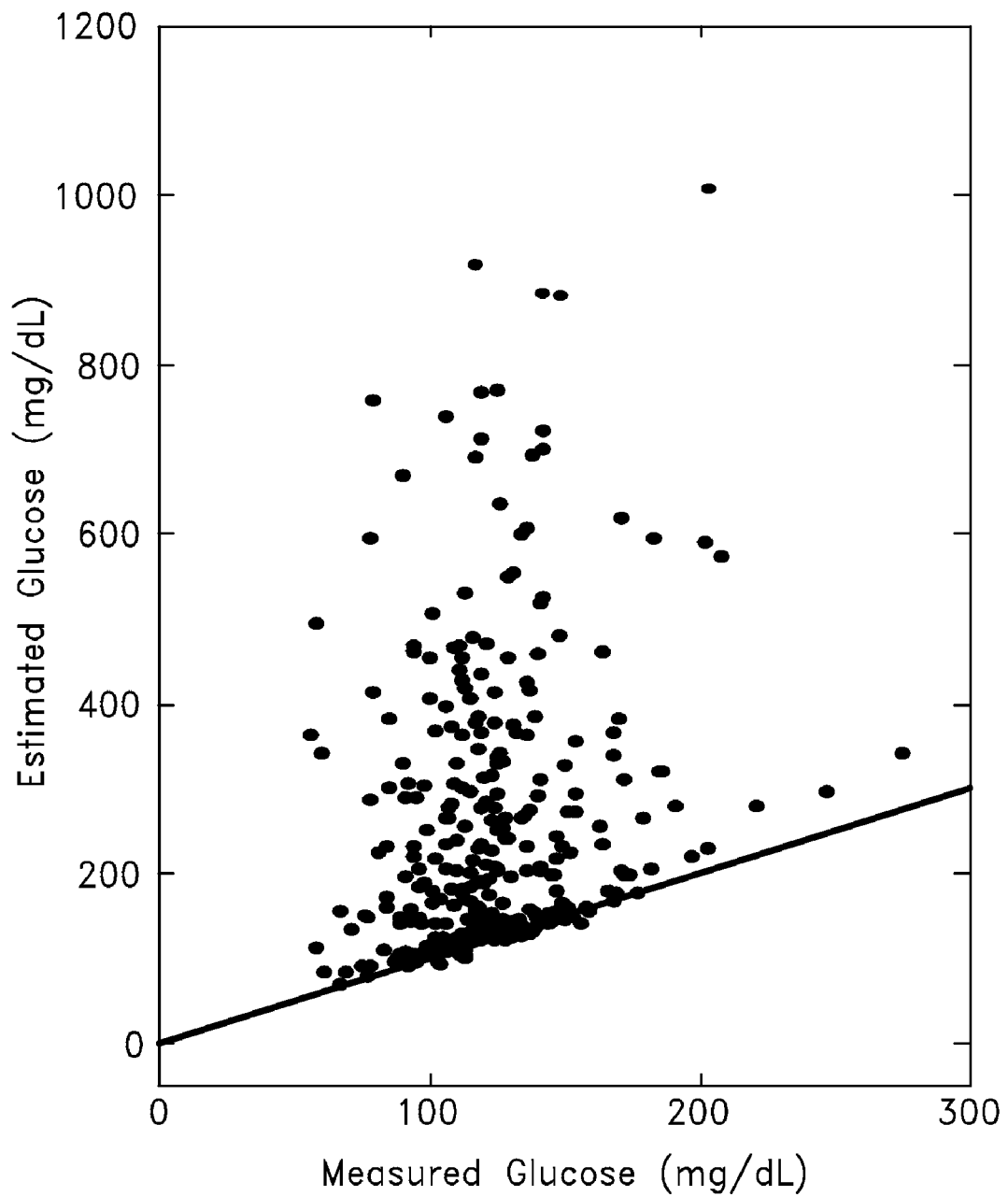
FIGS. 23A through 23D illustrate different examples of the results obtained by using various algorithms to estimate the concentration of an analyte in a sample.

FIG. 23A plots predicted versus measured glucose measurements for 55 measurements taken from 41 intensive care unit (ICU) patients. PLS regression method was applied to the infrared spectra of the patients' blood plasma to obtain the glucose measurements. In the example depicted in FIG. 23A, the Sample Population measurements include infrared spectra measurements and independently measured glucose concentrations for 92 individuals selected from the general population. This Sample Population is referred to herein, without limitation, as a "Normal Population." Some embodiments of a method can calculate the calibration constants that correspond to the infrared spectra of the Normal Population to obtain the predicted value of the glucose concentration. The population whose infrared spectra are intended to be analyzed by the analysis device and whose glucose concentration is intended to be predicted therefrom will be referred to herein as a "target population." The infrared spectra of that target population is referred to herein as the "target spectra".

From FIG. 23A it is observed that the estimated glucose values in the blood plasma of ICU patients do not always correspond to the measured glucose values. If the estimated glucose values matched the measured glucose values then all the dots would lie on the straight line 2380. The estimated or predicted glucose values have an average prediction error of 126 mg/dl and a standard deviation of prediction error of 164 mg/dl. Possible reasons for the high average prediction error and high standard deviation of prediction error could be a result of using a Sample Population that includes only the Normal Population and the fact that the predicted values were not corrected for possible interferents.

Example Experiment 2

Figure 23B:
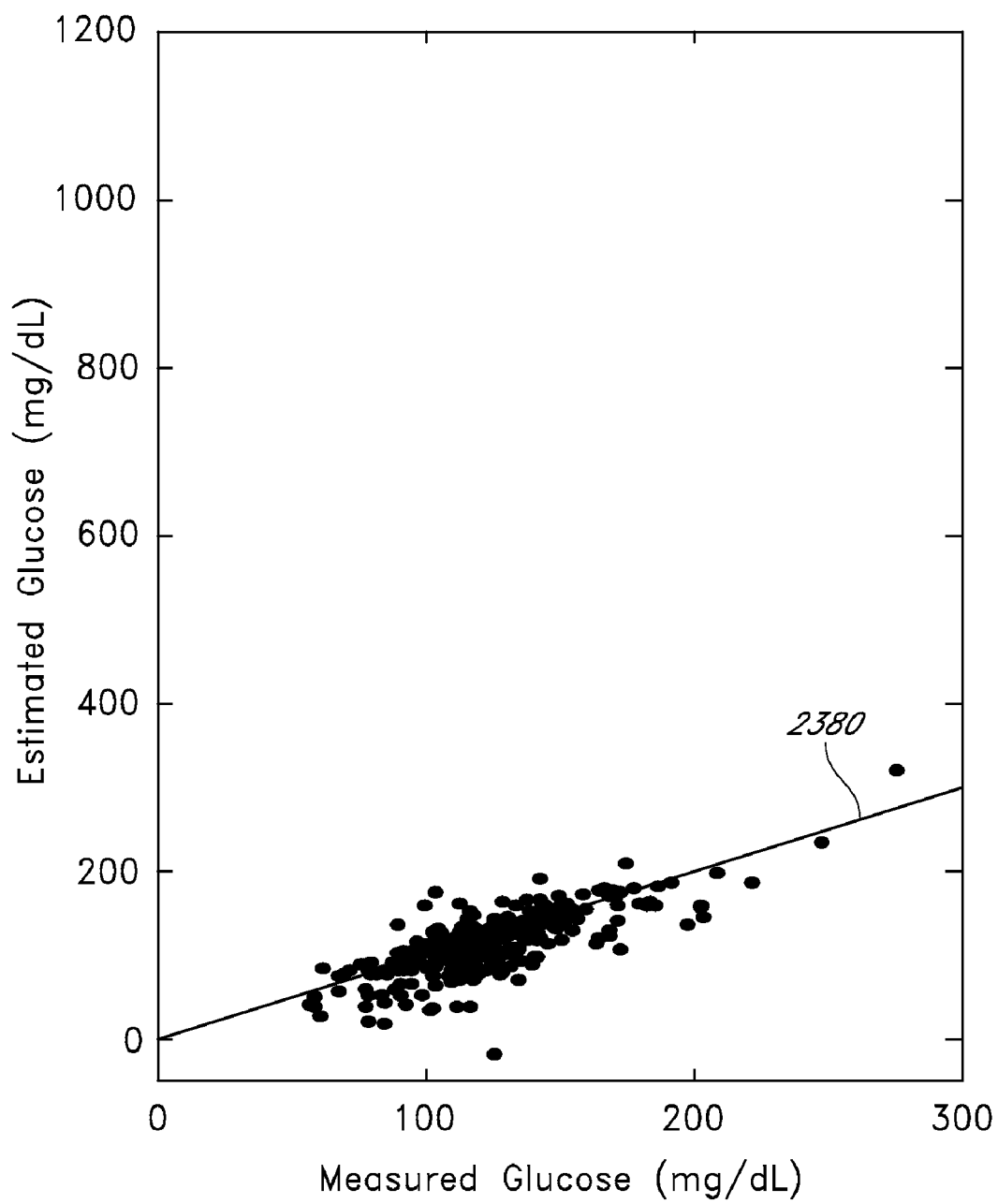

In example experiment 2, an embodiment of the Parameter-Free Interferent Rejection (PFIR) method was used to estimate glucose concentration for the same target population of patients in example experiment 1. To achieve better correlation between the predicted glucose value and the measured glucose value, a PFIR method can be applied to infrared spectra of the patient's blood plasma and the prediction can be corrected for interfering substances (e.g., those present in a library of interferents). FIG. 23B plots the predicted versus independently measured glucose values for the same patients as those of FIG. 23A, except that this time, the predicted glucose values are obtained using a PFIR method, and the prediction is corrected for interfering substances. The Sample Population was the Normal Population. In this example, calibration for Library Interferents was applied to the measured target spectra. The Library of Interferents included spectra of the 59 substances listed below:

| | | |
|---|---|---|
| Acetylsalicylic Acid | Hetastarch | Pyruvate Sodium |
| Ampicillin Sulbactam | Human Albumin | Pyruvic Acid |
| Azithromycin | Hydroxy Butyric Acid | Salicylate Sodium |
| Aztreonam | Imipenem Cilastatin | Sodium Acetate |
| Bacitracin | Iohexol | Sodium Bicarbonate |
| Benzyl Alcohol | L__Arginine | Sodium Chloride |
| Calcium Chloride | Lactate Sodium | Sodium Citrate |
| Calcium Gluconate | Magnesium Sulfate | Sodium Thiosulfate |
| Cefazolin | Maltose | Sulfadiazine |
| Cefoparazone | Mannitol | Urea |
| Cefotaxime Sodium | Meropenem | Uric Acid |
| Ceftazidime | Oxylate Potassium | Voriconazole |
| Ceftriaxone | Phenytoin | Xylitol |
| D__Sorbitol | Phosphates Potassium | Xylose |
| Dextran | Piperacillin | PC 1 of Saline covariance |
| Ertapenem | Piperacillin Tazobactam | PC 2 of Saline covariance |
| Ethanol | PlasmaLyteA | PC 3 of Saline covariance |
| Ethosuximide | Procaine HCl | PC 4 of Saline covariance |
| Glycerol | Propylene Glycol | ICU/Normal difference spectrum |
| Heparin | Pyrazinamide | |

In some embodiments, the calibration data set is determined according to two criteria: the calibration method itself (e.g., HLA, PLS, OLS, PFIR) and the intended application of the method. The calibration data set may comprise spectra and corresponding analyte levels derived from a set of plasma samples from the Sample Population. In some embodiments, e.g., those where an HLA calibration method is used, the calibration data set may also include spectra of the analyte of interest.

From FIG. 23B it is observed that by including the spectral effects of the interferents in the above table, the predicted glucose values are closer to the measured glucose values. The average prediction error in this case is approximately −6.8 mg/dL and the standard deviation of the prediction error is approximately 23.2 mg/dL. The difference in the average prediction error and the standard deviation of prediction error between FIG. 23A and FIG. 23B illustrates that the prediction is greatly improved when the model includes the effects of possible interferents.

In the example experiments 1 and 2, the Sample Population was the Normal Population. Thus, samples were drawn from a population of normal individuals who did not have identifiable medical conditions that might affect the spectra of their plasma samples. For example, the sample plasma spectra typically did not show effects of high levels of medications or other substances (e.g., ethanol), or effects of chemicals that are indicative of kidney or liver malfunction. Similarly, in the data presented in FIGS. 23A and 23B, the Sample Population samples are drawn from a population of normal individuals. These individuals do not have identifiable medical conditions that might affect the spectra of their plasma, for example, the spectra of their plasma may not exhibit high plasma levels of medications or other substances such as ethanol, or other chemicals that are indicative of kidney or liver malfunction.

In some embodiments, an analysis method may calibrate for deviations from the distribution defined by the calibration plasma spectra by identifying a "base" set of interferent spectra likely to be responsible for the deviation. The analysis method may then recalibrate with respect to an enhanced spectral data set. In some embodiments, the enhancement can be achieved by including the identified interferent spectra into the calibration plasma spectra. When it is anticipated that the target population may have been administered significant amounts of substances not present in the samples of the calibration set, or when the target population have many distinct interferents, estimation of the interferents present in the target spectrum may be subject to a large degree of uncertainty. In some cases, this may cause analyte estimation to be subject to errors.

Accordingly, in certain embodiments, the calibration data set may be enhanced beyond the base of "normal" samples to include a population of samples intended to be more representative of the target population. The enhancement of the calibration set may be generated, in some embodiments, by including samples from a sufficiently diverse range of individuals in order to represent the range of likely interferents (both in type and in concentration) and/or the normal variability in underlying plasma characteristics. The enhancement may, additionally or alternatively, be generated by synthesizing interferent spectra having a range of concentrations as described above (see, e.g., discussion of block 2310 in FIG. 23). Using the enhanced calibration set may reduce the error in estimating the analyte concentration in the target spectra.

Example Experiments 3 and 4

Example experiments 3 and 4 use the analysis methods of example experiments 1 and 2, respectively (PLS without interferent correction and PFIR with interferent correction). However, example experiments 3 and 4 use a Sample Population having blood plasma spectral characteristics different from the Normal Population used in example experiments 1 and 2. In example experiments 3 and 4, the Sample Population was modified to include spectra of both the Normal Population and spectra of an additional population of 55 ICU patients. These spectra will be referred to as the "Normal+Target Spectra." In experiments 3 and 4, the ICU patients included Surgical ICU patients, Medical ICU patients as well as victims of severe trauma, including a large proportion of patients who had suffered major blood loss. Major blood loss may necessitate replacement of the patient's total blood volume multiple times during a single day and subsequent treatment of the patient via electrolyte and/or fluid replacement therapies. Major blood loss may also require administration of plasma-expanding medications. Major blood loss may lead to significant deviations from the blood plasma spectra representative of a Normal Population. The population of 55 ICU patients (who provided the Target Spectra) has some similarities to the individuals for whom the analyses in experiments 1-4 were performed (e.g., all were ICU patients), but in these experiments, target spectra from individuals in the target population were not included in the Target Spectra.

Figure 23C:
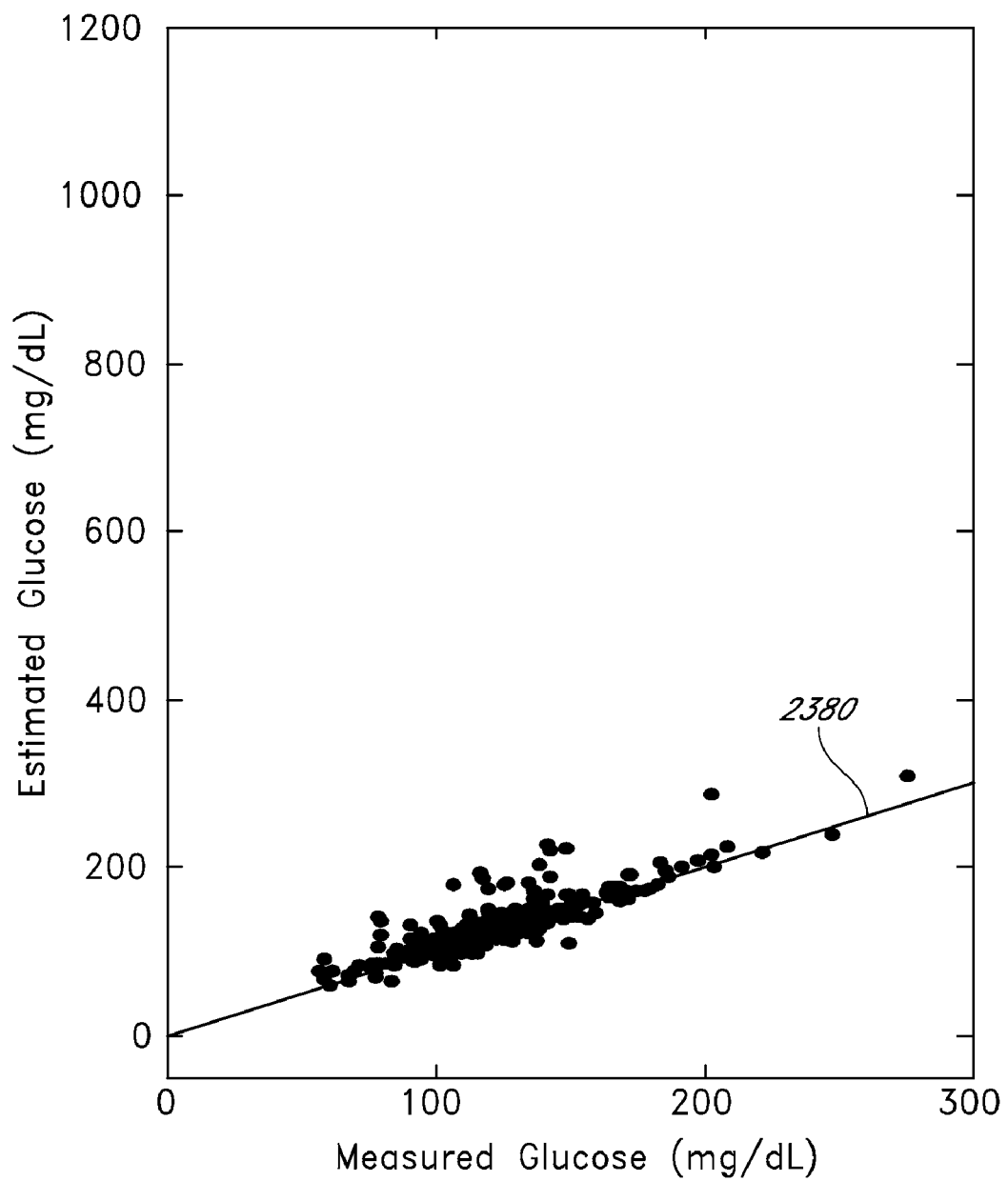
Figure 23D:
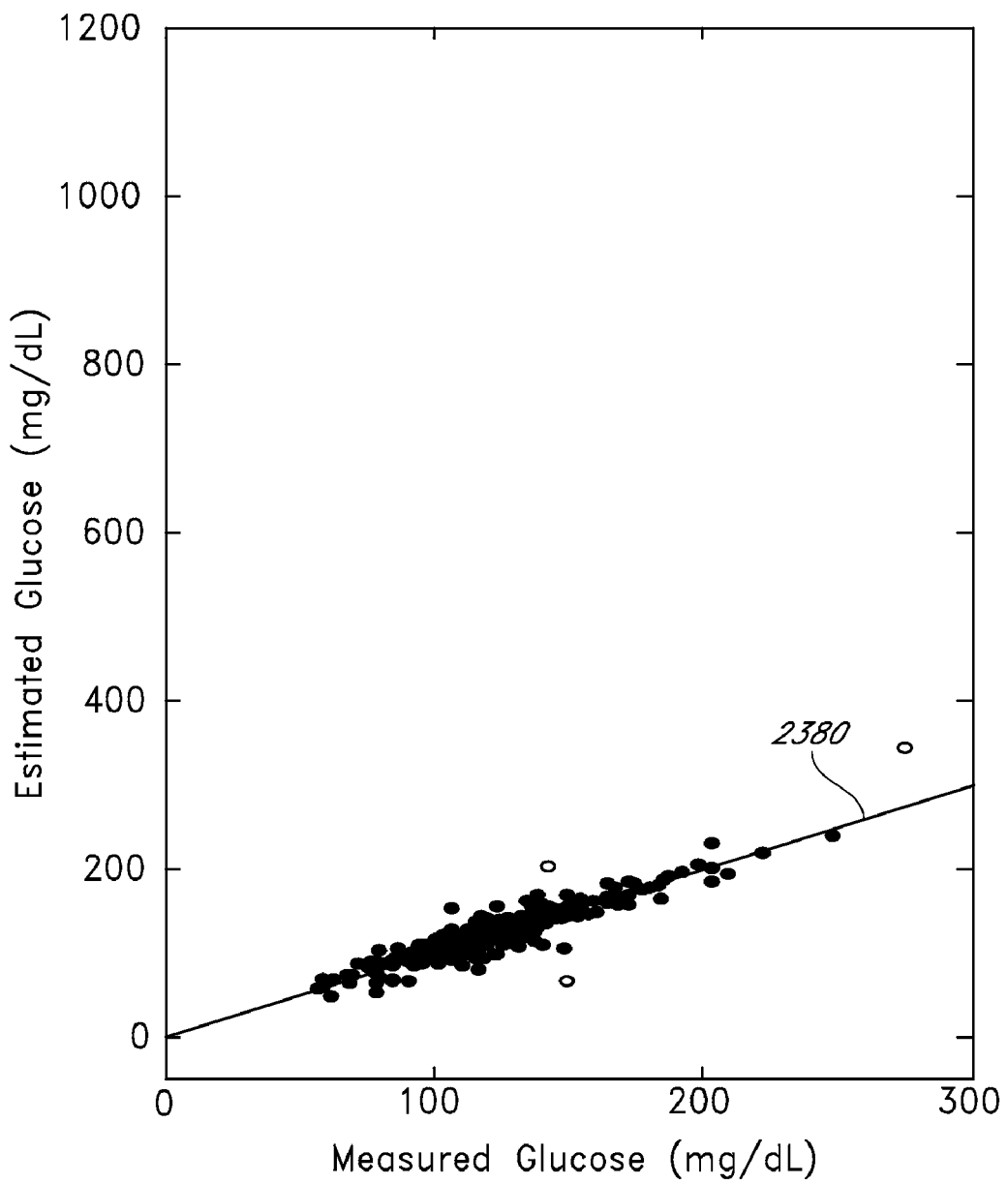

FIG. 23C and FIG. 23D illustrate the principles discussed with respect to Experiments 3 and 4. Specifically, to obtain the data presented in FIG. 23C, the method used to obtain the data of FIG. 23A is modified to include spectra of both Normal Population members and spectra of 55 ICU patients. (The target population, for such a method, can advantageously comprise ICU patients. For example, the spectra obtained from a target population of ICU patients can be similar in many ways to the spectra obtained from the 55 ICU patients.) This combined set of Spectra is referred to herein as the "Normal+Target Spectra." In this particular study, the ICU was a major trauma center, and the ICU patients were all victims of severe trauma, including a large proportion of patients who had suffered major blood loss. In such cases, researchers generally agree that this degree of blood loss—which may necessitate replacement of the patient's total blood volume multiple times during a single day and subsequent treatment of the patient via electrolyte/fluid replacement and the administration of plasma-expanding medications—can lead to significant spectral deviations from the blood plasma spectra of a Normal Population. A comparison of FIG. 23A and FIG. 23C shows that the predicted glucose values match the measured glucose values to a greater extent in FIG. 23C than in FIG. 23A. Statistical analysis of the data presented in FIG. 23C shows that the average prediction error of the predicted glucose value is approximately 8.2 mg/dl and the standard deviation of the prediction error is approximately 16.9 mg/dl. It should be noted that in predicting the glucose value in FIG. 23C, the presence of interferents was not taken into account.

The data shown in FIG. 23D, is obtained by modifying the method used to obtain the data for FIG. 23B (which included correction for possible interferents) to include spectra of the "Normal+Target Spectra." A comparison of FIG. 23B and FIG. 23D shows that the predicted glucose values match the measured glucose values to a greater extent in FIG. 23D than in FIG. 23B. Statistical analysis of the data presented in FIG. 23D shows that in this example, the average prediction error of the predicted glucose value is approximately 1.32 mg/dl and the standard deviation of the prediction error is approximately 12.6 mg/dl. It can be concluded from this example that determining calibration constants from a population that includes both normal spectra and spectra derived from individuals similar to those of the target population, and also correcting for possible interferents, provides a good match between the estimated value and the measured value.

Results of example experiments 1-4 are shown in the following table. The glucose concentrations estimated from the analysis method were compared to independently determined glucose measurements to provide an average prediction error and a standard deviation of the average prediction error. The table demonstrates that independent of the Sample Population used (e.g., either the Normal Population or the Normal+Target Population), calibrating for interferents reduces both the average prediction error and the standard deviation (e.g., compare the results for experiment 2 to the results for experiment 1 and compare the results for experiment 4 to the results for experiment 3). The table further demonstrates that independent of the analysis method used (e.g., either PLS or PFIR), using a Sample Population with more similarity to the target population (e.g., the Normal+Target Population) reduces both the average prediction error and the standard deviation (e.g., compare the results for experiment 3 to the results for experiment 1 and compare the results for experiment 4 to the results for experiment 2).

| Example Experiment No. | Interferent Calibration | Sample Population | Average Prediction Error (mg/dL) | Standard Deviation (mg/dL) |
| --- | --- | --- | --- | --- |
| 1 | NO | Normal | 126 | 164 |
| 2 | YES | Normal | −6.8 | 23.2 |
| 3 | NO | Normal + Target | 8.2 | 16.9 |
| 4 | YES | Normal + Target | 1.32 | 12.6 |

Accordingly, embodiments of analysis methods that use a Sample Population that includes both normal spectra and spectra from individuals similar to those of the target population and that calibrate for possible interferents provide a good match between the estimated glucose concentration and the measured glucose concentration. As discussed above, a suitable Sample Population may be assembled from the Population Database in order to include normal spectra plus suitable target spectra from individuals that match a desired target population including, for example, ICU patients, trauma patients, a particular demographic group, a group having a common medical condition (e.g., diabetes), and so forth.

User Interface

The system 400 can include a display system 414, for example, as depicted in FIG. 4. The display system 414 may comprise an input device including, for example, a keypad or a keyboard, a mouse, a touchscreen display, and/or any other suitable device for inputting commands and/or information. The display system 414 may also include an output device including, for example, an LCD monitor, a CRT monitor, a touchscreen display, a printer, and/or any other suitable device for outputting text, graphics, images, videos, etc. In some embodiments, a touchscreen display is advantageously used for both input and output.

The display system 414 can include a user interface 2400 by which users can conveniently and efficiently interact with the system 400. The user interface 2400 may be displayed on the output device of the system 400 (e.g., the touchscreen display). In some embodiments, the user interface 2400 is implemented and/or stored as one or more code modules, which may be embodied in hardware, firmware, and/or software.

FIGS. 24 and 25 schematically illustrate the visual appearance of embodiments of the user interface 2400. The user interface 2400 may show patient identification information 2402, which can include patient name and/or a patient ID number. The user interface 2400 also can include the current date and time 2404. An operating graphic 2406 shows the operating status of the system 400. For example, as shown in FIGS. 24 and 25, the operating status is "Running," which indicates that the system 400 is fluidly connected to the patient ("Jill Doe") and performing normal system functions such as infusing fluid and/or drawing blood. The user interface 2400 can include one or more analyte concentration graphics 2408, 2412, which may show the name of the analyte and its last measured concentration. For example, the graphic 2408 in FIG. 24 shows "Glucose" concentration of 150 mg/dL, while the graphic 2412 shows "Lactate" concentration of 0.5 mmol/L. The particular analytes displayed and their measurement units (e.g., mg/dL, mmol/L, or other suitable unit) may be selected by the user. The size of the graphics 2408, 2412 may be selected to be easily readable out to a distance such as, e.g., 30 feet. The user interface 2400 may also include a next-reading graphic 2410 that indicates the time until the next analyte measurement is to be taken. In FIG.

24, the time until next reading is 3 minutes, whereas in FIG. 25, the time is 6 minutes, 13 seconds.

The user interface 2400 can include an analyte concentration status graphic 2414 that indicates status of the patient's current analyte concentration compared with a reference standard. For example, the analyte may be glucose, and the reference standard may be a hospital ICU's tight glycemic control (TGC). In FIG. 24, the status graphic 2414 displays "High Glucose," because the glucose concentration (150 mg/dL) exceeds the maximum value of the reference standard. In FIG. 25, the status graphic 2414 displays "Low Glucose," because the current glucose concentration (79 mg/dL) is below the minimum reference standard. If the analyte concentration is within bounds of the reference standard, the status graphic 2414 may indicate normal (e.g., "Normal Glucose"), or it may not be displayed at all. The status graphic 2414 may have a background color (e.g., red) when the analyte concentration exceeds the acceptable bounds of the reference standard.

The user interface 2400 can include one or more trend indicators 2416 that provide a graphic indicating the time history of the concentration of an analyte of interest. In FIGS. 24 and 25, the trend indicator 2416 comprises a graph of the glucose concentration (in mg/dL) versus elapsed time (in hours) since the measurements started. The graph includes a trend line 2418 indicating the time-dependent glucose concentration. In other embodiments, the trend line 2418 can include measurement error bars and may be displayed as a series of individual data points. In FIG. 25, the glucose trend indicator 2416 is shown as well as a trend indicator 2430 and trend line 2432 for the lactate concentration. In some embodiments, a user may select whether none, one, or both trend indicators 2416, 2418 are displayed. In some embodiments, one or both of the trend indicators 2416, 2418 may appear only when the corresponding analyte is in a range of interest such as, for example, above or below the bounds of a reference standard.

The user interface 2400 can include one or more buttons 2420-2426 that can be actuated by a user to provide additional functionality or to bring up suitable context-sensitive menus and/or screens. For example, in the embodiments shown in FIG. 24 and FIG. 25, four buttons 2420-2426 are shown, although fewer or more buttons are used in other embodiments. The button 2420 ("End Monitoring") may be pressed when one or more removable portions (see, e.g., 710 of FIG. 7) are to be removed. In many embodiments, because the removable portions 710, 712 are not reusable, a confirmation window appears when the button 2420 is pressed. If the user is certain that monitoring should stop, the user can confirm this by actuating an affirmative button in the confirmation window. If the button 2420 were pushed by mistake, the user can select a negative button in the confirmation window. If "End Monitoring" is confirmed, the system 400 performs appropriate actions to cease fluid infusion and blood draw and to permit ejection of a removable portion (e.g., the removable portion 710).

The button 2422 ("Pause") may be actuated by the user if patient monitoring is to be interrupted but is not intended to end. For example, the "Pause" button 2422 may be actuated if the patient is to be temporarily disconnected from the system 400 (e.g., by disconnecting the tubes 306). After the patient is reconnected, the button 2422 may be pressed again to resume monitoring. In some embodiments, after the "Pause" button 2422 has been pressed, the button 2422 displays "Resume."

The button 2424 ("Delay 5 Minutes") causes the system 400 to delay the next measurement by a delay time period (e.g., 5 minutes in the depicted embodiments). Actuating the delay button 2424 may be advantageous if taking a reading would be temporarily inconvenient, for example, because a health care professional is attending to other needs of the patient. The delay button 2424 may be pressed repeatedly to provide longer delays. In some embodiments, pressing the delay button 2424 is ineffective if the accumulated delay exceeds a maximum threshold. The next-reading graphic 2410 automatically increases the displayed time until the next reading for every actuation of the delay button 2424 (up to the maximum delay).

The button 2426 ("Dose History") may be actuated to bring up a dosing history window that displays patient dosing history for an analyte or medicament of interest. For example, in some embodiments, the dosing history window displays insulin dosing history of the patient and/or appropriate hospital dosing protocols. A nurse attending the patient can actuate the dosing history button 2426 to determine the time when the patient last received an insulin dose, the last dose amount, and/or the time and amount of the next dose. The system 400 may receive the patient dosing history via wired or wireless communications from a hospital information system.

In other embodiments, the user interface 2400 can include additional and/or different buttons, menus, screens, graphics, etc. that are used to implement additional and/or different functionalities.

Related Components

Figure 26:
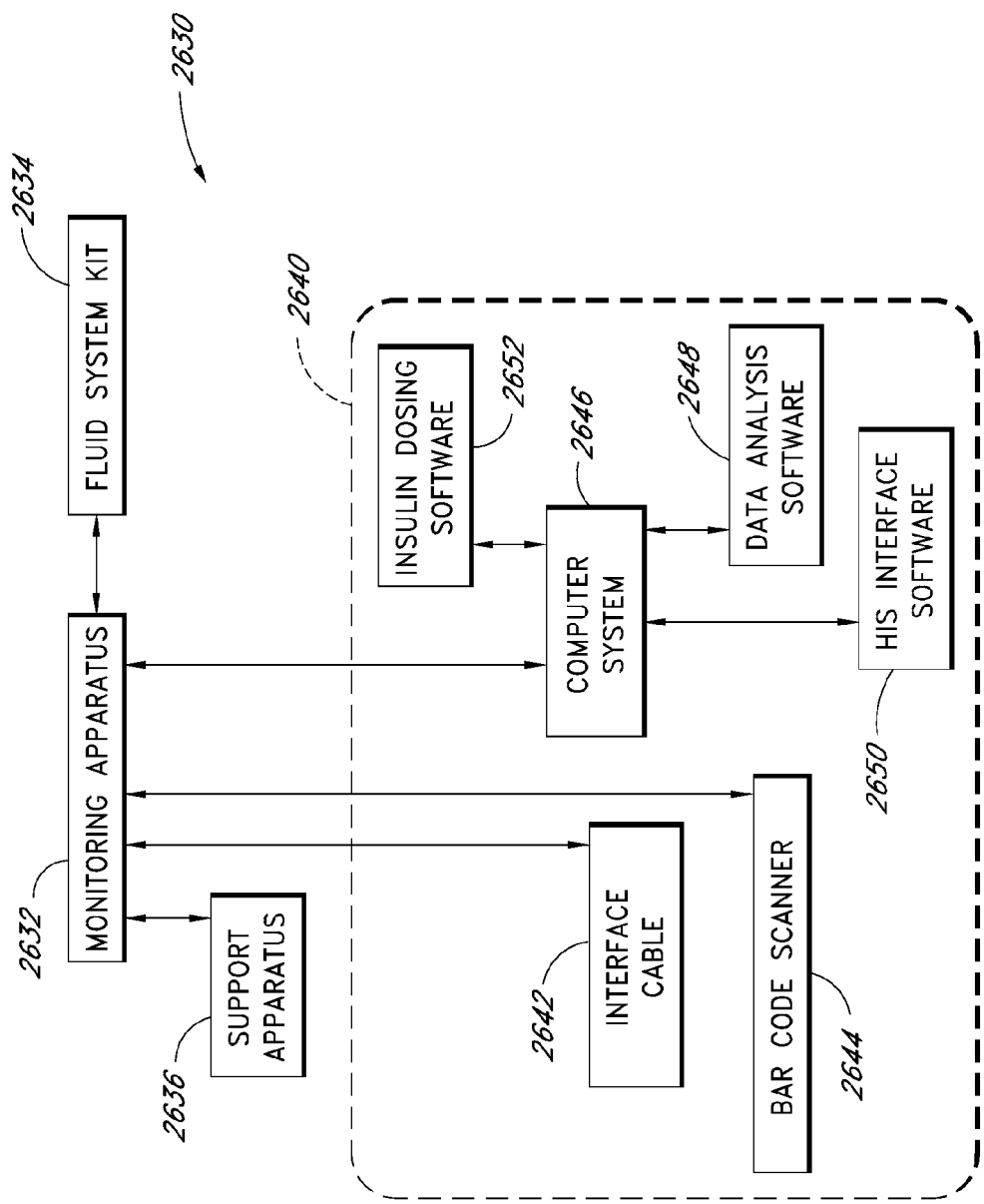
FIG. 26 schematically depicts various components and/or aspects of a patient monitoring system and the relationships among the components and/or aspects.

FIG. 26 schematically depicts various components and/or aspects of a patient monitoring system 2630 and how those components and/or aspects relate to each other. In some embodiments, the monitoring system 2630 can be the apparatus 100 for withdrawing and analyzing fluid samples. Some of the depicted components can be included in a kit containing a plurality of components. Some of the depicted components, including, for example, the components represented within the dashed rounded rectangle 2640 of FIG. 26, are optional and/or can be sold separately from other components.

The patient monitoring system 2630 shown in FIG. 26 includes a monitoring apparatus 2632. The monitoring apparatus 2632 can be the monitoring device 102, shown in FIG. 1 and/or the system 400 of FIG. 4. The monitoring apparatus 2632 can provide monitoring of physiological parameters of a patient. In some embodiments, the monitoring apparatus 2632 measures glucose and/or lactate concentrations in the patient's blood. In some embodiments, the measurement of such physiological parameters is substantially continuous. The monitoring apparatus 2632 may also measure other physiological parameters of the patient. In some embodiments, the monitoring apparatus 2632 is used in an intensive care unit (ICU) environment. In some embodiments, one monitoring apparatus 2632 is allocated to each patient room in an ICU.

The patient monitoring system 2630 can include an optional interface cable 2642. In some embodiments, the interface cable 2642 connects the monitoring apparatus 2632 to a patient monitor (not shown). The interface cable 2642 can be used to transfer data from the monitoring apparatus 2632 to the patient monitor for display. In some embodiments, the patient monitor is a bedside cardiac monitor having a display that is located in the patient room (see, e.g., the user interface 2400 shown in FIG. 24 and FIG. 25.) In some embodiments, the interface cable 2642 transfers data from the monitoring apparatus 2632 to a central station monitor and/or to a hospital information system (HIS). The ability to transfer data to a central station monitor and/or to a HIS may depend on the capabilities of the patient monitor system.

In the embodiment shown in FIG. 26, an optional bar code scanner 2644 is connected to the monitoring apparatus 2632. In some embodiments, the bar code scanner 2644 is used to enter patient identification codes, nurse identification codes, and/or other identifiers into the monitoring apparatus 2632. In some embodiments, the bar code scanner 2644 contains no moving parts. The bar code scanner 2644 can be operated by manually sweeping the scanner 2644 across a printed bar code or by any other suitable means. In some embodiments, the bar code scanner 2644 includes an elongated housing in the shape of a wand.

The patient monitoring system 2630 includes a fluid system kit 2634 connected to the monitoring apparatus 2632. In some embodiments, the fluid system kit 2634 includes fluidic tubes that connect a fluid source to an analytic subsystem. For example, the fluidic tubes can facilitate fluid communication between a blood source or a saline source and an assembly including a sample holder and/or a centrifuge. In some embodiments, the fluid system kit 2634 includes many of the components that enable operation of the monitoring apparatus 2632. In some embodiments, the fluid system kit 2634 can be used with anti-clotting agents (such as heparin), saline, a saline infusion set, a patient catheter, a port sharing IV infusion pump, and/or an infusion set for an IV infusion pump, any or all of which may be made by a variety of manufacturers. In some embodiments, the fluid system kit 2634 includes a monolithic housing that is sterile and disposable. In some embodiments, at least a portion of the fluid system kit 2634 is designed for single patient use. For example, the fluid system kit 2634 can be constructed such that it can be economically discarded and replaced with a new fluid system kit 2634 for every new patient to which the patient monitoring system 2630 is connected. In addition, at least a portion of the fluid system kit 2634 can be designed to be discarded after a certain period of use, such as a day, several days, several hours, three days, a combination of hours and days such as, for example, three days and two hours, or some other period of time. Limiting the period of use of the fluid system kit 2634 may decrease the risk of malfunction, infection, or other conditions that can result from use of a medical apparatus for an extended period of time.

In some embodiments, the fluid system kit 2634 includes a connector with a luer fitting for connection to a saline source. The connector may be, for example, a three-inch pigtail connector. In some embodiments, the fluid system kit 2634 can be used with a variety of spikes and/or IV sets used to connect to a saline bag. In some embodiments, the fluid system kit 2634 also includes a three-inch pigtail connector with a luer fitting for connection to one or more IV pumps. In some embodiments, the fluid system kit 2634 can be used with one or more IV sets made by a variety of manufacturers, including IV sets obtained by a user of the fluid system kit 2634 for use with an infusion pump. In some embodiments, the fluid system kit 2634 includes a tube with a low dead volume luer connector for attachment to a patient vascular access point. For example, the tube can be approximately seven feet in length and can be configured to connect to a proximal port of a cardiovascular catheter. In some embodiments, the fluid system kit 2634 can be used with a variety of cardiovascular catheters, which can be supplied, for example, by a user of the fluid system kit 2634.

As shown in FIG. 26, the monitoring apparatus 2632 is connected to a support apparatus 2636, such as an IV pole. The support apparatus 2636 can be customized for use with the monitoring apparatus 2632. A vendor of the monitoring apparatus 2632 may choose to bundle the monitoring apparatus 2632 with a custom support apparatus 2636. In some embodiments, the support apparatus 2636 includes a mounting platform for the monitoring apparatus 2632. The mounting platform can include mounts that are adapted to engage threaded inserts in the monitoring apparatus 2632. The support apparatus 2636 can also include one or more cylindrical sections having a diameter of a standard IV pole, for example, so that other medical devices, such as IV pumps, can be mounted to the support apparatus. The support apparatus 2636 can also include a clamp adapted to secure the apparatus to a hospital bed, an ICU bed, or another variety of patient conveyance device.

In the embodiment shown in FIG. 26, the monitoring apparatus 2632 is electrically connected to an optional computer system 2646. The computer system 2646 can comprise one or multiple computers, and it can be used to communicate with one or more monitoring devices. In an ICU environment, the computer system 2646 can be connected to at least some of the monitoring devices in the ICU. The computer system 2646 can be used to control configurations and settings for multiple monitoring devices (for example, the system can be used to keep configurations and settings of a group of monitoring devices common). The computer system 2646 can also run optional software, such as data analysis software 2648, HIS interface software 2650, and insulin dosing software 2652.

In some embodiments, the computer system 2646 runs optional data analysis software 2648 that organizes and presents information obtained from one or more monitoring devices. In some embodiments, the data analysis software 2648 collects and analyzes data from the monitoring devices in an ICU. The data analysis software 2648 can also present charts, graphs, and statistics to a user of the computer system 2646.

In some embodiments, the computer system 2646 runs optional hospital information system (HIS) interface software 2650 that provides an interface point between one or more monitoring devices and an HIS. The HIS interface software 2650 may also be capable of communicating data between one or more monitoring devices and a laboratory information system (LIS).

In some embodiments, the computer system 2646 runs optional insulin dosing software 2652 that provides a platform for implementation of an insulin dosing regimen. In some embodiments, the hospital tight glycemic control protocol is included in the software. The protocol allows computation of proper insulin doses for a patient connected to a monitoring device 2646. The insulin dosing software 2652 can communicate with the monitoring device 2646 to ensure (or at least improve the likelihood) that proper insulin doses are calculated. For example, the insulin dosing software 2652 can communicate with the computer system 2646 to perform the dosing calculations. The user interface 2400 can be used to communicate relevant information such as, for example, rate of dose and/or infusion, type of dose and/or infusion (e.g., bolus injection, basal infusion, steady state dose, treatment dose, etc.), to a health care practitioner so that the infusion rate and type of dose can be provided to the patient. The insulin dosing software 2652 and user interface can be implemented with the monitoring system 102 (FIG. 1), the system 400 (FIG. 4), or any other suitable patient monitoring system.

Analyte Control And Monitoring

In some embodiments, it can be advantageous to control a level of an analyte (e.g., glucose) in a patient using an embodiment of an analyte detection system described herein. Although certain examples of glucose control are described below, embodiments of the systems and methods disclosed herein can be used to monitor and/or control other analytes (e.g., lactate).

For example, diabetic individuals control their glucose levels by administration of insulin. If a diabetic patient is admitted to a hospital or ICU, the patient may be in a condition in which he or she cannot self-administer insulin. Advantageously, embodiments of the analyte detection systems disclosed herein can be used to control the level of glucose in the patient. Additionally, it has been found that a majority of patients admitted to the ICU exhibit hyperglycemia without having diabetes. In such patients it may be beneficial to monitor and control their blood glucose level to be within a particular range of values. Further, it has been shown that tightly controlling blood glucose levels to be within a stringent range may be beneficial to patients undergoing surgical procedures.

A patient admitted to the ICU or undergoing surgery can be administered a variety of drugs and fluids such as Hetastarch, intravenous antibiotics, intravenous glucose, intravenous insulin, intravenous fluids such as saline, etc., which may act as interferents and make it difficult to determine the blood glucose level. Moreover, the presence of additional drugs and fluids in the blood stream may require different methods for measuring and controlling blood glucose level. Also, the patient may exhibit significant changes in hematocrit levels due to blood loss or internal hemorrhage, and there can be unexpected changes in the blood gas level or a rise in the level of bilirubin and ammonia levels in the event of an organ failure. Embodiments of the systems and methods disclosed herein advantageously can be used to monitor and control blood glucose (and/or other analytes) in the presence of possible interferents to estimation of glucose and for patients experiencing health problems.

In some environments, Tight Glycemic Control (TGC) can include: (1) substantially continuous monitoring (which can include periodic monitoring, at relatively frequent intervals of every 15, 30, 45, and/or 60 minutes, for example) of glucose levels; (2) determination of substances that tend to increase glucose levels (e.g., sugars such as dextrose) and/or decrease glucose levels (e.g., insulin); and/or (3) responsive delivery of one or more of such substances, if appropriate under the controlling TGC protocol. For example, one possible TGC protocol can be achieved by controlling glucose within a relatively narrow range (for example between 70 mg/dL to 110 mg/dL). As will be further described, in some embodiments, TGC can be achieved by using an analyte monitoring system to make continuous and/or periodic but frequent measurements of glucose levels.

In some embodiments, the analyte detection system schematically illustrated in FIGS. 4, 5, and 6 can be used to regulate the concentration of one or more analytes in the sample in addition to determining and monitoring the concentration of the one or more analytes. In some cases, the analyte detection system can be used in an ICU to monitor (and/or control) analytes that may be present in patients experiencing trauma. In some implementations, the concentration of the analytes is regulated to be within a certain range. The range can be predetermined (e.g., according to a hospital protocol or a physician's recommendation), or the range can be adjusted as conditions change.

In an example of glycemic control, a system can be used to determine and monitor the concentration of glucose in the sample. If the concentration of glucose falls below a lower threshold, glucose from an external source can be supplied and/or delivery of insulin can be scaled back or halted altogether. If the concentration of glucose exceeds an upper threshold, insulin from an external source can be supplied and/or delivery of glucose can be scaled back or halted altogether. A treatment dose of glucose and/or insulin can be infused into a patient continuously over a certain time interval or can be injected in a relatively large quantity at once (referred to as "bolus injection"). Moreover, a steady-state or baseline (as opposed to a treatment) can be achieved as glucose and/or insulin can be infused into a patient relatively continuously at a low delivery rate (referred to as "basal infusion") to maintain the concentration of one or more analytes within a predetermined range. For example, in some cases a basal infusion can comprise a series of discrete doses designed to maintain a concentration of one or more analytes in a patient (e.g., concentration of glucose in a patient's blood stream). Such a serial infusion of discrete packets or doses can be referred to as "pulsatile" infusion. In some cases, instead of a series of discrete doses, a steady stream of infusion substance can be provided. The automatic and/or recommended basal infusion rate of glucose or insulin can be determined on the basis of one or more factors. For example, body weight, medical condition, medical history, presence or absence of other drugs and chemicals in the patient, etc. can all be factors that contribute to such a determination. Without contradicting the use of the term "basal" set forth above, the "basal infusion rate" can also refer to the rate of insulin needed to cover the "basal" metabolic functions (e.g. breathing, maintaining heart rate and other metabolic processes).

Various dosing protocols can be used to determine a dose of a treatment substance (e.g., a drug, glucose, dextrose, insulin, etc.). For example, in some embodiments, the dosing protocol used by personnel at a hospital is integrated into the glucose monitoring system to automatically determine the delivery rate of the treatment drug. In some embodiments, the system and method for recommending insulin bolus quantities to an insulin user disclosed in U.S. Pat. No. 7,291,107 B2 titled "INSULIN BOLUS RECOMMENDATION SYSTEM", by Hellwig et. al. can be used with the above described glucose monitoring system to determine the bolus dose of insulin to be delivered to the patient in the event of hyperglycemia or hypoglycemia. The entire content of U.S. Pat. No. 7,291,107 B2 is hereby incorporated by reference herein and is made a part of this specification.

In some embodiments, a hospital dosing protocol can be integrated into a glucose monitoring and control system. For example, the protocol instructions for a nurse can be accomplished automatically by the system rather than by the nurse. In some embodiments, a hospital or other health care provider can use its own protocol and program a monitoring system to incorporate the specific protocol. The procedure outline and corresponding tables below are an example of such a dosing protocol (the example provided can be referred to as the "Atlanta Protocol" and related information publically available at the following web address: "http://www.gha.org/pha/health/diabetes/Toolkit/guidelines/IVins80110/80-110chart_co11-16.pdf"). The following protocol can also be modified and incorporated into a monitoring system:

---

START infusion using the drip rate (ml/hr) shown in Column 2 for the current Blood Glucose Range.
To determine the new drip rate for each hourly measurement, compare the latest BG Range to the previous BG Range
If latest BG Range has decreased:
Stay in the same column -continued If latest BG Range has not changed or increased:
Move 1 column to the right
When hourly BG 80-110, stay in the same column to determine the new drip rate. (Do Not
Change Columns)
When BG <80, move one column to the left and treat for hypoglycemia

| Blood Glucose Ranges | 1 (ml/hr) | 2 (ml/hr) START | 3 (ml/hr) | 4 (ml/hr) | 5 (ml/hr) | 6 (ml/hr) | 7 (ml/hr) | 8 (ml/hr) | 9 (ml/hr) | 10 (ml/hr) |
|---|---|---|---|---|---|---|---|---|---|---|
| >450 | 4.4 | 8.8 | 13.2 | 17.6 | 22.0 | 26.4 | 30.8 | 35.2 | 39.6 | 44.0 |
| 385-450 | 3.6 | 7.2 | 10.8 | 14.4 | 18.0 | 21.6 | 25.2 | 28.8 | 32.4 | 36.0 |
| 326-384 | 3.0 | 6.0 | 9.0 | 12.0 | 15.0 | 18.0 | 21.0 | 24.0 | 27.0 | 30.0 |
| 290-333 | 2.5 | 5.0 | 7.5 | 10.0 | 12.5 | 15.0 | 17.5 | 20.0 | 22.5 | 25.0 |
| 251-289 | 2.1 | 4.2 | 6.3 | 8.4 | 10.5 | 12.6 | 14.7 | 16.8 | 18.9 | 21.0 |
| 217-250 | 1.7 | 3.4 | 5.1 | 7.2 | 8.5 | 10.2 | 11.9 | 13.6 | 15.3 | 17.0 |
| 188-216 | 1.4 | 2.8 | 4.2 | 5.6 | 7.0 | 8.4 | 9.8 | 11.2 | 12.6 | 14.0 |
| 163-187 | 1.2 | 2.4 | 3.6 | 4.8 | 6.0 | 7.2 | 8.4 | 9.6 | 10.8 | 12.0 |
| 141-162 | 1.0 | 2.0 | 3.0 | 4.0 | 5.0 | 6.0 | 7.0 | 8.0 | 9.0 | 10.0 |
| 119-140 | 0.8 | 1.6 | 2.4 | 3.2 | 4.0 | 4.8 | 5.6 | 6.4 | 7.2 | 8.0 |
| 111-120 | 0.6 | 1.2 | 1.8 | 2.4 | 3.0 | 3.6 | 4.2 | 4.8 | 5.4 | 6.0 |
| 106-110 | 0.5 | 1.0 | 1.5 | 2.0 | 2.5 | 3.0 | 3.5 | 4.0 | 4.5 | 5.0 |
| 101-105 | 0.4 | 0.9 | 1.3 | 1.8 | 2.2 | 2.7 | 3.1 | 3.6 | 4.0 | 4.5 |
| 96-100 | 0.4 | 0.8 | 1.2 | 1.6 | 2.0 | 2.4 | 2.8 | 3.2 | 3.6 | 4.0 |
| 91-95 | 0.3 | 0.7 | 1.0 | 1.4 | 1.7 | 2.1 | 2.4 | 2.8 | 3.2 | 3.5 |
| 86-90 | 0.3 | 0.6 | 0.9 | 1.2 | 1.5 | 1.8 | 2.1 | 2.4 | 2.7 | 3.0 |
| 80-85 | 0.2 | 0.5 | 0.7 | 1.0 | 1.2 | 1.5 | 1.7 | 2.0 | 2.3 | 2.5 |
| 75-79 | 0.2 | 0.4 | 0.6 | 0.8 | 1.0 | 1.2 | 1.4 | 1.6 | 1.8 | 2.0 |
| 70-74 | 0.1 | 0.3 | 0.4 | 0.6 | 0.7 | 0.9 | 1.0 | 1.2 | 1.3 | 1.5 |
| 60-70 | 0.1 | 0.2 | 0.3 | 0.4 | 0.5 | 0.6 | 0.7 | 0.8 | 0.9 | 1.0 |
| <60 | 0 | 0 | 0 | 0 | 0 | 0 | 0 | 0 | 0 | 0 |

| BG | D50W | ACTION |
|---|---|---|
| 70-79 | 10.0 ml IV push | Move 1 column to the left |
| 60-69 | 15.0 ml IV push | Recheck BG in 15 minutes |
| | | Repeat as necessary |
| 50-59 | 20.0 ml IV push | Move 1 column to the left |
| 30-49 | 25.0 ml IV push | Recheck BG in 15 minutes |
| <30 | 30.0 ml IV push | Repeat as necessary |
| | | Contact Physician if BG <60 for 2 consecutive BG measurements |

Notify Physician If:

BG is less <60 for 2 consecutive BG measurements
BG reverts to >200 for 2 consecutive BG measurements
Insulin requirement exceeds 24 units/hour
If the K+ level drops to <4
If drip rate (ml/hr) is 0.5 or less
If continuous enteral feeding, TPN, or IV insulin infusion is stopped or interrupted In some embodiments, a glycemic control system is capable of delivering glucose, dextrose, glycogen, and/or glucagon from an external source relatively quickly in the event of hypoglycemia. As discussed herein, embodiments of the glycemic control system are capable of delivering insulin from an external source relatively quickly in the event of hyperglycemia.

Returning to FIGS. 5 and 6, these figures schematically illustrate embodiments of a fluid handling system that comprise optional analyte control subsystems 2780. The analyte control subsystem 2780 can be used for providing control of an analyte such as, e.g., glucose, and may provide delivery of the analyte and/or related substances (e.g., dextrose solution and/or insulin in the case of glucose). The analyte control subsystem 2780 comprises a source 2782 such as, for example, the analyte (or a suitable compound related to the analyte) dissolved in water or saline. For example, if the analyte is glucose, the source 2782 may comprise a bag of dextrose solution (e.g., Dextrose or Dextrose 50%). The source 2782 can be coupled to an infusion pump (not shown). The source 2782 and the infusion pump can be provided separately from the analyte control subsystem 2780. For example, a hospital advantageously can use existing dextrose bags and infusion pumps with the subsystem 2780.

As schematically illustrated in FIGS. 5 and 6, the source 2782 is in fluid communication with the patient tube 512 via a tube 2784 and suitable connectors. A pinch valve 2786 can be disposed adjacent the tube 2784 to regulate the flow of fluid from the source 2782. A patient injection port can be located at a short distance from the proximal port of the central venous catheter or some other catheter connected to the patient.

In an example implementation for glycemic control, if the analyte detection system determines that the level of glucose has fallen below a lower threshold value (e.g., the patient is hypoglycemic), a control system (e.g., the fluid system controller 405 in some embodiments) controlling an infusion delivery system may close the pinch valves 521 and/or 542 to prevent infusion of insulin and/or saline into the patient. The control system may open the pinch valve 2786 and dextrose solution from the source 2782 can be infused (or alternatively injected as a bolus) into the patient. After a suitable amount of dextrose solution has been infused to the patient, the pinch valve 2786 can be closed, and the pinch valves 521 and/or 542 can be opened to allow flow of insulin and/or saline. In some systems, the amount of dextrose solution to be delivered as a basal infusion or as a bolus injection can be calculated based on one or more detected concentration levels of glucose. The source 2782 advantageously can be located at a short enough fluidic distance from the patient such that dextrose can be delivered to the patient within a time period of about one to about ten minutes of receiving an instruction (e.g. from a control system or a health care provider). In other embodiments, the source 2782 can be located at the site where the patient tube 512 interfaces with the patient so that dextrose can be delivered within about one minute of receiving an instruction (e.g. from a control system or a health care provider).

If the analyte detection system determines that the level of glucose has increased above an upper threshold value (e.g., the patient is hyperglycemic), the control system may close the pinch valves 542 and/or 2786 to prevent infusion of saline and/or dextrose into the patient. The control system may open the pinch valve 521, and insulin can be infused at a basal infusion rate (and/or injected as a bolus) into the patient. After a suitable amount of insulin has been infused (or bolus injected) to the patient, the control system can close the pinch valve 521 and open the pinch valves 542 and/or 2786 to allow flow of saline and/or glucose. The suitable amount of insulin can be calculated based on one or more detected concentration levels of glucose in the patient. In some embodiments, the insulin source can be connected to the infusion pump 518 which advantageously can be located at a short enough fluidic distance from the patient such that insulin can be delivered to the patient rapidly, e.g., within about one to about ten minutes. In some embodiments, the insulin source can be located at the site where the patient tube 512 interfaces with the patient so that insulin can be delivered to the patient rapidly, e.g., within about one minute.

In some embodiments, sampling bodily fluid from a patient and providing medication to the patient can be achieved through the same lines of the fluid handling system. For example, in some embodiments, a port to a patient can be shared by alternately drawing samples and medicating through the same line. In some embodiments, a insulin can be provided to the patient at regular intervals (in the same or different lines). For example, insulin can be provided to a patient after meals. In some embodiments, the medication can be delivered to the patient continuously at a basal infusion rate combined with intermittent bolus injections (e.g. after meals). In some embodiments, the medication can be delivered through a fluid passageway connected to the patient (e.g. patient tube 512 of FIG. 5). Intermittent injections can be provided to the patient by the same fluid passageway (e.g. patient tube 512 of FIG. 5). In some embodiments, a separate delivery system comprising a delivery pump can be used to provide the medication. In some embodiments comprising a shared line, medication can be delivered when returning part of a body fluid sample back to the patient. In some implementations, medication is delivered midway between samples (e.g., every 7.5 minutes if samples are drawn every 15 minutes). In some embodiments, a dual lumen tube can be used, wherein one lumen is used for the sample and the other lumen to medicate. In some embodiments, an analyte detection system (e.g., an "OptiScanner®" monitor) may provide suitable commands to a separate insulin pump (on a shared port or different line) to provide the recommended dose of insulin.

Example Method for Glycemic Control

Figure 27:
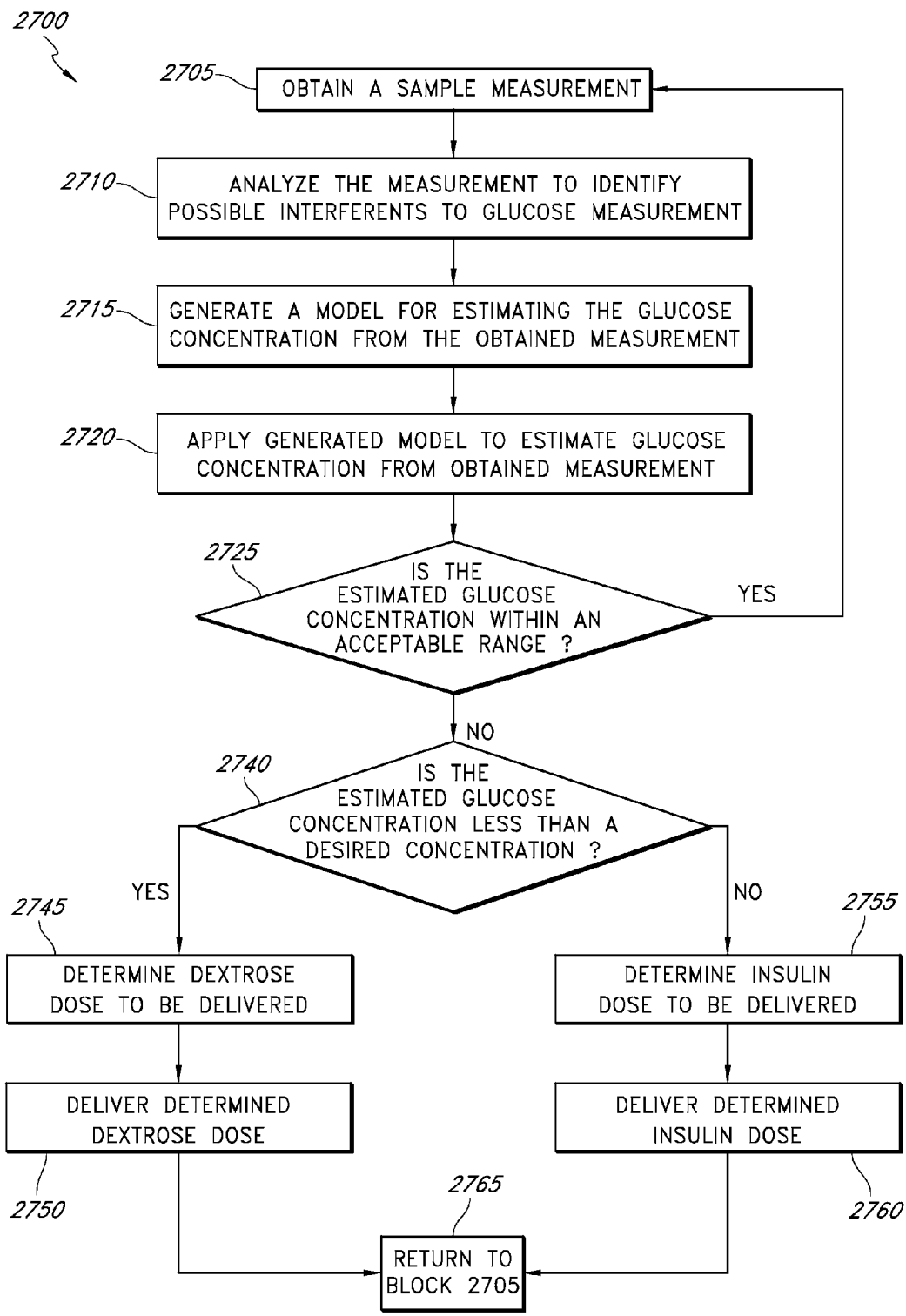
FIG. 27 is a flowchart that schematically illustrates an embodiment of a method of providing glycemic control.

FIG. 27 is a flowchart that schematically illustrates an example embodiment of a method 2700 of providing analyte control. The example embodiment is directed toward one possible implementation for glycemic control (including but not limited to tight glycemic control) and is intended to illustrate certain aspects of the method 2700 and is not intended to limit the scope of possible analyte control methods. In block 2705, a glucose monitoring apparatus (e.g., the monitoring apparatus 2632 of FIG. 26) draws a sample (e.g., a blood or blood plasma sample) from a sample source (e.g., a patient) and obtains a measurement from the sample (e.g., a portion of the drawn sample). The measurement may comprise an optical measurement such as, for example, an infrared spectrum of the sample. In block 2710, the measurement sample is analyzed to identify possible interferents to an estimation of the glucose concentration in the measurement sample. In block 2715, a model is generated for estimating the glucose concentration from the obtained measurement. In some embodiments, models developed from the algorithms describe above with reference to FIGS. 21-23 are used. The generated model may reduce or minimize effects of the identified interferents on the estimated glucose concentration, in certain embodiments. In block 2720, an estimated glucose concentration is determined from the model and the obtained measurement. In block 2725, the estimated glucose concentration in the sample is compared to an acceptable range of concentrations. The acceptable range can be determined according to a suitable glycemic control protocol such as, for example, a TGC protocol. For example, in certain TGC protocols the acceptable range can be a glucose concentration in a range from about 70 mg/dL to about 110 mg/dL. If the estimated glucose concentration lies within the acceptable range, the method 2700 returns to block 2705 to obtain the next sample measurement, which can be made after a relatively short or a relatively long time period has elapsed since the last measurement. For example, the next measurement can be taken within about one minute. In another example, the succeeding measurement can be taken after about one hour. In other examples, measurements are taken every fifteen minutes or less, every thirty minutes or less, ever forty-five minutes or less, etc. In some embodiments, a treatment substance (e.g. insulin or glucose) or drug can be continuously infused through the patient even if the estimated glucose concentration is already within the predetermined range. This can be advantageous when it is determined, for example, that without such a basal injection, the glucose concentration may drift outside the range, or when it is predicted that the glucose concentration would preferably be within another range.

In block 2725, if the estimated glucose concentration is outside the acceptable range of concentrations, then the method 2700 proceeds to block 2740 in which the estimated glucose concentration is compared with a desired glucose concentration. The desired glucose concentration can be based on, for example, the acceptable range of glucose concentrations, the parameters of the particular glycemic protocol, the patient's estimated glucose concentration, and so forth. If the estimated glucose concentration is below the desired concentration (e.g., the patient is hypoglycemic), a dose of dextrose to be delivered to the patient is calculated in block 2745. In some embodiments, this dose of dextrose can be delivered in addition to a low dose of the treatment substance (e.g. a drug, insulin, glucose, etc.) being delivered to the patient continuously at a steady rate. The calculation of the dose of dextrose may take into account various factors including, for example, one or more estimated glucose concentrations, presence of additional drugs in the patient's system, time taken for dextrose to be assimilated by the patient, and the delivery method (e.g., continuous infusion or bolus injection). In block 2750, a fluid delivery system (e.g., a system such as the optional subsystem 2780 shown in FIGS. 5 and 6) delivers the calculated dose of dextrose to the patient.

In block 2740, if the estimated glucose concentration is greater than the desired concentration (e.g., the patient is hyperglycemic), a dose of insulin to be delivered is calculated in block 2755. In some embodiments, this dose of insulin can be delivered in addition to a low dose of the treatment substance (e.g. a drug, insulin, glucose, etc.) being delivered to the patient continuously at a steady rate. The calculation of the dose of insulin may depend on various factors including, for example, one or more estimated glucose concentrations in the patient, presence of other drugs, type of insulin used, time taken for insulin to be assimilated by the patient, method of delivery (e.g., continuous infusion or bolus injection), etc. In block 2750, a fluid delivery system (e.g., the optional subsystem 2780 shown in FIGS. 5 and 6) delivers the calculated dose of insulin to the patient.

In block 2765, the method 2700 returns to block 2705 to await the start of the next measurement cycle, which can be within about one minute to about one hour (e.g., every fifteen minutes or less, every 30 minutes or less, every 45 minutes or less, etc.). In some embodiments, the next measurement cycle begins at a different time than normally scheduled in cases in which the estimated glucose concentration lies outside the acceptable range of concentrations under the glycemic protocol. Such embodiments advantageously allow the system to monitor response of the patient to the delivered dose of dextrose (or insulin). In some such embodiments, the time between measurement cycles is reduced so the system can more accurately monitor analyte levels in the patient.

Examples of Some Possible Additional or Alternative Analytes

Although examples of control and/or monitoring has been described in the illustrative context of glycemic control, embodiments of the systems and methods can be configured for control and/or monitoring of one or more of many possible analytes, in addition to or instead of glucose. Monitor and/or control of analytes can be particularly helpful in ICUs, which receive trauma patients. For example, another parameter that can be monitored is level of Hemoglobin (Hb). If the Hb level of a patient goes down without an apparent external reason, the patient could be suffering from internal bleeding. Indeed, many ICU patients (some estimate as many as 10%) suffer from what appears to be spontaneous internal bleeding that may not be otherwise detectable until the consequences are too drastic to easily overcome. In some embodiments, level of Hb can be measured indirectly, because its relationship to oxygen in the veins and arteries (at different points in the vasculature with respect to the heart and lungs) is understood. In some embodiments, the apparatus, systems and methods described herein can be useful for measuring a level of Hb.

Another parameter that can be monitored is lactate level, which can be related to sepsis or toxic shock. Indeed, high levels and/or rapid rise in lactate levels can be correlated to organ failure and oxygenation problems in the blood and organs. However, other direct measures of the biological effects related to lactate level problems can be difficult to measure, for example, only becoming measurable with a delay (e.g., 2-6 hours later). Thus, measurement of lactate level can help provide a valuable early warning of other medical problems. Indeed, if a problem with lactate levels is detected, a nurse or doctor may be able to prevent the correlated problems by providing more fluids.

Another parameter that can be monitored is central venous oxygen saturation (ScvO2). It can be advantageous to try to maintain an ScvO2 of 65-70% or greater in ICU patients (to help avoid sepsis, for example). In some embodiments, the apparatus, systems, and methods described herein can be useful for measuring a level of ScvO2.

Levels of lactate and ScvO2 in a patient can be used together to provide information and/or warnings to a health care provider, which can be especially useful in an ICU setting. For example, if lactate and ScvO2 are both high, a warning can be provided (e.g., automatically using an alarm). If lactate is high, but ScvO2 is low, a patient may benefit from additional fluids. If ScvO2 is high, but lactate is low, a cardiac problem may be indicated. Thus, a system that provides information about both lactate and ScvO2 can be very beneficial to a patient, especially, for example, in the ICU environment. Although lactate and ScvO2 have been used as an illustrative example, in other embodiments different combinations of analytes can be monitored and used to provide information and/or warnings (e.g., to a patient and/or health care provider).

Treatment Dosing System

Some implementations of a hospital's TGC protocol suffer from disadvantages. For example, in some healthcare environments (e.g., an ICU) healthcare providers such as nurses may not have readily available a paper insulin protocol that is sometimes used with IV insulin drips as part of the TGC protocol. As a result, such healthcare providers may have to "estimate" the next required insulin dose adjustment or may have to leave the patient's care in order to find the appropriate protocol. Further, when a new insulin dose is estimated, there is a risk that there may be a transcription error if the healthcare provider incorrectly inputs a new dose rate into an IV delivery pump. In such examples, an "estimated" rate is typically considered to be a deviation from the hospital's TGC protocol. Hospitals refine their insulin protocols and generally seek "high compliance" with the insulin protocol in order, for example, to improve quality of care. Accordingly, in some embodiments, the patient monitoring system (e.g. 2630 of FIG. 26) advantageously is configured to determine insulin doses in compliance with the TGC protocol.

In some embodiments, the insulin dose rate adjustments are determined from one or more previously-made glucose readings and the current glucose reading. One or both glucose readings can be determined by the patient monitoring system (e.g., by the monitoring apparatus 2632 of FIG. 26) and/or can be input to the patient monitoring system (e.g., via the HIS interface software 2650). Possible advantages of determining glucose readings with the system patient monitoring system include increased precision, reduced transcription errors, and near real-time access to the most current patient readings.

In some embodiments, the patient monitoring system may comprise a treatment dosing system including a treatment dosing software (e.g. insulin dosing software 2652 of FIG. 26). In some embodiments, the dosing software is configured to include a treatment dosing protocol (e.g. an insulin protocol and/or TGC protocol). For example, the dosing software may include the hospital's current, approved, local insulin protocol. If an adjustment to a patient's insulin dose should be made because of the patient's current glucose values, the patient monitoring system can be configured to calculate the next recommended (or suggested) treatment dose. The calculation of the next recommended treatment dose can be made at least in part based on the insulin dosing protocol for the particular hospital. In some embodiments, information related to the recommended treatment dose is output on the user interface (e.g., the user interface 2400 and/or a display graphic as shown in FIGS. 28A-F). For example, the user interface may display the current rate of dose and/or infusion, the dose type (e.g., bolus or steady (basal) rate), and the recommended dose. A healthcare provider may use the information output by the user interface to adjust the actual dose value, as needed by a specific patient condition, and may initiate infusion. In some embodiments, the patient monitoring system performs the calculation of recommended dose, makes the adjustments to the actual dose value, and provides this dose value to the patient, for example, by infusion with the fluid system kit 2634 of FIG. 26. In some embodiments, a control system (e.g. fluid system controller 405 of FIG. 4) in communication with the patient monitoring system can be configured to provide instructions to an infusion pump fluidically connected to the source of infusion fluid to start infusion. The control system may also be configured to adjust the pump rate of the infusion fluid to deliver the recommended dose to the patient at a basal rate or as a bolus injection.

Figure 28A:
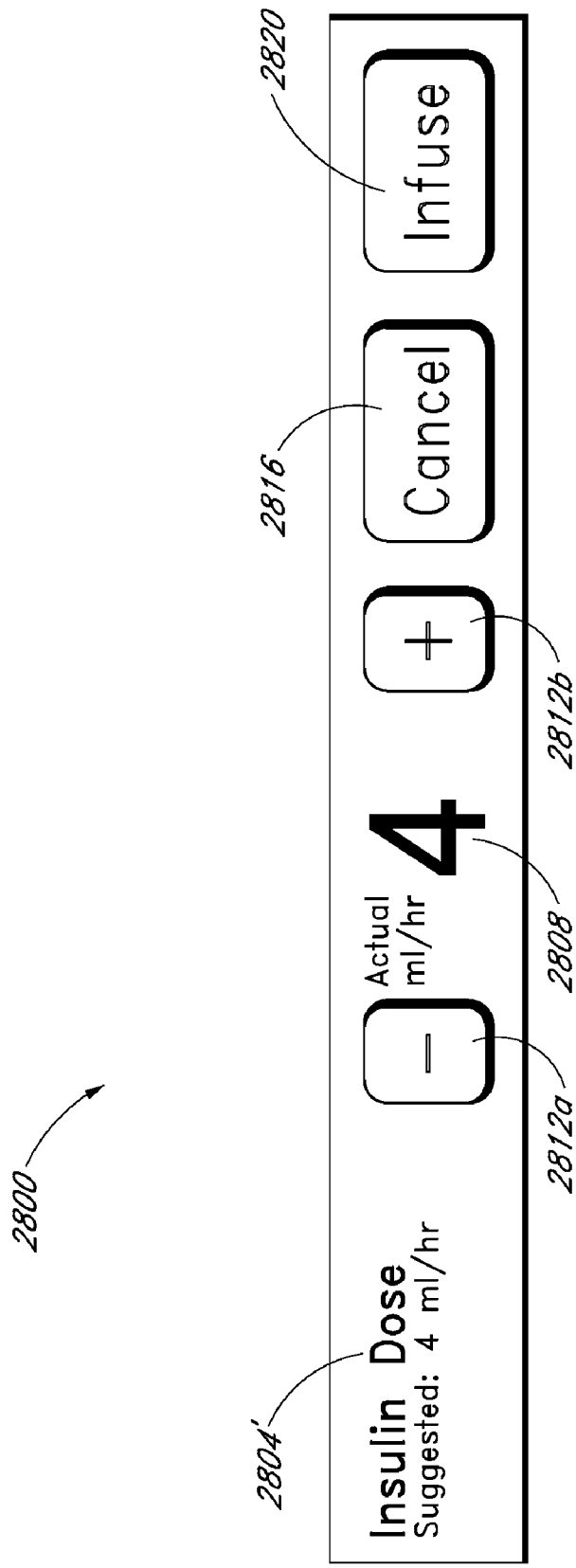
FIG. 28A schematically illustrates the visual appearance of an embodiment of a display graphic for providing information related to suggested and actual insulin dose for a patient.

FIG. 28A schematically illustrates an example of a display graphic 2800 for use with an embodiment of the user interface 2400. The display graphic 2800 can be output by, for example, a touchscreen display device so that a user can view the information on the display graphic 2800 and actuate suitable insulin dosing controls. In other embodiments, buttons, keys, a mouse, or other input device can be used instead of (or in addition to) touchscreen buttons. The embodiment of the display graphic 2800 shown in FIG. 28A includes a suggested dose graphic 2804, an actual dose graphic 2808, dose decrement and increment buttons 2812*a* and 2812*b*, and dosing control buttons 2816, and 2820. In other embodiments, the graphics and buttons schematically illustrated in FIG. 28A can be arranged differently, and the display graphic 2800 may include additional and/or different information and controls.

In this embodiment, the suggested dose graphic 2804 includes a suggested dose rate (e.g., 4 ml/hr) and a title graphic ("Insulin Dose"). As described above, the suggested dose rate can be calculated using the dosing software. The actual dose graphic 2708 includes a graphic representation of the current, actual dose (e.g., 4 ml/hr). In this embodiment, the suggested dose graphic 2808 and the actual dose graphic 2808 use alphanumeric graphics to output dose information. In other embodiments, the graphics 2804, 2808 may output dose information using, for example, trend graphs, bar or pie charts, symbols, and so forth. Advantageously, the values for the suggested and actual doses are displayed in a sufficiently large graphic font that a user can readily read the values, which reduces potential error in dosing the patient. In the example shown in FIG. 28A, a steady (basal) infusion rate (e.g., 4 ml/hr) is shown. In other embodiments, the display graphic 2800 may show a suggested bolus dose in addition to, or instead of, a steady state (basal) dose.

In this illustrative example, the actual dose and the recommended dose are the same (e.g., 4 ml/hr), but this is not a limitation. In a typical implementation, if the actual dose differs from the suggested dose, a user may adjust the actual dose value by actuating (e.g., pressing on a touchscreen) a decrement button 2812*a* and/or an increment button 2812*b* until the actual dose equals the suggested dose. The decrement and increment buttons 2812*a* and 2812*b* can be graduated in any suitable dose fractions (e.g., 0.1 ml/hr or some other amount).

The dosing control buttons include a cancel button 2816 and an infuse button 2820. The cancel button 2816 can be used to stop, and the infuse button 2820 can be used to actuate an infusion pump coupled to the infusion fluid source and start, infusion of the insulin dose. In other embodiments, additional or different infusion control buttons can be used.

In some embodiments, a control system (e.g. fluid system controller 405 of FIG. 4) configured to provide instructions to an infusion pump fluidically connected to a source of infusion fluid may comprise the display graphic 2800. A health care provider or a user may actuate the infusion pump or control the pump rate through the display graphic 2800 and the control system. Moreover, the patient monitoring system can allow a user to control delivery of infusion fluids using controls on a graphic user interface of the monitoring system, even if the infusion fluids are pumped by a separate system that is not contained within the same housing as the patient monitoring system. For example, the monitoring system can have built in wireless connectivity that can locate infusion pumps (e.g., those that have wireless capabilities) in the vicinity and establish communication with them. The monitoring system can allow a user to control those external infusion pumps through its own control interface (e.g., through its display graphic described herein). In some embodiments, the monitoring system can wirelessly search for an infusion pump delivering total parenteral nutrition (TPN), for example, and, with a handshake protocol, query that infusion pump for its hourly rate. This information can affect various outputs from the system (including, for example, a dose or rate suggested by the insulin dosing algorithm). The monitoring system can do the same with an infusion pump that is delivering insulin, and provide remote control of that pump through the monitoring system's graphic user interface, for example.

The display graphic 2800 can be output on to any suitable monitor or output device (e.g., a touchscreen display). For example, in some embodiments, the display graphic 2800 is displayed on the user interface 2400, e.g., adjacent an outer boundary of the example Ul graphic shown in FIGS. 24 and 25. In other embodiments, the display graphic 2800 is shown instead of the trend indicators 2816. In yet other embodiments, the display graphic 2800 is output with optional patient identification information. Many variations are possible.

Accordingly, certain embodiments of the patient monitoring system (e.g. system 2630 of FIG. 26) can be used as an infusion pump, actuatable using an embodiment of the display graphic 2800. In certain such embodiments, a healthcare provider advantageously will be able to control insulin delivery through the same patient IV access line. Embodiments of patient monitoring system that are configured to include a treatment dosing protocol (e.g. insulin protocol and/or a TGC protocol), to determine a patient treatment dose based on patient glucose reading(s), and to deliver a recommended treatment dose to the patient via a fluidic system (e.g. the fluid system kit 26134 of FIG. 26 or via an infusion pump, for example, infusion pump 518 of FIG. 5) may have one or more of the following potential benefits: increased compliance with a treatment dosing protocol, reduction in treatment dosing errors, time savings for healthcare providers, and greater IV access efficiency by delivery of some or all TGC-related medicaments through a common IV line (e.g., a proximal port of a central venous catheter or a lumen of a peripherally inserted central catheter).

FIGS. 28B-28F schematically illustrate embodiments of a display graphic comprising a graphic user interface. These figures illustrate how an analyte detection system can be configured to have a numerical display mode (see, e.g., 2822) and a trend display mode (see, e.g., 2824) to display the present and/or historical concentration of one or more analytes (e.g. glucose, ScvO2, lactate, etc.). Similar to the embodiment illustrated in FIG. 28A, the embodiments illustrated in FIGS. 28B-28F can also provide information related to suggested and/or actual insulin dose and enable the user or health care provider to control (e.g., start, cancel, increase, decrease, etc.) delivery of insulin.

Figure 28B:
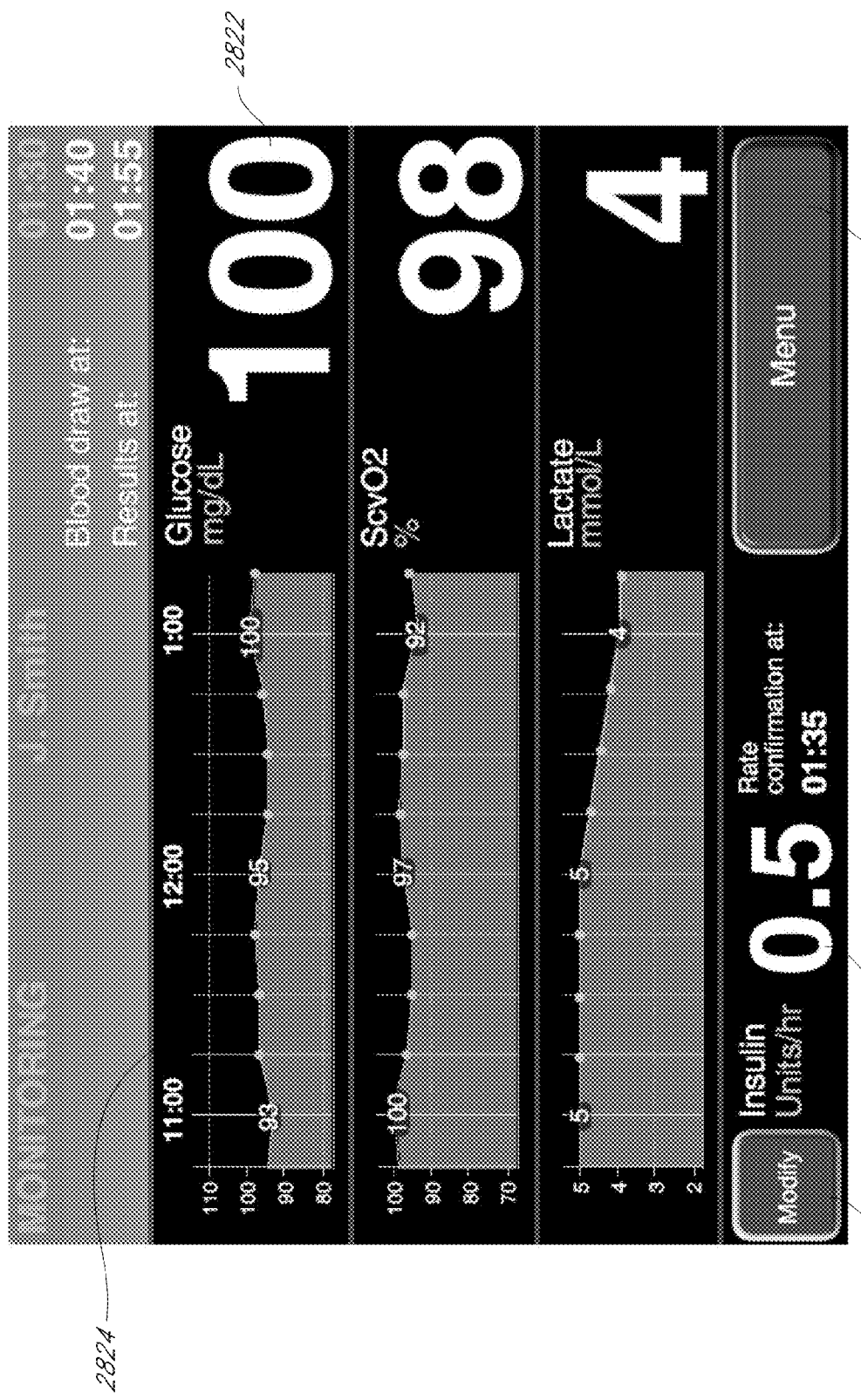
FIGS. 28B-28F schematically illustrate embodiments of a display graphic comprising a graphic user interface and illustrate examples of numerical display mode, trend display mode, suggested and actual insulin dose information, and controls for delivery of insulin.

FIG. 28B shows an example of an embodiment of the display graphic 2800. In this example, the concentrations of three analytes; glucose, ScvO2 and lactate are displayed on a screen of the display graphic 2800. The concentration can be displayed as a number (see, e.g., 2822) or as a trend line (see, e.g., 2824), or both. In some embodiments, the concentration can be displayed as a trend graph of the concentration versus time. The embodiments illustrated in FIG. 28B can also display the rate at which an infusion substance (e.g. insulin) is being delivered to the patient. For example reference numeral 2808 indicates that the amount of insulin being infused is 0.5 units/hr. In some embodiments, the display can be refreshed periodically to display the most current measured and/or stored values. The display can indicate when the last measurement was taken and/or the last time the display was refreshed (see, e.g., the text "rate confirmation at: 01:35").

The example illustrated in FIG. 28B also illustrates a button 2812 that can be used to modify the rate at which insulin is being infused or otherwise control an analyte level. The display graphic, 2800 of FIG. 28B can comprise additional buttons such as the Menu button 2828, which can provide additional functionalities.

Figure 28C:
Figure 28D:
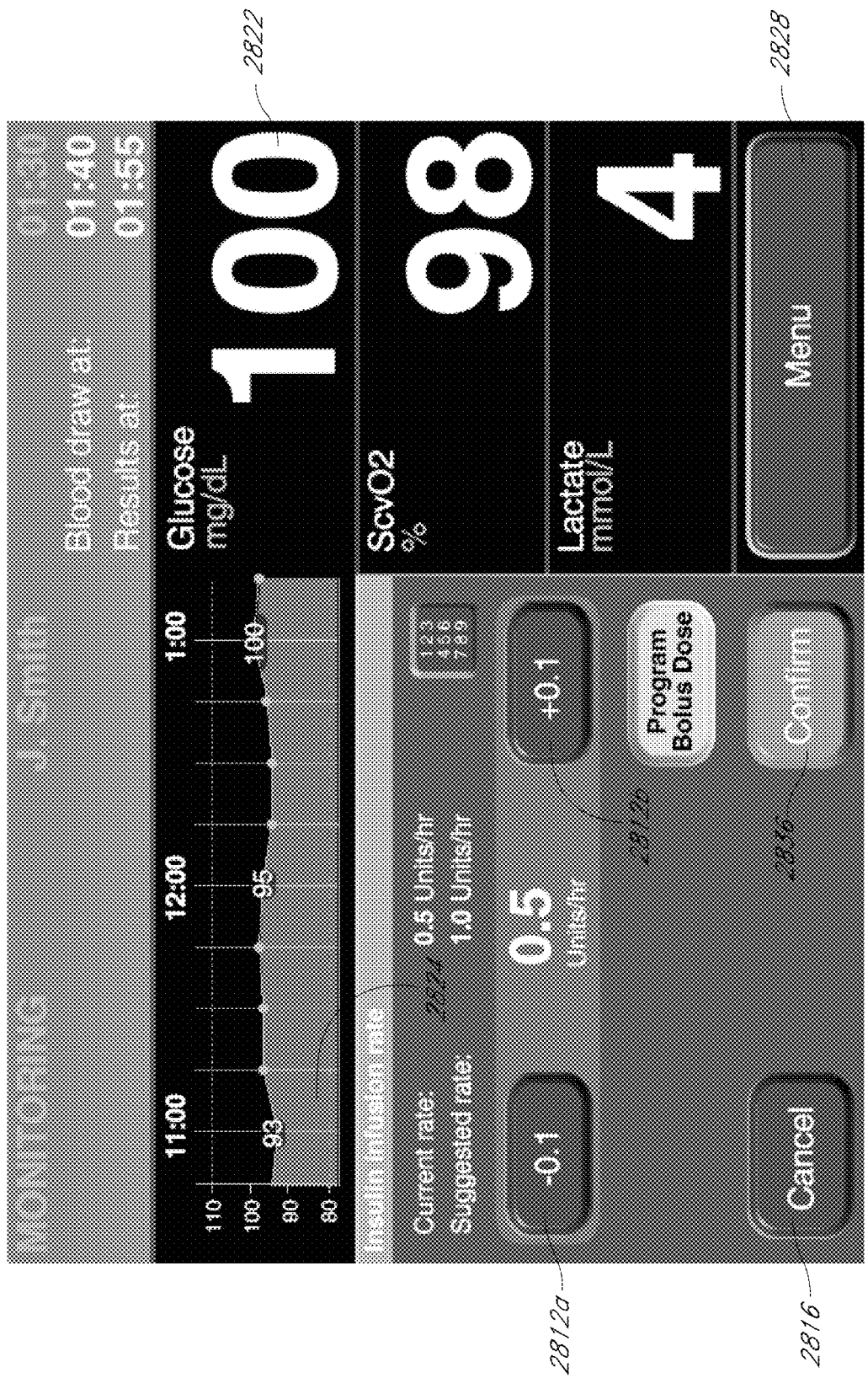
Figure 28E:
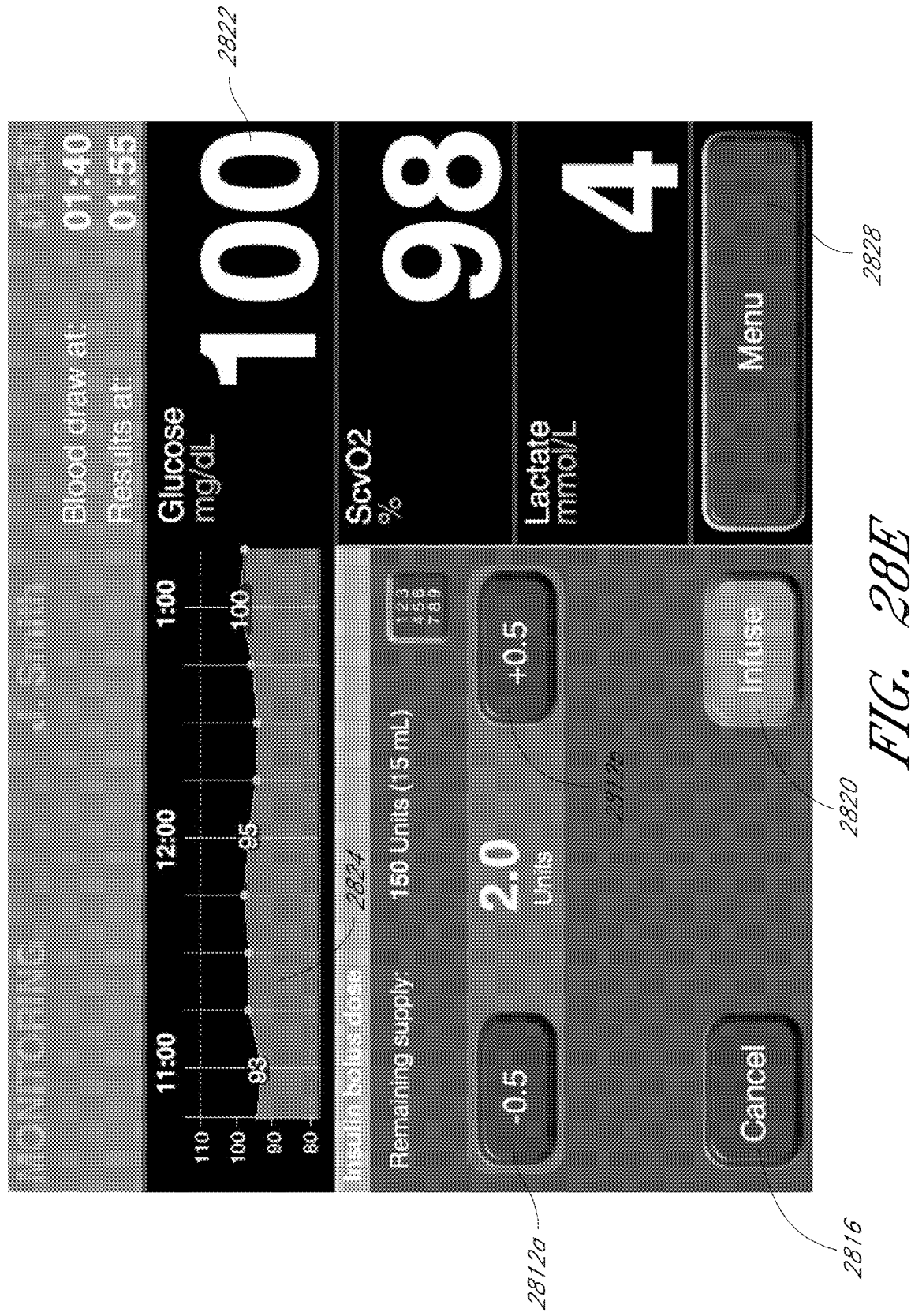
Figure 28F:

A user or a health care provider can activate the button 2812 of FIG. 28B to control infusion (e.g., modify the rate at which insulin or another infusion substance is delivered). In some embodiments, activating the button 2812 can display a secondary screen as illustrated in FIG. 28C. The secondary screen may display the current rate at which insulin is being infused and the suggested rate at which insulin should be infused. The secondary screen may comprise a dose increment button 2812a and a dose decrement button 2812b to increase or decrease the rate at which insulin is being infused. In some embodiments, a keypad may be provided so that the user or health care provider can input the value for the insulin infusion rate. The secondary screen may comprise controls (e.g. cancel button 2816 or confirm button 2836) to cancel or confirm the change in the insulin infusion rate. In the example embodiments illustrated in FIGS. 28C and 28D, a bolus dose button 2832 can be provided to program a bolus dose that can be delivered to the patient. If the user or the health care provider activates the bolus dose button 2832, the display graphic can display a bolus dose screen which displays a value for the bolus dose as illustrated in FIG. 28E. In some embodiments, the bolus dose screen may display the remaining supply of insulin as illustrated in FIG. 28E. The user or the health care provider can change the amount of insulin bolus to be delivered and instruct the system to deliver the bolus amount by activating the button 2820. A confirmation screen 2840 may be displayed on the display graphic 2800 as illustrated in FIG. 28F to confirm that the user or health care provider wished to proceed with the bolus delivery. The embodiments illustrated in FIGS. 28B-28F can comprise a touch screen to accept instructions and input from the user or the health care provider.

Although the insulin dosing software 2652 schematically illustrated in FIG. 26 and the display graphic 2800 schematically illustrated in FIGS. 28A-28F are shown and described with respect to delivery of an insulin dose, this is not a limitation, and in other embodiments, the dosing software 2652 and the display graphic 2800 can be used to provide suitable doses and information related thereto for any suitable item or items administered to a person, such as medicaments, drugs, foods or herbs, whether administered orally, intravenously, topically, etc. The dosing software 2652 of FIG. 26 may calculate a recommended dose based (at least in part) on readings of suitable analyte(s) of interest in the patient (e.g., glucose in the case of insulin dosing). The readings can be performed by the system 2630 (e.g., with the monitoring apparatus 2632) and/or by other analyte detection systems.

Examples Of Calculating Treatment Dose

In the method for providing glycemic control schematically illustrated in FIG. 27, the dextrose or insulin dose can be determined by a treatment dosing protocol. In some embodiments, the treatment dosing protocol may determine the amount of dextrose or insulin to be delivered by comparing the currently estimated value of glucose concentration with a target or desired value of glucose concentration. In some embodiments, the treatment dosing protocol may determine the treatment dose based on one or more of the following factors: the patient's medical condition and medical history, the effectiveness of the treatment dose, the presence or absence of other analytes, other drugs being administered, etc.

For example, in some embodiments, different types of insulin, listed in the table below, having different activation properties can be used to control the concentration of glucose in patients with hyperglycemia.

| Quick-acting, such as the insulin analog lispro | starts working: 5 to 15 mins; | active: 3 to 4 hrs. |
| Short-acting, such as regular insulin | starts working: 30 mins; | active: 5 to 8 hrs. |
| Intermediate-acting, such as NPH insulin, or lente insulin | starts working: 1 to 3 hrs; | active: 16 to 24 hrs. |
| Long-acting, such as ultralente insulin | starts working: 4 to 6 hrs; | active: 24 to 28 hrs. |
| Insulin glargine and Insulin detemir | start working: 1 to 2 hrs; | active, w/o peaks or dips: 24 hrs. |
| A mixture of NPH and regular insulin | starts working: 30 mins; | active: 16 to 24 hrs. |

In these embodiments, the insulin delivery rate can be calculated based on factors such as the type of insulin, the time taken by the insulin to start working, the time it remains active in the body, etc. In some embodiments the amount of treatment dose provided to control the analyte concentration can be adjusted no more frequently than once every hour. In these embodiments, determining the treatment dose only on the basis of the comparison of the currently estimated value of glucose concentration with a desired value of glucose concentration and a few other factors may be insufficient to accurately determine the treatment dose required to provide TGC. Thus treatment dosing protocols that determine the treatment dose by taking an average of two or more sequential glucose values or by calculating a rate of change of the glucose concentration over a period of time or both may be effective in providing glycemic control.

Figure 29:
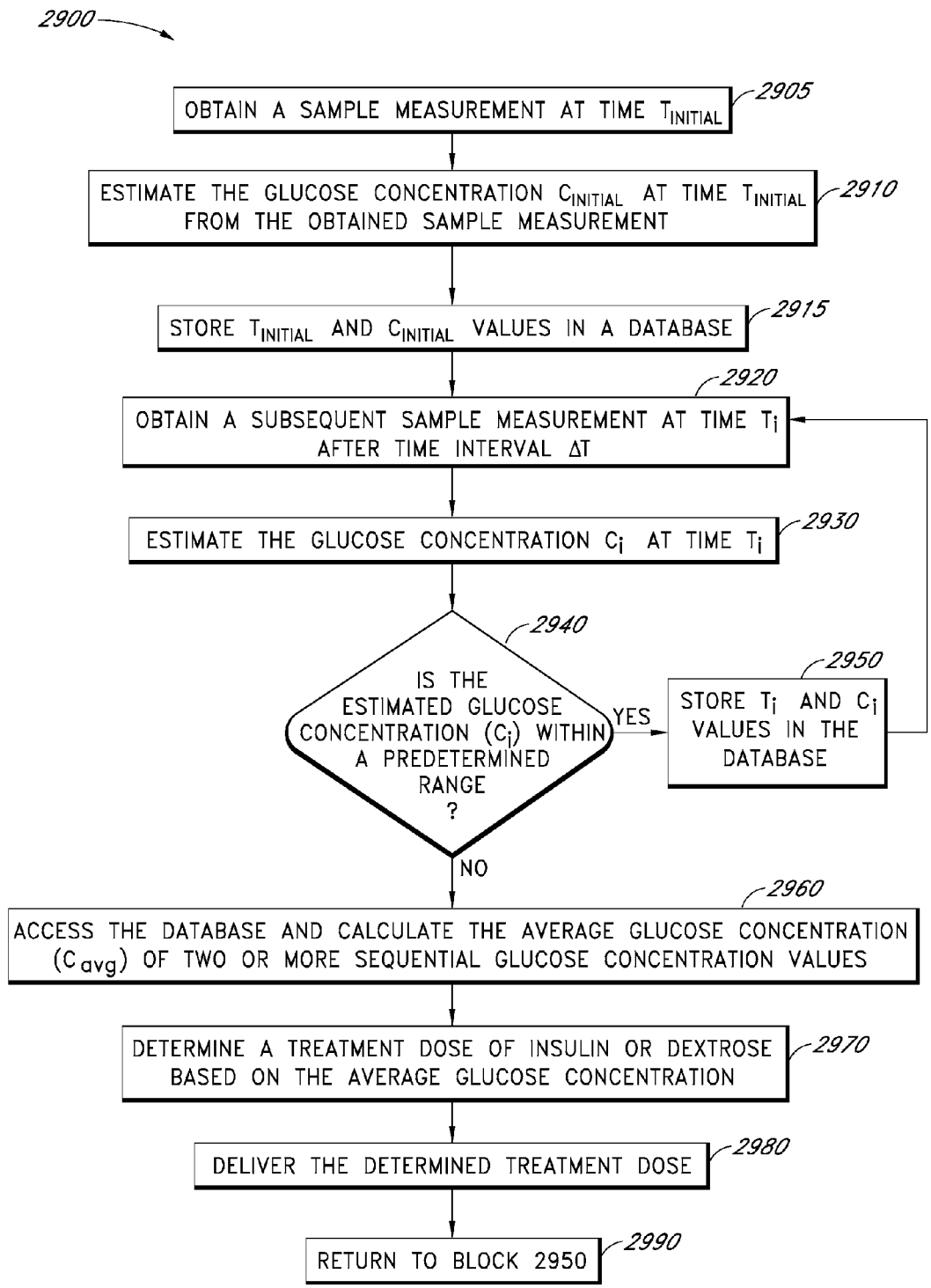
FIG. 29 is a flowchart that schematically illustrates an embodiment of a method of determining a treatment dose based on the average concentration of an analyte.

FIG. 29 is a flowchart that schematically illustrates an embodiment of a method 2900 of determining the treatment dose based on the average concentration of an analyte (e.g. glucose). In block 2905, an analyte monitoring system (e.g., the monitoring apparatus 2632 of FIG. 26) comprising a fluidic system (e.g. the fluid system kit 2634 of FIG. 26) obtains a sample of bodily fluid (e.g., a blood or blood plasma sample) from a source of bodily fluid (e.g., a patient) at an initial time $T_{initial}$. In some embodiments, the analyte monitoring system may further comprise an analyte detection system that spectroscopically analyzes the sample and obtains a measurement from the sample. The measurement may comprise an optical measurement such as, for example, an infrared spectrum of the sample. In block 2910, the initial concentration ($C_{initial}$) of an analyte (e.g. glucose) in the sample is estimated from the measurement by using any of the methods described above. In block 2915, the initial concentration $C_{initial}$ at time $T_{initial}$ is stored in an internal or an external database.

In some embodiments, the database can be located in a processing system (e.g. a computer system 2646 of FIG. 26) in electrical communication with the monitoring system. In some embodiments, the initial concentration $C_{initial}$ at time $T_{initial}$ can be stored in a memory location of a memory device. The memory device can be located in the monitoring system or the processing system. In some embodiments, the memory device can be located external to the monitoring system and be in electrical communication with the monitoring system. In some embodiments, an initial treatment dose $D_{initial}$ can be determined and delivered to the patient if the initial concentration $C_{initial}$ of the analyte is not within a predetermined range. The initial treatment dose $D_{initial}$ may also be stored in the database or the memory location.

At a later time $T_i$, a subsequent sample measurement is obtained as shown in block 2920. The time $T_i$ may occur after a time interval $\Delta T$ from time $T_{i-1}$ when a sample measurement was previously obtained. For example, a first sample measurement can be obtained at a first time $T_1$ which occurs after a time interval $\Delta T$ from the initial time $T_{initial}$ and a second sample measurement can be obtained at a second time $T_2$ which occurs after a time interval $\Delta T$ from the first time $T_1$ and so on. The time interval $\Delta T$ may range anywhere from 5 minutes to 15 minutes. In some embodiments, the time interval $\Delta T$ may be less than 5 minutes or greater than 15 minutes. In block 2930, the concentration $C_i$ of the same analyte at time $T_i$ is estimated from the obtained sample measurement. The method 2900 then proceeds to block 2940 wherein the estimated concentration $C_i$ of the analyte is compared to a predetermined range. The predetermined range can be determined by taking into account various factors such as a patient's medical condition, the medications and drugs being administered to the patient, etc. In some embodiments, the predetermined range is a glucose concentration in a range from about 70 mg/dL to about 110 mg/dL. If in block 2940, the concentration $C_i$ of the analyte is within the predetermined range, then the method 2900 moves to block 2950 where the value of the estimated concentration $C_i$ of the analyte at time $T_i$ is stored in the database or the memory location. The method 2900 then returns to block 2920 to obtain a next sample measurement after a time interval $\Delta T$.

However, if in block 2940, the estimated concentration of the analyte $C_i$ is determined to be not within the predetermined range, then the method 2900 proceeds to block 2960 wherein an average concentration $C_{avg}$ of the analyte is calculated. In some embodiments, the average concentration $C_{avg}$ can be calculated by taking an arithmetic mean of the estimated concentration $C_i$ and one or more previous concentration values stored in the database or the memory location and is given by the equation:

$$C_{avg} = \frac{C_i + \sum_{k=1}^{n} C_{i-k}}{n+1},$$

where n is an integer greater than or equal to 1.

In the above equation, the variable $C_i$ corresponds to the currently estimated concentration value and the variables $C_{i-1}, C_{i-2}, \ldots, C_{i-n}$ correspond to the concentration values previously obtained. In some embodiments, the average concentration $C_{avg}$ can be calculated by taking a weighted average of the estimated concentration $C_i$ and one or more previous concentration values and is given by the equation:

$$C_{avg} = \frac{w_i C_i + \sum_{k=1}^{n} w_{i-k} C_{i-k}}{w_i + \sum_{k=1}^{n} w_{i-k}},$$

where n can be an integer greater than or equal to 1.

The weights $w_i$ and $w_{i-k}$ can be determined in a variety of ways. For example, in some embodiments the weight $w_i$ associated with the current estimated concentration value $C_i$ may be greater than the weights $w_{i-k}$ associated with the previous concentration values. In some embodiments, a greater weight can be assigned to a concentration value that is either abnormally high or abnormally low. In some embodiments, by contrast a smaller weight can be assigned to a concentration value that is either abnormally high or abnormally low.

The method 2900 then proceeds to block 2970 where a treatment dose of dextrose or insulin can be determined according to a glycemic control protocol based at least in part on the calculated average concentration $C_{avg}$. In some embodiments, the treatment dose of dextrose or insulin can be determined according to a glycemic control protocol based on the calculated average concentration $C_{avg}$ and variety of factors such as patient's sensitivity to the treatment drug (e.g. insulin), the treatment dosing history, the effectiveness of the treatment dose, the presence or absence of other analytes, other drugs being administered, etc. In some embodiments, the determined treatment dose can be displayed to a health care provider on a display graphic (e.g. display graphic 2800 of FIG. 28). In block 2980 the determined treatment dose can be delivered to the patient by a fluid delivery system or a fluid infusion system (e.g., a system such as the subsystem 2780 shown in FIGS. 5 and 6). In some embodiments, a control system (e.g. fluid system controller 405 of FIG. 4) can be configured to provide instructions to an infusion pump fluidically connected to a source of infusion fluid to start infusion. The control system may also be configured to adjust the pump rate of the infusion fluid to deliver the recommended treatment dose to the patient at a basal rate or as a bolus injection. In some embodiments, the treatment dose can be delivered to the patient in addition to a low dose of the treatment drug (e.g. insulin or glucose) being delivered to the patient continuously at a steady rate. In some embodiments, the healthcare provider may actuate the infusion pump fluidically connected to a source of infusion fluid through a graphic user interface (e.g. display graphic 2800 of FIG. 28). In some embodiments, the health care provider may provide instructions regarding the pump rate to the infusion pump through a graphic user interface (e.g. display graphic 2800 of FIG. 28). In block 2990 the method 2900 returns to block 2950 where the value of the estimated concentration $C_i$ of the analyte at time $T_i$ is stored in the database or the memory location.

Figure 30:
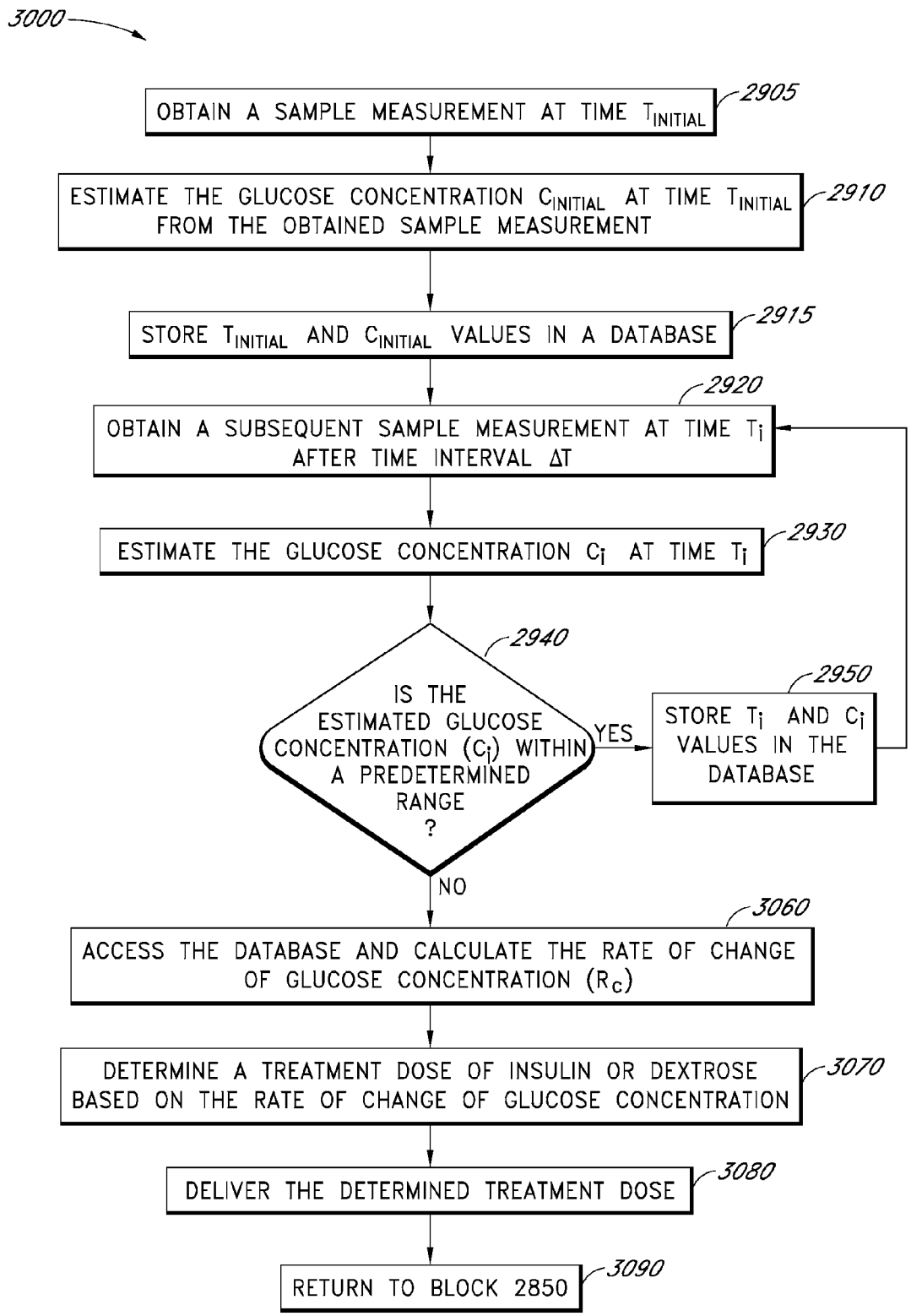
FIG. 30 is a flowchart that schematically illustrates an embodiment of a method of determining a treatment dose based on the rate of change of the concentration of an analyte.

FIG. 30 is a flowchart that schematically illustrates an embodiment of a method 3000 of determining the treatment dose based on the rate of change of the concentration of an analyte (e.g. glucose). The method 3000 differs from the method 2900 in that if in block 2940, the estimated concentration of the analyte $C_i$ is determined to be not within the predetermined range, then the method 3000 proceeds to block 3060 where a rate of change of the concentration $R_c$ of the analyte is calculated. The rate of change of the concentration of the analyte $R_c$ can be calculated in a variety of ways. In some embodiments, the rate $R_c$ can be calculated from the current estimated concentration of the analyte $C_i$ at time $T_i$ and the previously determined concentration of the analyte $C_{i-1}$ at time $T_{i-1}$ stored in the database or memory location and is given by the following equation:

$$R_c = \frac{C_i - C_{i-1}}{T_i - T_{i-1}}$$

In some embodiments, the rate $R_c$ can be calculated from the currently estimated concentration of the analyte $C_i$ at time $T_i$ and several previously determined values for the concentration of the analyte stored in the database or memory location. In the method 3000, the treatment dose is determined using a glycemic control protocol based at least in part on the rate of change $R_c$ of the concentration of the analyte as shown in block 3070. In some embodiments, determining the treatment dose based on the rate of change $R_c$ of the concentration of the analyte can ensure that the treatment dosing protocol responds to certain extreme conditions such as rapid change in the concentration of the analyte (e.g. glucose). In some embodiments, such rapid change in the concentration of the analyte can indicate that the patient's medical condition is unstable or critical. In some embodiments, the rapid change in the concentration can be an indicator of a failure of the measurement system or a part thereof.

Figure 31A:
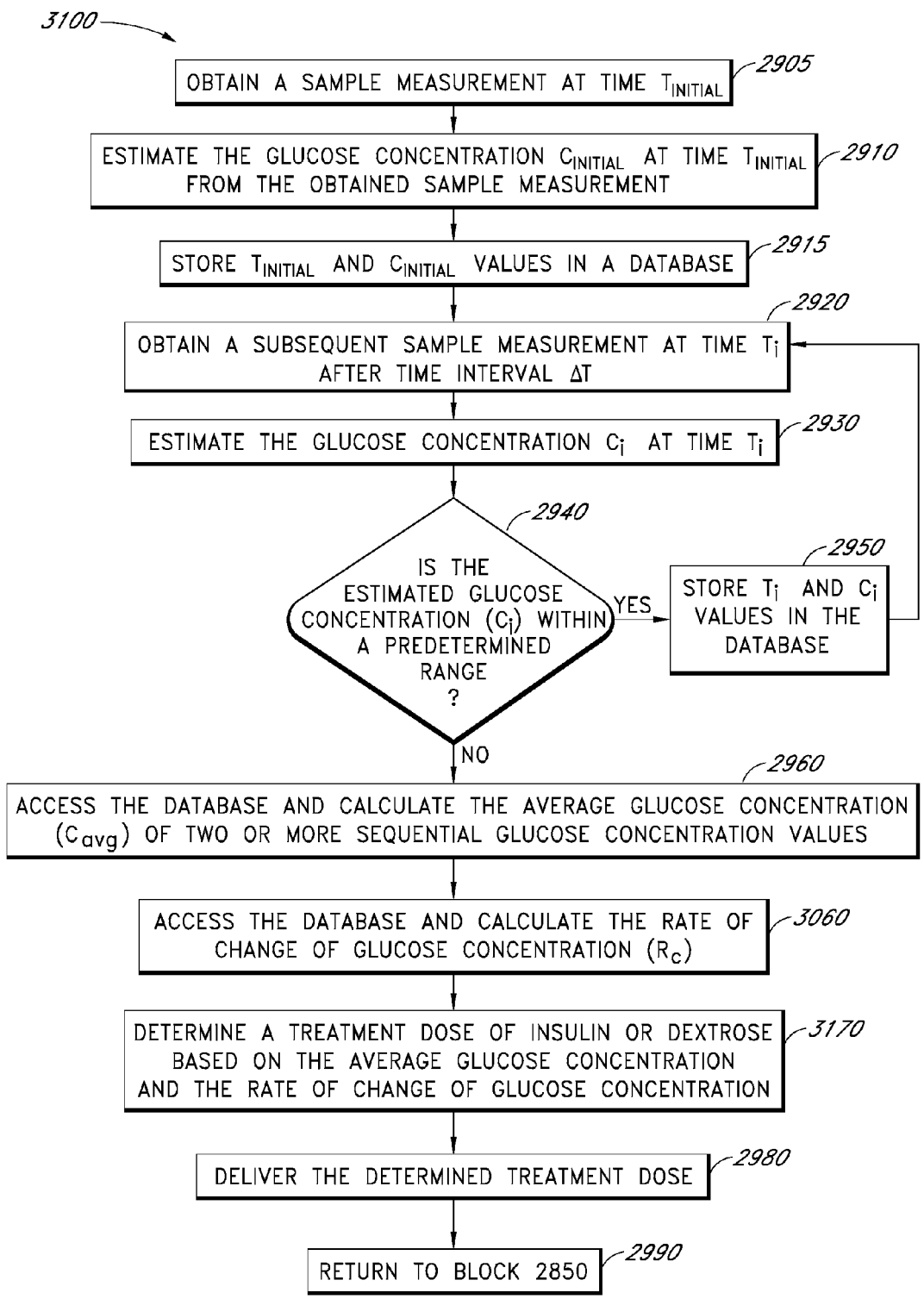
FIG. 31A is a flowchart that schematically illustrates an embodiment of a method of determining a treatment dose based on the average concentration of an analyte and the rate of change of the concentration of the analyte.
Figure 31B:
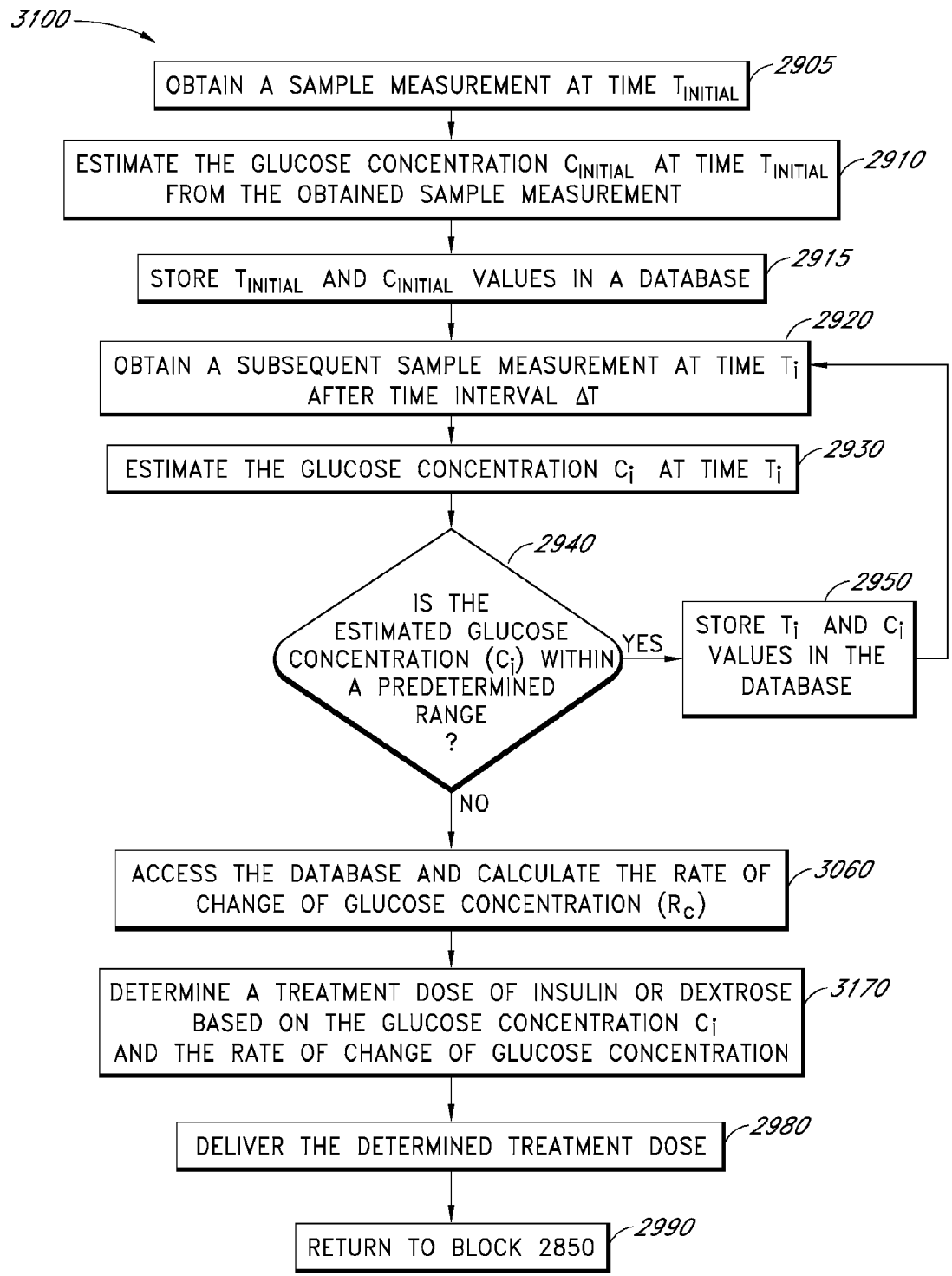
FIG. 31B is a flowchart that schematically illustrates an embodiment of a method of determining a treatment dose based on the current concentration of an analyte and the rate of change of the concentration of the analyte.

FIG. 31A is a flowchart that schematically illustrates an embodiment of a method 3100 of determining the treatment dose based on the current estimated concentration or the average concentration of an analyte (e.g. glucose) and the rate of change of the concentration of the analyte. The method 3100 determines the treatment dose using a glycemic control protocol based at least in part on the average concentration $C_{avg}$ of the analyte and the rate of change of the concentration $R_c$ of the analyte as shown in block 3170. The average concentration $C_{avg}$ and the rate of change of the concentration $R_c$ can be calculated by one or more of the methods described above. In some embodiments, as illustrated in FIG. 31B, the treatment dose can be determined using a glycemic control protocol based at least in part on the currently estimated concentration $C_i$ and the rate of change of the concentration $R_c$ of the analyte.

Treatment Dose Feedback System

As described above, in some embodiments, the analyte monitoring system can be configured to control the concentration of one or more analyte by infusing a treatment dose calculated by a treatment dosing protocol. However, the analyte monitoring system or the healthcare provider may not have feedback regarding the effectiveness of the treatment dose suggested by the treatment dosing protocol. Thus it may be advantageous to have a system that can both: (i) predict the concentration of an analyte (e.g. glucose) at a future time based on the treatment dose suggested by the treatment dosing protocol; and (ii) provide feedback to the healthcare provider.

As described above, an analyte monitoring apparatus comprising a fluidic system (e.g. the fluid system kit 2634 of FIG. 26) can obtain a sample of bodily fluid (e.g., a blood or blood plasma sample) from a source of bodily fluid (e.g., a patient) and estimate the concentration of one or more analytes in the sample several times during an hour. The concentration of the one or more analytes can be stored in a measurement history that can be accessed later. The measurement history may comprise one or more stored databases or memory locations.

Figure 32:
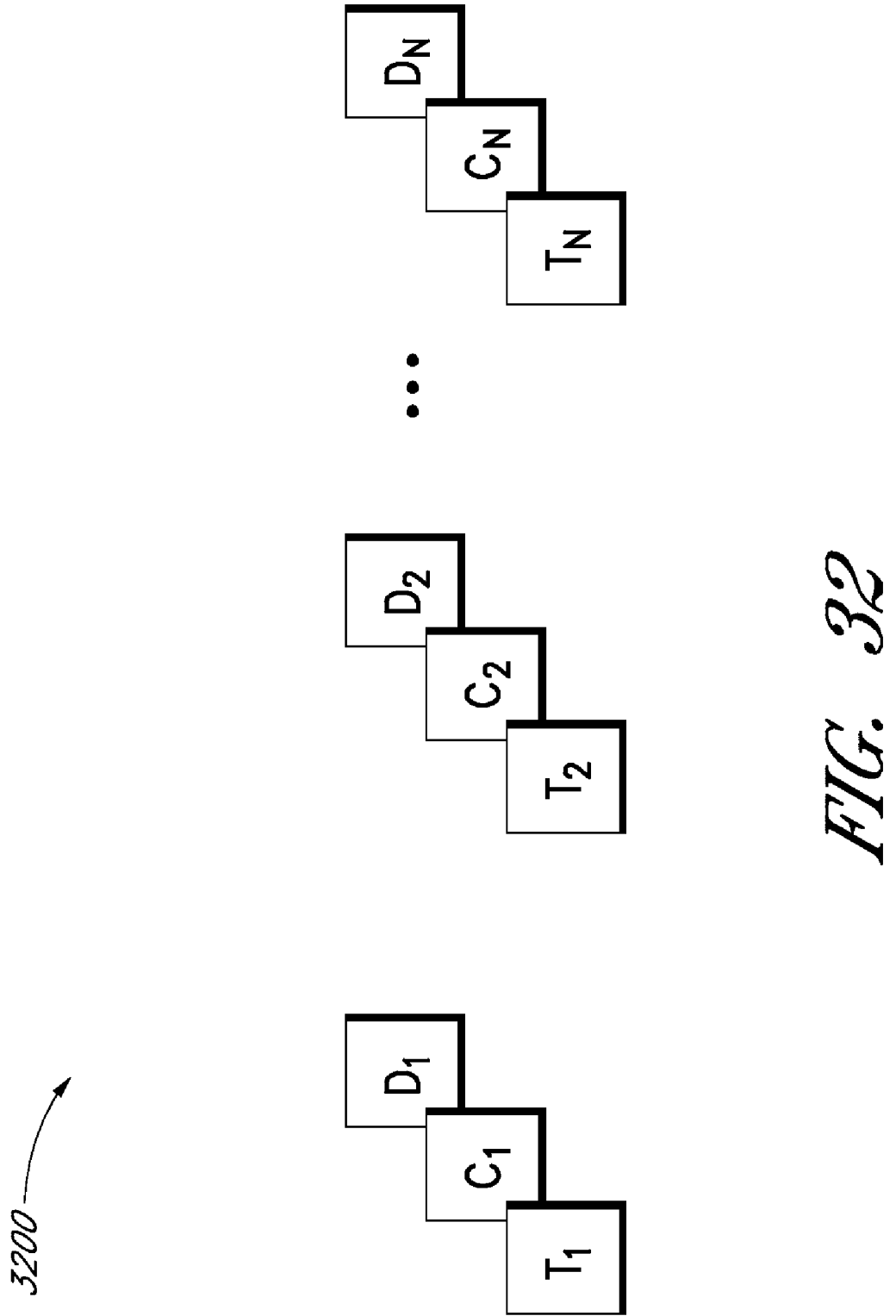
FIG. 32 schematically illustrates an embodiment of a history that stores the previously determined values for the concentration of an analyte and the values for a treatment dose previously administered.

In some embodiments, the measurement history can be located in a processing system (e.g. a computer system 2646 of FIG. 26) in electrical communication with the monitoring system. In some embodiments, the concentration of the one or more analytes can be stored in a memory location of a memory device. The memory device can be located in the monitoring system or the processing system. In some embodiments, the memory device can be located external to the monitoring system and be in electrical communication with the monitoring system. FIG. 32 illustrates an embodiment of a measurement history 3200 that stores the time of measurement $T_i$, the estimated or measured concentration of an analyte (e.g. glucose) $C_i$ and the treatment dose $D_i$ (of insulin or sugar, for example) administered to the patient. In some embodiments, the measurement history 3200 may store information regarding estimated or measured concentration of other analytes. Other embodiments of the measurement history are also possible.

Figure 33:
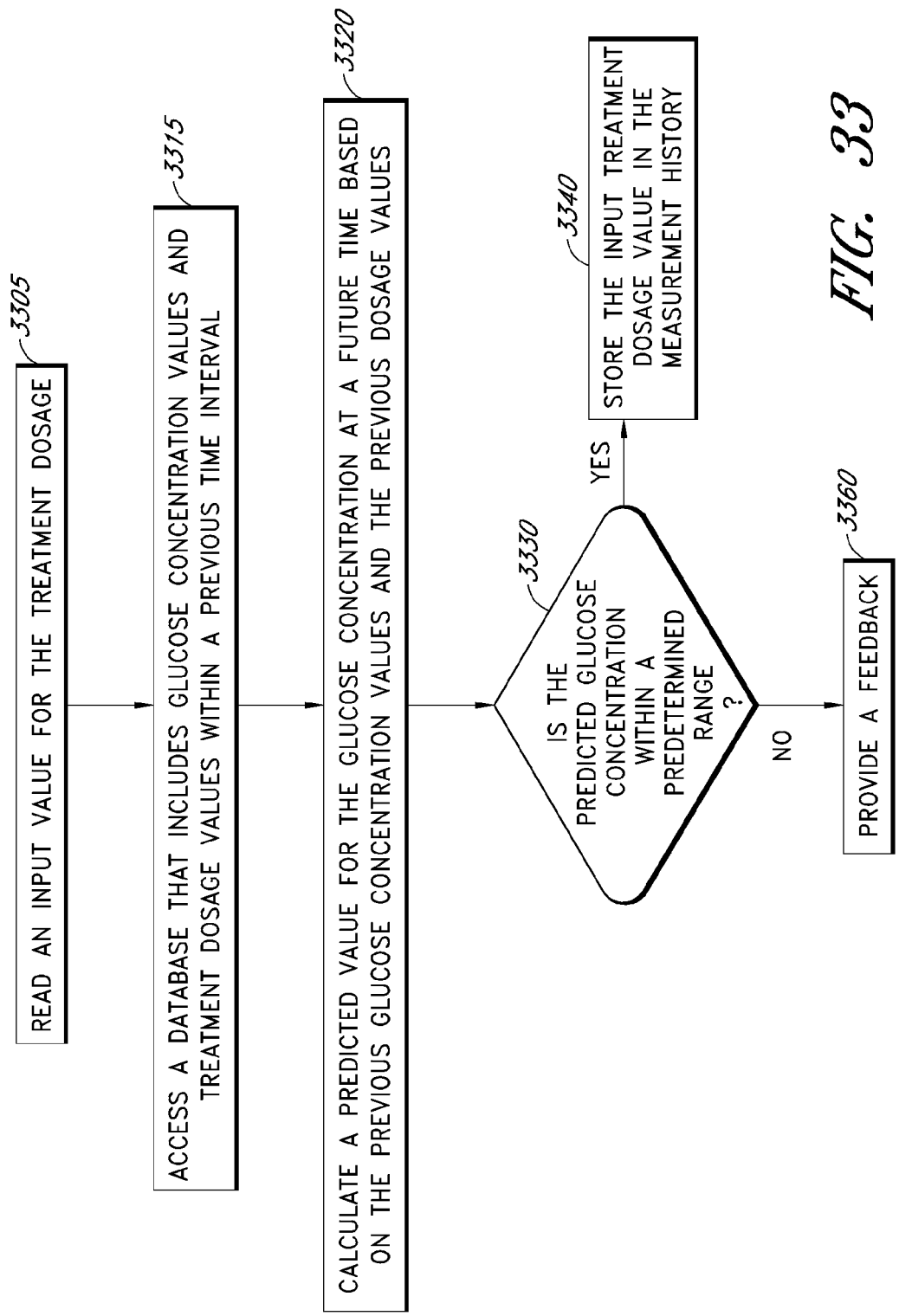
FIG. 33 is a flowchart that schematically illustrates steps in a method of providing feedback regarding a treatment dose.
Figure 34:
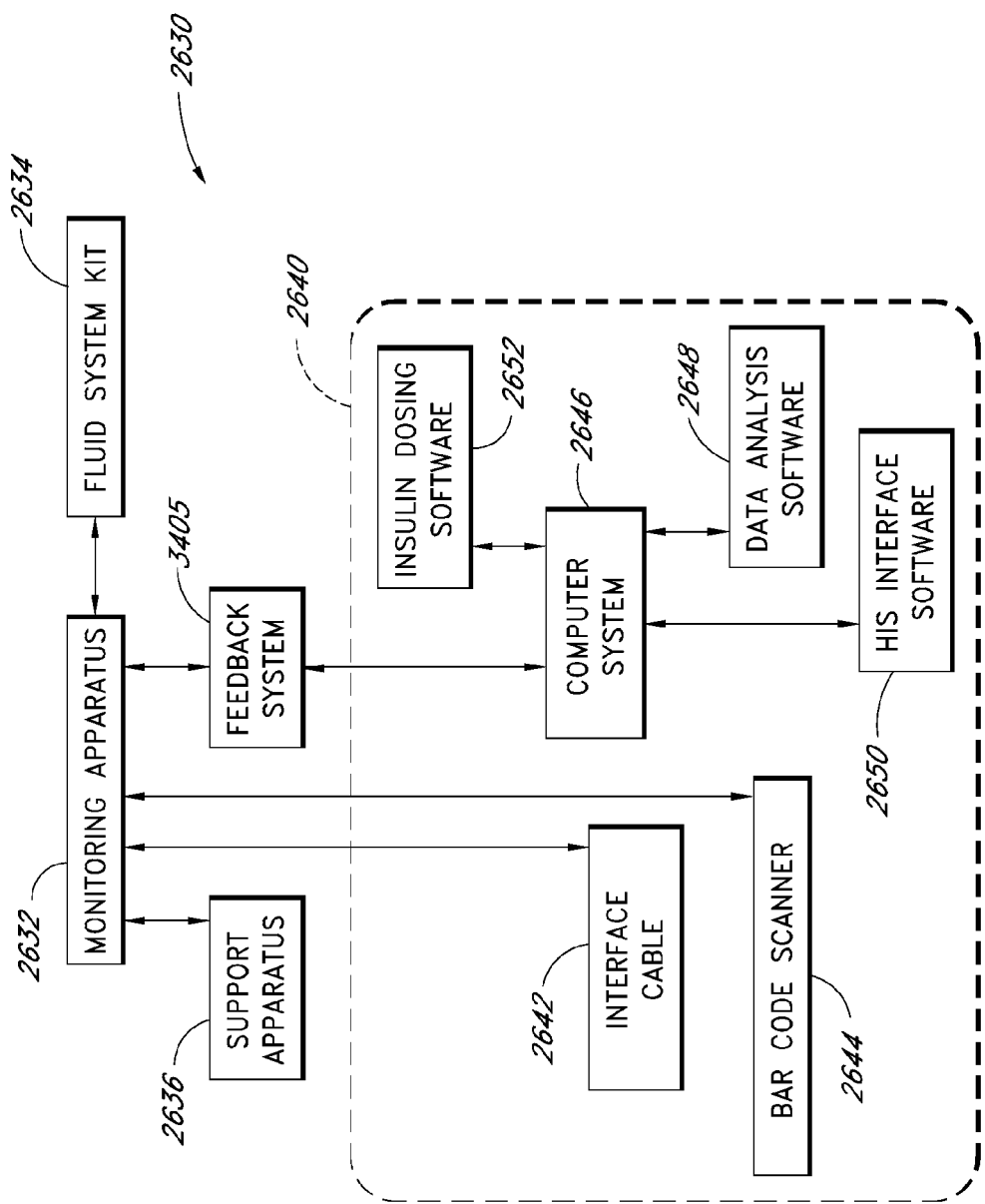
FIG. 34 schematically depicts a feedback system and the relationship between the feedback system and the other components and/or aspects of the patient monitoring system.

If the estimated or measured concentration of an analyte (e.g. glucose) is not within an acceptable range, then a healthcare provider may administer a treatment dose based on a treatment dosing protocol to bring the concentration of the analyte within the acceptable range. FIG. 33 schematically illustrates steps in a method to provide feedback to the monitoring and/or dosing system (and, e.g., the healthcare provider) regarding the effectiveness of the treatment dose suggested by the treatment dosing protocol. Feedback can be provided by a feedback system 3405 illustrated in FIG. 34 which is in electronic communication with the analyte monitoring apparatus 2632 and/or the computer system 2646 of FIG. 34. Referring to FIG. 33, in block 3305 the feedback system 3405 reads the treatment dose input by the healthcare provider or determined by the treatment dosing software. The treatment dose can be put in to the system in a variety of ways. For example, in one embodiment, the healthcare provider may input the treatment dose using a keyboard. In some embodiments, the healthcare provider may input the treatment dose using a touch screen. In some embodiments, the treatment dose can be provided automatically (e.g. by computer).

In block 3315 the feedback system 3405 accesses the measurement history (e.g. the measurement history 3200 illustrated in FIG. 32) that stores the previously determined values for the concentration of the analyte and the values for a treatment dose previously administered. The method 3300 then proceeds to block 3320 where the feedback system 3405 calculates a predicted value for the concentration of the analyte at a future time (e.g. in the next hour) based on the previously determined values for the concentration of the analyte and the treatment dosing history. In some embodiments, the calculation may predict the value for the concentration of the analyte at a future time by extrapolating the concentration of the analyte assuming that the patient's sensitivity to the treatment drug (e.g. insulin) remains the same and by further assuming that the amount of medications and drugs being administered to the patient remain the same. For example, in some embodiments, the feedback system 3405 may assume that treatment dose input by the healthcare provider will not change over the next several time durations.

In block 3330, the predicted value for the concentration of the analyte is compared with a predetermined range. The predetermined range can be determined by taking into account various factors such as a patient's medical condition, the medications and drugs being administered to the patient, etc. In some embodiments, the predetermined range may be a glucose concentration in a range from about 70 mg/dL to about 110 mg/dL. If in block 3330, the predicted concentration of the analyte is determined to be within the predetermined range, then the method 3300 moves to block 3340 where the treatment dose input by the healthcare provider is stored in the measurement history.

However, if in block 3330, the predicted concentration of the analyte is determined to be not within the predetermined range, then the method 3300 proceeds to block 3360 where feedback is provided (e.g. to the healthcare provider or analyte monitoring system) that the predicted concentration of the analyte at a future time may be outside the predetermined range if the treatment dose input to the system is delivered to the patient. The system or the healthcare provider may change the treatment dose based on the feedback. In some embodiments, the feedback system 3405 can be configured to automatically stop the flow of the infusion fluid (e.g. glucose or insulin) based on the trend or a value of the concentration of one or more analytes. For example, in the case where the analyte of interest is glucose and the infusion fluid is insulin, the feedback system 3405 may stop the flow of insulin if the concentration of glucose is low enough to be life threatening or if the trend of successive glucose measurements indicated that the concentration of glucose may drop to levels that may to harmful to the patient.

In some embodiments, the feedback system 3405 can provide feedback regarding one or more drugs being administered to the patient without requiring an input from the healthcare provider. In some embodiments the feedback system 3405 can spectroscopically analyze the infusion fluid as it flows out of the infusion pump and/or source of infusion fluid (e.g. 518, 520 or 2782 of FIG. 5) through the infusion fluid tubes (e.g. 514, 516 or 2784 of FIG. 5) to determine the contents of the infusion fluid. For example, in some embodiments the feedback system 3405 may irradiate the infusion fluid with three or more wavelengths. In some embodiments, the wavelengths can be selected from the wavelength range of approximately 275 nm to 310 nm. In some embodiments, the wavelengths can be selected from the near infrared or infrared range of wavelengths. The feedback system 3405 can then obtain one or more spectra from the radiation reflected, transmitted and/or scattered by the infusion fluid to determine the contents of the infusion fluid. The spectra obtained by the feedback system 3405 can be compared with a catalog of drug or chemical spectra to identify the contents of the infusion fluid. In some embodiments, the spectra can be further analyzed to determine the concentration of the various contents of the infusion fluid.

The feedback system 3405 can comprise a watch list including the drugs or chemicals that may be detrimental to the health of the patient. The identified contents of the infusion fluid can be compared with the watch list. If a particular drug or chemical present in the watch list is detected in the infusion fluid, then the feedback system 3405 can be configured to shut off the infusion system delivering that particular drug or chemical to the patient. In addition, the feedback system 3405 may provide alerts or warnings to the healthcare provider and request confirmation from the healthcare provider before resuming the flow of that particular drug or chemical. In some embodiments, the feedback system 3405 can be configured to prevent the flow of a drug or chemical if the concentration of that drug or chemical in the infusion fluid is determined to be outside an acceptable range. For example, the system can issue an alert or warning to the healthcare provider.

Dilution Calibration

As described above, in certain embodiments, the systems and methods determine a concentration of an analyte such as, for example, glucose, in a bodily fluid sample such as, for example, whole blood or blood plasma. In some cases, the concentration of a blood plasma analyte can be affected by dilution of the whole blood sample from which the plasma is obtained. Dilution of a sample may occur during processing of the sample (e.g., by addition of a diluent to the sample), during operation of the sampling apparatus (e.g., by mixing of the sample with diluents in the apparatus), and so forth. For example, dilution may occur if an anticoagulant (e.g., heparin) is added to a blood sample to prevent clotting. Also, dilution may occur as a fluid sample travels through the apparatus, for example, through accumulation of residual diluent fluids (e.g., saline solution) in tubing.

Generally, dilution of a bodily fluid sample will result in the analyte concentration measured from the diluted sample being less than the analyte concentration present in the patient's body. Because diluents are more likely to reside in the plasma portion of the blood, dilution effects may be greater for analyte concentrations measured in blood plasma. Accordingly, it may be advantageous to calibrate a measured analyte concentration for some or all of the effects of dilution. In some embodiments, a measured analyte concentration is corrected for dilution to provide an estimate of analyte concentration that is more representative of the concentration in the patient's body.

As described above, certain embodiments of the disclosed systems and methods are directed to the measurement of blood plasma analytes in samples of whole blood. Since fluid diluents typically reside in blood plasma rather than in non-plasma components, it may be advantageous to determine the relative amounts of plasma and non-plasma components in a whole blood sample.

Whole blood includes fluid components (e.g., blood plasma) and non-fluid components (e.g., red blood cells, white blood cells, platelets, etc.). In a typical sample of whole human blood, red blood cells constitute approximately 45% of the blood volume, and white blood cells constitute approximately 1% of the blood of the blood volume. Platelets are small, non-fluid blood components that typically remain in the plasma, even after the plasma is separated (e.g., via centrifuging). Consequently, blood plasma typically constitutes approximately 54% of the blood volume.

The relative amounts of plasma and corpuscles in a whole blood sample can be determined in many ways, for example, by using a hematocrit, which is an instrument that separates a blood sample by centrifugation. The hematocrit value (commonly referred to as "Ht" or "HCT") is the percentage of red blood cells in whole blood. The hematocrit value can be determined by centrifuging a sample of whole blood in a graduated tube, a process which packs the red blood cells into the bottom of the tube. Values of the volume of packed red blood cells and the total volume of the blood sample are measured, and the percentage of red blood cells in the total sample, Ht, is calculated as the ratio of these values. As noted above, red blood cells form the bulk of the non-plasma component of blood. Accordingly, the fraction of blood plasma in whole blood is approximately 1-Ht.

The hematocrit value can be estimated without separating red blood cells from whole blood in a centrifuge. One method for estimating Ht uses the fact that hemoglobin predominantly resides in the red blood cells. The concentration of hemoglobin in whole blood can be determined, for example, by optical spectroscopy of the blood sample. Apparatus and methods for optical measurements of blood are described, for example, in U.S. Pat. No. 5,385,539, issued Jan. 31, 1995, entitled "APPARATUS FOR MONITORING HEMATOCRIT LEVELS OF BLOOD," the entire disclosure of which is hereby incorporated by reference herein. The hematocrit, Ht, has been found to be related to the concentration of hemoglobin in whole blood, Hb, as follows:

$$Ht\ (\%) = 3Hb/(g/dL) \tag{1}$$

Accordingly, a measurement of hemoglobin concentration, Hb, can be converted into a measurement of hematocrit, Ht, (and vice versa) by application of Equation (1). Therefore, embodiments of analyte detection systems can be configured with hematocrit sensors, hemoglobin sensors, or a combination thereof to determine, as appropriate, hematocrit and/or hemoglobin concentration.

Hematocrit (and/or hemoglobin concentration) can be measured via other techniques as well. For example, one example method for estimating Ht uses changes in the electrical conductivity through whole blood, where blood cells act as electrical insulators. Electrical conductivity apparatus and methods are described, for example, in U.S. Pat. No. 6,058,934, issued May 9, 2000, entitled "PLANAR HEMATOCRIT SENSOR INCORPORATING A SEVEN-ELECTRODE CONDUCTIVITY MEASUREMENT CELL," the entire disclosure of which is hereby incorporated by reference herein. Another example method for estimating Ht uses acoustic ultrasound measurements to determine Ht, for example, as described in U.S. Pat. No. 4,854,170, issued Aug. 8, 1989, entitled "APPARATUS AND METHOD FOR USING ULTRASOUND TO DETERMINE HEMATOCRIT," the entire disclosure of which is hereby incorporated by reference herein. In other techniques, hematocrit and/or hemoglobin concentration can be measured using a combination of approaches such as, for example, optical and acoustic techniques as described in U.S. Pat. No. 6,751,490, issued Jun. 15, 2004, entitled "CONTINUOUS OPTOACOUSTIC MONITORING OF HEMOGLOBIN CONCENTRATION AND HEMATOCRIT," the entire disclosure of which is hereby incorporated by reference herein. Embodiments of the systems and methods disclosed herein may use one or more of the above-described example approaches (or other approaches) to measure hematocrit and/or hemoglobin concentration in a fluid sample.

In certain embodiments, an analyte concentration, g, is calibrated for the effects of dilution by determining or inferring a volume of diluent fluid added to the bodily fluid sample during processing of the sample, operation of the analyte detection system, and so forth. The estimated analyte concentration can be calibrated to account for the added diluent volume. For example, in some embodiments, one or more measurements of hematocrit (and/or hemoglobin concentration) in the fluid sample are made before and after dilution, and these measurements are used to at least partially correct an estimated analyte concentration for the effects of dilution. Examples of dilution calibration methods and systems will now be described.

Example Dilution Calibration Systems

Figure 35:
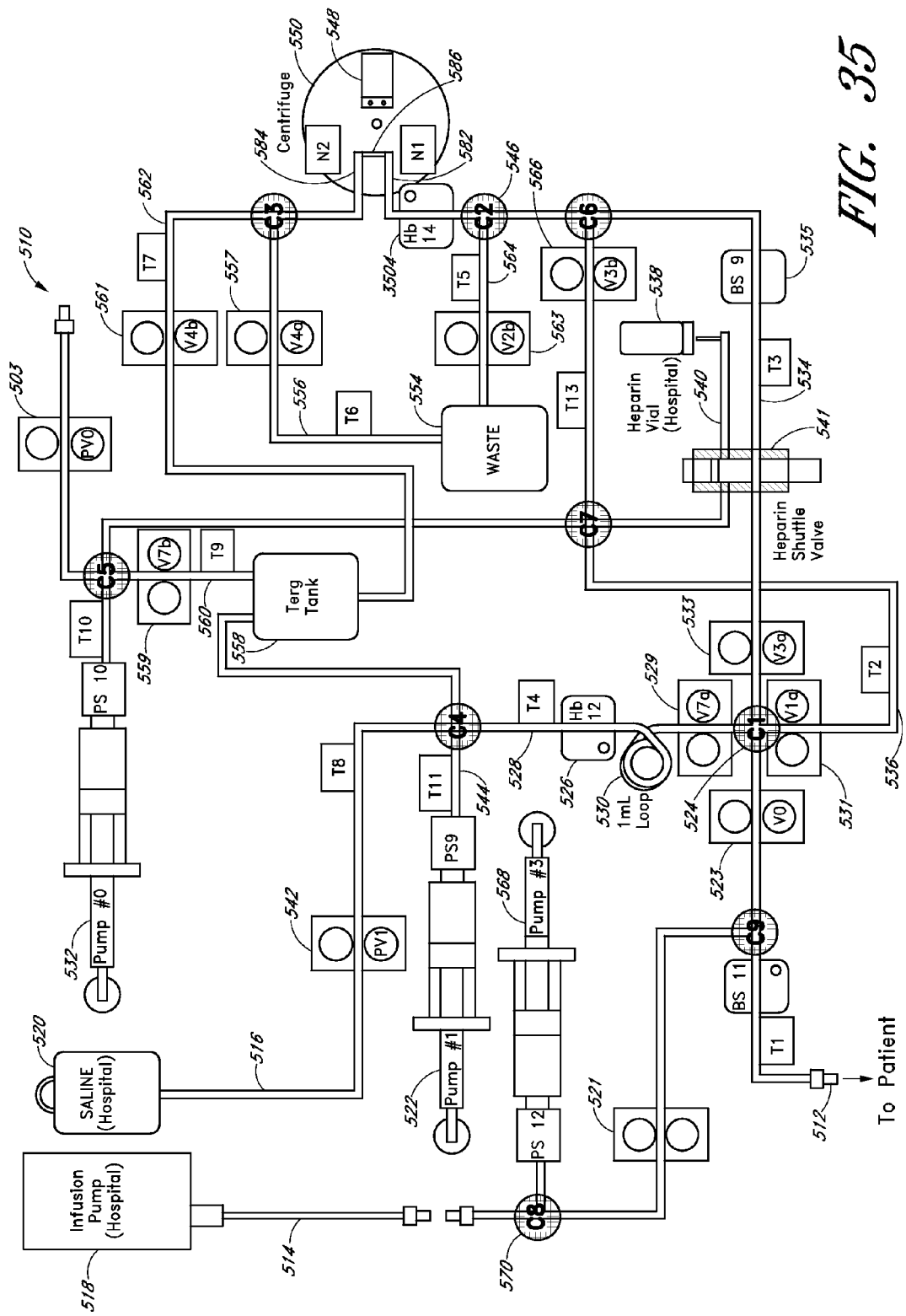
FIG. 35 schematically illustrates an embodiment of a fluid system that can be part of a system for withdrawing and analyzing fluid samples and calibrating the analyzed samples for sample dilution.
Figure 36:
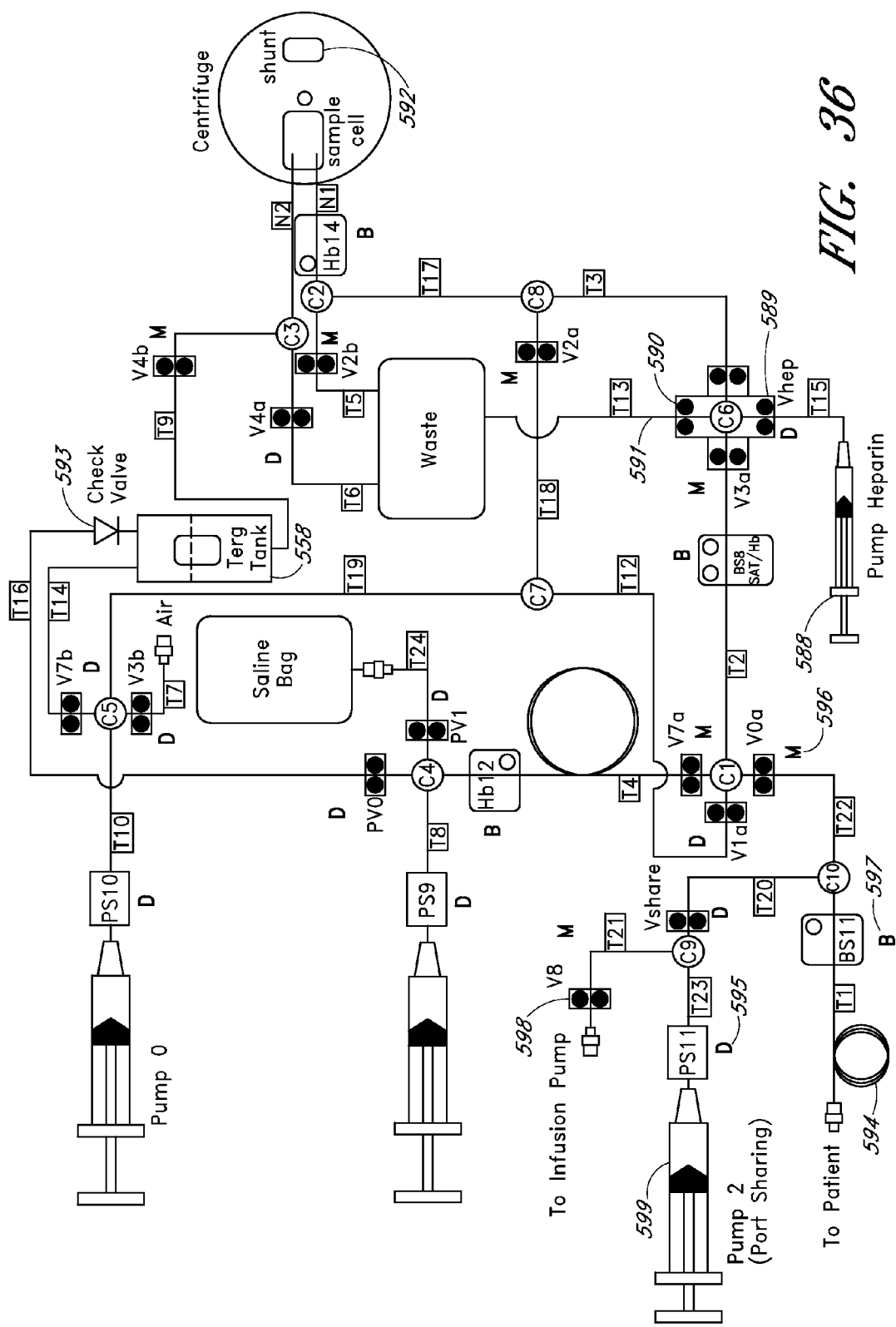
FIG. 36 schematically illustrates another embodiment of a fluid system that can be part of a system for withdrawing and analyzing fluid samples and calibrating the analyzed samples for sample dilution.

Any of the example analyte detection systems (and/or fluid handling systems) described herein can be used to provide dilution calibration. For example, FIGS. 35 and 36 schematically illustrate embodiments suitable for using hematocrit and/or hemoglobin concentration measurements to at least partially correct for dilution. Many of the components shown in FIGS. 35 and 36 have been described above with reference to FIGS. 5 and 6. In the embodiments depicted in FIGS. 35 and 36, the bubble sensor BS14 shown in FIG. 5 (reference numeral 552) and FIG. 6 has been interchanged with a hemoglobin sensor Hb14 (reference numeral 3504 in FIG. 35). In some embodiments, the hemoglobin sensor Hb14 is generally similar to the hemoglobin sensor 526 (Hb12) described above with reference to FIGS. 5 and 6. As will be described below, in these embodiments, the hemoglobin sensor Hb12 is used to measure hemoglobin concentration of the fluid sample after drawing from the body (and before substantial dilution has occurred). The hemoglobin sensor Hb14 is used to measure hemoglobin concentration after the fluid sample has traveled through the tubing to the vicinity of the centrifuge (and therefore after dilution may have occurred). These "before dilution" and "after dilution" measurements of hemoglobin concentration can be used to at least partially correct for the effects, if present, of dilution.

Although the embodiments shown in FIGS. 35 and 36 utilize a hemoglobin concentration sensor Hb14, in other embodiments either (or both) of the hemoglobin concentration sensors Hb12 and Hb14 may be hematocrit sensors. Further, although the bubble sensor BS14 (shown in FIGS. 5 and 6) has been interchanged with the hematocrit sensor Hb14 in the embodiments shown in FIGS. 35 and 36, in other embodiments, the hematocrit sensor Hb14 is provided in addition to the bubble sensor BS 14. Also, in other embodiments the sensors Hb12 and Hb14 can be disposed at locations in the fluid handling network that are different than shown in FIGS. 5, 6, 35, and 36. For example, the sensor Hb12 can be located closer to the patient tube 512 (T1), and the sensor Hb14 can be located closer to (but downstream of) the anticoagulant valve 541. It is advantageous for the sensors Hb12 and Hb14 to be disposed at locations in the fluid handling network such that substantially all the dilution of the fluid sample can be accounted for. Although two sensors Hb12 and Hb14 are shown in FIGS. 35 and 36, in other embodiments three, four, five, six, or more sensors can be used to measure dilution of the fluid sample. For example, in some embodiments, sensors are positioned upstream and downstream of the location where an anticoagulant (e.g., heparin) is added to the fluid sample. Such embodiments advantageously can be used to calibrate for dilution by the anticoagulant.

An example of collection of a fluid sample will now be described with reference to FIG. 35. With the valves 542 (PV1), 559 (V7b), and 561 (V4b) closed, a first pump 522 (pump #1) is actuated to draw sample fluid to be analyzed (e.g. blood) from a fluid source (e.g., a laboratory sample container, a living patient, etc.) up into the patient tube 512 (T1), through the tube past the two flanking portions of the open pinch-valve 523 (V0), through the first connector 524 (C1), into the looped tube 530, past the hemoglobin sensor 526 (Hb12), and into the Hb sensor tube 528 (T4). During this process, the valve 529 (V7a) and 523 (V0) are open to fluid flow, and the valves 531 (V1a), 533 (V3a), 542 (PV1), 559 (V7b), and 561 (V4b) can be closed and therefore block (or substantially block) fluid flow by pinching the tube.

Before drawing the sample, the tubes 512 (T1) and 528 (T4) are filled with saline and the hemoglobin (Hb) level is zero. The tubes that are filled with saline are in fluid communication with the sample source (e.g., the fluid source 402). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually a nondiluted sample fluid.

The hemoglobin sensor 526 (Hb12) detects the concentration of hemoglobin in the sample fluid. As blood starts to arrive at the hemoglobin sensor 526 (Hb12), the hemoglobin level rises. A hemoglobin level can be selected, and the system can be pre-set to determine when that level is reached. A controller such as the fluid system controller 405 of FIG. 4 can be used to set and react to the pre-set value, for example. In some embodiments, when the sensed hemoglobin level reaches the pre-set value, a substantially undiluted sample is present at the first connector 524 (C1). The preset value can depend, in part, on the length and diameter of any tubes and/or passages traversed by the sample. A nondiluted sample can be, for example, a blood sample that is not diluted with saline solution, but instead has the characteristics of the rest of the blood flowing through a patient's body. The hemoglobin sensor 526 (Hb12) can measure the hemoglobin concentration of this "before dilution" blood sample. A loop of tubing 530 (e.g., a 1-mL loop) can be advantageously positioned as illustrated to help insure that undiluted fluid (e.g., undiluted blood) is present at the first connector 524 (C1) when the hemoglobin sensor 526 (Hb12) registers that the preset Hb threshold is crossed. The loop of tubing 530 provides additional length to the Hb sensor tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1). Accordingly, a possible advantage of embodiments using the loop of tubing 530 is that the "before dilution" hemoglobin concentration measured by the sensor 526 (Hb12) is representative of the (non-diluted) hemoglobin concentration of the patient's body.

When sufficiently nondiluted blood is present at the first connector 524 (C1), the fluid sample can be directed through the tube 534 (T3), past the connectors C6 and C2, and to the sample cell 548 for analysis. While traveling through this tubing, the fluid sample can be diluted by accumulation of saline solution, cleaning solution, etc. that has been left behind on the tube walls after cleaning or purging. Additionally, in some embodiments, an amount of anticoagulant (e.g., heparin) can be introduced into the tube 534 (T3), and then the fluid sample is mixed with the anticoagulant. As described above, the anticoagulant can be shuttled from the tube 540 into the anticoagulant valve tube 534 (T3) to provide a controlled amount of anticoagulant into the tube 534 (T3), which thereby additionally dilutes the fluid sample. After addition of the anticoagulant (if desired), the fluid sample is pushed up the anticoagulant valve tube 534 (T3), through the connector C6, and through the second connector 546 (C2). Along this path, the fluid sample may experience further dilution from accumulation of fluids on the tube walls. After passing the connector C2, the sample comes into sensing contact with the hemoglobin sensor 3404 (Hb14), which determines an "after-dilution" hemoglobin concentration of the sample. The sample is then pushed into the sample cell 548, which can be located on the centrifuge rotor 550. The fluid in the sample cell is centrifuged, which separates blood corpuscles from the blood plasma and any diluents present in the plasma (e.g., heparin, saline, cleaning fluid, etc.). Concentration of analytes in the diluted blood plasma can be measured as described above.

An example of the collection of a fluid sample in the fluid handling embodiment schematically illustrated in FIG. 36 will be described. Collection of the fluid sample may be generally similar to the collection described above with reference to FIG. 35. For example, blood is drawn from a patient (or from a suitable extracorporeal conduit), through the tubes T1, T22, and T4 and into the loop. When the hemoglobin sensor Hb12 determines, via a "before dilution" hemoglobin measurement, that the loop contains undiluted blood, the blood sample is directed to connector C1 and into line T2. If desired, as the blood sample passes the connector C6 an anticoagulant (e.g., heparin) can be injected, which dilutes the blood sample. The blood sample is then directed through the tubes T3 and T17 and passes the connector C2, where the hemoglobin sensor Hb14 performs an "after dilution" hemoglobin measurement. The blood sample is then directed into the sample cell of the centrifuge, where the blood corpuscles are separated from a diluted volume of blood plasma. A measurement of analyte concentration may then be performed on the diluted plasma sample. As discussed above, as the blood sample travels from the sensor Hb12 to the sensor Hb14, the blood sample can be diluted due to 1) accumulation of fluids (e.g., saline, cleaning solution, etc.) left behind on the tube walls from a previous tube purging/cleaning, and/or 2) injection, if desired, of an amount of a anticoagulant at the connector C6.

Example Dilution Calibration Methods

Figure 37:
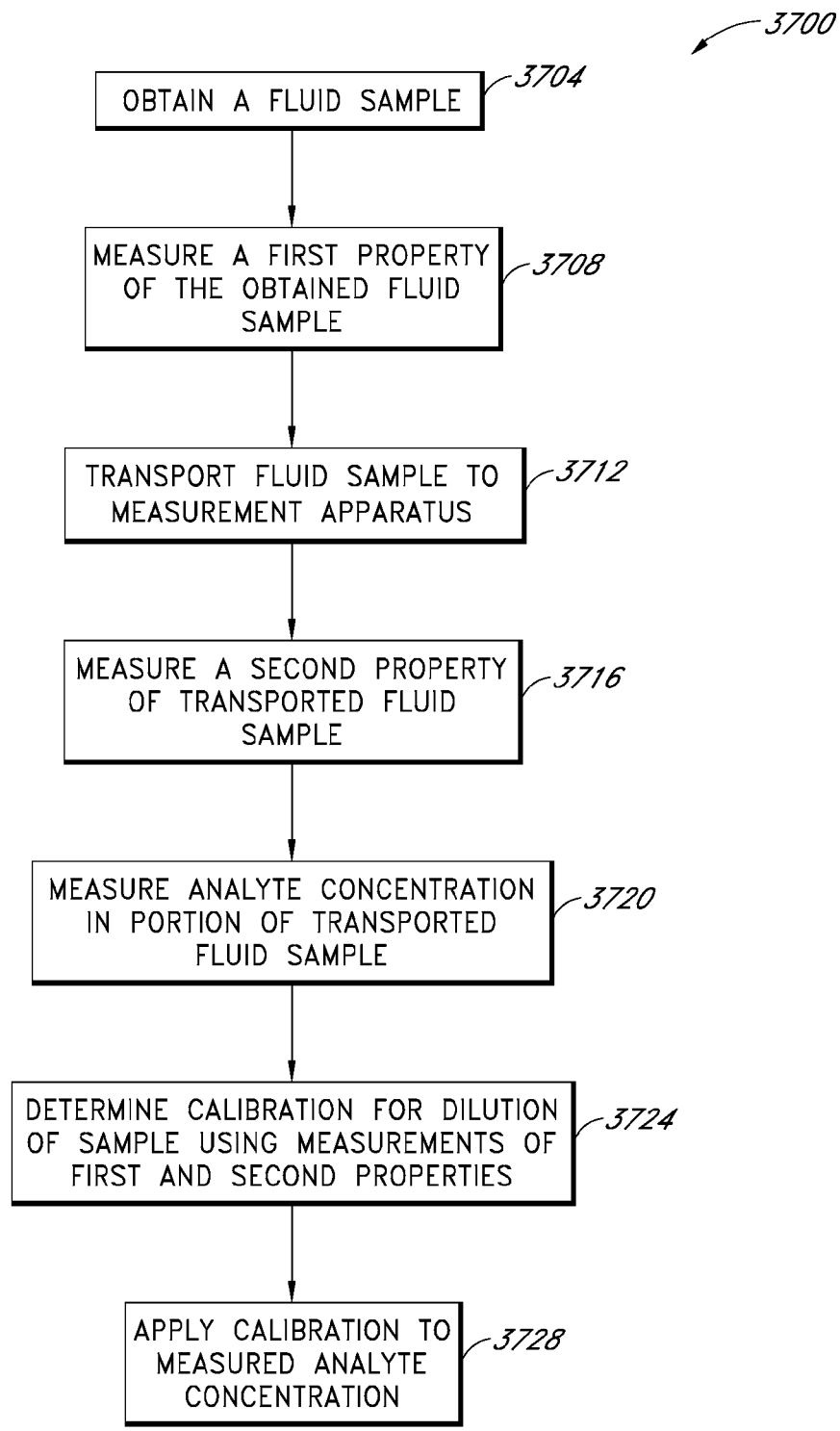
FIG. 37 is a flowchart that schematically illustrates an embodiment of a method for calibrating an analyte measurement in a fluid sample for effects of dilution of the fluid sample.

FIG. 37 is a flowchart illustrating an example method 3700 for calibrating an analyte measurement in a fluid sample for dilution of the fluid sample. In block 3704, a fluid sample is obtained for measurement. The fluid sample may comprise whole blood, blood plasma, interstitial body fluid, and so forth. The fluid sample can be obtained from a suitable fluid source (e.g., a laboratory sample container, a living patient, etc.). In many of the illustrative examples described herein, the fluid sample is a whole blood sample drawn from a patient, but this is not intended to be a limitation to embodiments of the calibration methods.

In block 3708, a first property of the fluid sample is measured. Advantageously, the first property may be sensitive to dilution of the sample. For example, in some embodiments the first property is hematocrit and/or hemoglobin concentration, and the first property is measured by a blood sensor such as, e.g., a hematocrit sensor and/or a hemoglobin sensor. In other embodiments, the first property may be a concentration of a particular component, analyte, or species in the fluid sample. Properties such as, for example, density and/or volume of the fluid sample can be measured. The first property may be a measurement of a single parameter or characteristic of the fluid sample or may include a group of measurements.

In block 3712, the obtained fluid sample is transported to a measurement site capable of providing a measurement of an analyte in the fluid sample. For example, the obtained fluid sample can be transported by a fluid handling network in an analyte detection system, such as, e.g., the fluid handling networks schematically depicted in FIGS. 35 and 36. While being transported, the fluid sample may experience dilution caused by, for example, processing of the fluid sample (e.g., addition of one or more diluents) and/or through routine operation of the fluid transport network (e.g., accumulation in the sample of diluents present in tubing in the fluid handling network). The amount of dilution can be known and/or unknown. For example, the amount (e.g., volume) of an anticoagulant added to the sample can be known (or determinable), while the amount of diluent accumulated from the fluid handling network can be unknown (and dependent on how the system has been operated prior to transport of the sample).

In block 3716, a second property of the fluid sample is measured. Advantageously, the second property may be sensitive to dilution of the sample such that the amount of dilution can be determined from comparison of the first property and the second property. As discussed above for the first property, the second property may include hematocrit, hemoglobin concentration, concentration of a particular component, analyte, or species in the fluid sample, density, and/or volume of the fluid sample. The second property may be a measurement of a single parameter or characteristic of the fluid sample or may include a group of measurements. The second property may be the same as the first property (e.g., both the first and the second property may be hematocrit), or the second property may be different from the first property (e.g., the first property may be hematocrit and the second property may be hemoglobin concentration).

In block 3720, a measuring apparatus performs a measurement of an analyte concentration in a portion of the fluid sample. For example, the measuring apparatus may comprise a spectroscopic analyte detection system configured to measure the concentration of an analyte (e.g., glucose) in plasma separated from a blood sample. The measuring apparatus may perform the analyte measurement on the fluid sample (e.g., a whole blood sample) and/or a component of the fluid sample (e.g., blood plasma separated from whole blood). Because of the possible effects of dilution of the fluid sample during transport in block 3712, the measured analyte concentration may not represent the analyte concentration in the nondiluted fluid sample obtained in block 3704. Accordingly, in blocks 3724 and 3728, the measured analyte concentration is calibrated for dilution of the fluid during transport. In some embodiments, the calibration at least partially corrects the measured analyte concentration for the dilution. For example, in block 3724 a calibration is determined based at least in part on the first property and the second property. Illustrative, non-limiting examples of the calculation of the calibration will be presented below. In block 3728, the calibration is applied to the analyte concentration measured in block 3720 to provide an at least partially dilution-calibrated estimate for analyte concentration.

In some embodiments, one or more general purpose and/or special purpose computers can be used to implement embodiments of the method 3700. Embodiments of the method 3700 can be represented as computer-executable instructions on a computer-readable medium. For example, the fluid system controller 405 may control the measurements of the first and second properties in blocks 3708 and 3716 (e.g., using measurement of hematocrit and/or hemoglobin concentration), and the algorithm processor 416 may control the measurement and calibration of the analyte concentration in blocks 3720-3728. In other embodiments, portions of the method 3700 can be executed by processors that are remote from analyte detection system. In certain embodiments, some (or all) of the blocks 3604-3728 can be combined or can be performed differently (or in different orders) than shown in the example method 3700 shown in FIG. 37. Many variations are possible.

An example procedure for calibrating an analyte measurement for the effects of dilution will now be described. This example is intended to be illustrative and not to limit the scope of the dilution calibration methods. In this example, a measurement of hematocrit and/or hemoglobin in a blood sample is performed "before dilution" (e.g., in block 3708) and another hematocrit and/or hemoglobin measurement is performed "after dilution" (e.g., in block 3716). For example, in the fluid system embodiments shown in FIGS. 35 and 36, the "before dilution" measurement can be provided by the hemoglobin sensor Hb12 and the "after dilution" measurement can be provided by the hemoglobin sensor Hb14. As described above, in other embodiments, additional hematocrit and/or hemoglobin measurements can be obtained. In such embodiments, the additional measurements can be used to improve accuracy and/or precision of the dilution calibration according to any suitable statistical techniques (e.g., regression, least squares, maximum likelihood, outlier analysis, etc.).

In this example procedure, "before dilution" measurements are indicated with a subscript "0," and "after dilution" measurements are indicated with a subscript "1." Further, in this example, the blood sample will be considered to include corpuscles, e.g., red and white blood cells, (subscript "c") and plasma (subscript "p"). In a volume of blood denoted by V, a volume $V_c$ contains corpuscles, and the remaining volume $V_p = V - V_c$ contains plasma. Thus, hematocrit, Ht, can be written as $$Ht = \frac{V_c}{V} = 1 - \frac{V_p}{V} \tag{2}$$

If hemoglobin concentration, Hb, is used to estimate Ht, Equation (1) can be used to convert Hb to Ht (or vice versa).

The total amount of glucose in the plasma is denoted by G, and equals the plasma glucose concentration, g, multiplied by the plasma volume $$G = gV_p \tag{3}$$

In this example, assume that as the blood sample is transported, it is diluted with a volume ΔV of fluid having no glucose and no solids. For example, ΔV may represent the controlled amount of anticoagulant mixed with the blood sample at the tube 534 (T3, shown in FIG. 35). Because no glucose and no solids are assumed to be added to the blood sample, the values of G and $V_c$ do not change during dilution. Consequently, $$G_0 = G_1 = G \tag{4}$$

$$V_{c0} = V_{c1} = V_c \tag{5}$$

The total blood volume and the plasma volume after dilution are related to the volumes before dilution and the dilution volume ΔV by $$V_1 = V_0 + \Delta V \tag{6}$$

$$V_{p1} = V_{p0} + \Delta V. \tag{7}$$

The plasma glucose concentration after dilution, $g_1$, is determined by the analyte detection system (e.g., in block 3720 of FIG. 37) and is thus a measured (known) quantity. Because the total amount of glucose, G, in the blood sample is assumed to be constant (no glucose is added by the diluent fluid), the value of the plasma glucose concentration before dilution, $g_0$, is unknown but may be related to $g_1$ from Equations (3) and (4): $G = g_0 V_{p0} g_1 V_{p1}$. Combining this relationship with Equation (7) yields $$\frac{g_0}{g_1} - 1 = \frac{\Delta V}{V_{p0}}, \tag{8}$$

hence, the calibration of the plasma glucose measurement is related to the amount of dilution, ΔV, of the blood sample. The "before dilution" plasma volume $V_{p0}$ can be replaced with the "before dilution" hematocrit, $Ht_0$, by using Equation (2), which yields $$\frac{g_0}{g_1} - 1 = \frac{\Delta V / V_0}{1 - Ht_0}, \tag{9}$$

where $V_0$ is the total blood volume before dilution.

In embodiments in which hemoglobin concentration, Hb, is measured instead of hematocrit, Ht, Equation (1) can be used in Equation (9) to yield $$\frac{g_0}{g_1} - 1 = \frac{\Delta V / V_0}{1 - 3Hb_0}, \quad (10)$$

where $Hb_0$ is measured in g/dL.

In some embodiments, the volumes $\Delta V$ and $V_0$ (or the ratio $\Delta V/V_0$) and the value $Hb_0$ are measured, and Equation (10) is used to adjust the measured plasma glucose concentration, $g_1$, to yield an estimate of the undiluted plasma glucose concentration, $g_0$. For example, in implementations where addition of an anticoagulant predominates dilution of the sample, the amount $\Delta V$ of the added anticoagulant can be measured (or otherwise know) and used in Equation (10) to calibrate the analyte concentration measurement.

In other embodiments, the diluted hematocrit, $Ht_1$ (and/or the diluted hemoglobin concentration $Hb_1$) is measured, and the volumes in Equation (10) are replaced with measured blood sample values. For example, because no solids are assumed to be added by the fluid diluent, the volume of corpuscles in the sample, $V_c$, is constant, and Equations (2) and (5) can be combined as $V_c = V_0 Ht_0 = V_1 Ht_1$. Equation (6) can be used eliminate $V_1$ to yield $$\frac{\Delta V}{V_0} = \frac{Ht_0}{Ht_1} - 1. \quad (11)$$

Consequently, measurements of hematocrit (and/or hemoglobin concentration) "before dilution" and "after dilution" can be used to provide an estimate of fractional sample dilution, $\Delta V/V_0$.

Substituting Equation (11) into Equation (9) provides another relationship that can be used to calibrate an "after dilution" glucose measurement to yield an estimate for the "before dilution" glucose measurement:

$$\frac{g_0}{g_1} - 1 = \frac{Ht_0/Ht_1 - 1}{1 - Ht_0}, \quad (12)$$

or if hemoglobin concentration Hb is measured (see, Eq. (1)), $$\frac{g_0}{g_1} - 1 = \frac{Hb_0/Hb_1 - 1}{1 - 3Hb_0}. \quad (13)$$

Equations (12) and (13) can be rewritten to show how the estimate for the "before dilution" analyte concentration $g_0$ is related to the measured "after dilution" analyte concentration $g_1$:

$$g_0 = g_1 \left[ \frac{Ht_0}{Ht_1} \frac{(1 - Ht_1)}{(1 - Ht_0)} \right], \quad (14)$$

$$g_0 = g_1 \left[ \frac{Hb_0}{Hb_1} \frac{(1 - 3Hb_1)}{(1 - 3Hb_0)} \right]. \quad (15)$$

If there is no measurable dilution of the sample, the "before dilution" and the "after dilution" Ht and/or Hb measurements will be substantially the same (e.g., the factors in square brackets will be approximately equal to one), and Equations (14) and (15) demonstrate that, as expected, $g_0 \approx g_1$. In some embodiments, the calibration shown in Equation (14) or (15) is not applied if the change between $Ht_1$ and $Ht_0$ (or $Hb_1$ and $Hb_0$) is more representative of measurement errors by hematocrit (and/or hemoglobin) sensors than dilution of the sample. If measurable dilution of the sample occurs, the "before dilution" and "after dilution" values for Ht (and/or Hb) will be different, and the factors in square brackets in Equations (14) and (15) provide an approximate correction factor that at least partially accounts for the dilution.

Thus, for example, in an embodiment in which $Hb_0$, $Hb_1$, and $g_1$ are measured (e.g., the embodiments shown in FIGS. 35 and 36), Equation (13) (or Eq. (15)) provides a relationship that can be used to estimate the "before dilution" analyte concentration $g_0$. Although the above example has been described in terms of glucose concentration, this is not a limitation, and the example procedure described herein can be used to calibrate concentration of any analyte measured in blood plasma. Further, Equations (2)-(15) can be readily modified if various assumptions that went into their derivation are relaxed. For example, an appropriate calibration for an analyte concentration can be derived if the diluent fluid added to the blood sample contains a known amount (or concentration) of the analyte of interest and/or blood solids. Also, Equations (12)-(15) can be modified if more than two hematocrit (and/or hemoglobin concentration) measurements are made while the blood sample is being transported between the patient (or an extracorporeal fluid container) and the analyte measurement apparatus (e.g., the centrifuge and spectroscopic analyzer). Many variations are contemplated, and an appropriate calibration may readily be determined for each such variation using the teachings herein. For example, in many implementations, the calibration will be a linear (e.g., affine) relationship, thus the "before dilution" concentration estimate will be related to the "after dilution" concentration measurement according to $g_0 = Cg_1 + D$, where C is a calibration factor and D is a calibration offset. In the example calibration procedure described above, the calibration offset $D=0$, and the calibration factor C is the quantity in the square brackets in Equation (14) (if hematocrit is measured) or Equation (15) (if hemoglobin concentration is measured). In other embodiments, the calibration offset is non-zero. For example, the calibration offset may at least partially correct for a diluent fluid that also includes the analyte of interest.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Embodiments of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. An analyte detection and treatment dosing system comprising:
    a fluid transport network configured to provide fluid communication with a body fluid in a patient through a patient end;
    a body fluid analyzer accessible via the fluid transport network, the body fluid analyzer configured to measure a characteristic of at least one analyte in the body fluid and determine a concentration of the at least one analyte from the measured characteristic;
    at least one pump system coupled to the fluid transport network, the pump system having a sampling mode in which the pump system is operable to withdraw a sample of bodily fluid from the patient end and transport said sample of bodily fluid toward the body fluid analyzer, and an infusion mode in which the pump system is operable to transport an infusion fluid to the patient; and
    a treatment dosing system in communication with the body fluid analyzer, said treatment dosing system including a treatment dosing protocol stored in a computer memory and configured to automatically determine a recommended dose of an infusion fluid configured to provide glycemic control, wherein the treatment dosing system determines the recommended dose based at least in part on the measured concentration of the analyte and the stored treatment dosing protocol,
    wherein the treatment dosing system is configured to:
        provide signals to a control system that is configured to vary the pump rate of the at least one pump system to deliver the recommended dose of the infusion fluid to the patient, and
        wherein the treatment dosing system is configured to provide signals to a control system to automatically and completely stop the delivery of the infusion fluid if the measured concentration of the analyte is below a certain threshold.

2. The analyte detection system of claim 1, wherein the treatment pump is configured to deliver infusion substance continuously at a basal rate through the patient end.

3. The analyte detection system of claim 1, wherein the treatment pump is configured to deliver the recommended dose of the infusion substance as a bolus injection through the patient end.

4. The analyte detection system of claim 1, wherein the treatment pump is configured to deliver the infusion substance continuously at a basal rate combined with intermittent bolus injections of the recommended dose.

5. The analyte detection system of claim 4, wherein a time interval between two bolus injections is determined based at least in part on the recommended dose and the basal rate.

6. The analyte detection system of claim 1, wherein the treatment pump is configured to deliver the recommended dose of the infusion substance to the patient through said patient end during the infusion mode of the pump system.

7. The analyte detection system of claim 1, wherein the body fluid analyzer comprises a spectroscopic analyzer.

8. The analyte detection system of claim 1, wherein the body fluid analyzer comprises an electro-chemical analyzer.

9. The analyte detection system of claim 1, wherein said at least one analyte comprises glucose.

10. The analyte detection system of claim 1, wherein the infusion, substance comprises a substance selected from the group consisting of insulin and dextrose.

11. The analyte detection system of claim 1, wherein the pump unit is selected from a group consisting of volumetric pump, syringe pump, peristaltic pump, vacuum pump, electrical pump, mechanical pump or hydraulic pump.

12. The analyte detection system of claim 1, wherein the dosing protocol comprises a tight glycemic control protocol.

13. The analyte detection system of claim 1, wherein the treatment dosing system is configured to access a measurement database, calculate an average concentration of the analyte based on one or more determinations by the body fluid analyzer of the concentration of the analyte and determine the recommended dose for the infusion substance based on the average concentration of the analyte.

14. The analyte detection system of claim 1, wherein the treatment dosing system is configured to access a measurement database, calculate a rate of change in the concentration of the analyte and determine the recommended dose for the infusion fluid based on the rate of change in the concentration of the analyte.

15. The analyte detection system of claim 1, further comprising a user interface including a dosing graphic that indicates information related to the recommended dose, an actual dose of the infusion substance, or both.

16. The analyte detection system of claim 15, wherein the user interface includes an input element configured to accept user input, the user interface further configured to adjust the actual dose of the infusion fluid based at least in part on the user input.

17. The analyte detection system of claim 16, wherein the user interface comprises a touchscreen display and the input element comprises a button on the touchscreen.

18. An analyte detection and treatment dosing system comprising:
a fluid transport network configured to provide fluid communication with a body fluid in a patient through a patient end;
at least one pump system coupled to the fluid transport network, the pump system having a sampling mode in which the pump system is operable to withdraw a sample of bodily fluid from the patient end and transport said sample of bodily fluid towards the body fluid analyzer, and an infusion mode in which the pump system is operable to transport an infusion fluid to the patient;
a body fluid analyzer accessible via the fluid transport network, the body fluid analyzer configured to measure a characteristic of at least one analyte in the body fluid and determine the concentration of the at least one analyte from the measured characteristic; and
a treatment dosing system in communication with the body fluid analyzer, said treatment dosing system including a treatment dosing protocol stored in a computer memory and configured to automatically determine a recommended dose of an infusion substance configured to provide glycemic control, wherein the recommended dose is determined based at least in part on one or more determinations by the body fluid analyzer of the concentration of the analyte and the treatment dosing protocol,
the treatment dosing system comprising a basal delivery system and a bolus injection system, both systems configured to deliver infusion substances to the patient through said patient end and through the same intravenous access line,
wherein the treatment dosing system is configured to provide signals to a control system to automatically stop the delivery of the infusion fluid if the concentration of the analyte falls below a threshold or if a trend in the concentration of the analyte indicates that the concentration will soon fall below the threshold.

19. The analyte detection system of claim 18, wherein the basal delivery system is configured to deliver infusion substance continuously at a basal rate through the patient end.

20. The analyte detection system of claim 18, wherein the bolus injection system is configured to deliver the recommended dose of the infusion substance as a bolus injection through the patient end.

21. The analyte detection system of claim 18, wherein the basal delivery system and the bolus injection system are controlled by a single treatment pump having a variable pump rate.

22. The analyte detection system of claim 18, wherein the basal delivery system and the bolus injection system have separate pumps, but each pump cooperates to infuse through the same intravenous access line.

23. An analyte detection and control system to determine and regulate the concentration of one or more analytes in a sample of bodily fluid, the system comprising:
a control system;
an analyte detector configured to measure a characteristic of at least one analyte in the sample of bodily fluid and determine a concentration of the analyte in the sample based on the measured characteristic;
a fluid handling system operatively coupled to the analyte detector, said fluid handling system comprising a fluid passageway in communication with a patient through a patient end;
a pump unit configured to engage the fluid handling system and draw a sample of bodily fluid from the patient periodically at draw intervals of less than 1 hour for analysis;
a source of infusion fluid configured to adjust glycemic levels in the patient, said infusion fluid source in fluid communication with the fluid handling system; and
a treatment dosing system in communication with the body fluid analyzer, said treatment dosing system including a treatment dosing protocol and configured to determine a recommended dose for the infusion fluid, wherein the recommended dose is determined based at least in part on one or more determinations by the body fluid analyzer of the concentration of the analyte and the treatment dosing protocol,
wherein the control system is configured to automatically stop the flow of the infusion fluid if one or more of the following conditions are met:
the body fluid analyzer determines that the concentration of the analyte is below a certain level; and
the body fluid analyzer determines that the concentration of the analyte is changing over time such that a fall below the level is imminent.

24. The system of claim 23, wherein the infusion fluid comprises glucose or Dextrose.

25. The analyte detection and control system of claim 23, wherein the infusion fluid comprises insulin.

26. The analyte detection and control system of claim 23 configured to draw a sample of bodily fluid at draw intervals of 45 minutes or less.

27. The analyte detection and control system of claim 23 configured to draw a sample of bodily fluid at draw intervals of 30 minutes or less.

28. The analyte detection and control system of claim 23 configured to draw a sample of bodily fluid at draw intervals of 15 minutes or less.

29. The analyte detection and control system of claim 23, wherein the infusion source is located within a short distance of the patient to allow infusion of the infusion fluid at intervals of less than the draw intervals.

30. The analyte detection and control system of claim 23, wherein the infusion source is located within a short fluid distance of the site where the patient end of the fluid passageway interfaces with the patient.

31. The analyte detection and control system of claim 23, wherein the infusion source delivers infusion fluid to the patient within 1 minute of receiving an instruction from the control system.

32. The analyte detection and control system of claim 23, wherein the infusion source delivers infusion fluid to the patient within 1-5 minutes of receiving an instruction from the control system.

33. The analyte detection and control system of claim 23, wherein the infusion source delivers infusion fluid to the patient within 1-10 minutes of receiving an instruction from the control system.

34. An analyte detection and treatment dosing system comprising:
  a fluid transport network configured to provide fluid communication with a body fluid in a patient;
  a body fluid analyzer accessible via the fluid transport network, the body fluid analyzer configured to measure a characteristic of at least one analyte in the body fluid and determine the concentration of the at least one analyte from the measured characteristic;
  a treatment dosing system in communication with the body fluid analyzer, said treatment dosing system including a treatment dosing protocol and configured to determine a recommended dose for an infusion fluid configured to provide glycemic control, wherein the recommended dose is determined based at least in part on one or more determinations by the body fluid analyzer of the concentration of the analyte and the treatment dosing protocol;
  a treatment pump coupled to the fluid transport network, the treatment pump operable to transport the infusion fluid to the patient through the patient end; and
  a fluid system controller comprising a graphic user interface, said fluid system controller configured to actuate the treatment pump, shut-off the treatment pump if the concentration of the at least one analyte is below a certain level and control the pump rate of the treatment pump;
  wherein the fluid system controller and the body fluid analyzer are both included within a single housing, the graphic user interface is located on the same housing, and the graphic user interface is configured to display the determined analyte concentration and the recommended dose.

35. The system of claim 34, wherein the graphic user interface includes an input element configured to accept user input, the user interface further configured to adjust the actual dose of the infusion fluid based at least in part on the user input.

36. The system of claim 35, wherein the graphic user interface is configured to display both the recommended dose and the actual dose, where both the recommended dose and the actual dose are expressed as infusion rates.

37. The system of claim 34, wherein the graphic user interface includes an input element configured to accept user input, the user interface configured to actuate the pump unit based at least in part on the user input.

38. An analyte monitoring system comprising:
  a fluidic system in fluid communication with a source of bodily fluid, said fluidic system being configured to obtain a first sample of bodily fluid from the source at a first time;
  an analyte detection system configured to analyze the first sample of bodily fluid or a component of the first sample of bodily fluid;
  a treatment dosing system; and
  a fluid infusion system;
  wherein the analyte detection system is configured to determine the concentration of an analyte in said first sample of the bodily fluid or a component of the first sample of the bodily fluid and store the value of the determined concentration in a measurement database,
  wherein the fluidic system further obtains a second sample of the bodily fluid at a second time and presents said second sample to the analyte detection system for analysis,
  wherein the analyte detection system analyzes the second sample or a component of the second sample and determines the concentration of the analyte in the second sample or the component of the second sample,
  wherein the treatment dosing system calculates a rate of change of the concentration of the analyte, and
  wherein the treatment dosing system communicates with the fluid infusion system to stop the flow of an infusion substance if:
    concentration of the analyte in the first or second sample is below a certain threshold; or
    the rate of change of the concentration of the analyte is below a certain prescribed value and the concentration of the analyte in the first or second sample is close to the threshold.

* * * * *